(12) United States Patent
Mathews et al.

(10) Patent No.: US 8,680,012 B2
(45) Date of Patent: Mar. 25, 2014

(54) 4-PHENYL-PYRANE-3,5-DIONES,4-PHENYL-THIOPYRANE-3,6-DIONES AND CYCLOHEXANETRIONES AS NOVEL HERBICIDES

(75) Inventors: Christopher John Mathews, Bracknell (GB); James Nicholas Scutt, Bracknell (GB); Michel Muehlebach, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 240 days.

(21) Appl. No.: 12/519,015

(22) PCT Filed: Dec. 12, 2007

(86) PCT No.: PCT/EP2007/010848
§ 371 (c)(1),
(2), (4) Date: Jan. 12, 2010

(87) PCT Pub. No.: WO2008/071405
PCT Pub. Date: Jun. 19, 2008

(65) Prior Publication Data
US 2010/0210466 A1    Aug. 19, 2010

(30) Foreign Application Priority Data

Dec. 14, 2006  (GB) .................................. 0624961.9
Mar. 15, 2007  (GB) .................................. 0705044.6

(51) Int. Cl.
| | | |
|---|---|---|
| A01N 43/54 | (2006.01) | |
| A01N 43/16 | (2006.01) | |
| A01N 43/02 | (2006.01) | |
| A01N 43/56 | (2006.01) | |
| A01N 43/40 | (2006.01) | |
| C07D 315/00 | (2006.01) | |
| C07D 311/94 | (2006.01) | |
| C07D 335/02 | (2006.01) | |
| C07D 231/06 | (2006.01) | |
| C07D 405/10 | (2006.01) | |
| C07D 401/10 | (2006.01) | |

(52) U.S. Cl.
USPC ........... 504/239; 504/292; 504/288; 504/280; 504/251; 548/364.4; 544/333; 546/282.1; 549/417; 549/397; 549/28

(58) Field of Classification Search
None
See application file for complete search history.

(56) References Cited

U.S. PATENT DOCUMENTS

| | | |
|---|---|---|
| 4,175,135 A | 11/1979 | Haines et al. |
| 4,209,532 A | 6/1980 | Wheeler et al. |
| 4,409,153 A | 10/1983 | Howdakowski et al. |
| 4,489,012 A | 12/1984 | Hodakowski |
| 4,526,723 A | 7/1985 | Wheeler et al. |
| 4,659,372 A | 4/1987 | Wheeler et al. |
| 5,801,120 A | 9/1998 | Lee et al. |
| 6,458,965 B1 | 10/2002 | Lieb et al. |
| 6,894,005 B1 | 5/2005 | Maetzke et al. |
| 8,058,210 B2 | 11/2011 | Lieb et al. |
| 8,084,649 B2 | 12/2011 | Muehlebach et al. |
| 2003/0216260 A1 | 11/2003 | Ruther et al. |
| 2005/0164883 A1 | 7/2005 | Maetzke et al. |
| 2006/0166829 A1 | 7/2006 | Fischer et al. |
| 2010/0113270 A1 | 5/2010 | Mathews et al. |
| 2010/0210466 A1 | 8/2010 | Muehlebach et al. |
| 2011/0152095 A1* | 6/2011 | Scutt et al. ..................... 504/103 |
| 2012/0040826 A1 | 2/2012 | Jeanmart et al. |

FOREIGN PATENT DOCUMENTS

| | | |
|---|---|---|
| CA | 2322158 | 8/2000 |
| CA | 2325526 | 9/2000 |
| CA | 2382432 | 2/2002 |
| CA | 2382435 | 2/2002 |
| CA | 2456776 | 2/2004 |
| DE | 2813341 | 4/1983 |
| EP | 1481970 | 12/2004 |
| WO | 99/43649 | 9/1999 |
| WO | 99/47525 | 9/1999 |
| WO | 99/48869 | 9/1999 |
| WO | 00/37437 | 6/2000 |
| WO | 01/17972 | 3/2001 |
| WO | 01/17973 | 3/2001 |
| WO | 01/74770 | 10/2001 |
| WO | 03/013249 | 2/2003 |
| WO | 2002048138 | 6/2003 |
| WO | 2004111042 | 12/2004 |
| WO | 2005/123667 | 12/2005 |
| WO | 2006034315 | 3/2006 |
| WO | 2006034446 | 3/2006 |
| WO | 2008/071405 | 6/2008 |
| WO | 2008/110307 | 9/2008 |
| WO | 2008/110308 | 9/2008 |

OTHER PUBLICATIONS

Preliminary_STN_12519015_07052011 (2011).*
Muehlebach, M., et al., "Discovery and SAR of pinoxaden: a new broad spectrum, postemergence cereal herbicide," in Pesticide Chemistry, Crop Protection, Public Health, Environmental Safety, ed. H. Ohkawa et al., Jun. 2007, pp. 101-110.
Wenger, J., and Nidermann, T., "Chapter 9: Acetyl-CoA Carboxylase Inhibitors", in Modern Crop Protection Compounds, ed. W. Kraemer et al., Wiley-VCH Verlag, Weinheim, 2007, pp. 335-357.
Wenger, et al.: "Chapter 11: Acetyl-CoA Carboxylase Inhibitors", in Modern Crop Protection Compounds, Second Edition, Jan. 2012, pp. 447-477.

* cited by examiner

*Primary Examiner* — Yong Chu
(74) *Attorney, Agent, or Firm* — R. Kody Jones

(57) ABSTRACT

Pyrandione, thiopyrandione and cyclohexanetrione compounds, which are suitable for use as herbicides.

42 Claims, No Drawings

4-PHENYL-PYRANE-3,5-DIONES, 4-PHENYL-THIOPYRANE-3,6-DIONES AND CYCLOHEXANETRIONES AS NOVEL HERBICIDES

This application is a 371 of International Application No. PCT/EP2007/010848 filed Dec. 12, 2007, which claims priority to GB 0624961.9 filed Dec. 14, 2006, and GB 0705044.6 filed on Mar. 15, 2007, the contents of which are incorporated herein by reference.

The present invention relates to novel, herbicidally active cyclic diones, and derivatives thereof, to processes for their preparation, to compositions comprising those compounds, and to their use in controlling weeds, especially in crops of useful plants, or in inhibiting plant growth.

Cyclic diones having herbicidal action are described, for example, in WO 01/74770.

Novel pyrandione, thiopyrandione and cyclohexanetrione compounds having herbicidal and growth-inhibiting properties have now been found.

The present invention accordingly relates to compounds of formula I

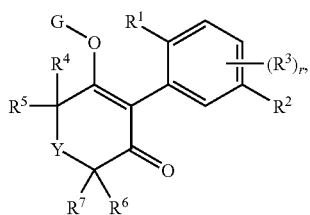

(I)

wherein
$R^1$ is halogen, $C_1$-$C_4$alkyl, $C_1$-$C_4$haloalkyl, $C_3$-$C_6$cycloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, nitro or cyano;
$R^2$ is optionally substituted aryl or optionally substituted heteroaryl;
r is 0, 1, 2 or 3;
$R^3$, if r is 1, is halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylthio, $C_1$-$C_6$alkylsulfinyl, $C_1$-$C_6$alkylsulfonyl, cyano or nitro; or the substituents $R^3$, if r is 2 or 3, independently of each other, are halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylthio, $C_1$-$C_6$alkylsulfinyl, $C_1$-$C_6$alkylsulfonyl, cyano or nitro;
$R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, cyclopropyl or cyclopropyl substituted by $C_1$- or $C_2$alkyl, $C_1$- or $C_2$haloalkyl or halogen; cyclobutyl or cyclobutyl substituted by $C_1$- or $C_2$alkyl; oxetanyl or oxetanyl substituted by $C_1$- or $C_2$alkyl; $C_5$-$C_7$cycloalkyl or $C_5$-$C_7$cycloalkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl or $C_4$-$C_7$cycloalkenyl substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; cyclopropyl$C_1$-$C_5$alkyl or cyclopropyl$C_1$-$C_5$alkyl substituted by $C_1$- or $C_2$alkyl, $C_1$- or $C_2$haloalkyl or halogen; cyclobutyl$C_1$-$C_5$alkyl or cyclobutylC$_1$-$C_5$alkyl substituted by $C_1$-$C_2$alkyl; oxetanyl$C_1$-$C_5$alkyl or oxetanyl$C_1$-$C_5$alkyl substituted by $C_1$- or $C_2$alkyl; $C_5$-$C_7$cycloalkyl$C_1$-$C_5$alkyl or $C_5$-$C_7$cycloalkyl$C_1$-$C_5$alkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl$C_1$-$C_5$ alkyl or $C_4$-$C_7$cycloalkenyl$C_1$-$C_5$alkyl which is substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylsulfinyl, $C_1$-$C_4$alkylsulfonyl or $C_1$-$C_4$alkylcarbonyl; benzyl or benzyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; or
$R^4$ and $R^5$, or $R^6$ and $R^7$, are joined to form a 5-7 membered saturated or unsaturated ring in which a methylene group is optionally replaced by an oxygen or sulfur atom, or a 5-7 membered saturated or unsaturated ring substituted by $C_1$- or $C_2$alkyl, where a methylene group of the ring is optionally replaced by an oxygen or sulfur atom; or
$R^4$ and $R^7$ are joined to form a 5-7 membered saturated or unsaturated ring unsubstituted or substituted by $C_1$- or $C_2$alkyl, $C_1$- or $C_2$alkoxy, $C_1$-$C_2$alkoxy$C_1$-$C_2$alkyl, hydroxy, halogen, phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl;
Y is O, C=O, $S(O)_m$ or $S(O)_nNR^8$; provided that when Y is C=O, $R^6$ and $R^7$ are different from hydrogen when either $R^4$ or $R^5$ is hydrogen, and $R^4$ and $R^5$ are different from hydrogen when either $R^6$ or $R^7$ is hydrogen;
m is 0 or 1 or 2 and n is 0 or 1;
$R^8$ is hydrogen, $C_1$-$C_6$alkyl, $C_3$-$C_6$cycloalkyl, $C_1$-$C_6$alkoxycarbonyl, tri($C_1$-$C_6$alkyl)silyl-ethyloxycarbonyl, $C_1$-$C_6$haloalkoxycarbonyl, cyano, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkylcarbonyl, $C_1$-$C_6$cycloalkylcarbonyl, phenylcarbonyl or phenylcarbonyl substituted by $R^9$; benzylcarbonyl or benzylcarbonyl substituted by $R^9$; pyridylcarbonyl or pyridylcarbonyl substituted by $R^9$; phenoxycarbonyl or phenoxycarbonyl substituted by $R^9$; benzyloxycarbonyl or benzyloxycarbonyl substituted by $R^9$;
$R^9$ is $C_1$-$C_6$haloalkyl, $C_1$-$C_6$alkoxycarbonyl, nitro, cyano, formyl, carboxyl or halogen, and
G is hydrogen, an agriculturally acceptable cation or a latentiating group.

In the substituent definitions of the compounds of the formula I, the alkyl substituents and alkyl moieties of alkoxy, alkylthio etc. having 1 to 6 carbon atoms are preferably methyl, ethyl, propyl, butyl, pentyl and hexyl, in the form of their straight and branched isomers. Higher alkyl groups of up to 10 carbon atoms comprise preferably octyl, nonyl and decyl, in form of their straight and branched isomers. The alkenyl and alkynyl radicals having 2 to 6 carbon atoms as well as up to 10 carbon atoms can be straight or branched and can contain more than 1 double or triple bond. Examples are vinyl, allyl, propargyl, butenyl, butynyl, pentenyl and pentynyl. Suitable cycloalkyl groups contain 3 to 7 carbon atoms and are for example cyclopropyl, cyclobutyl, cyclopentyl, cyclohexyl and cycloheptyl. Cyclopropyl, cyclobutyl, cyclopentyl and cyclohexyl are preferred. Preferred halogens are fluorine, chlorine and bromine. Preferred examples of aryls are phenyl and naphthyl. Preferred examples of heteroaryls are thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl and pyridazinyl, and, where appropriate, N-oxides and salts thereof. These aryls and heteroaryls can be substituted by one or more substituents, where preferred substituents are halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano. The group G denotes hydrogen, an agriculturally acceptable cation (such as an alkali metal cation, alkaline earth metal cation, sulfonium cation (preferably tri($C_1$-$C_6$) alkylsulfonium cation, ammonium cation, $C_1$-$C_6$alkylammonium cation, di($C_1$-$C_6$alkyl)ammonium cation, tri($C_1$-$C_6$alkyl)ammonium cation or tetra($C_1$-$C_6$) alkylammonium cation), or a latentiating group. These latentiating groups G are selected to allow its removal by one or a combination of biochemical, chemical or physical processes to afford compounds of formula I where G is H before, during or following application to the treated area or plants. Examples of these processes include enzymatic cleavage, chemical hydrolysis and photolysis. Compounds bearing such latentiating groups G may offer certain advantages, such as improved penetration of the cuticula of the plants treated, increased tolerance of crops, improved compatibility or stability in formulated mixtures containing other herbicides, herbicide safeners, plant growth regulators, fungicides or insecticides, or reduced leaching in soils. The latentiating group G is preferably selected from the groups G is $C_1$-$C_8$alkyl, $C_2$-$C_5$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ wherein $X^a$, $X^b$, $X^c$, $X^d$, $X^e$ and $X^f$ are independently of each other oxygen or sulfur;

$R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_5$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_6$alkyl)silyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, $R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_5$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_6$alkyl)silyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_6$trialkylsilyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl, (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, amino, $C_1$-$C_3$alkylamino, di($C_1$-$C_3$alkyl)amino, $C_1$-$C_3$alkoxy or $C_3$-$C_7$cycloalkylamino, di($C_3$-$C_7$cycloalkyl)amino or $C_3$-$C_7$cycloalkoxy or $R^c$ and $R^d$ may join together to form a 3-7 membered ring, optionally containing one heteroatom selected from O or S and optionally substituted by 1 or 2 $C_1$-$C_3$alkyl groups.

$R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_6$alkyl)silyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano, amino or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano, nitro, amino, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di($C_3$-$C_7$cycloalkyl)amino or $C_3$-$C_7$cycloalkoxy, $C_1$-$C_{10}$alkoxy, $C_1$-$C_{10}$haloalkoxy, $C_1$-$C_5$alkylamino or di($C_2$-$C_8$alkyl) amino $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, tri($C_3$-$C_6$alkyl)silyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro, heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro, heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro, diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro, phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, amino, hydroxyl, diphenylamino, or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro, or $C_3$-$C_7$cycloalkylamino, di($C_3$-$C_7$cycloalkyl)amino or $C_3$-$C_7$cycloalkoxy, $C_1$-$C_{10}$haloalkoxy, $C_1$-$C_5$alkylamino or di($C_2$-$C_8$alkyl)amino, benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro, and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_6$alkyl)silyl$C_1$-$C_5$alkyl, phenyl$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl, phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro, or heteroaryl, or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro.

In a preferred group of compounds of the formula I, $R^1$ is halogen, $C_1$-$C_4$alkyl, $C_1$-$C_4$haloalkyl, $C_2$-$C_4$alkenyl or $C_2$-$C_4$ alkynyl.

In another preferred group of compounds of the formula I, $R^2$ is aryl or heteroaryl; or aryl or heteroaryl both substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, phenoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_3$-$C_6$cycloalkyl, $C_1$-$C_4$alkylsulfonyloxy, $C_1$-$C_4$haloalkylsulfonyloxy, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, nitro, cyano, thiocyanato, hydroxy, amino, $C_1$-$C_6$alkylamino, $C_1$-$C_6$dialkylamino, $C_3$-$C_6$cycloalkylamino, morpholino, thiomorpholino, $C_1$-$C_6$alkylcarbonylamino, $C_1$-$C_6$alkoxycarbonylamino, $C_3$-$C_6$ alkenyloxycarbonylamino, $C_3$-$C_6$ alkynyloxycarbonylamino, $C_1$-$C_6$ alkylaminocarbonylamino, di($C_{1-6}$alkyl)aminocarbonylamino, formyl, $C_6$alkylcarbonyl, $C_2$-$C_6$alkenylcarbonyl, $C_2$-$C_6$alkynylcarbonyl, carboxy, $C_1$-$C_6$alkoxycarbonyl, $C_3$-$C_6$alkenyloxycarbonyl, $C_3$-$C_6$alkynyloxycarbonyl, carboxamido, $C_1$-$C_6$alkylaminocarbonyl, di($C_1$-$C_6$alkyl)aminocarbonyl, $C_1$-$C_6$alkylcarbonyloxy, $C_1$-$C_6$alkylaminocarbonyloxy, di($C_1$-$C_6$alkyl)aminocarbonyloxy or $C_1$-$C_6$alkylthiocarbonylamino;

Preferably, $R^2$ in the compounds of formula I is aryl or heteroaryl; or aryl or heteroaryl both substituted by halogen, $C_1$-$C_4$alkyl, $C_1$-$C_4$haloalkyl, phenoxy, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

More preferably, $R^2$ is phenyl, thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, pyridazinyl, oxadiazolyl and thiadiazolyl, and N-oxides and salts thereof, where these rings are unsubstituted or substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

In even more preferred compounds of the formula I, $R^2$ is phenyl or pyridyl or phenyl or pyridyl both substituted by halogen, nitro, cyano, $C_1$-$C_2$alkyl, $C_1$-$C_2$haloalkyl, $C_1$-$C_2$alkoxy or $C_1$-$C_2$haloalkoxy.

In an especially preferred group of compounds, $R^2$ is phenyl substituted at the para-position by halogen (in particular chlorine) and is optionally further substituted by halogen, nitro, $C_1$-$C_2$alkyl, $C_1$-$C_2$haloalkyl, $C_1$-$C_2$alkoxy or $C_1$-$C_2$haloalkoxy.

Preferably, $R^3$ is hydrogen (r is 0), halogen or $C_1$-$C_6$alkyl, especially hydrogen.

Preferably, $R^3$, if r is 1, is halogen or $C_1$-$C_3$alkyl.

Preferred are those compounds of the formula I, wherein $R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$ alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl; $C_5$-$C_7$cycloalkyl or $C_5$-$C_7$cycloalkyl substituted by $C_1$- or $C_2$alkyl or $C_1$- or $C_2$haloalkyl and in which a methylene group is optionally replaced by an oxygen or sulfur atom or a sulfinyl or sulfonyl group; $C_5$-$C_7$cycloalkyl$C_1$-$C_5$alkyl or $C_5$-$C_7$cycloalkyl$C_1$-$C_5$alkyl substituted by $C_1$-$C_2$alkyl or $C_1$- or $C_2$haloalkyl and in which a methylene group is optionally replaced by an oxygen or sulfur atom or a sulfinyl or sulfonyl group.

More preferably, $R^4$, $R^5$, $R^6$ and $R^7$, independently of each other, are hydrogen, $C_1$-$C_2$alkyl, $C_1$-$C_2$haloalkyl or $C_1$-$C_2$alkoxy$C_1$-$C_2$alkyl.

Preferred meanings of Y are O, C=O and S.

Y is O is especially preferred.

Preferably, G denotes $C(X^a)$—$R^a$ or $C(X^b)$—$X^c$—$R^b$, and the meanings of $X^a$, $R^a$, $X^b$, $X^c$ and $R^b$ are as defined above. Even more preferably, the latentiating group G is selected from the groups $C(X^a)$—$R^a$, $C(X^b)$—$X^c$—$R^b$, wherein $X^a$, $X^b$ and $X^c$ are oxygen, $R^a$ is $C_1$-$C_6$alkyl, $C_2$-$C_6$alkenyl, $C_2$-$C_6$alkynyl, $C_3$-$C_6$cycloalkyl or $C_1$-$C_4$alkoxy$C_1$-$C_4$alkyl and $R^b$ is $C_1$-$C_6$alkyl, $C_3$-$C_6$alkenyl, $C_3$-$C_6$alkynyl, $C_3$-$C_6$cycloalkyl or $C_1$-$C_4$alkoxy$C_1$-$C_4$alkyl.

More important groups G comprise hydrogen, an alkali metal or alkaline earth metal cation as an agriculturally acceptable cation, where hydrogen is particularly preferred.

In a preferred group of compounds of the formula (I), $R^1$ is $C_1$-$C_4$alkyl, $R^2$ is phenyl or phenyl substituted by halogen or $C_1$-$C_2$alkyl, $R^3$ is hydrogen, $R^4$, $R^5$, $R^6$ and $R^7$, independently of each other, are $C_1$-$C_2$alkyl, Y is O and G is hydrogen.

The invention relates also to the salts which the compounds of formula I are able to form with amines, alkali metal and alkaline earth metal bases or quaternary ammonium bases.

Among the alkali metal and alkaline earth metal hydroxides as salt formers, special mention should be made of the hydroxides of lithium, sodium, potassium, magnesium and calcium, but especially the hydroxides of sodium and potassium. The compounds of formula I according to the invention also include hydrates which may be formed during the salt formation.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and diisopropylamine.

Preferred quaternary ammonium bases suitable for salt formation correspond, for example, to the formula [N($R_a R_b R_c R_d$)]OH wherein $R_a$, $R_b$, $R_c$ and $R_d$ are each independently of the others $C_1$-$C_4$alkyl. Further suitable tetraalkylammonium bases with other anions can be obtained, for example, by anion exchange reactions.

Depending on the nature of the substituents G, $R^1$, $R^2$, $R^3$, $R^4$, $R^5$, $R^6$, $R^7$ and $R^8$, compounds of formula I may exist in different isomeric forms. When G is hydrogen, for example, compounds of formula I may exist in different tautomeric forms:

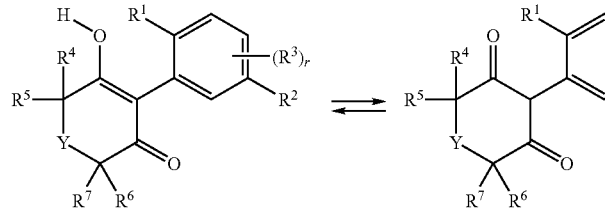

Furthermore, when Y is C=O and $R^4$ is hydrogen, further compounds of formula I may exist in different tautomeric forms:

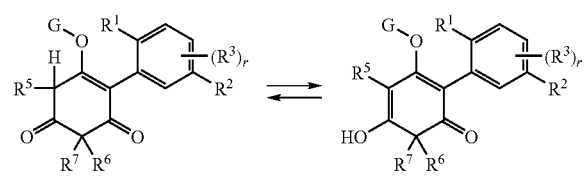

Also, when substituents contain double bonds, cis- and trans-isomers can exist. This invention covers all such isomers and tautomers and mixtures thereof in all proportions. These isomers, too, are within the scope of the claimed compounds of the formula I.

A compound of formula (I) wherein G is $C_1$-$C_8$alkyl, $C_2$-$C_8$haloalkyl, phenyl$C_1$-$C_8$alkyl (wherein the phenyl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), heteroaryl$C_1$-$C_8$alkyl (wherein the heteroaryl may optionally be substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsufinyl, $C_1$-$C_3$alkylsulfonyl, halogen, cyano or by nitro), $C_3$-$C_8$alkenyl, $C_3$-$C_8$haloalkenyl, $C_3$-$C_8$alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ or $CH_2$—$X^f$—$R^h$ where $X^a$, $X^b$, $X^c$, $X^d$, $X^e$, $X^f$, $R^a$, $R^b$, $R^c$, $R^d$, $R^e$, $R^f$, $R^g$ and $R^h$ are as defined above may be prepared by treating a compound of formula (A), which is a compound of formula (I) wherein G is H, with a reagent G-Z, wherein G-Z is an alkylating agent such as an alkyl halide (the definition of alkyl halides includes simple $C_1$-$C_8$ alkyl halides such as methyl iodide and ethyl iodide, substituted alkyl halides such as chloromethyl alkyl ethers, Cl—$CH_2$—$X^f$—$R^h$, wherein $X^f$ is oxygen, and chloromethyl alkyl sulfides Cl—$CH_2$—$X^f$—$R^h$, wherein $X^f$ is sulfur), a $C_1$-$C_8$alkyl sulfonate, or a di($C_1$-$C_8$alkyl) sulfate, or with a $C_3$-$C_8$alkenyl halide, or with a $C_3$-$C_8$alkynyl halide, or with an acylating agent such as a carboxylic acid, HO—$C(X^a)R^a$, wherein $X^a$ is oxygen, an acid chloride, Cl—$C(X^a)R^a$, wherein $X^a$ is oxygen, or acid anhydride, $[R^aC(X^a)]_2O$, wherein $X^a$ is oxygen, or an isocyanate, $R^cN$=C=O, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride Cl—$(X^d)$—$N(R^c)$—$R^d$ (wherein $X^d$ is sulfur and with the proviso that neither $R^c$ or $R^d$ is hydrogen) or a chloroformate, Cl—$C(X^b)$—$X^c$—$R^b$, (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate Cl—$C(X^b)$—$X^c$—$R^b$, (wherein $X^b$ and $X^c$ are sulfur), or an isothiocyanate, $R^cN$=C=S, or by sequential treatment with carbon disulfide and an alkylating agent, or with a phosphorylating agent such as a phosphoryl chloride, Cl—$P(X^e)(R^f)$—$R^g$ or with a sulfonylating agent such as a sulfonyl chloride Cl—$SO_2$—$R^e$, preferably in the presence of at least one equivalent of base. Where substituents $R^4$ and $R^5$ are not equal to substituents $R^6$ and $R^7$, these reactions may produce, in addition to a compound of formula (I), a second compound of formula (IA). This invention covers both a compound of formula (I) and a compound of formula (IA), together with mixtures of these compounds in any ratio.

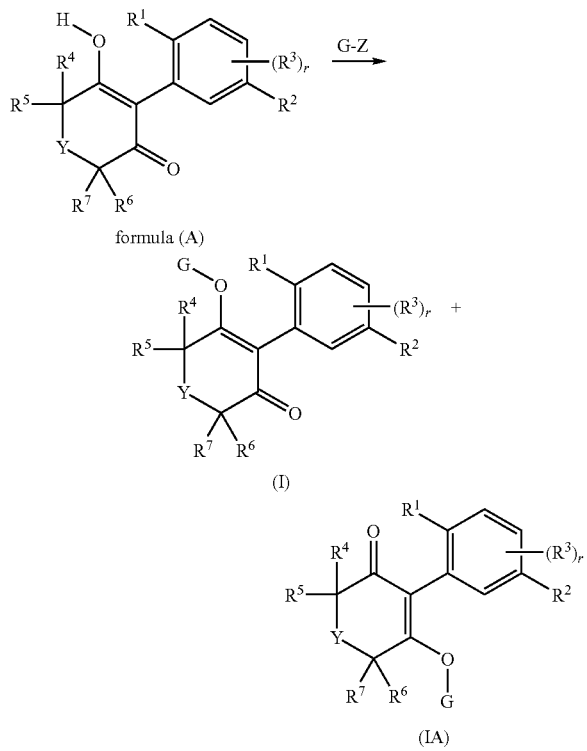

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M.

G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected by procedures similar to those described, for example, by R. Haines, U.S. Pat. No. 4,175,135, and by T. Wheeler, U.S. Pat. No. 4,422,870, U.S. Pat. No. 4,659,372 and U.S. Pat. No. 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform. Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of cyclic 1,3-diones may be effected using a phosphoryl halide or thiophosphoryl halide and a base by procedures analogous to those described by L. Hodakowski, U.S. Pat. No. 4,409,153.

Sulfonylation of a compound of formula (A) may be achieved using an alkyl or aryl sulfonyl halide, preferably in the presence of at least one equivalent of base, for example by the procedure of C. Kowalski and K. Fields, J. Org. Chem., (1981), 46, 197-201.

Compounds of formula (A), wherein Y is $S(O)_m$ and m is 1 or 2 may be prepared from compounds of formula (A) wherein Y is S by oxidation, according to a procedure analogous to that of E. Fehnel and A. Paul, J. Am. Chem. Soc., (1955), 77, 4241-4244.

A compound of formula (A), wherein Y is O, S or C=O may be prepared via the cyclisation of a compound of formula (B), preferably in the presence of an acid or base, and optionally in the presence of a suitable solvent, by analogous methods to those described by T. Wheeler, U.S. Pat. No. 4,209,532. The compounds of the formula (B) have been particularly designed as intermediates in the synthesis of the compounds of the formula I. Compounds of formula (B) wherein R is hydrogen or $C_1$-$C_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane.

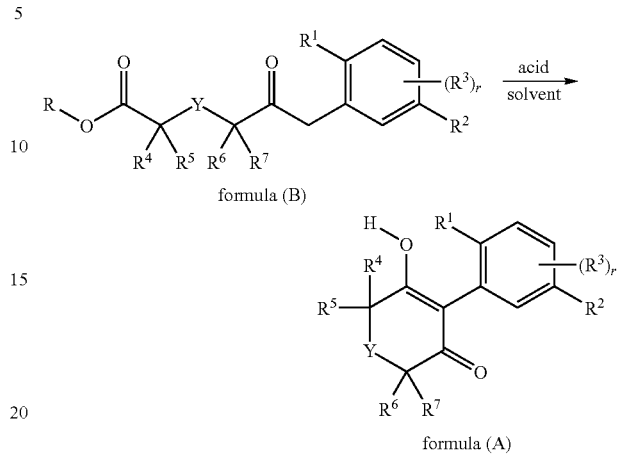

A compound of formula (B) wherein R is alkyl (preferably methyl or ethyl) may be cyclised under acidic or basic conditions, preferably under basic conditions in the presence of at least one equivalent of a strong base such as potassium tert-butoxide, lithium diisopropylamide, sodium bis(trimethylsilyl)amide or sodium hydride and in a solvent such as tetrahydrofuran, toluene, dimethylsulfoxide or N,N-dimethylformamide.

A compound of formula (B), wherein R is H may be esterified to a compound of formula (B), wherein R is alkyl, under known conditions (for example by treatment with an alcohol, R—OH, in the presence of an acid catalyst).

A compound of formula (B), wherein R is H may be prepared by hydrolysis of a compound of formula (C) wherein R is H or alkyl and R' is alkyl (preferably methyl or ethyl), followed by acidification of the reaction mixture to effect decarboxylation, by similar processes to those described by, for example, T. Wheeler, U.S. Pat. No. 4,209,532. Alternatively, a compound of formula (B), wherein R is alkyl (preferably methyl) may be prepared from a compound of formula (C), wherein R is alkyl (preferably methyl), through a Krapcho decarboxylation procedure under known conditions using known reagents (see for example G. Quallich, P. Morrissey, Synthesis, (1993), (1), 51-53).

A compound of formula (C) wherein R is alkyl may be prepared by treating a compound of formula (D) with a suitable carboxylic acid chloride of formula (E) wherein R is alkyl under basic conditions. Suitable bases include potassium tert-butoxide, sodium bis(trimethyl-silyl)amide and lithium diisopropylamide and the reaction is preferably conducted in a suitable solvent (such as tetrahydrofuran or toluene) at a temperature of between −80° C. and 30° C.:

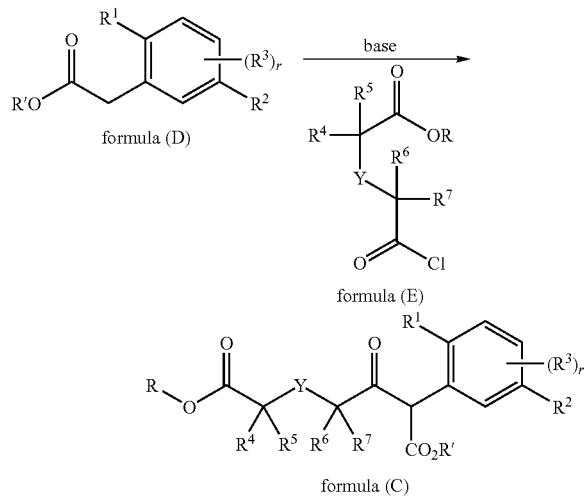

suitable temperature (between −80° C. and 30° C.) and reacting the resulting anion with a suitable anhydride of formula (F):

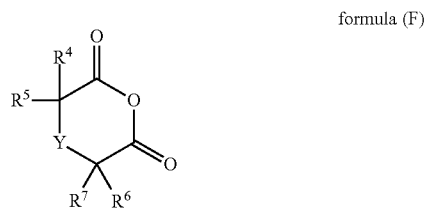

Compounds of formula (E) and formula (F) are known (see, for example T. Terasawa and T. Okada, J. Org. Chem., (1977), 42 (7), 1163-1169 and G. Bennett, W. Houlihan, R. Mason, and R. Engstrom, J. Med. Chem., (1976), 19 (5), 709-14) or may be made by similar methods from commercially available starting materials.

Using similar procedures to those outlined above, and starting from a halogenated phenylacetic acid ester of formula (G) (wherein Hal is chlorine, bromine or iodine), a compound of formula (H) may be prepared. In turn, this may be converted into a compound of formula (A) where $R^2$ is an aryl or heteroaryl, by reaction with a coupling partner such as an aryl or heteroaryl boronic acid, $R^2$—$B(OH)_2$, or a suitable salt or ester thereof, under palladium-catalysed conditions, preferably Suzuki-Miyaura conditions.

Alternatively, a compound of formula (C), wherein R is H, may be prepared by treating a compound of formula (D) with a suitable base (such as potassium tert-butoxide, sodium bis(trimethylsilyl)amide and lithium diisopropylamide) in a suitable solvent (such as tetrahydrofuran or toluene) at a The compound of the formula H has been particularly designed as an intermediate for the synthesis of the compounds of the formula (I).

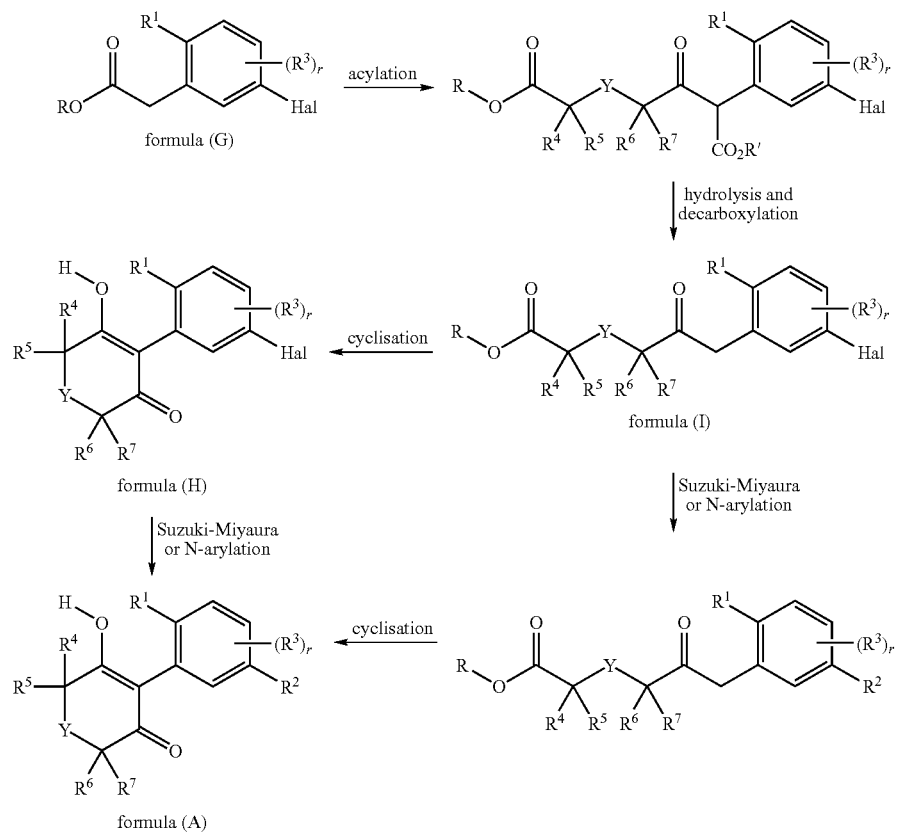

Conditions suitable for effecting the Suzuki-Miyaura cross-coupling of an aryl halide of formula (H) with an aryl- or heteroarylboronic acid of formula $R^2$—$B(OH)_2$, or a suitable salt or ester thereof, are known in the literature (see, for example K. Billingsley and S. Buchwald, J. Am. Chem. Soc., (2007), 129, 3358-3366; H. Stefani, R. Cella and A. Vieira, Tetrahedron, (2007), 63, 3623-3658; N. Kudo, M. Perseghini and G. Fu, Angew. Chem. Int. Ed., (2006), 45, 1282-1284; A. Roglans, A. Pla-Quintana and M. Moreno-Mañas, Chem. Rev., (2006), 106, 4622-4643; J-H Li, Q-M Zhu and Y-X Xie, Tetrahedron (2006), 10888-10895; S. Nolan et al., J. Org. Chem., (2006), 71, 685-692; M. Lysén and K. Köbler, Synthesis, (2006), 4, 692-698; K. Anderson and S. Buchwald, Angew. Chem. Int. Ed., (2005), 44, 6173-6177; Y. Wang and D. Sauer, Org. Lett., (2004), 6 (16), 2793-2796; I. Kondolff, H. Doucet and M, Santelli, Tetrahedron, (2004), 60, 3813-3818; F. Bellina, A. Carpita and R. Rossi, Synthesis (2004), 15, 2419-2440; H. Stefani, G. Molander, C-S Yun, M. Ribagorda and B. Biolatto, J. Org. Chem., (2003), 68, 5534-5539; A. Suzuki, Journal of Organometallic Chemistry, (2002), 653, 83; G. Molander and C-S Yun, Tetrahedron, (2002), 58, 1465-1470; G. Zou, Y. K. Reddy and J. Falck, Tetrahedron Lett., (2001), 42, 4213-7215; S. Darses, G. Michaud and J-P. Genêt, Eur. J. Org. Chem., (1999), 1877-1883; M. Beavers et al., WO2005/012243; J. Org. Chem. (1994), 59, 6095-6097; A. Collier and G. Wagner, Synthetic Communications, (2006), 36; 3713-3721).

Alternatively, a compound of formula (A) may be prepared by a Suzuki-Miyaura cross-coupling of a compound of formula (I), wherein Hal is chlorine, bromine, iodine or a pseudohalogen such as $C_1$-$C_4$haloalkylsulfonate, especially triflate, with an aryl or heteroaryl boronic acid, of formula $R^2$—$B(OH)_2$, or a suitable salt or ester thereof, followed by cyclisation under conditions previously described for a compound of formula (B).

In a further approach, a compound of formula (A) wherein $R^2$ is an azine N-oxide such as a pyridine N-oxide, a pyrimidine N-oxide, pyridazine N-oxide or pyrazine N-oxide, may be prepared from a compound of formula (H) by reaction with a suitable azine-N-oxide under conditions described by L. Campeau, S. Rousseaux and K. Fagnou, J. Am. Chem. Soc., (2005), 127, 18020 and by J-P. Leclerc and K. Fagnou, Angew. Chem. Int. Ed., (2006), 45, 7781-7786. The resulting N-oxide may be treated with known reagents under known conditions (for example reduction with hydrogen or ammonium formate in the presence of a suitable catalyst) to afford additional compounds of formula (I).

Additional compounds of formula (A), wherein $R^2$ is a heteroaromatic ring linked to the phenyl ring through a nitrogen atom, may be obtained by an Ullmann-type coupling (this reaction is also known in the literature as an N-arylation) of a compound of formula (H), or a compound of formula (I), with an N—H containing heteroaromatic compound, $R^2$—H, in the presence of a suitable catalyst, a suitable ligand, a suitable base and in a suitable solvent as described by, for example, M. Taillefer, N. Xia and A. Ouali, Angew. Chem. Int. Ed., (2007), 46 (6), 934-936; H. Zhang, Q. Cai, D. Ma, J. Org. Chem., (2005), 70, 5164-5173; J. Antilla, J. Baskin, T. Barder and S. Buchwald, J. Org. Chem., (2004), 69, 5578-5587 and A. Thomas and S. Ley, Angew. Chem. Int. Ed., 2003, 42, 5400-5449 and references therein.

In a further approach, a compound of formula (A) wherein Y is O, S or C=O, may be prepared by reaction of a compound of formula (J) with an aryllead tricarboxylate, in the presence of a suitable ligand and in a suitable solvent. Similar reactions are described in the literature (for example see, J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (K). Preferably the ligand is a nitrogen containing heterocycle such as N,N-dimethylaminopyridine, 1,10-phenanthroline pyridine, bipyridine, or imidazole, and one to ten equivalents of ligand with respect to a compound of formula (J) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.).

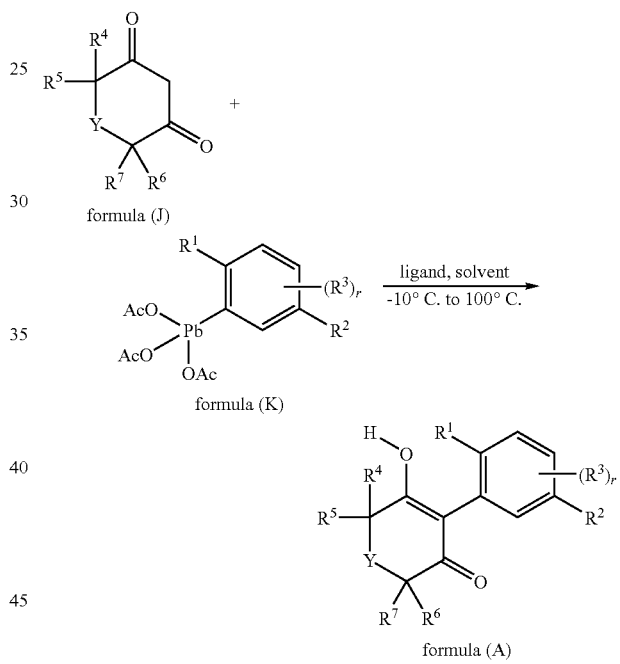

Compounds of formula (J), wherein Y is O, are known compounds or may be prepared by routes analogous to those described in the literature (see, for example, M. Morgan and E. Heyningen, J. Am. Chem Soc., (1957), 79, 422-424; I. Korobitsyna and K. Pivnitskii, Russian Journal of General Chemistry, (1960), 30, 4016-4023; T. Terasawa, and T. Okada, J. Org. Chem., (1977), 42 (7), 1163-1169; R. Anderson et al. U.S. Pat. No. 5,089,046; R. Altenbach, K. Agrios, I. Drizin and W. Carroll, Synth. Commun., (2004), 34 (4) 557-565; R. Beaudegnies et al., WO2005/123667; W. Li, G. Wayne, J. Lallaman, S. Chang, and S. Wittenberger, J. Org. Chem. (2006), 71, 1725-1727; R. Altenbach, M. Brune, S. Buckner, M. Coghlan, A. Daza, A. Fabiyi, M. Gopalakrishnan, R. Henry, A. Khilevich, M. Kort, I. Milicic, V. Scott, J. Smith, K. Whiteaker, and W. Carroll, J. Med. Chem, (2006), 49(23), 6869-6887; Carroll et al., WO 2001/083484 A1; J. K. Crandall, W. W. Conover, J. Org. Chem. (1978), 43(18), 3533-5; I. K. Korobitsyna, O. P. Studzinskii, Chemistry of Heterocyclic Compounds (1966), (6), 848-854). Compounds of formula (J), wherein Y is S, are known compounds or may be prepared by routes analogous to those described in the literature (see, for example, E. Fehnel and A. Paul, J. Am. Chem Soc., (1955), 77, 4241-4244; E. Er and P. Margaretha, Helvetica Chimica Acta (1992), 75(7), 2265-69; H. Gayer et al., DE 3318648 A1). Compounds of formula (J), wherein Y is C=O, are known compounds or may be prepared by routes analogous to those described in the literature (see, for example, R. Götz and N. Götz, WO2001/060776 R. Götz et al. WO 2000/075095; M. Benbakkar et al., Synth. Commun. (1989) 19(18) 3241-3247; A. Jain and T. Seshadri, Proc. Indian Acad. Sci. Sect. A, (1955), 42, 279); N. Ahmad et al., J. Org. Chem., (2007), 72(13), 4803-4815); F. Effenberger et al., Chem. Ber., (1986), 119, 3394-3404 and references therein).

A compound of formula (K) may be prepared from a compound of formula (L) by treatment with lead tetraacetate in a suitable solvent (for example chloroform) at 25° C. to 100° C. (preferably 25-50° C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

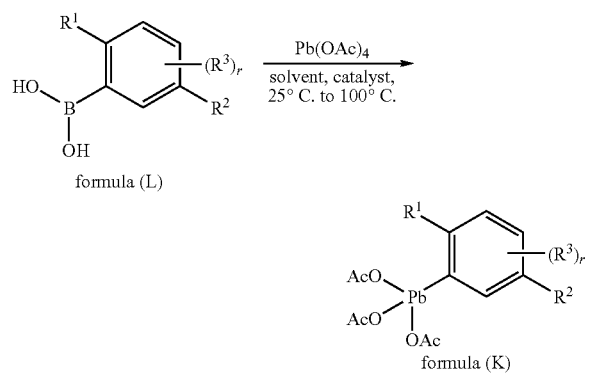

An aryl boronic acid of formula (L) may be prepared from an aryl halide of formula (M), wherein Hal is bromine or iodine by known methods (see, for example, W. Thompson and J. Gaudino, J. Org. Chem, (1984), 49, 5237-5243 and R. Hawkins et al., J. Am. Chem. Soc., (1960), 82, 3053-3059). Thus an aryl halide of formula (M) may be treated with an alkyl lithium or alkyl magnesium halide at low temperature, and the aryl magnesium or aryl lithium reagent obtained is allowed to react with a trialkyl borate, B(OR")$_3$, preferably trimethylborate, to give an aryl dialkylboronate which may be hydrolysed to the desired boronic acid of formula (L) under acidic conditions. Alternatively the same overall transformation of compound (M) to compound (L) may be achieved through a palladium-catalysed borylation reaction under known conditions using known reagents (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363), followed by hydrolysis of the intermediate boronate ester.

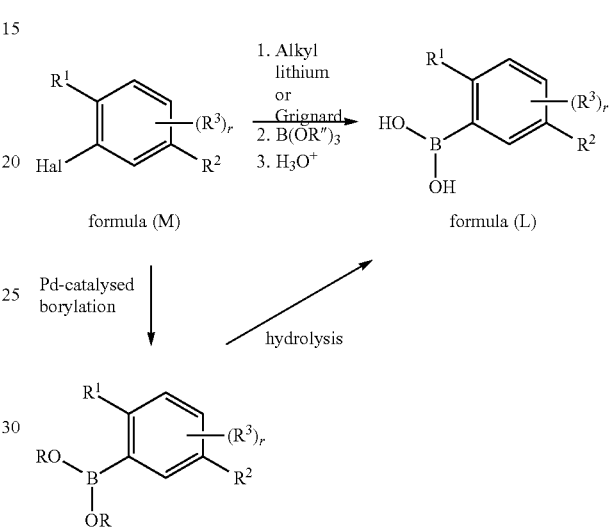

Aryl halides of formula (M) are known compounds or may be made by known methods from known compounds. For example, an aryl halide of formula (M) may be prepared from an aniline of formula (N) by known methods, for example the Sandmeyer reaction, via the corresponding diazonium salt (see, for example, J. March, Advanced Organic Chemistry, 3$^{rd}$ Edition, John Wiley and Sons, pages 647-648 and references therein. For additional examples see also W. Denney et al., J. Med. Chem., (1991), 34, 217-222; P. Knochel et al., Synthesis, (2007), No. 1, 81-84).

Additionally, a compound of formula (N) may be converted directly to a compound of formula (L) via a palladium-catalysed borylation of an intermediate aryl diazonium salt under known conditions using known reagents (see for example D. M. Willis, R. M. Strongin, Tetrahedron Lett. (2000), 41, 8683-8686), followed by hydrolysis of the intermediate boronate ester.

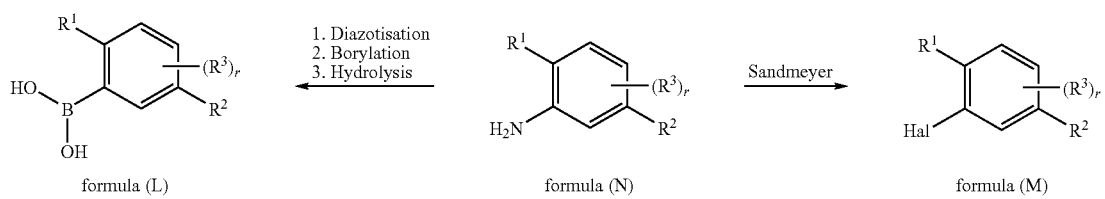

Anilines of formula (N) are known compounds, or may be made from known compounds by known methods. For example, an aniline of formula (N) may be prepared from an nitrobenzene of formula (O) (wherein Hal is chlorine, bromine, iodine, or a pseudohalogen such as $C_1$-$C_4$haloalkysulfonate, especially triflate) by reaction with an aryl- or heteroaryl boronic acid, $R^2$—$B(OH)_2$, or a suitable salt or ester thereof, under Suzuki-Miyaura conditions, or with an N—H containing heteroaromatic ring, $R^2$—H, under N-arylation conditions, followed by reduction of the nitro group by standard methods. Alternatively, a compound of formula (O) may first be reduced to an aniline, and the aniline cross-coupled under Suzuki-Miyaura conditions (see, for example A. Maj, L. Delaude, A. Demonceau and A. Noels, Tetrahedron, (2007), 63, 2657-2663; F. Bellina, A. Carpita and R. Rossi, Synthesis (2004), 15, 2419-2440 and A. Suzuki, Journal of Organometallic Chemistry, (2002), 653, 83-90)

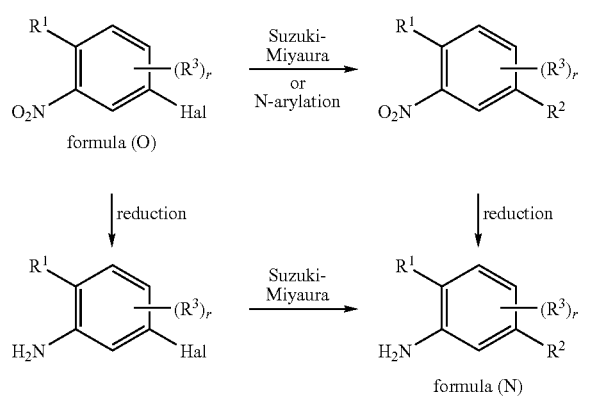

Nitrobenzenes of formula (O) are known compounds, or may be prepared from known compounds, by known methods.

In a further approach, a compound of formula (A) may be prepared from a compound of formula (P) by reaction with an aryl boronic acid of formula (L) in the presence of a suitable palladium catalyst and a base, preferably in a suitable solvent. Suitable palladium catalysts are generally palladium(II) or palladium(0) complexes, for example palladium(II) dihalides, palladium(II) acetate, palladium(II) sulfate, bis(triphenylphosphine)palladium(II) dichloride, bis(tricyclopentylphosphine)palladium(II) dichloride, bis(tricyclohexylphosphine)palladium(II) dichloride, bis(dibenzylideneacetone)palladium(0) or tetrakis(triphenylphosphine)-palladium(0). The palladium catalyst can also be prepared "in situ" from palladium(II) or palladium(0) compounds by complexing with the desired ligands, by, for example, combining the palladium(II) salt to be complexed, for example palladium(II) dichloride ($PdCl_2$) or palladium(II) acetate ($Pd(OAc)_2$), together with the desired ligand, for example triphenyl-phosphine ($PPh_3$), tricyclopentylphosphine or tricyclohexylphosphine and the selected solvent, with a compound of formula (P), a compound of formula (L) and a base. Also suitable are bidendate ligands, for example 1, 1'-bis(diphenylphosphino)ferrocene or 1,2-bis(diphenylphosphino)ethane. By heating the reaction medium, the palladium(II) complex or palladium(0) complex desired for the C—C coupling reaction is thus formed "in situ", and then initiates the C—C coupling reaction.

The palladium catalysts are used in an amount of from 0.001 to 50 mol %, preferably in an amount of from 0.1 to 15 mol %, based on the compound of formula (P). More preferably the palladium source is palladium acetate, the base is lithium hydroxide and the solvent is a mixture of 1,2-dimethoxyethane and water in a ratio of 4:1 to 1:4. The reaction may also be carried out in the presence of other additives, such as tetralkylammonium salts, for example, tetrabutylammonium bromide:

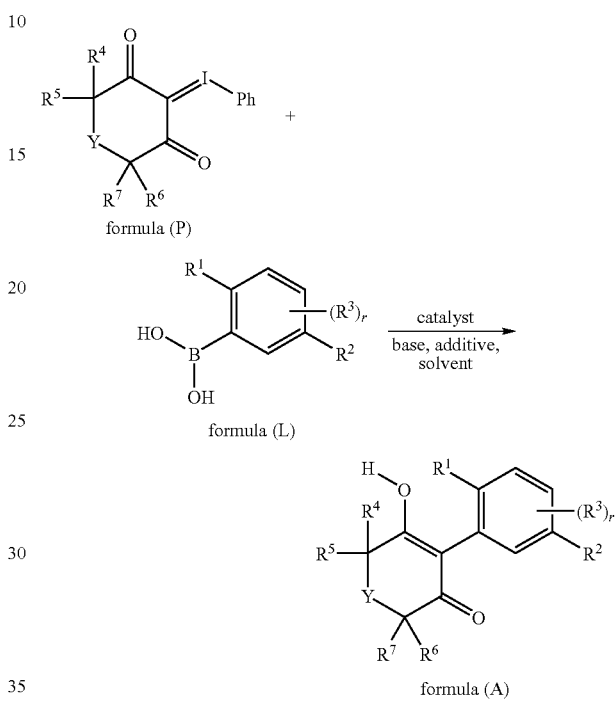

A compound of formula (P) may be prepared from a compound of formula (J) by treatment with (diacetoxy)iodobenzene according to the procedures of K. Schank and C. Lick, Synthesis, (1983), 392-395, or of Z Yang et al., Org. Lett., (2002), 4 (19), 3333-3336:

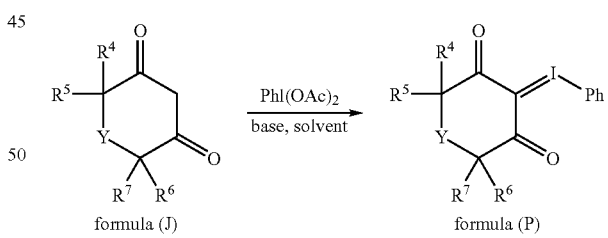

In a further approach a compound of formula (A) may be prepared via the rearrangement of a compound of formula (Q), in the presence of a reagent which promotes rearrangement, such as a metal alkoxide (preferably in an amount equal to or greater than 100% with respect to compound of formula (Q)) or cyanide anion (for example 0.001-25% potassium cyanide, 0.001-25% sodium cyanide), or a cyanohydrin (preferably 0.001-25% acetone cyanohydrin with respect to a compound of formula (Q)). This reaction is optionally performed in a suitable solvent (for example acetonitrile) at a suitable temperature (typically 25-100° C.) and with a suitable base (such as triethylamine).

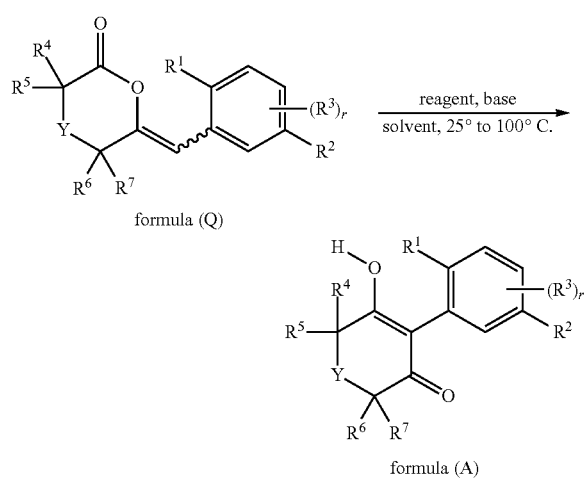

formula (Q)

formula (A)

A compound of formula (Q) may be prepared from a compound of formula (R) by treatment with a catalyst which promotes lactonisation (such as palladium(II) dichloride, gold(I) chloride or silver carbonate), preferably 0.001-50% silver carbonate with respect to compound of formula (R), in the presence of a suitable solvent (for example acetonitrile) at a suitable temperature (typically 25° C. to 150° C.), and optionally under microwave irradiation. Similar lactonisations are known in the literature (see for example P. Huang and W. Zhou, Tetrahedron Asymmetry (1991), 2 (9), 875-878; and H. Harkat, J-M. Weibel, P. Pale, Tetrahedron Letters (2006), 47(35), 6273-6276).

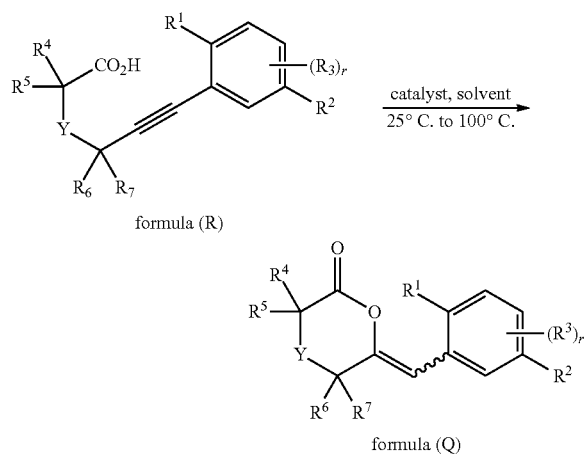

formula (R)

formula (Q)

A compound of formula (R) may be prepared by the hydrolysis of a compound of formula (S) where R' is alkyl (preferably methyl or ethyl), and a compound of formula (S) may be prepared from a compound of formula (T) by Sonogashira coupling with a compound of formula (M) in the presence of a suitable palladium catalyst (for example bis(triphenylphosphine) palladium(II) dichloride, tetrakis(triphenylphosphine)palladium(0) or palladium acetate in the presence of a suitable ligand), in an amount typically 0.001-25% of compound of formula (T), optionally in the presence of a suitable copper co-catalyst (for example copper(I) iodide in an amount typically 0.001-50% of compound of formula (T), a suitable base (such as diethylamine, triethylamine, piperidine or pyrrolidine) which may also be used as the solvent, or optionally in an alternative solvent such as 1,4-dioxane, N,N-dimethylacetamide or N,N-dimethylformamide, and optionally under microwave irradiation. Similar Sonogashira couplings are known in the literature (see for example see, J. Vara Prasad, F. Boyer, L. Chupak, M. Dermyer, Q. Ding, K. Gavardinas, S. Hagen, M. Huband, W. Jiao, T. Kaneko, S. N. Maiti, M. Melnick, K. Romero, M. Patterson, X. Wu, Bioorganic and Medicinal Chemistry Letters (2006), 16(20), 5392-5397, N. Leadbeater and B. Tominack, Tetrahedron Lett., (2003), 8653-8656, Z. Gan and R. Roy, Canadian Journal of Chemistry (2002), 80 (8), 908-916 and K. Sonogashira, J. Organomet. Chem., (2002), 653, 46-49 and references therein).

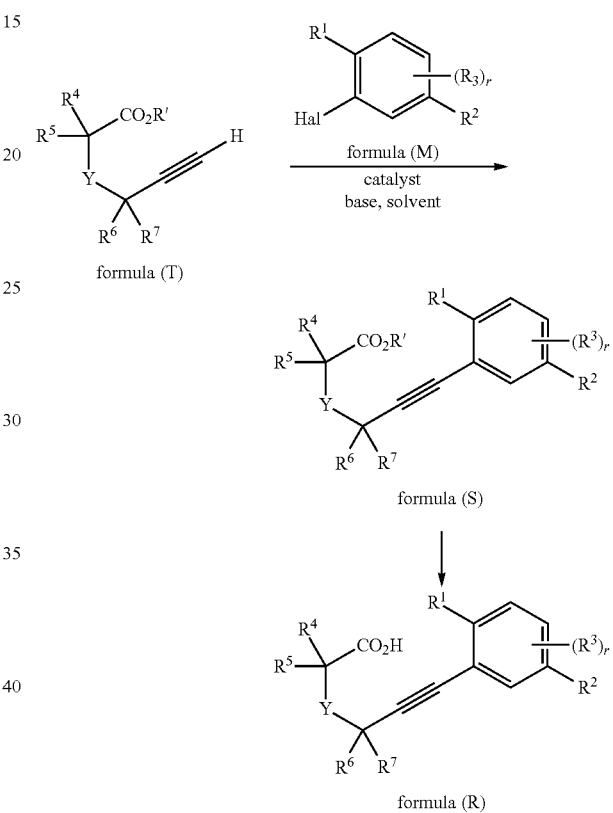

formula (T)

formula (M)

formula (S)

formula (R)

Compounds of formula (T) are known compounds or may be prepared by routes analogous to those described in the literature (see, for example, I. Drizin et al, WO2001/066544; M. Yamamoto, Journal of Chemical Research, Synopses (1991), (7), 165; P. Machin, U.S. Pat. No. 4,774,253; M. Morgan and E. Heyningen, J. Am. Chem Soc., (1957), 79, 422-424; N. Petiniot, A. J. Anciaux, A. F. Noels, A. J. Hubert, P. Teyssie, Tetrahedron letters, 1978, 14, 1239-42, and A. F. Noels, A. Demonceau, N. Petiniot, A. J. Hubert, P. Teyssie, Tetrahedron (1982), 38(17), 2733-9).

In a further approach, a compound of formula (A) may be prepared from a compound of formula (I) or (1A) (wherein G is $C_{1-4}$ alkyl) by hydrolysis, preferably in the presence of an acid catalyst such as hydrochloric acid and optionally in the presence of a suitable solvent such as tetrahydrofuran. A compound of formula (I) or (1A) (wherein G is preferably $C_{1-4}$ alkyl) may be prepared by reacting a compound of formula (U) (wherein G is preferably $C_{1-4}$ alkyl, and Hal is a halogen, preferably bromine or iodine), with an aryl boronic acid of formula (L) in the presence of a suitable palladium catalyst (for example 0.001-50% palladium(II) acetate with respect to compound (U)) and a base (for example 1 to 10 equivalents potassium phosphate with respect to compound (U)) and preferably in the presence of a suitable ligand (for example 0.001-50% (2-dicyclohexylphosphino)-2',6'-dimethoxybiphenyl with respect to compound (U)), and in a suitable solvent (for example toluene), preferably between 25° C. and 200° C. Similar couplings are known in the literature (see for example, Y. Song, B. Kim and J.-N. Heo, Tetrahedron Letters (2005), 46 (36), 5987-5990).

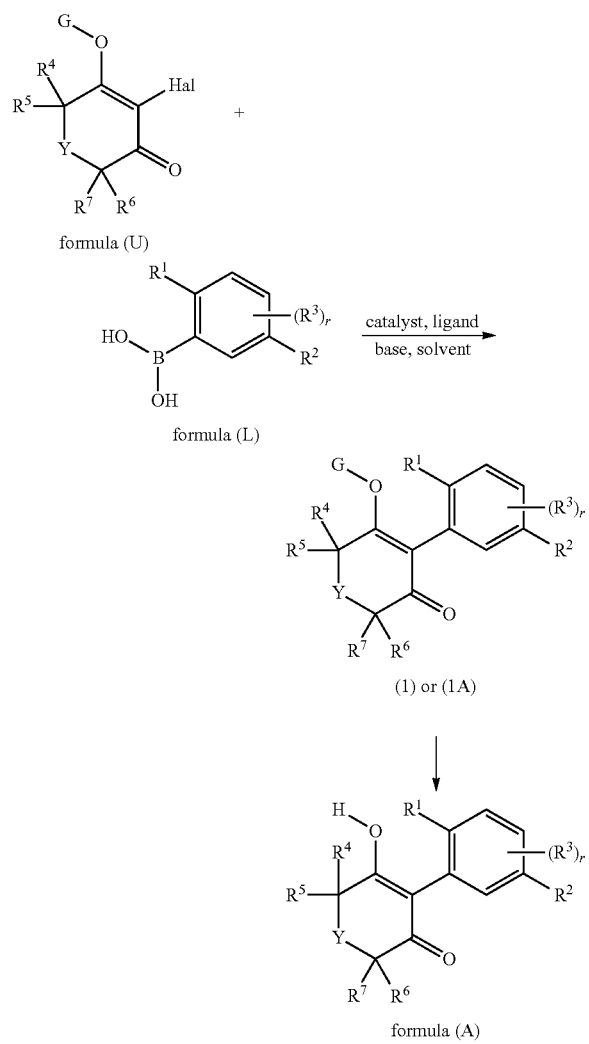

A compound of formula (U) may be prepared by halogenating a compound of formula (J), followed by alkylation of the resulting halide of formula (V) with a $C_{1-4}$ alkyl halide or tri-$C_{1-4}$-alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690). Alternatively, a compound of formula (U) may be prepared by alkylating a compound of formula (J) with an alkylating agent such as $C_{1-4}$ alkyl halide or a tri-$C_{1-4}$-alkylorthoformate, and halogenating the resulting enone of formula (W) under known conditions (see for example Y. Song, B. Kim and J.-N. Heo, Tetrahedron Letters (2005), 46(36), 5987-5990).

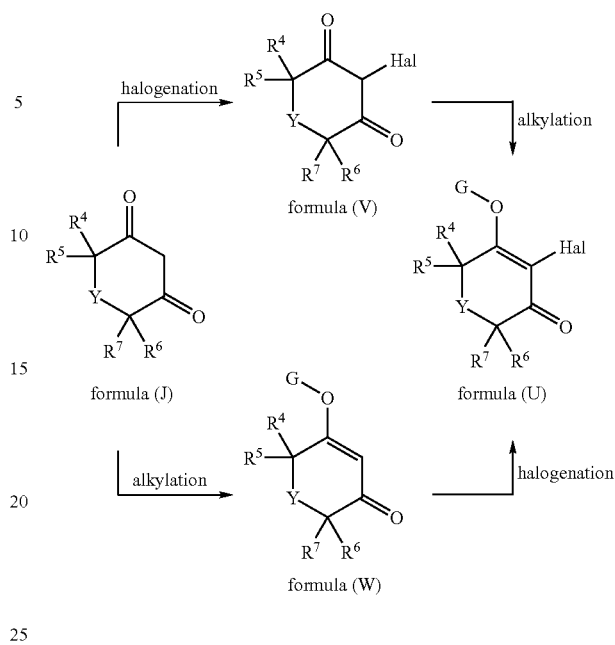

In a further approach, a compound of formula (A) may be prepared by reacting a compound of formula (J) with a compound of formula (M) in the presence of a suitable palladium catalyst (for example 0.001-50% palladium(II) acetate with respect to compound (J)) and a base (for example 1 to 10 equivalents potassium phosphate with respect to compound (J)) and preferably in the presence of a suitable ligand (for example 0.001-50% (2-dicyclohexylphosphino)-2',4',6'-tri-isopropylbiphenyl with respect to compound (J)), and in a suitable solvent (for example dioxane), preferably between 25° C. and 200° C. and optionally under microwave heating. Similar couplings are known in the literature (see for example, J. Fox, X. Huang, A. Chieffi, S. Buchwald, J. Am. Chem. Soc. (2000), 122, 1360-1370; B. Hong et al. WO 2005/000233). Alternatively, a compound of formula (A) may be prepared by reacting a compound of formula (J) with a compound of formula (M) in the presence of a suitable copper catalyst (for example 0.001-50% copper(I) iodide with respect to compound (J)) and a base (for example 1 to 10 equivalents cesium carbonate with respect to compound (J)) and preferably in the presence of a suitable ligand (for example 0.001-50% L-proline with respect to compound (J)), and in a suitable solvent (for example dimethylsulfoxide), preferably between 25° C. and 200° C. Similar couplings are known in the literature (see for example, Y. Jiang, N. Wu, H. Wu, M. He, Synlett, (2005), 18, 2731-2734, X. Xie, G. Cai, D. Ma, Organic Letters (2005), 7(21), 4693-4695).

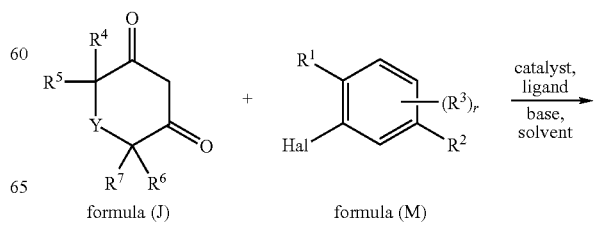

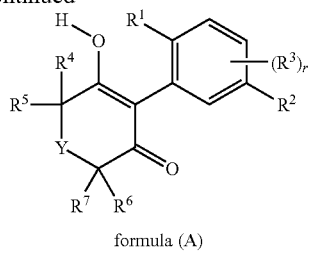

formula (A)

In a further approach, a compound of formula (A) may be prepared from a compound of formula (X) by cross coupling with an aryl- or heteroaryl-halide, $R^2$—Hal, where Hal is preferably chlorine, bromine, iodine or a pseudohalide such as $C_1$-$C_4$ haloalkylsulfonate, especially triflate, under Suzuki-Miyaura conditions described previously, or with an N—H containing heteroaromatic compound, $R^2$—H, under copper-catalysed conditions as described, for example, by P. Lam et al., Tetrahedron Lett., (1998), 39 (19), 2941-2944, and P. Lam, G. Vincent, C. G. Clark, S. Deudon, P. K. Jadhav, Tetrahedron Lett., (2001), 42, 3415-3418). The compound of the formula X has been particularly designed as an intermediate for the synthesis of the compounds of the formula (I).

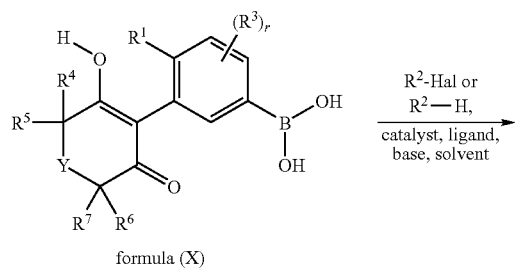

formula (X)

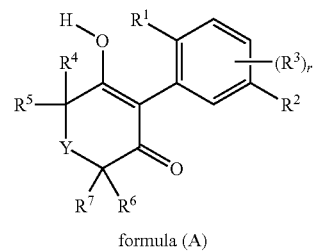

formula (A)

A compound of formula (X) may be prepared from a compound of formula (H) (wherein Hal is preferably iodine or bromine) by treatment with a suitable base (such as sodium hydride or potassium hydride), in a suitable solvent (such as tetrahydrofuran or diethyl ether) followed by a metal-halogen exchange reaction (preferably by treatment with an alkyl-lithium reagent such as n-butyllithium, sec-butyllithium or tert-butyllithium, or an organomagnesium reagent such as isopropyl magnesium chloride) and subsequent treatment with a trialkylborate, $B(OR'')_3$, (preferably trimethylborate) to give an arylboronate of formula (Y). A compound of formula (Y) may be hydrolysed under acidic conditions to give a boronic acid of formula (X). Alternatively a compound of formula (X) may be prepared from a compound of formula (H) (wherein Hal is preferably iodine, bromine, chlorine or a pseudohalide such as a $C_1$-$C_4$ haloalkylsulfonate, especially triflate) under known palladium-catalysed borylation conditions similar to those referenced for the preparation of compound (L).

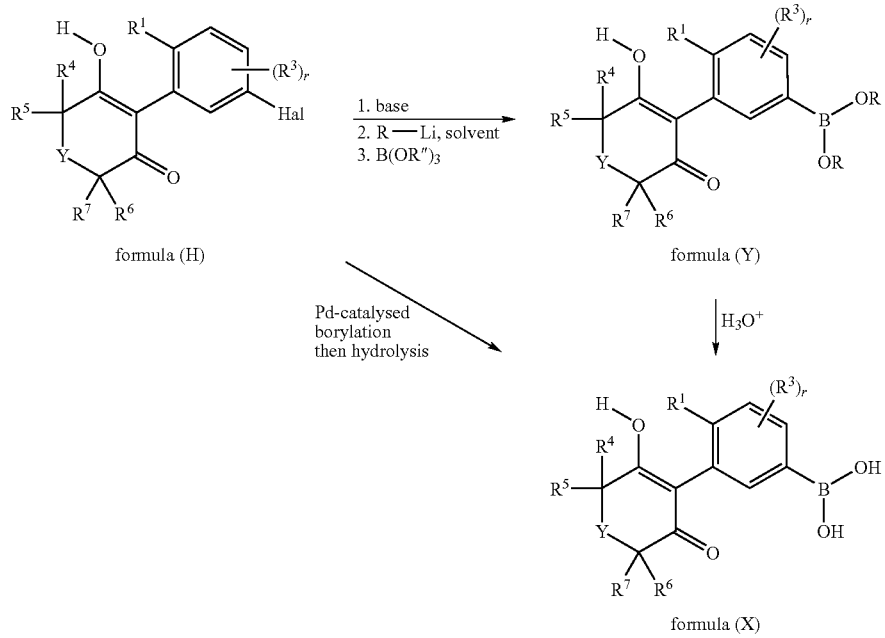

A compound of formula (H) may be prepared as described previously. Alternatively, a compound of formula (H) may be prepared from a compound of formula (J) by reaction with a compound of formula (Z) under conditions similar to those used for the preparation of a compound of formula (A) from a compound of formula (K).

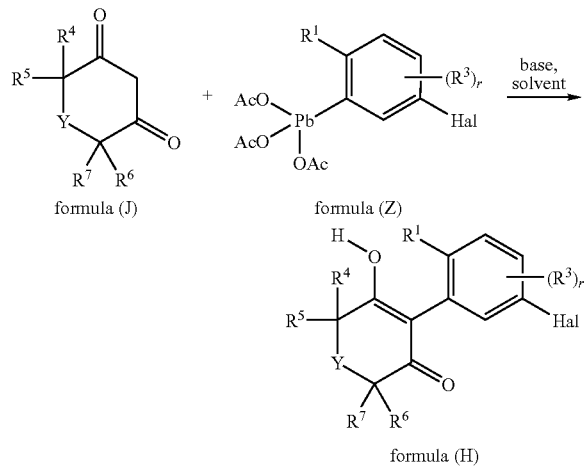

A compound of formula (Z) may be prepared from a compound of formula (Y) by methods similar to those described above for the preparation of a compound of formula (K) from a compound of formula (L).

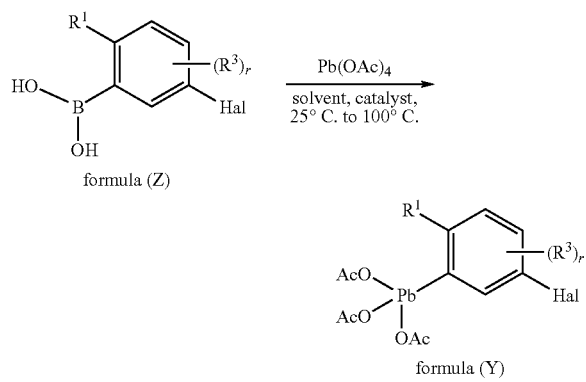

Compounds of formula (Z) are known compounds (see, for example, R. Bhatt et al., US2004/0204386), or may be made by known methods from known compounds, as described, for example, for the preparation of compounds of formula (L).

The compounds of formula I according to the invention can be used as herbicides in unmodified form, as obtained in the synthesis, but they are generally formulated into herbicidal compositions in a variety of ways using formulation adjuvants, such as carriers, solvents and surface-active substances. The formulations can be in various physical forms, for example in the form of dusting powders, gels, wettable powders, water-dispersible granules, water-dispersible tablets, effervescent compressed tablets, emulsifiable concentrates, microemulsifiable concentrates, oil-in-water emulsions, oil flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. Such formulations can either be used directly or are diluted prior to use. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be formulated with other adjuvants, for example finely divided solids, mineral oils, vegetable oils, modified vegetable oils, organic solvents, water, surface-active substances or combinations thereof. The active ingredients can also be contained in very fine microcapsules consisting of a polymer. Microcapsules contain the active ingredients in a porous carrier. This enables the active ingredients to be released into their surroundings in controlled amounts (e.g. slow release). Microcapsules usually have a diameter of from 0.1 to 500 microns. They contain active ingredients in an amount of about from 25 to 95% by weight of the capsule weight. The active ingredients can be present in the form of a monolithic solid, in the form of fine particles in solid or liquid dispersion or in the form of a suitable solution. The encapsulating membranes comprise, for example, natural and synthetic gums, cellulose, styrene-butadiene copolymers, polyacrylonitrile, polyacrylate, polyester, polyamides, polyureas, polyurethane or chemically modified polymers and starch xanthates or other polymers that are known to the person skilled in the art in this connection. Alternatively it is possible for very fine microcapsules to be formed wherein the active ingredient is present in the form of finely divided particles in a solid matrix of a base substance, but in that case the microcapsule is not encapsulated.

The formulation adjuvants suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylenes carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol (PEG 400), propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and higher molecular weight alcohols, such as amyl alcohol, tetrahydrofurfuryl alcohol, hexanol, octanol, ethylene glycol, propylene glycol, glycerol, N-methyl-2-pyrrolidone and the like. Water is generally the carrier of choice for the dilution of the concentrates. Suitable solid carriers are, for example, talc, titanium dioxide, pyrophyllite clay, silica, attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in CFR 180.1001. (c) & (d).

A large number of surface-active substances can advantageously be used both in solid and in liquid formulations, especially in those formulations which can be diluted with a carrier prior to use. Surface-active substances may be anionic, cationic, non-ionic or polymeric and they may be used as emulsifying, wetting or suspending agents or for other purposes. Typical surface-active substances include, for example, salts of alkyl sulfates, such as diethanolammonium lauryl sulfate; salts of alkylarylsulfonates, such as calcium dodecyl-benzenesulfonate; alkylphenol-alkylene oxide addition products, such as nonylphenol ethoxylate; alcohol-alkylene oxide addition products, such as tridecyl alcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further adjuvants which can usually be used in pesticidal formulations include crystallisation inhibitors, viscosity-modifying substances, suspending agents, dyes, anti-oxidants, foaming agents, light absorbers, mixing aids, anti-foams, complexing agents, neutralising or pH-modifying substances and buffers, corrosion-inhibitors, fragrances, wetting agents, absorption improvers, micronutrients, plasticisers, glidants, lubricants, dispersants, thickeners, anti-freezes, microbiocides, and also liquid and solid fertilisers.

The formulations may also comprise additional active substances, for example further herbicides, herbicide safeners, plant growth regulators, fungicides or insecticides.

The compositions according to the invention can additionally include an additive comprising an oil of vegetable or animal origin, a mineral oil, alkyl esters of such oils or mixtures of such oils and oil derivatives. The amount of oil additive used in the composition according to the invention is generally from 0.01 to 10%, based on the spray mixture. For example, the oil additive can be added to the spray tank in the desired concentration after the spray mixture has been prepared. Preferred oil additives comprise mineral oils or an oil of vegetable origin, for example rapeseed oil, olive oil or sunflower oil, emulsified vegetable oil, such as AMIGO® (Rhône-Poulenc Canada Inc.), alkyl esters of oils of vegetable origin, for example the methyl derivatives, or an oil of animal origin, such as fish oil or beef tallow. A preferred additive contains, for example, as active components essentially 80% by weight alkyl esters of fish oils and 15% by weight methylated rapeseed oil, and also 5% by weight of customary emulsifiers and pH modifiers. Especially preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid, being important. Those esters are known as methyl laurate (CAS-111-82-0), methyl palmitate (CAS-112-39-0) and methyl oleate (CAS-112-62-9). A preferred fatty acid methyl ester derivative is Emery® 2230 and 2231 (Cognis GmbH). Those and other oil derivatives are also known from the Compendium of Herbicide Adjuvants, 5th Edition, Southern Illinois University, 2000.

The application and action of the oil additives can be further improved by combining them with surface-active substances, such as non-ionic, anionic or cationic surfactants. Examples of suitable anionic, non-ionic and cationic surfactants are listed on pages 7 and 8 of WO 97/34485. Preferred surface-active substances are anionic surfactants of the dodecyl-benzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available surfactants are the Genapol types (Clariant AG). Also preferred are silicone surfactants, especially polyalkyl-oxide-modified heptamethyltrisiloxanes, which are commercially available e.g. as Silwet L-77®, and also perfluorinated surfactants. The concentration of surface-active substances in relation to the total additive is generally from 1 to 30% by weight. Examples of oil additives that consist of mixtures of oils or mineral oils or derivatives thereof with surfactants are Edenor ME SU®, Turbocharge® (Syngenta AG, CH) and Actipron® (BP Oil UK Limited, GB).

The said surface-active substances may also be used in the formulations alone, that is to say without oil additives.

Furthermore, the addition of an organic solvent to the oil additive/surfactant mixture can contribute to a further enhancement of action. Suitable solvents are, for example, Solvesso® (ESSO) and Aromatic Solvent® (Exxon Corporation). The concentration of such solvents can be from 10 to 80% by weight of the total weight. Such oil additives, which may be in admixture with solvents, are described, for example, in U.S. Pat. No. 4,834,908. A commercially available oil additive disclosed therein is known by the name MERGE® (BASF Corporation). A further oil additive that is preferred according to the invention is SCORE® (Syngenta Crop Protection Canada.)

In addition to the oil additives listed above, in order to enhance the activity of the compositions according to the invention it is also possible for formulations of alkylpyrrolidones, (e.g. Agrimax®) to be added to the spray mixture. Formulations of synthetic latices, such as, for example, polyacrylamide, polyvinyl compounds or poly-1-p-menthene (e.g. Bond®, Courier® or Emerald®) can also be used. Solutions that contain propionic acid, for example Eurogkem Pene-trate®, can also be mixed into the spray mixture as activity-enhancing agents.

The herbicidal formulations generally contain from 0.1 to 99% by weight, especially from 0.1 to 95% by weight, of a compound of formula I and from 1 to 99.9% by weight of a formulation adjuvant, which preferably includes from 0 to 25% by weight of a surface-active substance. Whereas commercial products will preferably be formulated as concentrates, the end user will normally employ dilute formulations.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied at a rate of 1 to 4000 g/ha, especially from 5 to 1000 g/ha.

Preferred formulations have especially the following compositions:
(%=percent by weight):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%

Dusts:
active ingredient: 0.1 to 10%, preferably 0.1 to 5%
solid carrier: 99.9 to 90%, preferably 99.9 to 99%

Suspension Concentrates:
active ingredient: 5 to 75%, preferably 10 to 50%
water: 94 to 24%, preferably 88 to 30%
surface-active agent: 1 to 40%, preferably 2 to 30%

Wettable Powders:
active ingredient: 0.5 to 90%, preferably 1 to 80%
surface-active agent: 0.5 to 20%, preferably 1 to 15%
solid carrier: 5 to 95%, preferably 15 to 90%

Granules:
active ingredient: 0.1 to 30%, preferably 0.1 to 15%
solid carrier: 99.5 to 70%, preferably 97 to 85%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP | — | — | 10% | 20% |
| arom. hydrocarbon mixture $C_9$-$C_{12}$ | 85% | 78% | 55% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | — | 20% | 20% | — |
| polyethylene glycol MW 400 | 20% | 10% | — | — |
| NMP | — | — | 30% | 10% |
| arom. hydrocarbon mixture $C_9$-$C_{12}$ | 75% | 60% | — | — |

The solutions are suitable for application in the form of microdrops.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly disperse silicic acid | 0.9% | 2% | 2% |
| inorg. carrier (diameter 0.1-1 mm) e.g. $CaCO_3$ or $SiO_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly disperse silicic acid | 0.9% | 1% | 2% |
| inorg. carrier (diameter 0.1-1 mm) e.g. $CaCO_3$ or $SiO_2$ | 98.0% | 92% | 80% |

The finely ground active ingredient is applied uniformly, in a mixer, to the carrier moistened with polyethylene glycol. Non-dusty coated granules are obtained in this manner.

| F6. Extruder granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, yielding a suspension concentrate from which suspensions of any desired concentration can be prepared by dilution with water.

The invention relates also to a method for the selective control of grasses and weeds in crops of useful plants, which comprises treating the useful plants or the area under cultivation or the locus thereof with a compound of formula I.

Crops of useful plants in which the compositions according to the invention can be used include cereals, cotton, soybeans, sugar beet, sugar cane, plantation crops, rape, maize and rice, and for non-selective weed control. The compositions according to the invention are particularly useful for the selective control of grasses and weeds in cereals, maize and rice, especially rice. The term "crops" is to be understood as also including crops that have been rendered tolerant to herbicides or classes of herbicides (for example ALS, GS, EPSPS, PPO, ACCase and HPPD inhibitors) as a result of conventional methods of breeding or genetic engineering. An example of a crop that has been rendered tolerant e.g. to imidazolinones, such as imazamox, by conventional methods of breeding is Clearfield® summer rape (Canola). Examples of crops that have been rendered tolerant to herbicides by genetic engineering methods include e.g. glyphosate- and glufosinate-resistant maize varieties commercially available under the trade names RoundupReady® and LibertyLink®. The weeds to be controlled may be both monocotyledonous and dicotyledonous weeds, such as, for example, *Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum, Rottboellia, Cyperus, Abutilon, Sida, Xanthium, Amaranthus, Chenopodium, Ipomoea, Chrysanthemum, Galium, Viola* and *Veronica*.

Crops are also to be understood as being those which have been rendered resistant to harmful insects by genetic engineering methods, for example Bt maize (resistant to European corn borer), Bt cotton (resistant to cotton boil weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

Areas under cultivation are to be understood as including land where the crop plants are already growing as well as land intended for the cultivation of those crop plants.

The compounds of formula I according to the invention can also be used in combination with other herbicides. The following mixtures of the compound of formula I are especially important. Preferably, in these mixtures, the compound of the formula I is one of those compounds listed in Tables 1 to 294 below:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atrazine, formula I+aviglycine, formula I+azafenidin, compound of formula I+azimsulfuron, compound of formula I+BCPC, compound of formula I+beflubutamid, compound of formula I+benazolin, formula I+bencarbazone, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, formula I+bromophenoxim, compound of formula I+bromoxynil, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, formula I+desmetryn, compound of formula I+dicamba, compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, formula I+dipropetryn, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, formula I+ethephon, compound of formula I+ethofumesate, compound of formula I+ethoxyfen, compound of formula I+ethoxysulfuron, compound of formula I+etobenzanid, compound of formula I+fenoxaprop-P, compound of formula I+fenoxaprop-P-ethyl, compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, formula I+fluazolate, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, formula I+flumetralin, compound of formula I+flumetsulam, compound of formula I+flumiclorac, compound of formula I+flumiclorac-pentyl, compound of formula I+flumioxazin, formula I+flumipropin, compound of formula I+fluometuron, compound of formula I+fluoroglycofen, compound of formula I+fluoroglycofen-ethyl, formula I+fluoxaprop, formula I+flupoxam, formula I+flupropacil, compound of formula I+flupropanate, compound of formula I+flupyrsulfuron, compound of formula I+flupyrsulfuron-methyl-sodium, compound of formula I+flurenol, compound of formula I+fluridone, compound of formula I+fluorochloridone, compound of formula I+fluoroxypyr, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glyphosate, compound of formula I+halosulfuron, compound of formula I+halosulfuron-methyl, compound of formula I+haloxyfop, compound of formula I+haloxyfop-P, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+isoproturon, compound of formula I+isouron, compound of formula I+isoxaben, compound of formula I+isoxachlortole, compound of formula I+isoxaflutole, formula I+isoxapyrifop, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+methabenzthiazuron, formula I+methazole, compound of formula I+methylarsonic acid, compound of formula I+methyldymron, compound of formula I+methyl isothiocyanate, compound of formula I+metobenzuron, formula I+metobromuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, formula I+NDA-402989, compound of formula I+neburon, compound of formula I+nicosulfuron, formula I+nipyraclofen, formula I+n-methyl glyphosate, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, formula I+prohexadione-calcium, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyzamide, compound of formula I+prosulfocarb, compound of formula I+prosulfuron, compound of formula I+pyraclonil, compound of formula I+pyraflufen, compound of formula I+pyraflufen-ethyl, formula I+pyrasulfotole, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, formula I+pyroxasulfone (KIH-485), formula I+pyroxulam, compound of formula I+quinclorac, compound of formula I+quinmerac, compound of formula I+quinoclamine, compound of formula I+quizalofop, compound of formula I+quizalofop-P, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, formula I+tebutam, compound of formula I+tebuthiuron, formula I+tefuryltrione, compound of formula 1+tembotrione, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazafluoron, compound of formula I+thiazopyr, compound of formula I+thifensulfuron, compound of formula I+thiencarbazone, compound of formula I+thifensulfuron-methyl, compound of formula I+thiobencarb, compound of formula I+tiocarbazil, compound of formula I+topramezone, compound of formula I+tralkoxydim, compound of formula I+triallate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+trinexapac-ethyl, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), compound of formula 1+2-chloro-5-[3,6-dihydro-3-methyl-2,6-dioxo-4-(trifluoromethyl)-1(2H)-pyrimidinyl]-4-fluoro-N-[[methyl(1-methylethyl)amino]sulfonyl]benzamide (CAS RN 372137-35-4), and compound of formula I+4-hydroxy-3-[[2-(3-methoxypropyl)-6-(difluoromethyl)-3-pyridinyl]carbonyl]bicyclo[3.2.1]oct-3-en-2-one.

The mixing partners for the compound of formula I may also be in the form of esters or salts, as mentioned e.g. in The Pesticide Manual, 12th Edition (BCPC) 2000.

The compounds of formula (I) according to the invention can also be used in combination with safeners. Preferably, in these mixtures, the compound of the formula (I) is one of those compounds listed in Tables 1 to 294 below. The following mixtures with safeners, especially, come into consideration:
compound of formula (I)+cloquintocet-mexyl, compound of formula (I)+cloquintocet acid and salts thereof, compound of formula (I)+fenchlorazole-ethyl, compound of formula (I)+fenchlorazole acid and salts thereof, compound of formula (I)+mefenpyr-diethyl, compound of formula (I)+mefenpyr diacid, compound of formula (I)+isoxadifen-ethyl, compound of formula (I)+isoxadifen acid, compound of formula (I)+furilazole, compound of formula (I)+furilazole R isomer, compound of formula (I)+benoxacor, compound of formula (I)+dichlormid, compound of formula (I)+AD-67, compound of formula (I)+oxabetrinil, compound of formula (I)+cyometrinil, compound of formula (I)+cyometrinil Z-isomer, compound of formula (I)+fenclorim, compound of formula (I)+cyprosulfamide, compound of formula (I)+naphthalic anhydride, compound of formula (I)+flurazole, compound of formula (I)+N-(2-methoxybenzoyl)-4-[(methylaminocarbonyl)amino]benzenesulfonamide, compound of formula (I)+CL 304,415, compound of formula (I)+dicyclonon, compound of formula (I)+fluxofenim, compound of formula (I)+DKA-24, compound of formula (I)+R-29148 and compound of formula (I)+PPG-1292. A safening effect can also be observed for the mixtures compound of the formula (I)+dymroni, compound of the formula (I)+MCPA, compound of the formula (I)+mecoprop and compound of the formula (I)+mecoprop-P.

The above-mentioned safeners and herbicides are described, for example, in the Pesticide Manual, Twelfth Edition, British Crop Protection Council, 2000. R-29148 is described, for example by P. B. Goldsbrough et al., Plant Physiology, (2002), Vol. 130 pp. 1497-1505 and references therein, PPG-1292 is known from WO09211761 and N-(2-methoxybenzoyl)-4-[(methylaminocarbonyl)amino]benzenesulfonamide is known from EP365484.

Preferred compositions according to the present invention contain in addition to comprising the compound of formula I, a further herbicide as mixing partner and a safener.

The following Examples illustrate the invention further but do not limit the invention.

Those skilled in the art will appreciate that certain compounds described below are β-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 and P1, are drawn as an arbitrary single enol tautomer, but it should be inferred that this description covers both the diketone form and any possible enols which could arise through tautomerism. Furthermore, some of the compounds shown below, and in Table A, Table B, Table C and Table D, are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

PREPARATION EXAMPLES

Example 1

Preparation of 4-(4'-chloro-4-methylbiphenyl-3-yl)-2,2,6,6-tetramethylpyran-3,5-dione

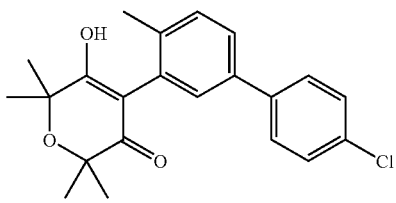

Step 1: Preparation of 3-amino-4'-chloro-4-methylbiphenyl

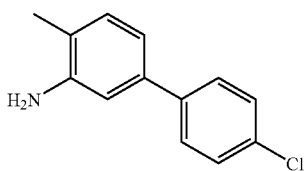

Tetrakis(triphenylphosphine)palladium (0) (3.7 g, 0.003 mol) and 4-chlorophenylboronic acid (20.2 g, 0.13 mol) are added to a solution of 5-bromo-2-methylaniline (20 g, 0.1 mol) in 1,2-dimethoxyethane (200 ml). After stirring the reaction mixture for 15 minutes at 20° C., a solution of 20% aqueous sodium carbonate (300 ml) is added to the mixture, and the resulting mixture is heated at reflux for 24 hours. The reaction mixture is cooled to room temperature, diluted with water (600 ml) and extracted using ethyl acetate. The combined organic extracts are dried over anhydrous sodium sulfate, filtered and the filtrate evaporated in vacuo. The residue is further purified by column chromatography on silica gel, eluting with 7% ethyl acetate in hexane to give 3-amino-4'-chloro-4-methylbiphenyl (21.0 g).

Step 2: Preparation of 3-bromo-4'-chloro-4-methylbiphenyl

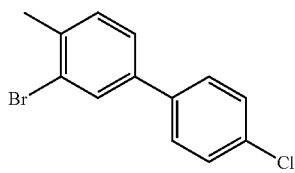

Hydrobromic acid (48% wt. in water, 120 ml) is added dropwise to a suspension of 3-amino-4'-chloro-4-methylbiphenyl (21 g, 0.09 mol) in water (80 ml), and the mixture stirred until the solid is dissolved. The mixture is cooled to −5° C. and a solution of sodium nitrite (10.12 g, 0.14 mol) in water (50 ml) is added dropwise, maintaining the temperature at 0-5° C. The reaction mixture is stirred for 1 hour, then added to a pre-cooled solution of cuprous bromide (17.9 g, 0.12 mol) in hydrobromic acid (48% wt. in water, 120 ml) at 0° C. The reaction mixture is stirred and allowed to warm to room temperature overnight. The mixture is extracted with ethyl acetate, and the organic extracts are combined, dried over anhydrous sodium sulfate, filtered and the filtrate concentrated in vacuo. The residue is further purified by column chromatography on silica gel, eluting with 2% ethyl acetate in hexane to give 3-bromo-4'-chloro-4-methylbiphenyl (15.0 g).

Step 3: Preparation of 4'-chloro-4-methylbiphenyl-3-ylboronic acid

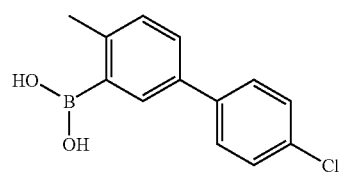 [SMILES: Cc1ccc(-c2ccc(Cl)cc2)cc1B(O)O]

3-Bromo-4'-chloro-4-methylbiphenyl (5.0 g, 0.02 mol) is dissolved in anhydrous tetrahydrofuran (125 ml), and the mixture is cooled to −78° C. n-Butyllithium (1.33 molar solution in hexanes, 17.3 ml) is added dropwise over 30 minutes, maintaining the temperature at approximately −78° C. The reaction mixture is stirred for one and a half hours at −78° C., then trimethylborate (2.58 g, 0.024 mol) is added dropwise and the reaction mixture stirred for three and a half hours, allowing it to warm to 0° C. A solution of 2N aqueous hydrochloric acid (50 ml) is then added dropwise, and once the addition is complete the mixture is stirred for 2 hours. The mixture is concentrated in vacuo to remove most of the tetrahydrofuran, then diluted with water (~80 ml) and extracted with diethyl ether. The organic extracts are combined, dried over anhydrous sodium sulfate, filtered and the filtrate evaporated in vacuo. The residue is further purified by flash column chromatography on silica gel, eluting with 7% ethyl acetate in hexane to give 4'-chloro-4-methylbiphenyl-3-ylboronic acid (2.5 g).

Step 4: Preparation of 4'-chloro-4-methylbiphenyl-3-yllead triacetate

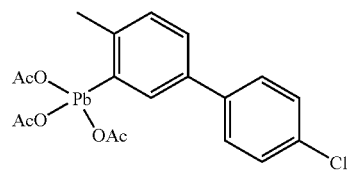

Step 4a

To a mixture of lead tetraacetate (2.44 g, 5.50 mmol) and mercuric diacetate (0.16 g, 0.50 mmol), thoroughly flushed with nitrogen, is added anhydrous chloroform (6 ml). This mixture is warmed to 40° C., and 4'-chloro-4-methylbiphenyl-3-ylboronic acid (1.23 g, 5.00 mmol) is added in one portion, and the suspension is heated at this temperature for 5 hours. After cooling to room temperature the mixture is concentrated to a small volume, then triturated with hexanes and filtered to yield crude 4'-chloro-4-methylbiphenyl-3-yllead triacetate (2.93 g).

Step 4b

Crude 4'-chloro-4-methyl-biphenyl-3-yllead triacetate (1.50 g) is dissolved in anhydrous chloroform (20 ml), to which is added powdered anhydrous potassium carbonate (0.59 g, 4.24 mmol) followed by rapid stirring for 5 minutes. Solids are removed by filtration, and the organic solution is concentrated to afford pure 4'-chloro-4-methylbiphenyl-3-yllead triacetate (1.121 g) as a bright orange solid.

Step 5: Preparation of 4-(4'-chloro-4-methylbiphenyl-3-yl)-2,2,6,6-tetramethylpyran-3,5-dione

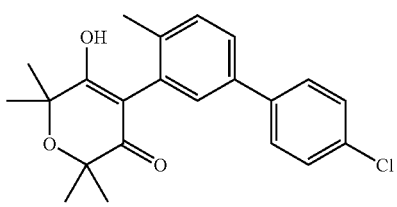

To a mixture of 2,2,6,6-tetramethylpyran-3,5-dione (described in U.S. Pat. No. 5,089,046A) (0.296 g, 1.74 mmol) and N,N-dimethylaminopyridine (1.06 g, 8.70 mmol) is added anhydrous chloroform (20 ml), followed by stirring at room temperature until dissolution. To this solution is added anhydrous toluene (5 ml), followed by 4'-chloro-4-methylbiphenyl-3-yllead triacetate (1.12 g, 1.91 mmol) in one portion and the reaction mixture heated at 80° C. for 1-2 hours. The mixture is allowed to cool to room temperature, then diluted with dichloromethane (150 ml) and dilute aqueous hydrochloric acid (30 ml), followed by stirring for 5 minutes and filtration through diatomaceous earth to remove inorganic residues (additional washing with solvents). All organic fractions are combined, dried over anhydrous magnesium sulfate and concentrated in vacuo. The crude product is purified by column chromatography (100% hexane to hexane/ethyl acetate 5:1 ratio) then triturated with hexanes to afford 4-(4'-chloro-4-methylbiphenyl-3-yl)-2,2,6,6-tetramethylpyran-3,5-dione (0.318 g) as a cream powder.

Example 2

Preparation of 4-(4'-chloro-4-ethylbiphenyl-3-yl)-2,2,6,6-tetramethylpyran-3,5-dione

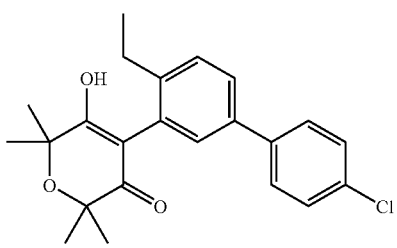

Step 1: Preparation of 4-ethyl-3-nitroaniline

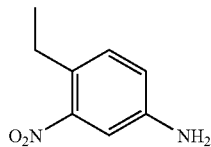

Ammonium nitrate (39.6 g, 0.49 mol) is added portionwise to a chilled (ice-bath) solution of 4-ethylaniline (20 g, 0.16 mol) in concentrated sulfuric acid (100 ml), maintaining the temperature at −10° to 0° C. by external cooling. The reaction mixture is stirred for two hours, then poured onto crushed ice, and the precipitate is collected by filtration. The solid is taken up in water, the solution made neutral by addition of dilute aqueous sodium hydroxide solution and extracted with ethyl acetate. The organic extracts are combined, dried over anhydrous sodium sulfate, filtered and the filtrate is evaporated in vacuo to give 4-ethyl-3-nitroaniline (20 g).

Step 2: Preparation of 4-bromo-1-ethyl-2-nitrobenzene

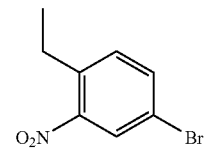

Hydrobromic acid (48% wt. in water, 240 ml) is added dropwise to a suspension of 4-ethyl-3-nitroaniline (20 g, 0.12 mol) in water (80 ml), and the mixture is stirred until the solid dissolves. The mixture is cooled to −5° C. and a solution of sodium nitrite (19.8 g, 0.28 mol) in water (100 ml) is added dropwise, maintaining the temperature at 0-5° C. Once the addition is complete, the cooling bath is removed and the reaction mixture is stirred for one hour at room temperature. The mixture is added dropwise to a pre-cooled solution of cuprous bromide (22.4 g, 0.16 mol) in hydrobromic acid (48% wt. in water) at 0° C. The reaction mixture is stirred and allowed to warm to room temperature over three hours. The mixture is extracted with diethyl ether, and the organic extracts are combined, dried over anhydrous sodium sulfate, filtered and the filtrate is concentrated in vacuo. The residue is further purified by column chromatography on silica gel, eluting with hexane to give 4-bromo-1-ethyl-2-nitrobenzene (18 g)

Step 3: Preparation of 4'-chloro-4-ethyl-3-nitrobiphenyl

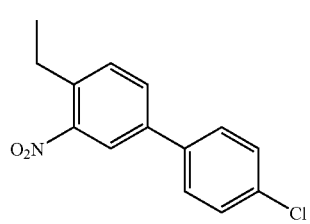

To 4-bromo-1-ethyl-2-nitrobenzene (20.0 g, 0.087 mol) in 150 ml 1,2-dimethoxyethane is added, at room temperature, 4-chlorophenylboronic acid (14.98 g, 0.096 mol) and tetrakis (triphenylphosphine)palladium(0) (2.0 g, 0.00174 mol) and nitrogen gas is bubbled through the mixture. After stirring for 10 minutes at 20° C., a solution of sodium carbonate (73.8 g, 0.696 mol) in water (350 ml) is added and mixture is refluxed for 16 hours. The reaction mixture is cooled to room temperature, filtered through diatomaceous earth, washing with 200 ml of ethyl acetate. The mixture is poured into a separating funnel and the two phases are separated. The aqueous phase is extracted with ethyl acetate. The organic extracts are combined, dried over anhydrous magnesium sulfate, filtered and the filtrate is evaporated in vacuo to give 4'-chloro-4-ethyl-3-nitrobiphenyl (23.84 g) as a brown oil used without further purification in the next step.

Step 4: Preparation of
3-amino-4'-chloro-4-ethylbiphenyl

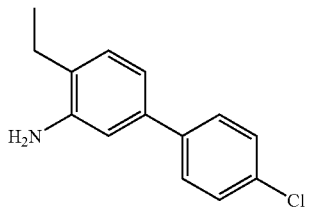 [SMILES: CCc1ccc(-c2ccc(Cl)cc2)cc1[N+](=O)[O-]]

4'-Chloro-4-ethyl-3-nitrobiphenyl (22.6 g, 0.086 mol) is suspended in methanol (250 ml) and the reaction mixture is stirred at room temperature. Distilled water (100 ml) is added, followed by zinc dust (39.0 g, 0.60 mol) and ammonium chloride (13.8 g, 0.26 mol) and the mixture is heated to reflux for 1 hour. The reaction mixture is cooled to room temperature, filtered through diatomaceous earth and the filtrate is evaporated in vacuo to remove most of the methanol. The residue is partitioned between ethyl acetate (200 ml) and water and the aqueous phase is re-extracted with ethyl acetate (200 ml). The organic extracts are combined, washed with water and brine, dried over anhydrous magnesium sulfate, filtered and the filtrate is evaporated in vacuo to give 3-amino-4'-chloro-4-ethylbiphenyl (15.0 g) as a colourless solid. The product is used directly without further purification in Step 5.

Step 5: Preparation of
3-bromo-4'-chloro-4-ethylbiphenyl

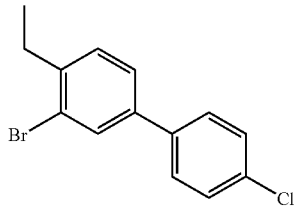 [SMILES: CCc1ccc(-c2ccc(Cl)cc2)cc1Br]

Step 5a

3-Amino-4'-chloro-4-ethylbiphenyl (60.0 g, 0.26 mol) is added portionwise to a mixture of hydrobromic acid (48% wt. in water, 350 ml) and water (250 ml), and once the addition is complete the mixture is heated to 40° C. and stirred for 20 minutes, before being cooled to 5° C. in an ice bath. A solution of sodium nitrite (20.65 g, 0.30 mol) in water (100 ml) is added dropwise over 45 minutes, and once the addition is complete the mixture is stirred at 5° C. for a further 45 minutes.

Step 5b

Meanwhile, hydrobromic acid (48% wt. in water, 400 ml) is heated and stirred at 70° C. and copper sulfate pentahydrate (74.75 g, 0.30 mol) is added in one portion and the mixture is stirred at 70° C. for two minutes to give a dark purple solution, and then copper powder (26.44 g, 0.42 mol) is added in one portion, resulting in a pink suspension.

Step 5c

The mixture containing the diazonium salt (prepared in step 5a) is added portionwise over 70 minutes to the stirred mixture prepared in Step 5b at 70° C. (in between additions the mixture containing the diazonium salt is kept cold in an ice bath). Once the addition is complete the mixture is stirred at 70° C. for a further 30 minutes and then allowed to cool to room temperature, and extracted with ethyl acetate (3×500 ml). The organic extracts are combined, washed with water and brine, dried over anhydrous magnesium sulfate, filtered and the filtrate is evaporated in vacuo. Purification by column chromatography on silica gel affords 3-bromo-4'-chloro-4-ethylbiphenyl (52.1 g) as a yellow oil Step 6: Preparation of
4'-chloro-4-ethylbiphenyl-3-ylboronic acid

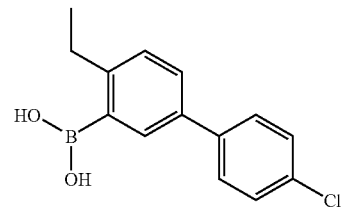 [SMILES: CCc1ccc(-c2ccc(Cl)cc2)cc1B(O)O]

3-Bromo-4'-chloro-4-ethylbiphenyl (10 g, 0.03 mol) is dissolved in tetrahydrofuran (250 ml), and the temperature is cooled to −78° C. n-Butyllithium (1.33 molar solution in hexanes, 34.6 ml) is added dropwise over 30 minutes, maintaining the temperature at around −78° C. The reaction mixture is stirred for one and a half hours, then trimethylborate (4.9 g, 0.05 mole) is added dropwise and the reaction mixture is stirred for two hours. A solution of 2N aqueous hydrochloric acid (100 ml) is added dropwise, and once the addition is complete the mixture is stirred for two hours. The mixture is concentrated to remove most of the tetrahydrofuran, then diluted with water and extracted with diethyl ether. The organic extracts are washed with water and brine, combined, dried over anhydrous sodium sulfate, filtered and the filtrate is evaporated in vacuo. The residue is further purified by flash column chromatography on silica gel, eluting with 7% ethyl acetate in hexane to give 4'-chloro-4-ethylbiphenyl-3-ylboronic acid (5.4 g).

Step 7: Preparation of 4'-chloro-4-ethylbiphenyl-3-yllead triacetate

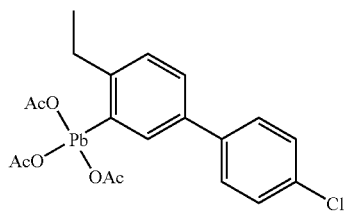

Step 7a

To a mixture of lead tetraacetate (2.15 g, 4.85 mmol) and mercuric diacetate (0.15 g, 0.47 mmol), thoroughly flushed with nitrogen, is added anhydrous chloroform (6 ml). This mixture is warmed to 40° C., and 4'-chloro-4-ethylbiphenyl-3-ylboronic acid (1.17 g, 4.50 mmol) is added in one portion and the suspension is heated at this temperature for 5 hours. The mixture is then cooled to room temperature, concentrated to a small volume and triturated with hexanes and filtered to yield crude 4'-chloro-4-ethylbiphenyl-3-yllead triacetate (2.70 g).

Step 7b

Crude 4'-chloro-4-ethylbiphenyl-3-yllead triacetate (1.50 g) is dissolved in anhydrous chloroform (20 ml), to which is added powdered anhydrous potassium carbonate (0.58 g, 4.16 mmol) followed by rapid stirring for 5 minutes. Solids are removed by filtration, and the organic solution is concentrated to afford pure 4'-chloro-4-ethylbiphenyl-3-yllead triacetate (1.176 g) as a bright orange solid.

Step 8: Preparation of 4-(4'-chloro-4-ethylbiphenyl-3-yl)-2,2,6,6-tetramethylpyran-3,5-dione

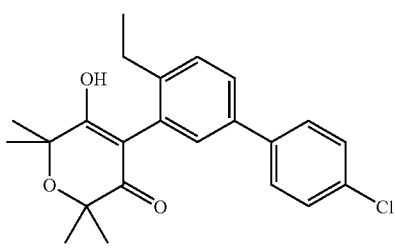

To a mixture of 2,2,6,6-tetramethylpyran-3,5-dione (described in U.S. Pat. No. 5,089,046A) (0.303 g, 1.78 mmol) and N,N-dimethylaminopyridine (1.09 g, 8.90 mmol) is added anhydrous chloroform (20 ml), followed by stirring at room temperature until dissolution. To this solution is added anhydrous toluene (5 ml), followed by 4'-chloro-4-ethylbiphenyl-3-yllead triacetate (1.17 g, 1.96 mmol) in one portion and the mixture heated at 80° C. for 1-2 hours. The mixture is allowed to cool to room temperature, then diluted with dichloromethane (150 ml) and dilute aqueous hydrochloric acid (30 ml), followed by stirring for 5 minutes and filtration through diatomaceous earth to remove inorganic residues (additional washing with solvents). All organic fractions are combined, dried over anhydrous magnesium sulfate and concentrated in vacuo. The crude product is purified by column chromatography (100% hexane to hexane/ethyl acetate 5:1 ratio) then triturated with hexanes to afford 4-(4'-chloro-4-ethylbiphenyl-3-yl)-2,2,6,6-tetramethylpyran-3,5-dione (0.46 g) as a cream powder.

Example 3

Preparation of 4-(3',4'-difluoro-4-methylbiphenyl-3-yl)-2,2,6,6-tetramethylpyran-3,5-dione

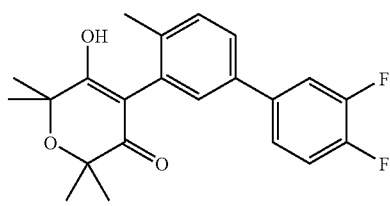 [SMILES: Cc1ccc(-c2ccc(F)c(F)c2)cc1C1=C(O)C(C)(C)OC(C)(C)C1=O]

Step 1: Preparation of 5-chloro-2-methylphenyllead triacetate

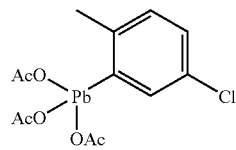

To a mixture of lead tetraacetate (2.15 g, 4.85 mmol) and mercuric diacetate (0.15 g, 0.47 mmol), thoroughly flushed with nitrogen, is added anhydrous chloroform (6 ml). This mixture is warmed to 40° C., and 5-chloro-2-methylphenylboronic acid (0.76 g, 4.46 mmol) is added in one portion, and the suspension is heated at this temperature for 5 hours. After cooling to room temperature the mixture is concentrated to a small volume then triturated with hexanes and filtered to yield crude 5-chloro-2-methylphenyllead triacetate (2.27 g).

Step 2: Preparation of 4-(5-chloro-2-methylphenyl)-2,2,6,6-tetramethylpyran-3,5-dione

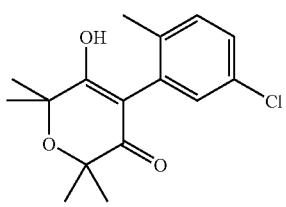 [SMILES: Cc1ccc(Cl)cc1C1=C(O)C(C)(C)OC(C)(C)C1=O]

To a mixture of 2,2,6,6-tetramethylpyran-3,5-dione (described in U.S. Pat. No. 5,089,046A) (0.504 g, 2.96 mmol) and N,N-dimethylaminopyridine (1.45 g, 11.84 mmol) is added anhydrous chloroform (40 ml). To this solution is added crude 5-chloro-2-methylphenyllead triacetate (2.26 g, 4.44 mmol) in one portion, and the mixture is then heated at 40° C. for 17 hours (analysis), then for a further 23 hours at 45-50° C. The mixture is allowed to cool to room temperature, then diluted with ethyl acetate (100 ml) and washed with dilute aqueous hydrochloric acid (3×30 ml). The organic phase is dried over anhydrous magnesium sulfate, then concentrated to give a yellow gum which is purified by column chromatography (ethyl acetate/hexane/acetic acid 8:18:1 ratio) then triturated with hexanes to afford 4-(5-chloro-2-methylphenyl)-2,2,6,6-tetramethylpyran-3,5-dione (0.53 g) as a white solid.

Step 3: Preparation of 4-(3',4'-difluoro-4-methylbiphenyl-3-yl)-2,2,6,6-tetramethylpyran-3,5-dione

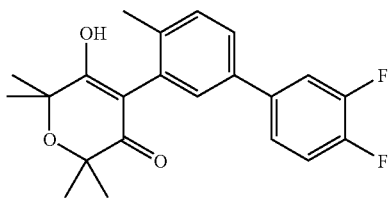 [SMILES: Cc1ccc(-c2ccc(F)c(F)c2)cc1C1=C(O)C(C)(C)OC(C)(C)C1=O]

To a microwave vial is added 4-(5-chloro-2-methylphenyl)-2,2,6,6-tetramethyl-pyran-3,5-dione (0.20 g, 0.68 mmol), 3,4-difluoro-phenylboronic acid (0.107 g, 0.68 mmol), potassium phosphate (0.722 g, 3.40 mmol), palladium(II) acetate (1.6 mg, 0.0068 mmol) and sodium S-phos-3'-sulphonate (7.0 mg, 0.0136 mmol). Distilled, degassed water (0.75 ml) is next added (washing-down any solids from the slides of the vial), followed by stirring for 5 minutes and flushing with argon. This mixture is then heated at 160° C. under microwave irradiation for 15 minutes, followed by the addition of extra 3,4-difluorophenylboronic acid (0.107 g, 0.68 mmol) and potassium phosphate (0.144 g, 0.68 mmol), then further heating at 160° C. under microwave irradiation for 15 minutes. After cooling to room temperature the reaction mixture is diluted with ethyl acetate (3 ml) and acidified to pH2 with dilute aqueous hydrochloric acid.

The organic phase is separated and the aqueous phase is further extracted with ethyl acetate (3×3 ml). All organics are then combined, filtered through a silica plug and evaporated to give a crude product which is dissolved in N,N-dimethylformamide (2.5 ml) and purified by preparative reverse phase HPLC to afford 4-(3',4'-difluoro-4-methylbiphenyl-3-yl)-2,2,6,6-tetramethylpyran-3,5-dione (0.190 g) as a white solid.

Example 4

Preparation of (1R*,5S*)-3-(4'-chloro-4-ethylbiphenyl-3-yl)-1-methyl-8-oxa-bicyclo[3.2.1]octane-2,4-dione

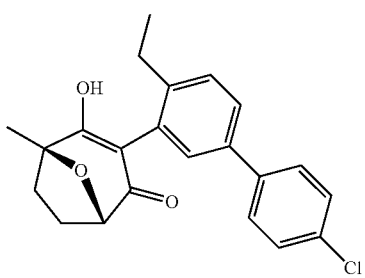 [SMILES: CCc1ccc(-c2ccc(Cl)cc2)cc1C1=C(O)[C@@]2(C)CC[C@H](O2)C1=O]

Step 1: Preparation of (1R*,5S*)-2,3,4,4-tetrachloro-1-methyl-8-oxabicyclo[3.2.1]octa-2,6-diene

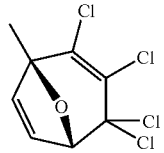

Pentachlorocyclopropane (100 g, 0.467 mol) is added to a suspension of potassium hydroxide (31.4 g, 0.56 mol) in 1,4-dioxane (3600 ml) and the mixture is stirred at room temperature for 30 minutes and then heated to 65° C. for a further 30 minutes. 2-Methylfuran (38.36 g, 0.467 mol) is added to the reaction mixture, the temperature is raised to 85-90° C. and the mixture is stirred for 16 hours. The reaction mixture is cooled to room temperature, filtered through a plug of diatomaceous earth and the filtrate evaporated in vacuo to give (1R*,5S*)-2,3,4,4-tetrachloro-1-methyl-8-oxabicyclo[3.2.1]octa-2,6-diene (83 g), used without further purification in the next step.

Step 2: Preparation of (1R*,5S*)-3,4-dichloro-5-methyl-8-oxabicyclo[3.2.1]octa-3,6-dien-2-one

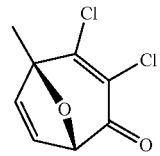

Silver nitrate (166 g, 0.982 mol) is added to a stirred mixture of (1R*,5S*)-2,3,4,4-tetrachloro-1-methyl-8-oxabicyclo[3.2.1]octa-2,6-diene (83 g, 0.491 mol), acetone (1500 ml) and water (1500 ml) and the mixture is heated at 65° C. for 16 hours. The reaction mixture is cooled to room temperature, and a saturated solution of aqueous sodium bicarbonate is added to adjust the pH to 7-8. The mixture is filtered through a plug of diatomaceous earth, and the filtrate is concentrated in vacuo to remove most of the acetone. The aqueous mixture is extracted with ethyl acetate (3×500 ml) and the organic extracts are combined, dried over anhydrous sodium sulfate, filtered and the filtrate is evaporated. The residue is purified by flash column chromatography on silica gel to give (1R*,5S*)-3,4-dichloro-5-methyl-8-oxabicyclo[3.2.1]octa-3,6-dien-2-one (29.5 g) as a yellow oil.

Step 3: Preparation of 3-chloro-1-methyl-4-oxo-spiro (1,3-dioxolane-2,2'-[8]oxa-bicyclo[3.2.1]oct-6-ene)

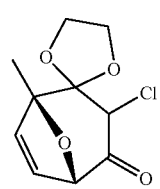

Sodium (4.41 g, 0.204 mol) is added cautiously to ethylene glycol (99.75 g) and the mixture is stirred at 35-40° C. under an atmosphere of nitrogen until the sodium is completely dissolved. A solution of (1R*,5S*)-3,4-dichloro-5-methyl-8-oxabicyclo[3.2.1]octa-3,6-dien-2-one (28 g, 0.136 mol) in tetrahydrofuran (200 ml) is added dropwise over 30 minutes, and once the addition is complete, the mixture is stirred for 90 minutes at room temperature. The reaction mixture is neutralised by addition of 10% aqueous sodium dihydrogen phosphate, and extracted with ethyl acetate (3×100 ml). The organic extracts are combined, dried over anhydrous sodium sulfate, filtered and the filtrate is evaporated. The residue is purified by flash column chromatography on silica gel to give 3-chloro-1-methyl-4-oxo-spiro(1,3-dioxolane-2,2'-[8]oxabicyclo[3.2.1]oct-6-ene) (24.5 g) as a gum.

Step 4: Preparation of (1R*,5S*)-1-methyl-4-oxo-spiro(1,3-dioxolane-2,2'-[8]oxa-bicyclo[3.2.1]oct-6-ene)

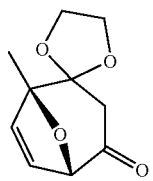

Zinc powder (13.88 g, 0.212 mol) is added to a solution of 3-chloro-1-methyl-4-oxo-spiro(1,3-dioxolane-2,2'-[8]oxabicyclo[3.2.1]oct-6-ene) (24.5 g, 0.016 mol) in acetic acid (122.5 ml) and the reaction mixture stirred at room temperature for 24 hours. The mixture is diluted with water (612.5 ml) and extracted with ethyl acetate (3×150 ml). The organic extracts are combined, dried over anhydrous sodium sulfate, filtered and the filtrate is evaporated to give (1R*,5S*)-1-methyl-4-oxo-spiro(1,3-dioxolane-2,2'-[8]oxabicyclo[3.2.1]oct-6-ene) (20 g) as a yellow oil, used without further purification in the next step.

Step 5: Preparation of (1R*,5S*)-1-methyl-8-oxabicyclo[3.2.1]oct-6-ene-2,4-dione

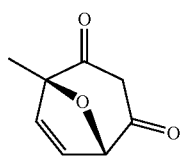

Hydrochloric acid (50 ml) is added, in three portions, to a mixture of (1R*,5S*)-1-methyl-4-oxo-spiro(1,3-dioxolane-2,2'-[8]oxabicyclo[3.2.1]oct-6-ene) (20 g, 0.102 mol) in acetone (500 ml) and water (250 ml) and the reaction mixture is stirred at 65-70° C. for 48 hrs. The mixture is cooled to room temperature, most of the acetone is removed by evaporation under reduced pressure and the resulting aqueous solution is extracted with ethyl acetate (3×100 ml). The organic extracts are combined, dried over anhydrous sodium sulfate, filtered and the filtrate is evaporated. The residue is purified by flash column chromatography on silica gel to give (1R*,5S*)-1-methyl-8-oxabicyclo[3.2.1]oct-6-ene-2,4-dione (10.0 g) as a yellow oil.

Step 6: Preparation of (1R*,5S*)-1-methyl-8-oxabicyclo[3.2.1]octane-2,4-dione

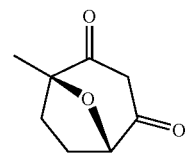

To a solution of (1R*,5S*)-1-methyl-8-oxabicyclo[3.2.1]oct-6-ene-2,4-dione (12.0 g, 0.079 mol) in ethyl acetate (100 ml) is added 10% palladium on carbon (2.4 g), followed by stirring under a 1 bar hydrogen atmosphere for 24 hours. The reaction mixture is then filtered through diatomaceous earth and concentrated to give a crude product which is purified by flash chromatography (hexane/ethyl acetate) to afford (1R*,5S*)-1-methyl-8-oxabicyclo[3.2.1]octane-2,4-dione (6.90 g) as pale yellow solid.

Step 7: Preparation of (1R*,5S*)-3-(4'-chloro-4-ethylbiphenyl-3-yl)-1-methyl-8-oxa-bicyclo[3.2.1]octane-2,4-dione

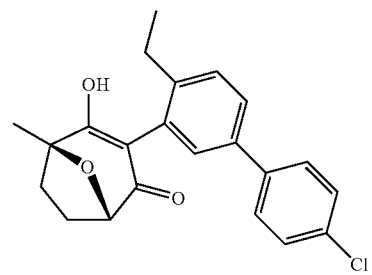 [SMILES: CCc1ccc(-c2ccc(Cl)cc2)cc1C1=C(O)[C@@]2(C)CC[C@H](O2)C1=O]

To a mixture of chloroform (2.0 ml) and toluene (0.5 ml) is added (1R*,5S*)-1-methyl-8-oxa-bicyclo[3.2.1]octane-2,4-dione (0.10 g, 0.6 mmol) and N,N-dimethylamino-pyridine (0.395 g, 3.2 mmol) under a nitrogen atmosphere with stirring. To this reaction mixture is added 4'-chloro-4-ethylbiphenyl-3-yllead triacetate (0.42 g, 0.70 mmol) in one portion, then the mixture is heated at 80° C. for 1-2 hours. The reaction mixture is cooled to room temperature, acidified with dilute aqueous hydrochloric acid then filtered through diatomaceous earth to remove inorganic residues (subsequent washing with dichloromethane). The aqueous fractions are extracted with dichloromethane (2×5 ml), all organic fractions are combined, dried over sodium sulfate then concentrated under vacuum to give the crude product which is purified by flash chromatography (hexane/ethyl acetate) to give (1R*,5S*)-3-(4'-chloro-4-ethylbiphenyl-3-yl)-1-methyl-8-oxabicyclo[3.2.1]octane-2,4-dione (0.150 g) as a white solid.

Example 5

Preparation of (1R*,5S*)-3-(4'-chloro-4-methylbiphenyl-3-yl)-1-methyl-8-oxa-bicyclo[3.2.1]octane-2,4-dione

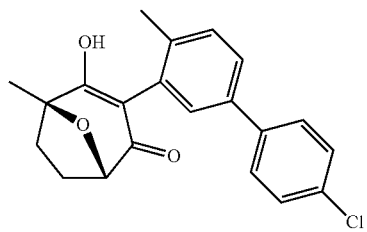 [SMILES: Cc1ccc(-c2ccc(Cl)cc2)cc1C1=C(O)[C@@]2(C)CC[C@H](O2)C1=O]

To a mixture of chloroform (3.5 ml) and toluene (0.75 ml) is added (1R*,5S*)-1-methyl-8-oxa-bicyclo[3.2.1]octane-2,4-dione (0.25 g, 1.62 mmol) and N,N-dimethylaminopyridine (0.99 g, 8.11 mmol) under a nitrogen atmosphere with stirring. To this reaction mixture is then added 4'-chloro-4-methylbiphenyl-3-yllead triacetate (1.05 g, 1.78 mmol) in one portion, then the mixture heated at 80° C. for 1-2 hours. The reaction mixture is cooled to room temperature, acidified with dilute aqueous hydrochloric acid then filtered through diatomaceous earth to remove inorganic residues (subsequent washing with dichloromethane). Aqueous fractions are extracted with dichloromethane (2×10 ml), then all organic fractions are combined, dried over sodium sulfate and concentrated under vacuum to give crude product which is purified by flash chromatography (hexane/ethyl acetate) to give (1R*,5S*)-3-(4'-chloro-4-methylbiphenyl-3-yl)-1-methyl-8-oxabicyclo[3.2.1]octane-2,4-dione (0.240 g) as a white solid.

Example 6

Preparation of 4-(4'-chloro-4-methylbiphenyl-3-yl)-2,2-dimethylpyran-3,5-dione

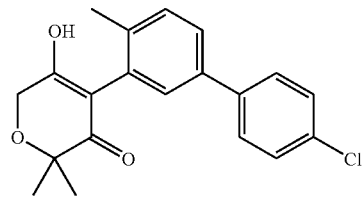 [SMILES: Cc1ccc(-c2ccc(Cl)cc2)cc1C1=C(O)COC(C)(C)C1=O]

Step 1: Preparation of [3-(4'-chloro-4-methylbiphenyl-3-yl)-1,1-dimethylprop-2-ynyloxy]acetic acid methyl ester

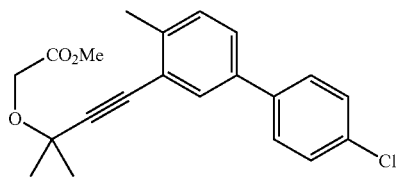 [SMILES: COC(=O)COC(C)(C)C#Cc1cc(-c2ccc(Cl)cc2)ccc1C]

To a solution of 3-bromo-4'-chloro-4-methylbiphenyl (12.6 g, 44.7 mmol) and (1,1-dimethylprop-2-ynyloxy)acetic acid methyl ester (prepared according to WO2001/066544) (8.4 g, 53.8 mmol) in triethylamine (70 ml) is added bis(triphenylphosphine)palladium(II) dichloride (0.63 g, 0.9 mmol) and copper(I) iodide (0.34 g, 1.8 mmol). The reaction mixture is degassed and flushed with nitrogen (×3), then stirred under nitrogen at 80° C. for one hour. The cooled mixture is filtered through diatomaceous earth to remove the catalyst, and the filtrate evaporated in vacuo. The residue is resubjected to the same reaction conditions (8.4 g 1,1-dimethylprop-2-ynyloxy)acetic acid methyl ester, 0.63 g bis(triphenylphosphine)-palladium(II) dichloride, 0.34 g copper(I) iodide in 70 ml triethylamine under nitrogen) and stirred at 80° C. for one hour. The cooled mixture is filtered through diatomaceous earth, then concentrated in vacuo and purified by flash chromatography (hexane/ethyl acetate 3:1) to afford [3-(4'-chloro-4-methylbiphenyl-3-yl)-1,1-dimethylprop-2-ynyloxy]acetic acid methyl ester (6.70 g) as an oil.

Step 2: Preparation of [3-(4'-chloro-4-methylbiphenyl-3-yl)-1,1-dimethylprop-2-ynyloxy]acetic acid

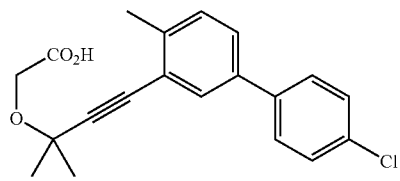 [SMILES: Cc1ccc(-c2ccc(Cl)cc2)cc1C#CC(C)(C)OCC(=O)O]

Potassium hydroxide (1.105 g, 19.7 mmol) is added to a solution of [3-(4'-chloro-4-methyl-biphenyl-3-yl)-1,1-dimethylprop-2-ynyloxy]acetic acid methyl ester (6.7 g, 18.8 mmol) in dioxane (20 ml) and water (20 ml). After stirring for four hours at 20° C., the reaction mixture is extracted twice with dichloromethane. The aqueous layer is acidified at 0° C. to pH 2-3 using 1N aqueous hydrochloric acid and extracted twice with ethyl acetate. The combined organic extracts are dried over anhydrous sodium sulfate, filtered and the filtrate evaporated in vacuo. The residue is stirred in hexane and filtered to afford [3-(4'-chloro-4-methylbiphenyl-3-yl)-1,1-dimethylprop-2-ynyloxy]acetic acid (4.50 g) as a white solid (m.p. 125° C.).

Step 3: Preparation of 6-[1-(4'-chloro-4-methylbiphenyl-3-yl)methylidene]-5,5-dimethyl-[1,4]dioxan-2-one

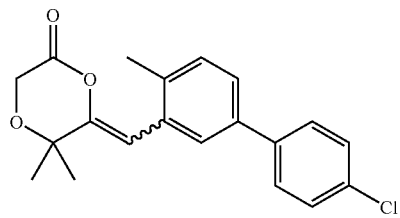 [SMILES: Cc1ccc(-c2ccc(Cl)cc2)cc1C=C1OC(=O)COC1(C)C]

Silver carbonate (0.17 g, 0.61 mmol) is added to a solution of [3-(4'-chloro-4-methyl-biphenyl-3-yl)-1,1-dimethylprop-2-ynyloxy]acetic acid (2.1 g, 6.13 mmol) in anhydrous acetonitrile (15 ml) in a microwave vial. The reaction mixture is stirred and heated to 120° C. for 40 minutes under microwave irradiation to give a brown suspension. The mixture is evaporated in vacuo, then diluted with water and extracted with ethyl acetate. The combined organic extracts are dried over anhydrous sodium sulfate, filtered and the filtrate evaporated in vacuo to give 6-[1-(4'-chloro-4-methylbiphenyl-3-yl)methylidene]-5,5-dimethyl-[1,4]dioxan-2-one (1.75 g) as a solid.

Step 4: Preparation of 4-(4'-chloro-4-methylbiphenyl-3-yl)-2,2-dimethylpyran-3,5-dione

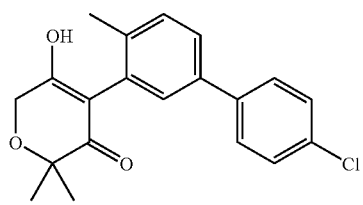 [SMILES: Cc1ccc(-c2ccc(Cl)cc2)cc1C1=C(O)COC(C)(C)C1=O]

To a suspension of 6-[1-(4'-chloro-4-methylbiphenyl-3-yl)methylidene]-5,5-dimethyl-[1,4]dioxan-2-one (1.5 g, 4.38 mmol) in anhydrous acetonitrile (22 ml) is added triethylamine (0.67 ml, 4.81 mmol) and potassium cyanide (30 mg, 0.46 mmol). The reaction mixture is stirred under reflux for two hours. The cooled mixture is diluted with ethyl acetate, and 0.5N aqueous hydrochloric acid is added at 0° C. The organic layer is separated and the aqueous phase extracted twice with ethyl acetate. The combined organic extracts are dried over anhydrous sodium sulfate, filtered and the filtrate evaporated in vacuo. The residue is purified by flash chromatography (heptane/ethyl acetate 1:1 ratio) to afford 4-(4'-chloro-4-methylbiphenyl-3-yl)-2,2-dimethylpyran-3,5-dione (1.35 g) as a foam. A sample of the product is stirred in hexane/diisopropyl ether (4:1 ratio) and filtered to give a white solid with a melting point of 186-188° C.

Example 7

Preparation of 4-(4'-chloro-4-ethyl-2'-fluorobiphenyl-3-yl)-2,2,6,6-tetramethyl-pyran-3,5-dione

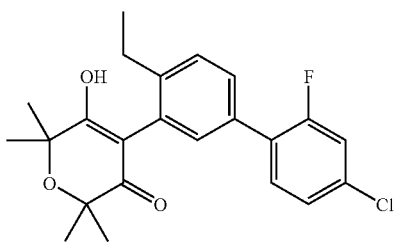

Step 1: Preparation of 5-bromo-2-ethylaniline

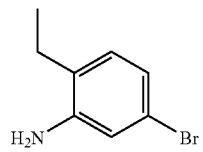

To a solution of 2-ethyl-5-bromo nitrobenzene (9.71 g, 230 mmol) in ethanol (125 ml) is added tin(II) chloride dihydrate (35.72 g, 225.71 mmol), followed by heating at 70° C. for 2 hours. After cooling to room temperature the solution is poured into crushed ice (1 litre) then diluted with ethyl acetate (200 ml). Solid sodium carbonate is cautiously added until pH 7 is achieved, at which stage the viscous mixture is filtered through diatomaceous earth (further washing with ethyl acetate/aqueous sodium carbonate) and the phases separated. After additional extraction of the aqueous phase, all organic phases are combined, dried over anhydrous magnesium sulfate then concentrated in vacuo. The crude oil is purified by flash column chromatography on silica gel (hexane/ethyl acetate 8:2 ratio) to afford 5-bromo-2-ethylaniline (7.89 g) as a brown oil.

Step 2: Preparation of 4-bromo-1-ethyl-2-iodobenzene

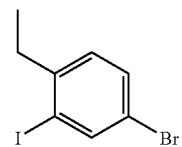

To a stirred mixture of 5-bromo-2-ethylaniline (3.39 g, 200 mmol) in distilled water (110 ml) is added concentrated sulfuric acid (5.60 ml), followed by brief heating at reflux until dissolution. The mixture is allowed to cool to room temperature, producing a fine precipitate, then further cooled to approximately 0° C. in an ice/salt bath. To this slurry is added an aqueous solution of sodium nitrite (1.17 g, 16.94 mmol) in distilled water (10 ml) dropwise over 15 minutes, maintaining a temperature below 5° C., followed by additional stirring for 30 minutes. The reaction mixture is next filtered then added to a second solution of aqueous potassium iodide (8.44 g, 50.83 mmol) in distilled water (45 ml) dropwise at room temperature. After the addition is complete the solution is briefly heated to 80° C. then allowed to cool to room temperature again. The reaction mixture is extracted with ethyl acetate (3×50 ml), and the organic phase is washed with 1M aqueous hydrochloric acid (30 ml) and aqueous sodium thiosulfate (2×30 ml). After drying over anhydrous magnesium sulfate and concentration in vacuo 4-bromo-1-ethyl-2-iodobenzene (4.90 g) is furnished as an orange liquid.

Step 3: Preparation of 5-bromo-2-ethylphenylboronic acid

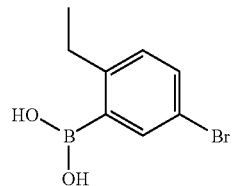

To a solution of 4-bromo-1-ethyl-2-iodobenzene (10.00 g, 32.20 mmol) in anhydrous tetrahydrofuran (60 ml) at −78° C. is added a solution of isopropylmagnesium chloride (16.90 ml, 33.80 mmol, 2M solution in tetrahydrofuran) dropwise, maintaining a temperature below −60° C. After stirring for 20 minutes the reaction mixture is allowed to slowly warm to room temperature followed by an additional hour of stirring. The solution is re-cooled to −78° C. and trimethylborate (7.18 ml, 64.32 mmol) is added dropwise, after which the mixture is again allowed to warm to room temperature with further stirring for 2 hours. Dilute aqueous hydrochloric acid (30 ml) is added, and the crude product is extracted into ethyl acetate (100 ml). The aqueous phase is washed with ethyl acetate (2×100 ml), and all organics are combined, dried over anhydrous magnesium sulfate then concentrated in vacuo to give a light brown solid which is triturated with hexanes to afford 5-bromo-2-ethylphenylboronic acid (6.46 g) as a cream powder.

Step 4: Preparation of 5-bromo-2-ethylphenyllead triacetate

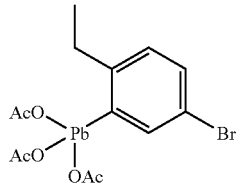

To a mixture of lead tetraacetate (13.7 g, 31.00 mmol) and mercuric diacetate (0.47 g, 1.50 mmol), thoroughly flushed with nitrogen, is added anhydrous chloroform (42 ml). This mixture is warmed to 40° C., and 5-bromo-2-ethylphenylboronic acid (6.50 g, 28.00 mmol) is added in one portion and the suspension is heated at this temperature for 5 hours. The mixture is then allowed to cool to room temperature, followed by further cooling to 0° C. then addition of powdered anhydrous potassium carbonate (3.22 g) with rapid stirring for 5 minutes then filtration. The filtrate is concentrated to half its volume, followed by the addition of hexanes to induce precipitation. This mixture is further concentrated, the solvent decanted, and the solid washed with hexanes to afford 5-bromo-2-ethylphenyllead triacetate (10.69 g) as a sandy coloured solid.

Step 5: Preparation of 4-(5-bromo-2-ethylphenyl)-2,2,6,6-tetramethylpyran-3,5-dione

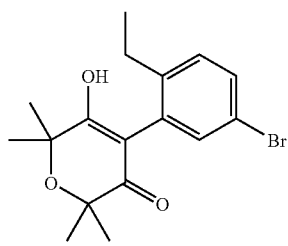 [SMILES: CCc1ccc(Br)cc1C1=C(O)C(C)(C)OC(C)(C)C1=O]

To a mixture of 2,2,6,6-tetramethylpyran-3,5-dione (3.57 g, 21.00 mmol) and N,N-dimethylaminopyridine (13.50 g, 111.00 mmol) is added anhydrous chloroform (120 ml), followed by stirring at room temperature until dissolution. To this solution is added anhydrous toluene (37 ml), followed by 5-bromo-2-ethylphenyllead triacetate (10.69 g, 24.00 mmol) in one portion and the reaction mixture is heated at 80° C. for 2 hours, then allowed to stand overnight at room temperature. The mixture is diluted with dichloromethane (185 ml) and dilute aqueous hydrochloric acid (185 ml), followed by swirling for 5 minutes and filtration to remove inorganic residues (additional washing with dichloromethane). All organic fractions are combined, washed with brine, dried over anhydrous magnesium sulfate, then concentrated in vacuo to afford a crude oil which is further purified by flash column chromatography (hexane/ethyl acetate 5:1 ratio) to give the product as a yellow solid (4.47 g). Lead residues are removed by dissolving this solid in chloroform (50 ml) and stirring with 3-mercaptopropyl-functionalized silica gel (5.50 g, 1.20 mmol/g loading) overnight. After filtration and concentration 4-(5-bromo-2-ethylphenyl)-2,2,6,6-tetramethylpyran-3,5-dione (4.36 g) is afforded as a cream powder.

Step 6: Preparation of 4-(4'-chloro-4-ethyl-2'-fluoro-biphenyl-3-yl)-2,2,6,6-tetramethylpyran-3,5-dione

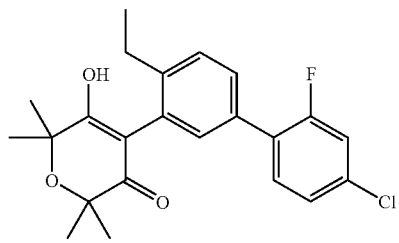

To a mixture of 4-(5-bromo-2-ethylphenyl)-2,2,6,6-tetramethylpyran-3,5-dione (0.278 g, 0.79 mmol), cesium fluoride (1.19 g, 7.90 mmol), 4-chloro-2-fluorophenylboronic acid (0.194 g, 1.11 mmol) and [1,1'-bis(diphenylphosphino)ferrocene]dichloro-palladium(II) (0.102 g, 0.12 mmol) is added degassed dimethoxyethane (2 ml), and the resulting suspension is stirred under nitrogen for 45 minutes then heated at 80° C. for 20 hours. After cooling to room temperature the reaction mixture is partitioned between ethyl acetate and 1M aqueous hydrochloric acid. The aqueous phase is further extracted with ethyl acetate, then all organic fractions are combined, dried over anhydrous magnesium sulfate and concentrated in vacuo. The resulting material is purified by column chromatography on silica gel (hexane/ethyl acetate 3:1 ratio) to afford 4-(4'-chloro-4-ethyl-2'-fluorobiphenyl-3-yl)-2,2,6,6-tetramethyl-pyran-3,5-dione (0.248 g) as a white solid.

Example 8

Preparation of 4-(2',4'-dichloro-4-ethylbiphenyl-3-yl)-2,2,6,6-tetramethylpyran-3,5-dione

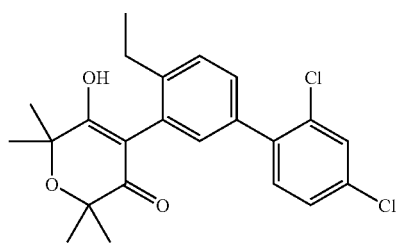

To a mixture of 4-(5-bromo-2-ethylphenyl)-2,2,6,6-tetramethylpyran-3,5-dione (0.278 g, 0.79 mmol), cesium fluoride (1.19 g, 7.90 mmol) and 2,4-dichlorophenyl boronic acid (0.30 g, 1.58 mmol) is added degassed dioxane (2.5 ml), and the resulting suspension is stirred under nitrogen for 45 minutes over which time a milky suspension is formed. To this suspension is then added [1,1'-bis(diphenylphosphino)ferrocene]-dichloropalladium(II) (0.102 g, 0.12 mmol) in one portion, and the mixture is heated at approximately 100° C. for 3 hours. After cooling to room temperature dichloromethane (150 ml) is added, and the solution washed with 1M hydrochloric acid (150 ml). The organic phase is separated, dried over anhydrous magnesium sulfate, filtered and the filtrate is concentrated in vacuo to afford a crude oil which is purified by column chromatography (hexane/ethyl acetate 5:1 ratio) to give the product as a foam. Trituration with hexanes affords 4-(2',4'-dichloro-4-ethyl-biphenyl-3-yl)-2,2,6,6-tetramethylpyran-3,5-dione (0.250 g) as a white solid.

Example 9

Preparation of 4-(4'-chloro-4-ethyl-2'-methylbiphenyl-3-yl)-2,2,6,6-tetramethyl-pyran-3,5-dione

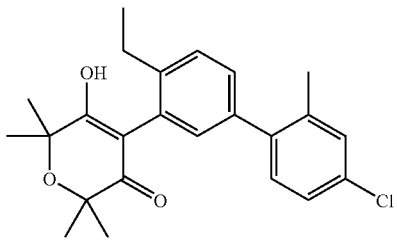

To a microwave vial is added palladium(II) acetate (3.3 mg, 0.015 mmol), tris(3-sulfophenyl)phosphine trisodium salt (22 mg, 0.038 mmol), 4-chloro-2-methylphenyl boronic acid (0.152 g, 0.89 mmol), 4-(5-bromo-2-ethyl-phenyl)-2,2,6,6-tetramethylpyran-3,5-dione (0.208 g, 0.59 mmol) and potassium phosphate (0.625 g, 2.95 mmol). A degassed mixed solution of acetonitrile/distilled water (1.5 ml, 1:1 ratio) is next added (washing-down any solids from the slides of the vial), followed by stirring for 5 minutes and flushing with argon.

This mixture is then heated at 160° C. under microwave irradiation for 15 minutes. After cooling to room temperature the reaction mixture is diluted with ethyl acetate (3 ml) and acidified to pH2 with dilute aqueous hydrochloric acid. The organic phase is separated and the aqueous phase is further extracted with ethyl acetate (2×3 ml). All organics are then combined, filtered through a silica plug and evaporated to give a crude product which is dissolved in N,N-dimethylformamide (2.5 ml) and purified by preparative reverse phase HPLC to afford 4-(4'-chloro-4-ethyl-2'-methylbiphenyl-3-yl)-2,2,6,6-tetramethylpyran-3,5-dione (0.139 g) as a white powder.

Example 10

Preparation of 4-(4'-chloro-4-ethyl-3'-trifluoromethylbiphenyl-3-yl)-2,2,6,6-tetramethylpyran-3,5-dione

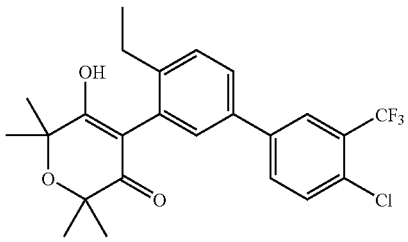 [SMILES: CCc1ccc(-c2ccc(Cl)c(C(F)(F)F)c2)cc1C1=C(O)C(C)(C)OC(C)(C)C1=O]

To a microwave vial is added palladium(II) acetate (3.3 mg, 0.015 mmol), tris(3-sulfophenyl)phosphine trisodium salt (22 mg, 0.038 mmol), 4-chloro-3-trifluoromethylphenyl boronic acid (0.200 g, 0.89 mmol), 4-(5-bromo-2-ethylphenyl)-2,2,6,6-tetramethylpyran-3,5-dione (0.208 g, 0.59 mmol) and potassium phosphate (0.625 g, 2.95 mmol). A degassed mixed solution of acetonitrile/distilled water (1.5 ml, 1:1 ratio) is next added (washing-down any solids from the slides of the vial), followed by stirring for 5 minutes and flushing with argon. This mixture is then heated at 160° C. under microwave irradiation for 15 minutes. After cooling to room temperature the reaction mixture is diluted with ethyl acetate (3 ml) and acidified to pH2 with dilute aqueous hydrochloric acid. The organic phase is separated and the aqueous phase is further extracted with ethyl acetate (2×3 ml). All organics are then combined, filtered through a silica plug and evaporated to give a crude product which is dissolved in N,N-dimethylformamide (2.5 ml) and purified by preparative reverse phase HPLC to afford 4-(4'-chloro-4-ethyl-3'-trifluoromethylbiphenyl-3-yl)-2,2,6,6-tetramethylpyran-3,5-dione (0.143 g) as a white powder.

Example 11

Preparation of 4-(4'-bromo-4-ethylbiphenyl-3-yl)-2,2,6,6-tetramethylpyran-3,5-dione

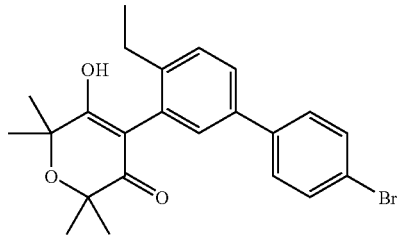

Step 1a 4-(4'-Amino-4-ethylbiphenyl-3-yl)-2,2,6,6-tetramethylpyran-3,5-dione (0.260 g, 0.71 mmol) is added portionwise to a mixture of hydrobromic acid (48% wt. in water, 1.7 ml) and water (1.2 ml), and once the addition is complete the mixture is heated to 40° C. and stirred for 20 minutes, before being cooled to 5° C. in an ice bath. A solution of sodium nitrite (0.099 g, 1.40 mmol) in water (1.2 ml) is added dropwise over 20 minutes, and once the addition is complete the mixture is stirred at 5° C. for a further 45 minutes.

Step 1b

Meanwhile, to a solution of hydrobromic acid (48% wt. in water, 3.3 ml) at 70° C. is added copper sulfate pentahydrate (0.388 g, 1.55 mmol) in one portion and the mixture is stirred at 70° C. for two minutes to give a dark purple solution, and then copper powder (0.135 g, 2.15 mmol) and (0.030 g, 0.47 mmol) is added, resulting in a pink suspension.

Step 1c

The mixture containing the diazonium salt (prepared in step 1a) is added portionwise to the stirred mixture prepared in Step 1b at 5° C., followed by heating at 70° C. for a further 45 minutes. After cooling to room temperature the reaction mixture is extracted with ethyl acetate, washed with water and brine, then dried over anhydrous magnesium sulfate and concentrated in vacuo. Purification by flash column chromatography (hexane/ethyl acetate 3:1 ratio) yields a crude solid which is triturated with hexanes/diethyl ether to afford 4-(4'- bromo-4-ethylbiphenyl-3-yl)-2,2,6,6-tetramethylpyran-3,5-dione (0.045 g) as a white solid.

Example 12

Preparation of 4-(4'-iodo-4-ethylbiphenyl-3-yl)-2,2,6,6-tetramethylpyran-3,5-dione

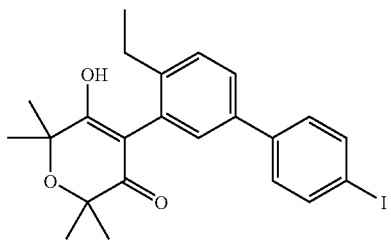 [SMILES: CCc1ccc(-c2ccc(I)cc2)cc1C1=C(O)C(C)(C)OC(C)(C)C1=O]

To a solution of para-toluenesulfonic acid monohydrate (1.03 g, 5.40 mmol) in acetonitrile (11 ml) is added 4-(4'-amino-4-ethylbiphenyl-3-yl)-2,2,6,6-tetramethyl-pyran-3,5-dione (0.65 g, 1.80 mmol), followed by stirring for 10 minutes at room temperature then cooling to 10° C. To this mixture is then added a second mixed solution of sodium nitrite (0.25 g, 3.60 mmol) and potassium iodide (0.76 g, 4.50 mmol) in distilled water (1.3 ml), and the mixture is then stirred at 10° C. for 20 minutes then at room temperature for 2 hours. Aqueous sodium bicarbonate solution is added until pH 9-10 is achieved, followed by dilution with ethyl acetate and washing with saturated aqueous sodium metabisulfite (20 ml). After additional extraction of the aqueous phase using ethyl acetate (×2) all organic fractions are combined, washed with distilled water and brine, then dried over anhydrous magnesium sulfate and concentrated in vacuo. This crude product is purified by flash column chromatography on silica gel (hexane/ethyl acetate 3:1 ratio) to yield an orange gum, which is triturated with hexanes to afford 4-(4'-iodo-4-ethylbiphenyl-3-yl)-2,2,6,6-tetramethylpyran-3,5-dione (0.413 g) as a white solid.

Example 13

Preparation of 4-(4-ethyl-4'-ethynylbiphenyl-3-yl)-2,2,6,6-tetramethylpyran-3,5-dione Step 1: Preparation of 4-[4-ethyl-4'-(trimethylsilylethynyl)biphenyl-3-yl]-2,2,6,6-tetramethyl-pyran-3,5-dione

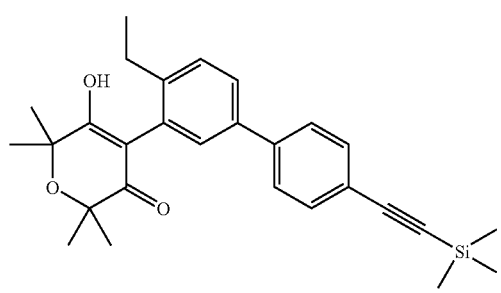

A mixture of 4-(4'-iodo-4-ethyl-biphenyl-3-yl)-2,2,6,6-tetramethylpyran-3,5-dione (0.200 g, 0.42 mmol), trimethylsilylacetylene (0.10 ml, 0.47 mmol), copper(I) iodide (4 mg, 0.023 mmol), bis(triphenylphosphine)palladium(II) chloride (0.016 g, 0.023 mmol), triphenylphosphine (0.022 g, 0.084 mmol) and diethylamine (0.65 ml) in anhydrous N,N-dimethylformamide (0.25 ml) is heated at 120° C. under microwave irradiation for 25 minutes. This mixture is then allowed to cool to room temperature and filtered through diatomaceous earth (additional washing with dichloromethane). The solvent is removed under reduced pressure and the residue is purified by flash column chromatography on silica gel (hexane/ethyl acetate 9:1 to 3:1 ratio) to yield 4-[4-ethyl-4'-(trimethylsilylethynyl)biphenyl-3-yl]-2,2,6,6-tetramethylpyran-3,5-dione (0.143 g) as a white solid which is used without further purification in the next step.

Step 2: Preparation of 4-(4-ethyl-4'-ethynylbiphenyl-3-yl)-2,2,6,6-tetramethylpyran-3,5-dione

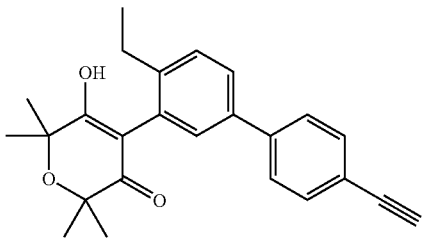 [SMILES: C#Cc1ccc(-c2ccc(CC)c(C3=C(O)C(C)(C)OC(C)(C)C3=O)c2)cc1]

To a solution of 4-[4-ethyl-4'-(trimethylsilylethynyl)biphenyl-3-yl]-2,2,6,6-tetramethyl-pyran-3,5-dione (0.143 g, 0.32 mmol) in methanol (6.5 ml) is added powdered potassium carbonate (0.177 g, 1.28 mmol), and the mixture is stirred at room temperature for 1 hour. Water is then added to dissolve all inorganics, and the mixture is concentrated in vacuo. 2M hydrochloric acid is added to achieve pH 2-3, then the desired material is extracted with ethyl acetate (×3). All organics are combined, washed with brine, dried over anhydrous magnesium sulfate then concentrated in vacuo. The residue is further purified by flash column chromatography on silica gel (hexane/ethyl acetate 4:1 ratio) to afford 4-(4-ethyl-4'-ethynylbiphenyl-3-yl)-2,2,6,6-tetramethylpyran-3,5-dione (0.070 g) as a yellow solid.

Example 14

Preparation 4-[5-(3,5-dichloropyridin-2-yl)-2-methylphenyl]-2,2,6,6-tetramethyl-pyran-3,5-dione

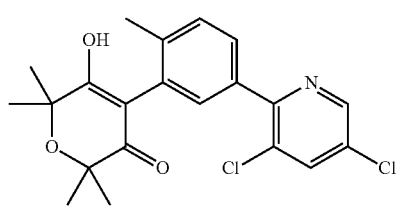 [SMILES: Cc1ccc(-c2ncc(Cl)cc2Cl)cc1C1=C(O)C(C)(C)OC(C)(C)C1=O]

Step 1: Preparation of 5-bromo-2-methylphenyllead triacetate

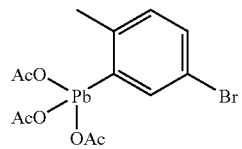

To a mixture of lead tetraacetate (11.25 g, 25.40 mmol) and mercuric diacetate (0.40 g, 1.27 mmol), thoroughly flushed with nitrogen, is added anhydrous chloroform (35 ml). This mixture is warmed to 40° C., and 5-bromo-2-methylphenyl-boronic acid (4.96 g, 23.10 mmol) is added in one portion and the suspension is heated at this temperature for 5 hours. The mixture is then allowed to cool to room temperature, followed by further cooling to 0° C. then powdered anhydrous potassium carbonate (1.61 g) is added with rapid stirring for 5 minutes. The mixture is filtered, the filtrate is concentrated to half its volume, and hexanes added to induce precipitation. This mixture is further concentrated, the solvent decanted, and the solid washed with hexanes to afford 5-bromo-2-methylphenyllead triacetate (10.10 g) as a sandy coloured solid.

Step 2: Preparation of 4-(5-bromo-2-methylphenyl)-2,2,6,6-tetramethylpyran-3,5-dione

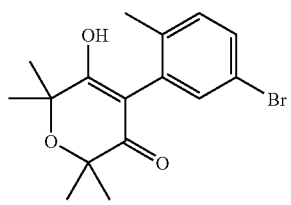 [SMILES: Cc1ccc(Br)cc1C1=C(O)C(C)(C)OC(C)(C)C1=O]

To a mixture of 2,2,6,6-tetramethylpyran-3,5-dione (6.00 g, 35.29 mmol) and N,N-dimethylaminopyridine (21.62 g, 177.21 mmol) is added anhydrous chloroform (200 ml), followed by stirring at room temperature until dissolution. To this solution is added anhydrous toluene (55 ml), followed by 5-bromo-2-methylphenyllead triacetate (21.60 g, 38.99 mmol) in one portion and the reaction mixture is heated at 80° C. for 2 hours. The mixture is allowed to cool to room temperature, then diluted with dichloromethane (300 ml) and aqueous hydrochloric acid (300 ml), and the mixture is swirled for 5 minutes and filtered to remove inorganic residues. The filter cake is washed with dichloromethane, and all organic fractions are combined, dried over anhydrous magnesium sulfate, filtered and the filtrate is concentrated in vacuo to afford a crude solid which is recrystallised from dichloromethane/hexanes. This material is then further purified by flash column chromatography (hexane/ethyl acetate 5:1 ratio). The lead residues are removed by dissolving the resulting solid (approximately 6.50 g) in chloroform (100 ml) and stirring with 3-mercaptopropyl-functionalized silica gel (6.50 g, 1.20 mmol/g loading) overnight. The mixture is filtered and the filtrate concentrated in vacuo to afford 4-(5-bromo-2-methyl-phenyl)-2,2,6,6-tetramethylpyran-3,5-dione (6.50 g) as a cream powder.

Step 3: Preparation of 4-methyl-3-(2,2,6,6-tetramethyl-3,5-dioxotetrahydropyran-4-yl)phenylboronic acid

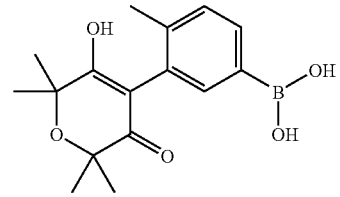 [SMILES: Cc1ccc(B(O)O)cc1C1=C(O)C(C)(C)OC(C)(C)C1=O]

4-(5-Bromo-2-methyl-phenyl)-2,2,6,6-tetramethyl-pyran-3,5-dione (5 g, 0.0147 mol) is dissolved in anhydrous tetrahydrofuran (150 ml), the reaction mixture is cooled to 0° C. and sodium hydride (708 mg, 0.0294 mol, 60% dispersion in oil) is added. The mixture is stirred for 30 minutes, then cooled to −78° C. n-Butyl lithium (14.7 ml, 0.0294 mol, 2M solution in cyclohexane) is added, dropwise over approximately 10 minutes and reaction mixture is stirred for 15 minutes before trimethylborate (4.95 ml, 0.0442 mol) is added. The reaction mixture is stirred for a further 45 minutes, allowed to warm to ambient temperature and then stirred a further 1.5 hours before quenching with 2M aqueous hydrochloric acid. The reaction mixture is stirred for 1 hour and then extracted with dichloromethane. After separation of the organic phase solvents are removed under reduced pressure to give a pale yellow gum. Trituration with iso-hexane affords 4-methyl-3-(2,2,6,6-tetramethyl-3,5-dioxo-tetrahydropyran-4-yl)phenylboronic acid (2.01 g) as a white solid.

Step 4: Preparation 4-[5-(3,5-dichloropyridin-2-yl)-2-methylphenyl]-2,2,6,6-tetra-methylpyran-3,5-dione

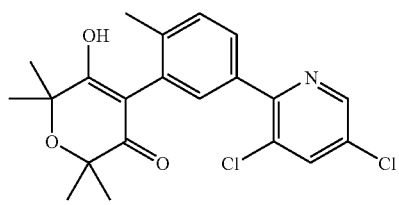

To a microwave vial is added 4-methyl-3-(2,2,6,6-tetramethyl-3,5-dioxo-tetrahydropyran-4-yl)phenylboronic acid (200 mg, 0.657 mmol), 2-bromo-3,5-dichloropyridine (149 mg, 0.657 mmol), palladium acetate (3.7 mg, 0.0164 mmol), tris(3-sulfophenyl)phosphine trisodium salt (22 mg, 0.0394 mmol) and potassium phosphate (697 mg, 3.28 mol), followed by a degassed solvent mixture of water/acetonitrile (1.6 ml, 2:1 ratio). The mixture is flushed with nitrogen then stirred at ambient temperature for 5 minutes before heating at 160° C. under microwave irradiation for 15 minutes. After cooling to room temperature the reaction is partitioned between 2M aqueous hydrochloric acid and dichloromethane, and the organic phase is separated. The aqueous phase is further extracted with dichloromethane and all organic fractions are combined then evaporated. The residue is purified by preparative reverse phase HPLC to give 4-[5-

(3,5-dichloropyridin-2-yl)-2-methylphenyl]-2,2,6,6-tetramethylpyran-3,5-dione (113 mg).

Example 15

Preparation of 4-[2-methyl-5-(4-methylthiazol-2-yl)phenyl]-2,2,6,6-tetramethylpyran-3,5-dione

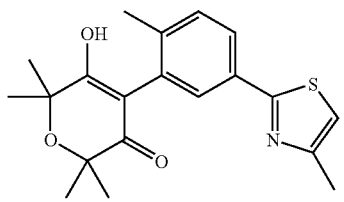 [SMILES: Cc1csc(-c2ccc(C)c(C3=C(O)C(C)(C)OC(C)(C)C3=O)c2)n1]

To a mixture of 4-(5-bromo-2-methylphenyl)-2,2,6,6-tetramethylpyran-3,5-dione (200 mg, 0.589 mmol), 4-methylthiazole (70 mg, 0.707 mmol), silver carbonate (814 mg, 2.94 mmol), triphenylphosphine (15 mg, 0.0589 mmol) and [1,1-bis(diphenylphosphino)-ferrocene]palladium(II)chloride (24 mg, 0.0294 mmol) is added a degassed solvent mixture of water/acetonitrile (1.5 ml, 1:1 ratio), followed by subsequent purging with nitrogen then heating at 65° C. for 65 hours with shaking. After cooling to room temperature the reaction mixture is then partitioned between 2M aqueous hydrochloric acid and dichloromethane, and the organic phase is separated. The aqueous layer is washed with a further aliquot of dichloromethane, and the combined organic layers are evaporated under reduced pressure to give a brown solid which is purified by preparative reverse phase HPLC to give 4-[2-methyl-5-(4-methylthiazol-2-yl)phenyl]-2,2,6,6-tetramethylpyran-3,5-dione as a pale yellow solid (36 mg).

Example 16

Preparation of 4-[2-methyl-5-(1-oxypyridin-2-yl)phenyl]-2,2,6,6-tetramethyl-pyran-3,5-dione

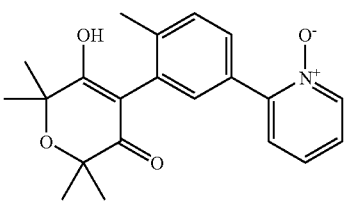

A mixture of 4-(5-bromo-2-methylphenyl)-2,2,6,6-tetramethyl-pyran-3,5-dione (30 mg, 0.0888 mmol), pyridine-N-oxide (33.7 mg, 0.355 mmol), palladium acetate (1 mg, 0.0044 mmol), potassium carbonate (24.5 mg, 0.1775 mmol) and tri-tert-butylphosphonium tetrafluoroborate (3.86 mg, 0.0133 mmol) in toluene (1 ml) is heated at 110° C. for 18 hours with shaking. After cooling to room temperature the reaction mixture is evaporated under reduced pressure and the residue purified by preparative reverse phase HPLC to give 4-[2-methyl-5-(1-oxy-pyridin-2-yl)phenyl]-2,2,6,6-tetramethylpyran-3,5-dione (5.2 mg) as a colourless gum.

Example 17

Preparation of 4-(4'-Difluoromethyl-4-ethylbiphenyl-3-yl)-2,2,6,6-tetramethyl-pyran-3,5-dione

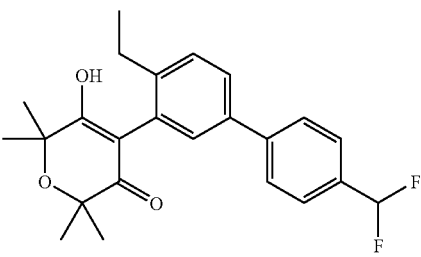 [SMILES: CCc1ccc(-c2ccc(C(F)F)cc2)cc1C1=C(O)C(C)(C)OC(C)(C)C1=O]

To a solution of 4-(4'-carbaldehyde-4-ethylbiphenyl-3-yl)-2,2,6,6-tetramethylpyran-3,5-dione (0.110 g, 0.3 mmol) in anhydrous dichloromethane (4 ml) is added (diethylamino)sulfur trifluoride (0.14 ml, 1.06 mmol) dropwise at 0° C. After stirring for 1 hour the mixture is allowed to warm to room temperature, and the solution is further stirred overnight. The solution is next cooled in an ice-bath and saturated aqueous sodium carbonate (4 ml) is added with vigorous stirring over 30 minutes. The reaction mixture is diluted with ethyl acetate (×2) then the two layers are separated and the aqueous phase further extracted with ethyl acetate. The organic extracts are combined, washed with brine, and dried over anhydrous magnesium sulfate. The mixture is filtered, the filtrate is evaporated in vacuo and the residue is purified by preparative reverse phase chromatography to afford 4-(4'-difluoromethyl-4-ethylbiphenyl-3-yl)-2,2,6,6-tetramethylpyran-3,5-dione (0.015 g) as a white solid.

Example 18

Preparation of 4-(4,4'-dichlorobiphenyl-3-yl)-2,2,6,6-tetramethylpyran-3,5-dione

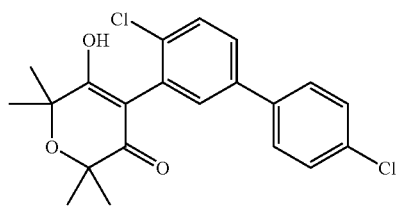

Step 1: Preparation of 4-bromo-1-chloro-2-iodobenzene

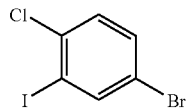

tert-Butyl nitrite (3 ml, 25 mmol) is added to a suspension of copper(II) chloride (2.71 g, 20 mmol) in acetonitrile (60 ml) and the mixture is heated with stirring to 60° C. A solution of 4-bromo-2-iodoaniline (5 g, 17 mmol) in acetonitrile (15 ml) is added dropwise, and once the addition is complete the mixture is stirred at 60° C. for 2.5 hours. The mixture is cooled to room temperature, poured into 20% aqueous hydrochloric acid and extracted with diethyl ether. The organic extract is dried over anhydrous magnesium sulfate, filtered and the filtrate evaporated in vacuo. The residue is further purified by column chromatography on silica gel to give 4-bromo-1-chloro-2-iodobenzene (4.32 g) as an oil.

Step 2: Preparation of 5-bromo-2-chlorophenylboronic acid

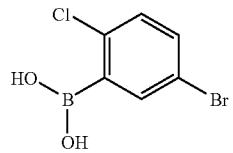 [SMILES: OB(O)c1cc(Br)ccc1Cl]

4-Bromo-1-chloro-2-iodobenzene (10.35 g, 33 mmol) is dissolved in anhydrous tetrahydrofuran (60 ml) and the solution is cooled to −75° C. under an atmosphere of argon. Isopropylmagnesium chloride (17.1 ml, 34 mmol, 2M solution in tetrahydrofuran) is added dropwise over 30 minutes, maintaining the internal temperature below −70° C. by external cooling. Once the addition is complete, the reaction mixture is stirred at approximately −70° C. for 30 minutes and then allowed to warm to room temperature and stirred for 1 hour. The reaction mixture is then cooled to −78° C. and trimethyl borate (7.3 ml, 65 mmol) is added dropwise. The mixture is stirred at −78° C. for 30 minutes and then the cooling bath is removed and the mixture stirred at room temperature for 1.5 hours. 2M Aqueous hydrochloric acid (30 ml) is added, and the crude product is then extracted with ethyl acetate. The organic phase is washed with water and brine, dried over anhydrous magnesium sulfate, filtered and the filtrate evaporated in vacuo. Trituration with hexane gives 5-bromo-2-chlorophenylboronic acid (6.16 g) as an off-white solid.

Step 3: Preparation of 5-bromo-2-chlorophenyllead triacetate

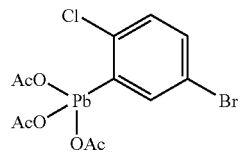

To a mixture of lead tetraacetate (1.46 g, 3.3 mmol) and mercuric diacetate (42 mg, 0.13 mmol), thoroughly flushed with nitrogen, is added anhydrous chloroform (2.5 ml) is introduced and the reaction mixture is stirred and heated to 40° C. 5-Bromo-2-chlorophenylboronic acid (0.62 g, 2.6 mmol) is added in one portion, and the reaction mixture is stirred at 40° C. for 4 hours. After cooling to room temperature potassium carbonate (0.18 g) is added, the mixture stirred vigorously for 5 minutes and then filtered.

The filtrate is concentrated in vacuo to give 5-bromo-2-chlorophenyllead triacetate (1.23 g), used without further purification in the next step.

Step 4: Preparation of 4-(5-bromo-2-chlorophenyl)-2,2,6,6-tetramethylpyran-3,5-dione

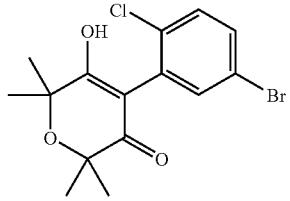 [SMILES: CC1(C)OC(C)(C)C(O)=C(c2cc(Br)ccc2Cl)C1=O]

To a mixture of 2,2,6,6-tetramethylpyran-3,5-dione (2.78 g, 16.3 mmol) and N,N-dimethylaminopyridine (9.97 g, 81.6 mmol) is added anhydrous chloroform (120 ml). To this solution is added anhydrous toluene (30 ml), followed by 5-bromo-2-chlorophenyllead triacetate (10.32 g, 18 mmol) in one portion and the reaction mixture is heated at 80° C. overnight. The mixture is allowed to cool to room temperature, then diluted with dichloromethane (120 ml) and 2M aqueous hydrochloric acid (250 ml), followed by filtration through diatomaceous earth to remove inorganic residues. The filter cake is washed with dichloromethane, and all organic fractions are combined, washed with 2M hydrochloric acid, water and brine, dried over anhydrous magnesium sulfate then concentrated in vacuo. This material is finally purified by flash column chromatography on silica gel to afford 4-(5-bromo-2-chlorophenyl)-2,2,6,6-tetramethylpyran-3,5-dione (0.44 g) of sufficient purity to use directly in the next step.

Step 5: Preparation of 4-(4,4'-dichlorobiphenyl-3-yl)-2,2,6,6-tetramethylpyran-3,5-dione

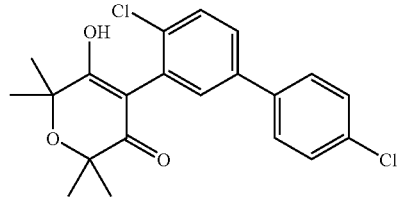

A mixture of 4-(5-bromo-2-chlorophenyl)-2,2,6,6-tetramethylpyran-3,5-dione (0.22 g, 0.6 mmol), 4-chlorophenylboronic acid (0.14 g, 0.9 mmol), and cesium fluoride (0.28 g, 1.8 mmol) are stirred together in 1,2-dimethoxyethane (2.4 ml) under an atmosphere of nitrogen at room temperature for 45 minutes. [1,1'-bis(diphenyl-phosphino)ferrocene]dichloropalladium(II) (80 mg, 0.098 mmol) is added and the reaction mixture is heated at 80° C. overnight. The reaction mixture is filtered through diatomaceous earth, washing the filter cake with dichloromethane (7 ml) and water (3 ml). The mixture is acidified to pH1 by addition of 2M aqueous hydrochloric acid, and the organic phase is separated. The aqueous phase is extracted with dichloromethane, and all organic extracts are combined, dried over anhydrous magnesium sulfate, filtered and the filtrate evaporated. The residue is dissolved in N,N-dimethylformamide (approximately 1 ml) and purified by preparative reverse phase HPLC to give 4-(4,4'-dichlorobiphenyl-3-yl)-2,2,6,6-tetramethylpyran-3,5-dione (80 mg).

Example 19

Preparation of 4-(4-bromo-4'-chlorobiphenyl-3-yl)-2,2,6,6-tetramethylpyran-3,5-dione

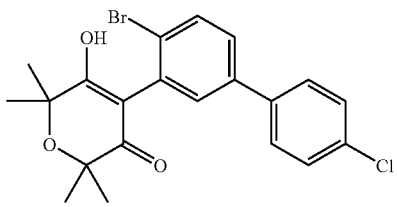

Step 1: Preparation of
4'-chloro-3-iodobiphenyl-4-ylamine

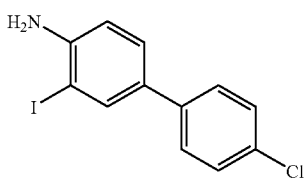 [SMILES: Nc1ccc(-c2ccc(Cl)cc2)cc1I]

To a solution of 4'-chlorobiphenyl-4-ylamine (2.03 g, 0.01 mmol) in a mixed solvent system of methanol (10 ml) and distilled water (40 ml) is added potassium chlorate (0.830 g, 6.77 mmol) and potassium iodide (3.32 g, 0.02 mol). After heating the reaction mixture to 80° C., concentrated hydrochloric acid (0.60 ml) is added, and the mixture is further heated overnight at this temperature. The solution is cooled to room temperature and the crude product is extracted with diethyl ether (×3), followed by washing of the combined organic fractions with 5% aqueous sodium thiosulfate solution and distilled water. The organic phase is dried over anhydrous magnesium sulfate, filtered and the filtrate evaporated in vacuo to give a dark solid, which is triturated with hexanes to afford 4'-chloro-3-iodobiphenyl-4-ylamine (2.94 g) as light brown solid.

Step 2: Preparation of
4-bromo-4'-chloro-3-iodobiphenyl

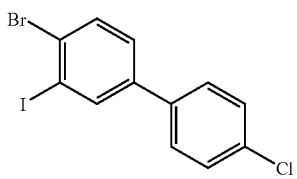 [SMILES: Clc1ccc(-c2ccc(Br)c(I)c2)cc1]

4'-Chloro-3-iodobiphenyl-4-ylamine (13.5 g, 0.041 mol) is ground to a fine powder and suspended in a mixture of 48% aqueous hydrogen bromide (54 ml) and distilled water (42 ml). This suspension is then heated to 45° C. for 30 minutes, then cooled to 0-5° C. and a solution of sodium nitrite (3.54 g, 0.0125 mol) in distilled water (6 ml) is added dropwise, maintaining internal temperature below 5° C. throughout. This mixture is then added portionwise to a second preformed suspension of copper(II) sulfate pentahydrate (15 g, 0.06 mol) and copper powder (5.29 g, 0.084 mol) in 48% aqueous hydrogen bromide (80 ml) at 80° C. When the addition is complete the reaction mixture is stirred at 80° C. for an additional 90 minutes. After cooling to room temperature, ethyl acetate is added and the reaction mixture is poured into distilled water and the two layers separated. The aqueous phase is further extracted with ethyl acetate (×2), and the combined organic extracts are washed with distilled water until a neutral pH is achieved, then dried over anhydrous magnesium sulfate. The mixture is filtered, the filtrate is evaporated in vacuo, and the residue is further purified by flash column chromatography on silica gel (hexane eluant) to afford 4-bromo-4'-chloro-3-iodobiphenyl (10.5 g) as a pale orange liquid.

Step 3: Preparation of
4-bromo-4'-chlorobiphenyl-3-ylboronic acid

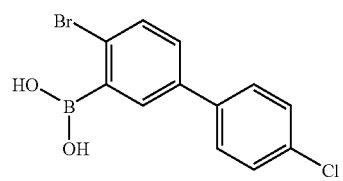 [SMILES: OB(O)c1cc(-c2ccc(Cl)cc2)ccc1Br]

To a solution of 4-bromo-4'-chloro-3-iodobiphenyl (8.00 g, 20.40 mmol) in a mixed solvent system of anhydrous diethyl ether (80 ml) and anhydrous tetrahydrofuran (80 ml) at −75° C. is added isopropylmagnesium bromide (31.60 ml, 15% in tetrahydrofuran) dropwise, maintaining the temperature of the reaction mixture below −70° C. When the addition is complete the mixture is stirred at −75° C. for an additional 2 hours, then allowed to warm to −25° C. at which point trimethyl borate (3.15 g, 30.60 mmol) is added dropwise. After the addition is complete the reaction is allowed to warm to room temperature and stir overnight, followed by cooling in an ice-bath and acidification with 2M aqueous hydrochloric acid. The crude product is extracted with ethyl acetate (×3), and the organic fractions are combined, washed with brine, then dried over anhydrous magnesium sulfate. The mixture is filtered and the filtrate is evaporated in vacuo to give a solid which is further triturated with hexanes to afford 4-bromo-4'-chlorobiphenyl-3-yl-boronic acid (5.20 g) as a white solid.

Step 4: Preparation of
4-bromo-4'-chlorobiphenyl-3-yllead triacetate

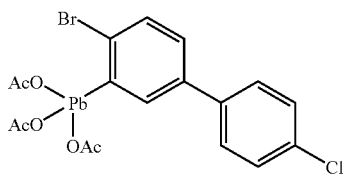

To a mixture of lead tetraacetate (3.76 g, 8.49 mmol) and mercuric diacetate (0.27 g, 0.85 mmol), thoroughly flushed with nitrogen, is added anhydrous chloroform (25 ml). This mixture is warmed to 40° C., and 4-bromo-4'-chlorobiphenyl-3-yl-boronic acid (2.40 g, 7.72 mmol) is added in one portion, and the mixture is stirred and heated at this temperature for 4 hours. After cooling to room temperature, the mixture is diluted with chloroform (25 ml), cooled in an ice-bath, and powdered anhydrous potassium carbonate (2.75 g) is added rapidly, followed by rapid stirring for 5 minutes. The solids are removed by filtration, and the filtrate is concentrated to approximately a quarter of its volume. Hexane is added to induce crystallisation, and the solvents evaporated in vacuo. Trituration with hexane gives 4-bromo-4'-chlorobiphenyl-3-yllead triacetate (3.25 g), used without further purification in the next step.

Step 5: Preparation of 4-(4-bromo-4'-chlorobiphenyl-3-yl)-2,2,6,6-tetramethylpyran-3,5-dione

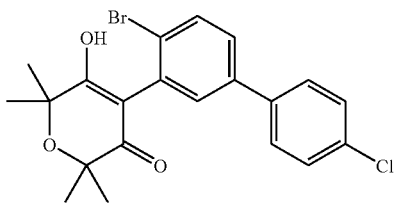

To a mixture of 2,2,6,6-tetramethylpyran-3,5-dione (0.75 g, 4.9 mmol) and N,N-dimethylaminopyridine (2.52 g, 20.6 mmol) is added anhydrous chloroform (40 ml), followed by stirring at room temperature until dissolution. To this solution is added anhydrous toluene (12 ml), followed by 4-bromo-4'-chlorobiphenyl-3-yllead triacetate (3.25 g, 5.1 mmol) in one portion and the reaction mixture is heated at 80° C. for 2 hours. The mixture is cooled to room temperature, diluted with chloroform (50 ml) and 1M aqueous hydrochloric acid (50 ml), and the mixture is stirred for 5 minutes. The precipitate is removed by filtration, the two phases separated, and the organic phase is washed with brine, dried over anhydrous magnesium sulfate, filtered and the filtrate is evaporated in vacuo. The residue is purified by flash column chromatography on silica gel, and fractions containing the desired compound are combined and evaporated to give a residue which is further purified by preparative reverse phase HPLC to give 4-(4-bromo-4'-chlorobiphenyl-3-yl)-2,2,6,6-tetramethylpyran-3,5-dione (0.013 g).

Example 20

Preparation of 4-(4'-chloro-4-cyclopropylbiphenyl-3-yl)-2,2,6,6-tetramethyl-pyran-3,5-dione

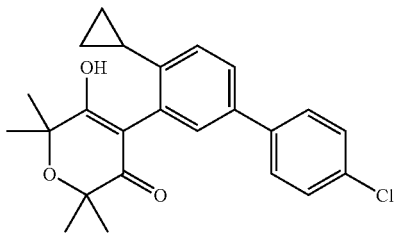 [SMILES: CC1(C)OC(C)(C)C(O)=C(c2cc(-c3ccc(Cl)cc3)ccc2C2CC2)C1=O]

To a stirred solution of 4-(4-bromo-4'-chlorobiphenyl-3-yl)-2,2,6,6-tetramethylpyran-3,5-dione (0.390 g, 0.90 mmol), cyclopropylboronic acid (0.100 g, 1.16 mmol), potassium phosphate (0.665 g, 3.14 mmol) and tricyclohexylphosphine (0.025 g, 0.09 mmol) in a mixed solvent system of toluene (4 ml) and distilled water (0.2 ml) is added palladium acetate (0.010 g, 0.044 mmol). This mixture is then heated at 100° C. overnight. After cooling to room temperature the solution is diluted with ethyl acetate and distilled water, then filtered through diatomaceous earth (additional washing with ethyl acetate/distilled water). The aqueous phase is acidified with 2M aqueous hydrochloric acid to pH3, then the organic phase is separated and the aqueous phase extracted again with ethyl acetate (×2). All organic fractions are combined, washed with brine, then dried over anhydrous magnesium sulfate and filtered. After concentration in vacuo the crude oil is purified by preparative reverse phase HPLC then triturated with hexanes to afford 4-(4'-chloro-4-cyclopropylbiphenyl-3-yl)-2,2,6,6-tetramethylpyran-3,5-dione (0.011 g) as a white solid.

Example 21

Preparation of 4-(4'-chloro-4-vinylbiphenyl-3-yl)-2,2,6,6-tetramethylpyran-3,5-done

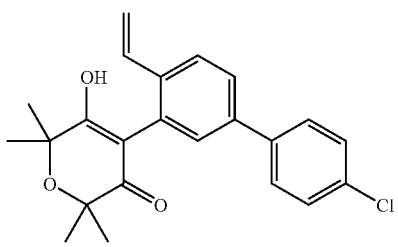

A solution of 4-(4-bromo-4'-chlorobiphenyl-3-yl)-2,2,6,6-tetramethylpyran-3,5-dione (0.314 g, 0.72 mmol), vinylboronic anhydride pyridine complex (0.175 g, 0.73 mmol), lithium hydroxide monohydrate (0.177 g, 4.22 mmol), 1,3-bis(diphenylphosphino)propane (0.015 g, 0.036 mmol) and palladium acetate (0.010 g, 0.044 mmol) is stirred in a mixed solvent system of 1,2-dimethoxyethane (5 ml) and distilled water (1 ml) at 80° C. for 3 hours. After cooling to room temperature the mixture is filtered through diatomaceous earth, followed by washing with ethyl acetate and distilled water. The aqueous phase is acidified with 2M aqueous hydrochloric acid to pH3, then the organic phase is separated and the aqueous phase extracted again with ethyl acetate. All organic fractions are combined, then dried over anhydrous magnesium sulphate and filtered. After concentration in vacuo the crude oil is purified by preparative reverse phase HPLC then triturated with hexanes to afford 4-(4'-chloro-4-vinylbiphenyl-3-yl)-2,2,6,6-tetramethylpyran-3,5-dione (0.038 g) as a white solid.

Example 22

Preparation of 4-(4'-chloro-4-ethylbiphenyl-3-yl)-2-methoxymethyl-2,6,6-trimethylpyran-3,5-dione

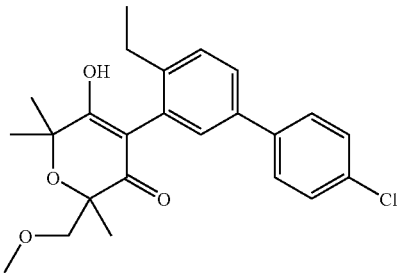 [SMILES: CCc1ccc(-c2ccc(Cl)cc2)cc1C1=C(O)C(C)(C)OC(C)(COC)C1=O]

Step 1: Preparation of 1-methoxy-2,5-dimethylhex-3-yne-2,5-diol

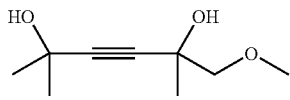

To a solution of anhydrous diethyl ether at 0-5° C. is added ethyl magnesium bromide (37.33 ml, 112 mmol, 3M solution in diethyl ether), then 2-methyl-3-butyn-2-ol (4.70 g, 55.87 mmol) dropwise. The mixture is allowed to warm to room temperature, followed by stirring at this temperature for 30 minutes, then at 40° C. until gas evolution ceases (approximately 1 hour). The viscous mixture is next cooled to room temperature and methoxyacetone (3.78 g, 42.90 mmol) is added dropwise, followed by heating to 40° C. for 1 hour. After cooling to room temperature the suspension is poured into a mixture of ice and saturated aqueous ammonium chloride, and the product is extracted with diethyl ether (2×50 ml) then dichloromethane (2×50 ml, 2×100 ml). The organic extracts are combined, washed with brine, dried over anhydrous magnesium sulfate then concentrated in vacuo to afford 1-methoxy-2,5-dimethylhex-3-yne-2,5-diol (6.98 g) as a clear oil.

Step 2: Preparation of 5-methoxymethyl-2,2,5-trimethyldihydrofuran-3-one and 2-methoxymethyl-2,5,5-trimethyldihydrofuran-3-one

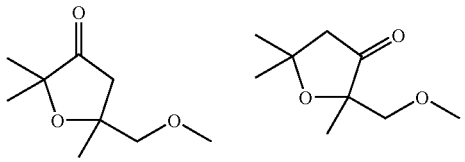

To mercury oxide (0.05 g, 0.231 mmol) is added a solution of trichloroacetic acid (0.02 g, 0.122 mmol) in methanol (0.053 ml), then boron trifluoride-diethyl etherate (0.053 ml, 0.37 mmol). The mixture is briefly stirred then heated until a cream paste is produced (approximately 5 minutes), followed by dilution with additional methanol (1 ml). To this suspension is then added a solution of 1-methoxy-2,5-dimethylhex-3-yne-2,5-diol (1.22 g, 7.09 mmol) in methanol (1 ml) dropwise, and the resulting mixture is heated at 50° C. for 3 hours. After cooling to room temperature the reaction mixture is filtered through diatomaceous earth (washing with additional methanol) then concentrated at 40° C./150 mbar to give a crude oil. This material is further diluted with diethyl ether, stirred over solid sodium bicarbonate then filtered and concentrated at 40° C./150 mbar to afford a mixture of 5-methoxymethyl-2,2,5-trimethyldihydrofuran-3-one and 2-methoxymethyl-2,5,5-trimethyldihydrofuran-3-one (0.73 g) as a brown oil, used without further purification in the next step.

Step 3: Preparation of 2-methoxymethyl-2,5,5-trimethylfuran-3,4-dione

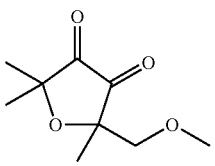

A stirred solution of selenium dioxide (2.10 g, 18.91 mmol) in moist dioxane (17 ml, containing 0.5% distilled water by volume) is heated to 100° C., at which point a second (mixed) solution of 5-methoxymethyl-2,2,5-trimethyldihydrofuran-3-one and 2-methoxymethyl-2,5,5-trimethyldihydrofuran-3-one (2.55 g, 14.82 mmol) in moist dioxane (5 ml, containing 0.5% distilled water by volume) is added dropwise over 40 minutes, then further heated at this temperature for 3 hours. After cooling to room temperature the mixture is filtered through diatomaceous earth (washing with diethyl ether) then the solvents are removed at 40° C./50 mbar to give a viscous red-brown oil. This material is purified by bulb to bulb distillation to afford 2-methoxymethyl-2,5,5-trimethylfuran-3,4-dione (2.15 g) as a bright red oil.

Step 4: Preparation of 2-methoxymethyl-2,6,6-trimethyl-3,5-dioxotetrahydropyran-4-carboxylic acid ethyl ester

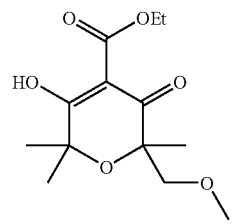

To a solution of zinc chloride (11.80 ml, 11.80 mmol, 1M solution in diethyl ether) at 8° C. is carefully added a second solution of 2-methoxymethyl-2,5,5-trimethylfuran-3,4-dione (2.15 g, 11.56 mmol) in tert-butyl methyl ether (8 ml). This mixture is allowed to warm to 15° C. at which stage a solution of ethyl diazoacetate (1.35 g, 11.84 mmol) in tert-butyl methyl ether (6 ml) is added dropwise over 1 hour, maintaining an internal temperature below 21° C. with further stirring at room temperature overnight. The mixture is diluted with tert-butyl methyl ether (15 ml), washed with 1M hydrochloric acid (3×20 ml) and extracted with 1M sodium hydroxide (2×100 ml). To this aqueous phase is added solid sodium chloride, followed by acidification with concentrated hydrochloric acid then the mixture is extracted with dichloromethane. The organic extract is dried over anhydrous magnesium sulfate, filtered and the filtrate is concentrated in vacuo to afford 2-methoxymethyl-2,6,6-trimethyl-3,5-dioxotetrahydropyran-4-carboxylic acid ethyl ester (2.11 g) as a pink oil.

Step 5: Preparation of 2-methoxymethyl-2,6,6-trimethylpyran-3,5-dione

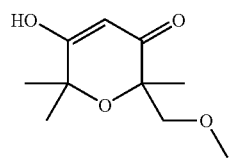

To a solution of 2-methoxymethyl-2,6,6-trimethyl-3,5-dioxotetrahydropyran-4-carboxylic acid ethyl ester (2.11 g, 7.72 mmol) in dioxane (2.5 ml) is added 20% aqueous sulfuric acid (2.5 ml) and the mixture is heated at 110° C. for 2.5 hours. The mixture is cooled to room temperature, diluted with saturated brine and extracted with dichloromethane. The crude material is extracted into aqueous sodium hydroxide, the aqueous phase washed with dichloromethane, then acidified with concentrated hydrochloric acid and extracted into dichloromethane (2×15 ml). The organic phase is concentrated in vacuo to give a crude oil which is purified by flash column chromatography on silica gel (isohexane/diethyl ether 7.5:1.5 ratio) to afford 2-methoxymethyl-2,6,6-trimethylpyran-3,5-dione (0.250 g) as a pink solid.

Step 6: Preparation of 4-(4'-chloro-4-ethylbiphenyl-3-yl)-2-methoxymethyl-2,6,6-trimethyl-pyran-3,5-dione

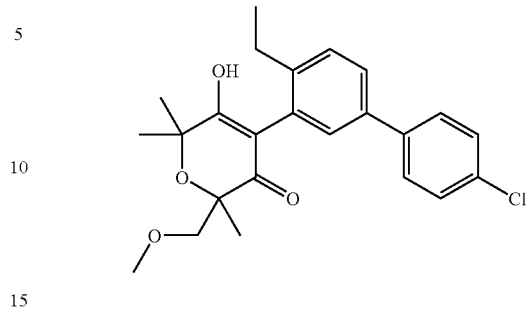

To a mixture of 2-methoxymethyl-2,6,6-trimethylpyran-3,5-dione (0.141 g, 0.705 mmol) and N,N-dimethylaminopyridine (0.43 g, 3.52 mmol) in a mixed solvent system of anhydrous chloroform (7.5 ml) and anhydrous toluene (1.75 ml), is added 4'-chloro-4-ethylbiphenyl-3-yllead triacetate (0.465 g, 0.775 mmol) in one portion and the mixture heated at 80° C. for 2 hours. The mixture is allowed to cool to room temperature, diluted with dichloromethane and dilute aqueous hydrochloric acid, and stirred for 5 minutes then filtered through diatomaceous earth to remove inorganic residues (additional washing with solvents). The organic fractions are combined, dried over anhydrous magnesium sulfate, filtered and the filtrate is concentrated in vacuo. The residue is purified by column chromatography on silica gel (hexane/ethyl acetate 4:1 ratio). Fractions containing the desired product are combined and evaporated in vacuo. Trituration with hexanes affords 4-(4'-chloro-4-ethylbiphenyl-3-yl)-2-methoxymethyl-2,6,6-trimethylpyran-3,5-dione (0.070 g) as a white solid.

Additional compounds in Table A were prepared by analogous procedures, from appropriate starting materials. It should be noted that certain compounds of the invention exist as a mixture of atropisomers, or other isomers noted above, under the conditions used to obtain the $^1$H nmr data. Where this has occurred, the characterising data are reported for individual isomers, isomer A and isomer B, which together represent the mixture of atropisomers, or other isomers, present at ambient temperature in the specified solvent.

TABLE A

| Compound Number | Structure | $^1$H nmr (CDCl$_3$ unless stated) or other physical data |
|---|---|---|
| A-1 | 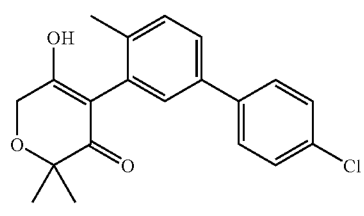 [SMILES: Cc1ccc(-c2ccc(Cl)cc2)cc1C1=C(O)COC(C)(C)C1=O] | δ 7.50-7.44 (m, 3H, isomers A and B), 7.40-7.32 (m, 3H, isomers A and B), 7.25 (m, 1H, isomers A and B), 5.86 (br. s, 0.58H, isomer A), 5.78 (br. s, 0.42H, isomer B), 4.56 (br. s, 1.16H, isomer A), 4.33 (br. s, 0.84, isomer B) 2.14 (s, 3H, isomers A and B), 1.57 (br. s, 3H, isomers A and B), 1.45 (br. s, 3H, isomers A and B). |
| A-2 | 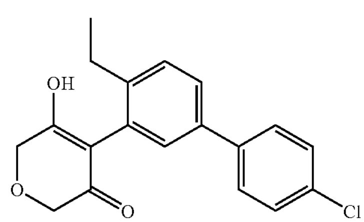 [SMILES: CCc1ccc(-c2ccc(Cl)cc2)cc1C1=C(O)COCC1=O] | δ 7.50 (dd, 1H), 7.45 (m, 2H), 7.37 (d, 1H), 7.37 (m, 2H), 7.21 (d, 1H), 4.33 (br. q, 4H), 2.48 (q, 2H), 1.12 (t, 3H). |

TABLE A-continued

| Compound Number | Structure | ¹H nmr (CDCl₃ unless stated) or other physical data |
|---|---|---|
| A-3 | 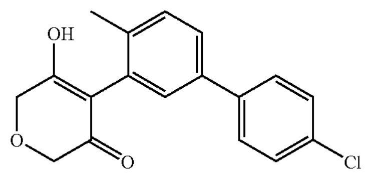 [SMILES: Cc1ccc(-c2ccc(Cl)cc2)cc1C1=C(O)COCC1=O] | δ 7.52 (dd, 1H), 7.50 (m, 2H), 7.40 (m, 2H), 7.39 (d, 1H), 7.30 (d, 1H), 4.39 (m, 4H), 2.20 (s, 3H). |
| A-4 | 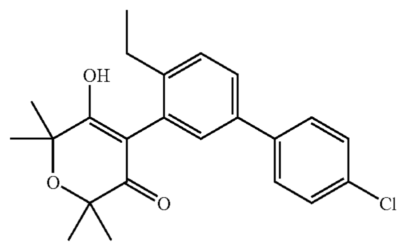 [SMILES: CCc1ccc(-c2ccc(Cl)cc2)cc1C1=C(O)C(C)(C)OC(C)(C)C1=O] | δ 7.55 (dd, 1H), 7.52-7.50 (m, 2H), 7.42 (d, 1H), 7.40-7.38 (m, 2H), 7.24 (d, 1H), 5.61 (br. s, 1H), 2.53-2.42 (m, 2H), 1.62 (br. s, 6H), 1.51 (app. d, 6H), 1.15 (t, 3H). |
| A-5 | 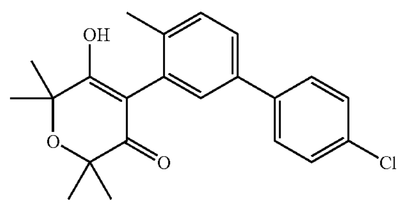 | δ 7.51-7.49 (m, 3H), 7.40-7.38 (m, 3H), 7.27 (d, 1H), 5.63 (s, 1H), 2.18 (s, 3H), 1.62 (br. S, 6H), 1.51 (app. d, 6H). |
| A-6 | 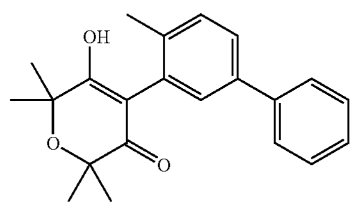 [SMILES: Cc1ccc(-c2ccccc2)cc1C1=C(O)C(C)(C)OC(C)(C)C1=O] | δ 7.58 (m, 2H), 7.55 (dd, 1H), 7.42 (m, 2H), 7.41 (d, 1H), 7.34 (t, 1H), 7.31 (d, 1H), 5.70 (br. s, 1H), 2.19 (s, 3H), 1.60 (d, 6H), 1.51 (d, 6H). |
| A-7 | 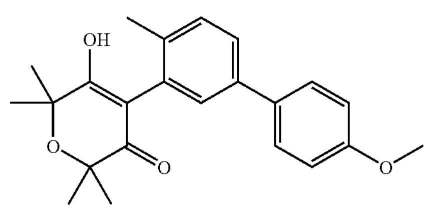 | δ 7.50 (dd, 1H), 7.50 (m, 2H), 7.36 (d, 1H), 7.27 (d, 1H), 6.97 (m, 2H), 5.71 (br. s, 1H), 3.83 (s, 3H), 2.17 (s, 3H), 1.58 (d, 6H), 1.50 (d, 6H). |
| A-8 | 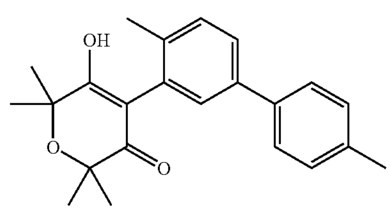 | δ 7.59 (dd, 1H), 7.51 (m, 2H), 7.40 (d, 1H), 7.32 (d, 1H), 7.30 (m, 2H), 5.81 (br. s, 1H), 2.45 (s, 3H), 2.21 (s, 3H), 1.68 (d, 6H), 1.57 (d, 6H). |
| A-9 | 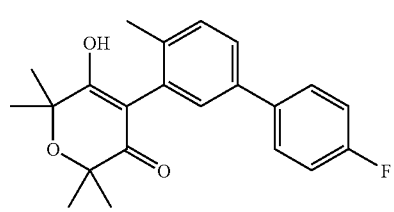 | δ 7.50 (dd, 1H), 7.50 (m, 2H), 7.39 (d, 1H), 7.25 (d, 1H), 7.10 (m, 2H), 6.05 (br. s, 1H), 2.17 (s, 3H), 1.60 (br. s, 6H), 1.51 (br. d, 6H). |

TABLE A-continued

| Compound Number | Structure | ¹H nmr (CDCl₃ unless stated) or other physical data |
|---|---|---|
| A-10 | 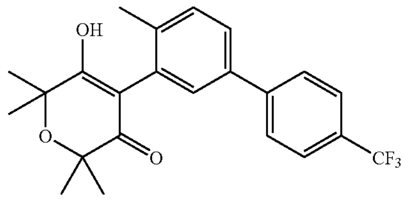 [SMILES: Cc1ccc(-c2ccc(C(F)(F)F)cc2)cc1C1=C(O)C(C)(C)OC(C)(C)C1=O] | δ 7.69 (s, 4H), 7.55 (dd, 1H), 7.41 (d, 1H), 7.31 (d, 1H), 5.60 (s, 1H), 2.20 (s, 3H), 1.62 (s, 6H), 1.50 (d, 6H). |
| A-11 | 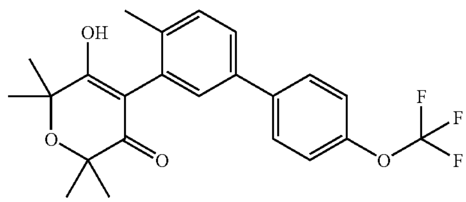 [SMILES: Cc1ccc(-c2ccc(OC(F)(F)F)cc2)cc1C1=C(O)C(C)(C)OC(C)(C)C1=O] | δ 7.59 (m, 2H), 7.51 (dd, 1H), 7.40 (d, 1H), 7.27 (m, 2H), 7.27 (d, 1H), 5.60 (s, 1H), 2.20 (s, 3H), 1.62 (s, 6H), 1.50 (d, 6H). |
| A-12 | 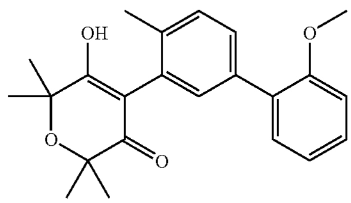 | δ 7.49 (dd, 1H), 7.30-7.37 (m, 3H), 7.22 (d, 1H), 7.01 (t, 1H), 6.99 (d, 1H), 6.00 (br. s, 1H), 3.80 (s, 3H), 2.19 (s, 3H), 1.60 (s, 6H), 1.49 (s, 6H). |
| A-13 | 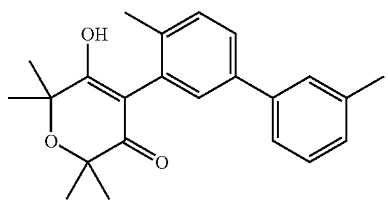 | δ 7.52 (dd, 1H), 7.37 (m, 3H), 7.32 (d, 1H), 7.29 (d, 1H), 7.15 (d, 1H), 5.90 (br. s, 1H), 2.41 (s, 3H), 2.19 (s, 3H), 1.61 (br. s, 6H), 1.50 (br. s, 6H). |
| A-14 | 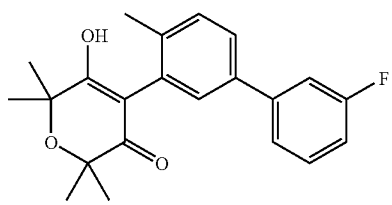 [SMILES: Cc1ccc(-c2cccc(F)c2)cc1C1=C(O)C(C)(C)OC(C)(C)C1=O] | δ 7.41-7.32 (m, 3H), 7.30-7.23 (m, 2H), 7.29 (d, 1H), 7.03 (m, 1H), 5.76 (br. s, 1H), 2.19 (s, 3H), 1.61 (br. s, 6H), 1.50 (br. s, 6H). |
| A-15 | 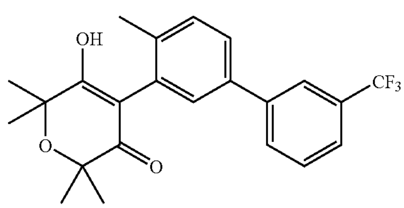 [SMILES: Cc1ccc(-c2cccc(C(F)(F)F)c2)cc1C1=C(O)C(C)(C)OC(C)(C)C1=O] | δ 7.80 (s, 1H), 7.75 (d, 1H), 7.60 (d, 1H), 7.56 (t, 1H), 7.56 (dd, 1H), 7.41 (d, 1H), 7.30 (d, 1H), 5.69 (br. s, 1H), 2.20 (s, 3H), 1.61 (d, 6H), 1.51 (s, 6H). |
| A-16 | 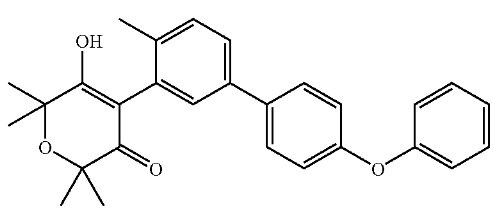 [SMILES: Cc1ccc(-c2ccc(Oc3ccccc3)cc2)cc1C1=C(O)C(C)(C)OC(C)(C)C1=O] | δ 7.53 (m, 2H), 7.51 (dd, 1H), 7.37 (d, 1H), 7.34 (m, 2H), 7.27 (d, 1H), 7.12 (t, 1H), 7.05 (m, 4H), 5.77 (br. s, 1H), 2.18 (s, 3H), 1.61 (br. s, 6H), 1.51 (br. d, 6H). |

TABLE A-continued

| Compound Number | Structure | ¹H nmr (CDCl₃ unless stated) or other physical data |
|---|---|---|
| A-17 | 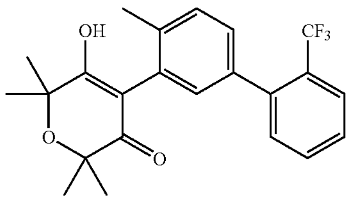 | δ 7.73 (d, 1H), 7.57 (t, 1H), 7.47 (t, 1H), 7.39 (d, 1H), 7.37 (d, 1H), 7.30 (dd, 1H), 7.09 (s, 1H), 5.87 (br. s, 1H), 2.20 (s, 3H), 1.60 (d, 6H), 1.51 (s, 3H), 1.49 (s, 3H). |
| A-18 | 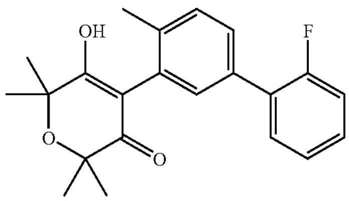 [SMILES: Cc1ccc(-c2ccccc2F)cc1C1=C(O)C(C)(C)OC(C)(C)C1=O] | δ 7.50 (dt, 1H), 7.44 (dt, 1H), 7.39 (d, 1H), 7.31 (m, 1H), 7.26 (d, 1H), 7.20 (dt, 1H), 7.15 (m, 1H), 6.01 (br. s, 1H), 2.20 (s, 3H), 1.62 (s, 6H), 1.50 (d, 6H). |
| A-19 | 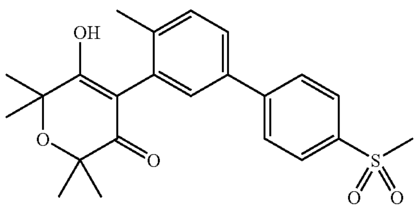 | δ 7.95 (m, 2H), 7.72 (m, 2H), 7.54 (dd, 1H), 7.41 (d, 1H), 7.31 (d, 1H), 5.85 (br. s, 1H), 3.09 (s, 3H), 2.20 (s, 3H), 1.58 (br. s, 12H). |
| A-20 | 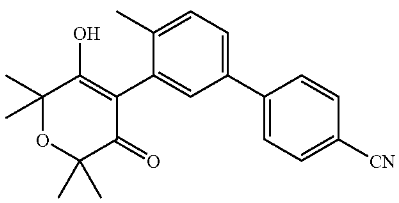 [SMILES: Cc1ccc(-c2ccc(C#N)cc2)cc1C1=C(O)C(C)(C)OC(C)(C)C1=O] | δ 7.69 (m, 4H), 7.54 (dd, 1H), 7.42 (d, 1H), 7.30 (d, 1H), 5.60 (br. s, 1H), 2.20 (s, 3H), 1.61 (s, 6H), 1.50 (d, 6H). |
| A-21 | 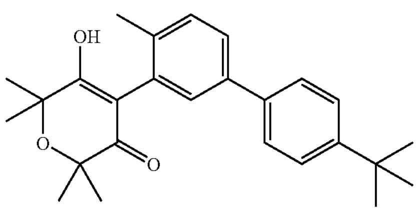 [SMILES: Cc1ccc(-c2ccc(C(C)(C)C)cc2)cc1C1=C(O)C(C)(C)OC(C)(C)C1=O] | δ 7.55 (dd, 1H), 7.51 (m, 2H), 7.45 (m, 2H), 7.39 (d, 1H), 7.30 (d, 1H), 5.69 (s, 1H), 2.18 (s, 3H), 1.61 (s, 6H), 1.50 (d, 6H), 1.35 (s, 9H). |
| A-22 | 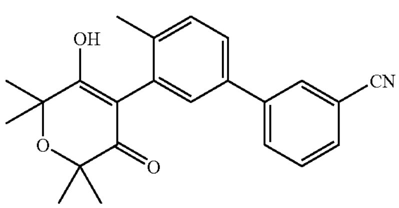 [SMILES: Cc1ccc(-c2cccc(C#N)c2)cc1C1=C(O)C(C)(C)OC(C)(C)C1=O] | δ 7.84 (d, 1H), 7.80 (dd, 1H), 7.61 (dd, 1H), 7.53 (d, 1H), 7.51 (m, 1H), 7.42 (d, 1H), 7.30 (d, 1H), 5.70 (s, 1H), 2.20 (s, 3H), 1.62 (d, 6H), 1.50 (s, 6H). |
| A-23 | 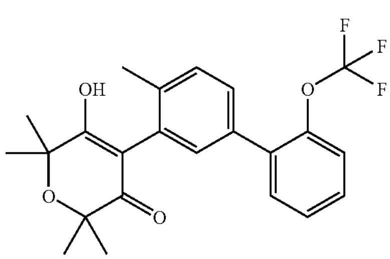 [SMILES: Cc1ccc(-c2ccccc2OC(F)(F)F)cc1C1=C(O)C(C)(C)OC(C)(C)C1=O] | δ 7.44-7.30 (m, 6H), 7.20 (d, 1H), 6.01 (br. s, 1H), 2.20 (s, 3H), 1.60 (d, 6H), 1.50 (d, 6H). |

TABLE A-continued

| Compound Number | Structure | ¹H nmr (CDCl₃ unless stated) or other physical data |
|---|---|---|
| A-24 | 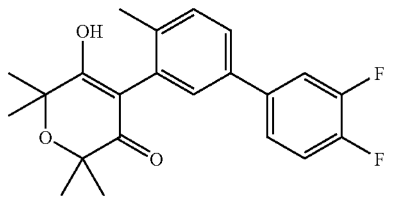 [SMILES: Cc1ccc(-c2ccc(F)c(F)c2)cc1C1=C(O)C(C)(C)OC(C)(C)C1=O] | δ 7.47 (dd, 1H), 7.39 (d, 1H), 7.36 (dd, 1H), 7.29 (m, 1H), 7.24 (d, 1H), 7.21 (m, 1H), 5.60 (s, 1H), 2.19 (s, 3H), 1.61 (s, 6H), 1.50 (d, 6H). |
| A-25 | 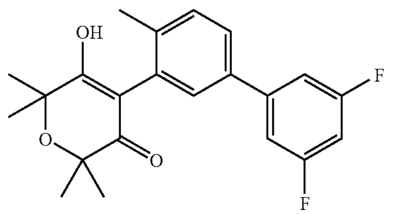 [SMILES: Cc1ccc(-c2cc(F)cc(F)c2)cc1C1=C(O)C(C)(C)OC(C)(C)C1=O] | δ 7.50 (dd, 1H), 7.40 (d, 1H), 7.26 (d, 1H), 7.09 (m, 2H), 6.78 (m, 1H), 5.64 (s, 1H), 2.18 (s, 3H), 1.62 (d, 6H), 1.50 (s, 6H). |
| A-26 | 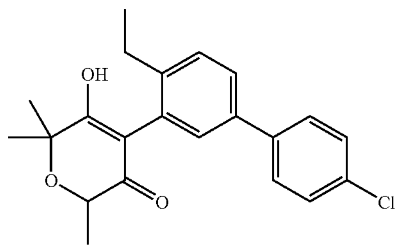 [SMILES: CCc1ccc(-c2ccc(Cl)cc2)cc1C1=C(O)C(C)(C)OC(C)C1=O] | δ 7.57-7.48 (m, 3H, isomers A and B), 7.43-7.37 (m, 3H, isomers A and B), 7.27 (ddd, 0.5H, isomer A or B), 7.22 (ddd, 0.5H, isomer A or B), 5.59 (app. d, 0.5H, isomer A or B), 5.48 (app. d, 0.5H, isomer A or B), 4.77 (m, 0.5H, isomer A or B), 4.45 (m, 0.5H, isomer A or B), 2.55-2.36 (m, 2H, isomers A and B), 1.63-1.45 (m, 9H, isomers A and B), 1.17-1.12 (m, 3H, isomers A and B). |
| A-27 | 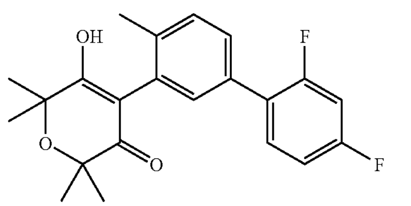 [SMILES: Cc1ccc(-c2ccc(F)cc2F)cc1C1=C(O)C(C)(C)OC(C)(C)C1=O] | δ 7.49-7.38 (m, 3H), 7.21 (s, 1H), 6.98-6.88 (m, 2H), 5.70 (s, 1H), 2.20 (s, 3H), 1.61 (s, 6H), 1.50 (d, 6H). |
| A-28 | 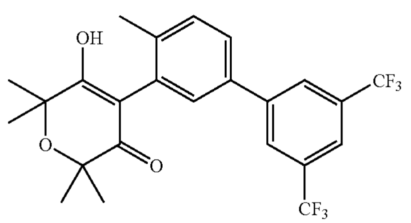 [SMILES: Cc1ccc(-c2cc(C(F)(F)F)cc(C(F)(F)F)c2)cc1C1=C(O)C(C)(C)OC(C)(C)C1=O] | δ 8.00 (s, 2H), 7.85 (s, 1H), 7.58 (dd, 1H), 7.47 (d, 1H), 7.31 (d, 1H), 5.56 (s, 1H), 2.20 (s, 3H), 1.63 (app. d, 6H), 1.55 (s, 3H), 1.50 (s, 3H). |
| A-29 | 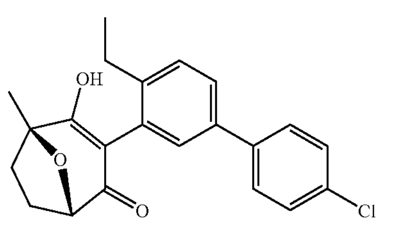 [SMILES: CCc1ccc(-c2ccc(Cl)cc2)cc1C1=C(O)[C@@]2(C)CC[C@H](O2)C1=O] | δ 7.5-7.3 (m, 6H, isomers A and B), 7.23 (d, 0.59H, isomer A), 7.06 (d, 0.41H, isomer B), 5.8 (app. br. d, 1H, isomers A and B), 4.79 (app. d, 0.59H, isomer A), 4.60 (app. d, 0.41H, isomer B), 2.6-1.8 (m, 6H, isomers A and B), 1.59 (s, 1.77H, isomer A), 1.51 (s, 1.23H, isomer B), 1.09 (t, 1.23H, isomer B), 1.04 (t, 1.77H, isomer A). |
| A-30 | 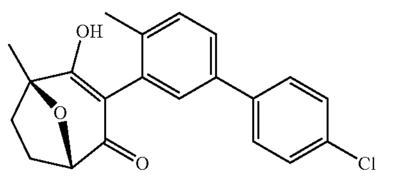 [SMILES: Cc1ccc(-c2ccc(Cl)cc2)cc1C1=C(O)[C@@]2(C)CC[C@H](O2)C1=O] | δ 7.46-7.27 (m, 6H, isomers A and B), 7.25 (d, 0.55H, isomer A), 7.1 (d, 0.45H, isomer B), 5.8 (app. br. d, 0.45H, isomer B), 5.64 (app. br. s, 0.55H, isomer A), 4.79 (app. d, 0.55H, isomer A), 4.6 (app. dd, 0.45H, isomer B), 2.5-2.3 (m, 1H, isomers A and B), 2.13 (s, 1.35H, isomer B), 2.02 (s, 1.65H, isomer A), 2.1-1.8 (m, 3H, isomers A and B), 1.61 (s, 1.35H, isomer B), 1.52 (s, 1.65H, isomer A). |

TABLE A-continued

| Compound Number | Structure | $^1$H nmr (CDCl$_3$ unless stated) or other physical data |
|---|---|---|
| A-31 | 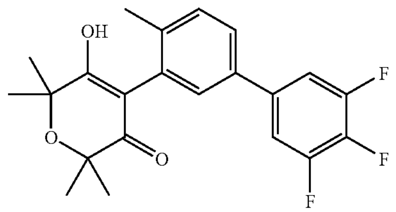 [SMILES: Cc1ccc(-c2cc(F)c(F)c(F)c2)cc1C1=C(O)C(C)(C)OC(C)(C)C1=O] | δ 7.47 (dd, 1H), 7.40 (d, 1H), 7.21 (d, 1H), 7.19 (dd, 2H), 5.55 (s, 1H), 2.19 (s, 3H), 1.62 (d, 6H), 1.50 (s, 6H). |
| A-32 | 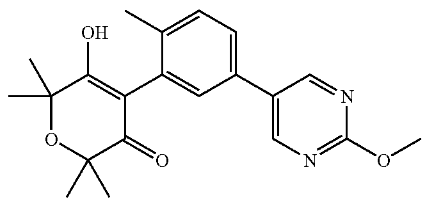 | δ 8.60 (s, 2H), 7.28 (br. s, 1H), 7.28 (br. s, 1H), 7.24 (br. s, 1H), 4.04 (s, 3H), 2.20 (s, 3H), 1.63 (d, 6H), 1.50 (s, 6H). |
| A-33 | 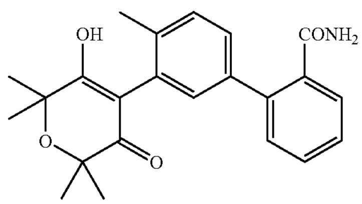 [SMILES: Cc1ccc(-c2ccccc2C(N)=O)cc1C1=C(O)C(C)(C)OC(C)(C)C1=O] | δ 7.65 (d, 1H), 7.52 (dt, 1H), 7.45-7.38 (m, 2H), 7.36-7.30 (m, 2H), 7.17 (d, 1H), 5.88-5.82 (m, 1H), 2.18 (s, 3H), 1.55 (br. s, 12H). |
| A-34 | 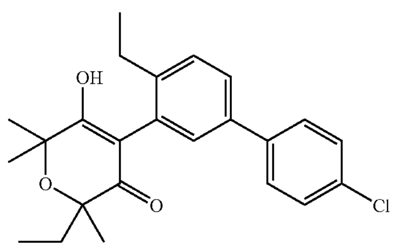 [SMILES: CCc1ccc(-c2ccc(Cl)cc2)cc1C1=C(O)C(C)(C)OC(C)(CC)C1=O] | δ 7.57-7.38 (m, 5H, isomers A and B), 7.23-7.19 (m, 2H, isomers A and B), 5.60-5.48 (m, 1H, isomers A and B), 2.57-2.39 (m, 2H, isomers A and B), 2.05-1.91 (m, 1H, isomer A or B), 1.80-1.68 (m, 1H, isomer A or B), 1.65-1.46 (m, 9H, isomers A and B), 1.18-1.13 (m, 3H, isomers A and B), 1.01-0.93 (m, 3H, isomers A and B). |
| A-35 | 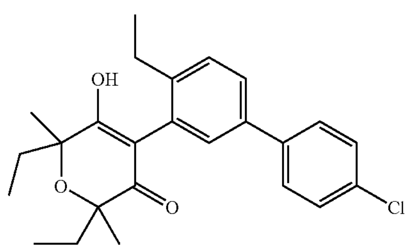 [SMILES: CCc1ccc(-c2ccc(Cl)cc2)cc1C1=C(O)C(C)(CC)OC(C)(CC)C1=O] | δ 7.57-7.38 (m, 5H), 7.23-7.18 (m, 2H), 5.57-5.46 (m, 1H), 2.57-2.42 (m, 2H), 2.07-1.61 (m, 4H), 1.64-1.41 (m, 6H), 1.19-1.13 (m, 3H), 1.04-0.94 (m, 6H). |
| A-36 | 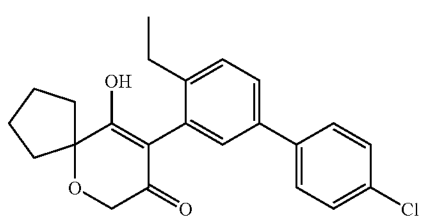 [SMILES: CCc1ccc(-c2ccc(Cl)cc2)cc1C1=C(O)C2(CCCC2)OCC1=O] | δ 7.57 (dd, 1H), 7.50 (d, 2H), 7.43 (d, 1H), 7.39 (d, 2H), 7.27 (m, 1H), 5.66 (br. s, 1H), 4.53-4.31 (m, 2H), 2.49 (m, 2H), 2.19-1.74 (m, 8H), 1.15 (t, 3H). |
| A-37 | 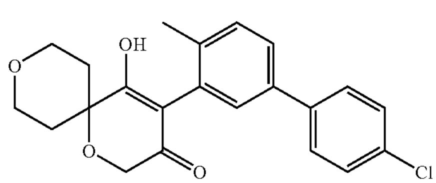 [SMILES: Cc1ccc(-c2ccc(Cl)cc2)cc1C1=C(O)C2(CCOCC2)OCC1=O] | δ 7.53-7.45 (m, 3H, isomers A and B), 7.40-7.34 (m, 3H, isomers A and B), 7.26 (m, 1H, isomers A and B), 6.04 (br. s, 0.61H, isomer A), 5.94 (br. s, 0.39H, isomer B), 4.54 (s, 1.22H, isomer A), 4.32 (s, 0.78H, isomer B), 3.90-3.81 (m, 2H, isomers A and B), 3.80-3.71 (m, 2H, isomers A and B), 2.30-2.03 (m, 2H, isomers A and B), 2.16 (s, 1.17H, isomer B), 2.14 (s, 1.83H, isomer A), 1.95-1.72 (m, 2H, isomers A and B). |

TABLE A-continued

| Compound Number | Structure | $^1$H nmr (CDCl$_3$ unless stated) or other physical data |
|---|---|---|
| A-38 | 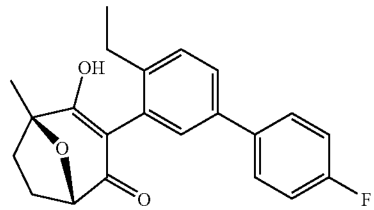 [SMILES: CCc1ccc(-c2ccc(F)cc2)cc1C1=C(O)[C@@]2(C)CC[C@H](O2)C1=O] | m.p. 165-167° C.; LC-MS (ES+) 353 (M + H)$^+$ |
| A-39 | 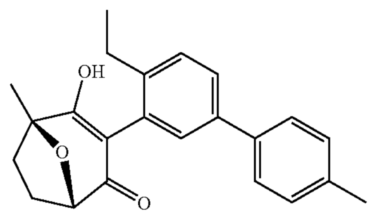 | δ 7.14-7.56 (m, 7H, isomers A and B), 6.1 (br. s, 1H, isomers A and B), 4.7 (d, 1H, isomer A), 4.6 (d, 1H, isomer II), 2.1-2.6 (m, 6H, isomers A and B), 2.0 (s, 3H, isomers A and B), 1.66 (s, 3H, isomers A and B), 1.16 (t, 3H, isomer A) 1.11 (s, 3H, isomer B). |
| A-40 | 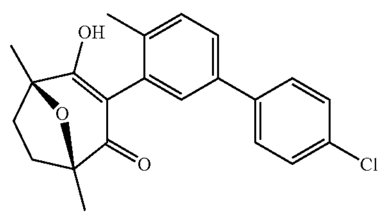 [SMILES: Cc1ccc(-c2ccc(Cl)cc2)cc1C1=C(O)[C@@]2(C)CC[C@](C)(O2)C1=O] | δ 7.16-7.48 (m, 7H), 5.65 (br. s, 1H), 2.0-2.2 (m, 7H), 1.64 (s, 3H), 1.55 (s, 3H). |
| A-41 | 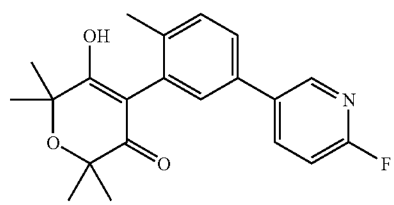 [SMILES: Cc1ccc(-c2ccc(F)nc2)cc1C1=C(O)C(C)(C)OC(C)(C)C1=O] | δ 8.10 (d, 1H), 7.94 (dt, 1H), 7.24-7.32 (m, 3H), 6.94 (dd, 1H), 2.19 (s, 3H), 1.65 (app. d, 6H), 1.51 (app. d, 6H). |
| A-42 | 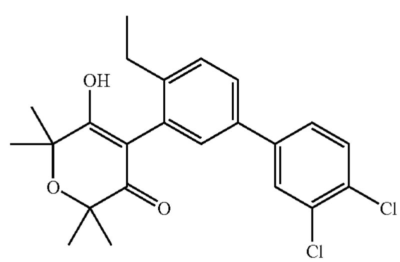 [SMILES: CCc1ccc(-c2ccc(Cl)c(Cl)c2)cc1C1=C(O)C(C)(C)OC(C)(C)C1=O] | δ 7.66 (dd, 1H), 7.55 (d, 1H), 7.48 (d, 1H), 7.43 (d, 1H), 7.40 (d, 1H), 7.24 (d, 1H), 5.52 (br. s, 1H), 2.49 (m, 2H), 1.63 (app d, 6H), 1.52 (s, 6H), 1.15, (t, 3H). |
| A-43 | 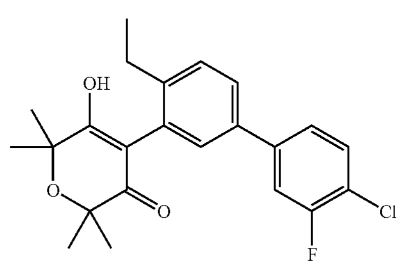 [SMILES: CCc1ccc(-c2ccc(Cl)c(F)c2)cc1C1=C(O)C(C)(C)OC(C)(C)C1=O] | δ 7.56 (dd, 1H), 7.44 (d, 1H), 7.42 (d, 1H), 7.36 (d, 1H), 7.31 (d, 1H), 7.24 (d, 1H), 5.52 (br. s, 1H), 2.48 (m, 2H), 1.62 (s, 6H), 1.51 (s, 6H), 1.15 (t, 3H). |

TABLE A-continued

| Compound Number | Structure | ¹H nmr (CDCl₃ unless stated) or other physical data |
|---|---|---|
| A-44 | 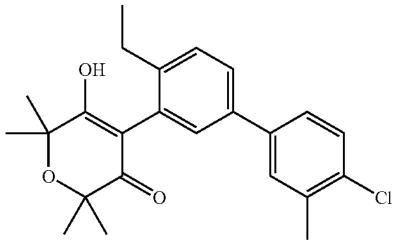 [SMILES: CCc1ccc(-c2ccc(Cl)c(C)c2)cc1C1=C(O)C(C)(C)OC(C)(C)C1=O] | δ 7.55 (dd, 1H), 7.42 (d, 1H), 7.40 (d, 1H), 7.36 (d, 1H), 7.32 (d, 1H), 7.23 (d, 1H), 5.58 (br. s, 1H), 2.48 (m, 2H), 2.44 (s, 3H), 1.63 (s, 6H), 1.52 (s, 6H), 1.16 (t, 3H). |
| A-45 | 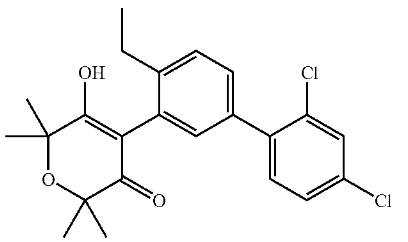 | δ 7.48 (d, 1H), 7.43 (m, 2H), 7.30 (m, 2H), 7.13 (d, 1H), 5.71 (br. s, 1H), 2.55-2.44 (m, 2H), 1.62 (s, 6H), 1.49 (app. d, 6H), 1.17 (t, 3H). |
| A-46 | 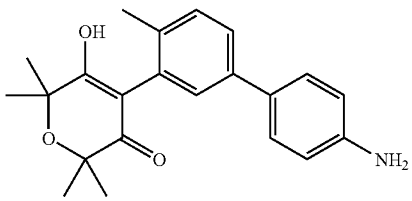 [SMILES: Cc1ccc(-c2ccc(N)cc2)cc1C1=C(O)C(C)(C)OC(C)(C)C1=O] | δ 7.12 (br. s, 4H), 6.91 (br. m, 3H), 6.52 (br. S, 1H), 2.04 (s, 3H), 1.49 (br. d, 12H). |
| A-47 | 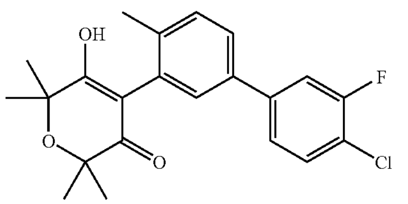 | δ 7.49 (dd, 1H), 7.43 (d, 1H), 7.39 (d, 1H), 7.35 (d, 1H), 7.30 (d, 1H), 7.23 (d, 1H), 5.65 (br. s, 1H), 2.18 (s, 3H), 1.63 (s, 6H), 1.51 (s, 6H). |
| A-48 | 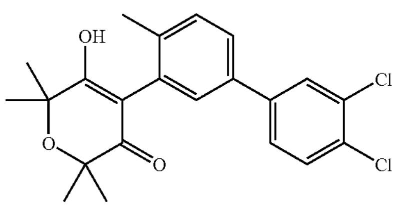 | δ 7.67 (dd, 1H), 7.50 (m, 2H), 7.40 (m, 2H), 7.24 (d, 1H), 5.54 (br. s, 1H), 2.19 (s, 3H), 1.63 (app. d, 6H), 1.52 (app. d, 6H). |
| A-49 | 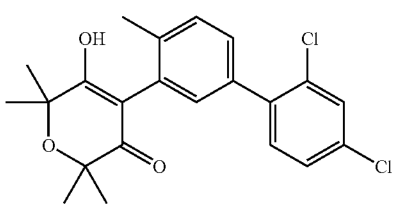 | δ 7.48 (dd, 1H), 7.43 (m, 2H), 7.30 (m, 2H), 7.15 (d, 1H), 5.78 (br. s, 1H), 2.20 (s, 3H), 1.60 (app. d, 6H), 1.50 (app. d, 6H). |
| A-50 | 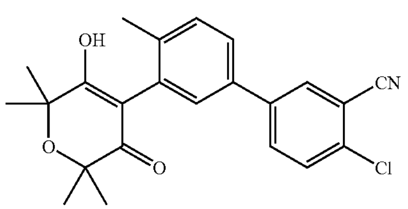 [SMILES: Cc1ccc(-c2ccc(Cl)c(C#N)c2)cc1C1=C(O)C(C)(C)OC(C)(C)C1=O] | δ 7.87 (d, 1H), 7.73 (dd, 1H), 7.57 (d, 1H), 7.50 (d, 1H), 7.45 (d, 1H), 7.24 (d, 1H), 5.52 (br. s, 1H), 2.20 (s, 3H), 1.63 (app. d, 6H), 1.51 (s, 6H). |

TABLE A-continued

| Compound Number | Structure | $^1$H nmr (CDCl$_3$ unless stated) or other physical data |
|---|---|---|
| A-51 | 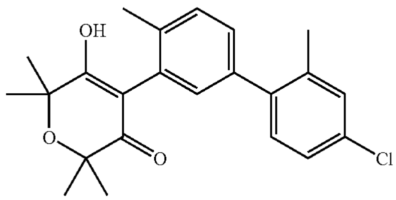 | δ 7.36 (dd, 1H), 7.25 (d, 1H), 7.22 (d, 1H), 7.19 (d, 1H), 7.17 (d, 1H), 7.03 (d, 1H), 5.64 (br. s, 1H), 2.27 (s, 3H), 2.18 (s, 3H), 1.62 (app. d, 6H), 1.50 app. d, 6H). |
| A-52 | 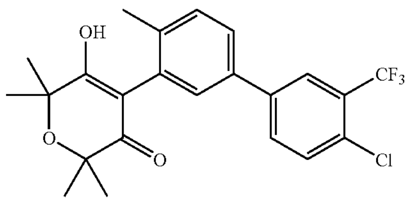 [SMILES: Cc1ccc(-c2ccc(Cl)c(C(F)(F)F)c2)cc1C1=C(O)C(C)(C)OC(C)(C)C1=O] | δ 7.86, (d, 1H), 7.67 (dd, 1H), 7.54 (d, 1H), 7.51 (dd, 1H), 7.42 (d, 1H), 7.27 (d, 1H), 5.64 (br. s, 1H), 2.19 (s, 3H), 1.63 (s, 6H), 1.52 (s, 6H). |
| A-53 | 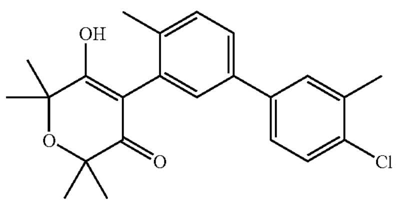 | δ 7.54-7.30 (m, 6H), 5.90 (br. s, 1H), 2.52 (s, 3H), 2.24 (s, 3H), 1.68 (s, 6H), 1.57 (s, 6H). |
| A-54 | 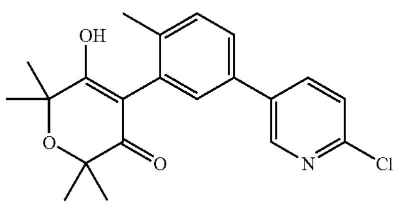 [SMILES: Cc1ccc(-c2ccc(Cl)nc2)cc1C1=C(O)C(C)(C)OC(C)(C)C1=O] | δ 8.52 (s, 1H), 7.84 (dd, 1H), 7.47 (d, 1H), 7.40 (d, 1H), 7.36 (d, 1H), 7.24 (s, 1H), 5.90 (br. s, 1H), 2.20 (s, 3H), 1.63 (s, 6H), 1.51 (s, 1H). |
| A-55 | 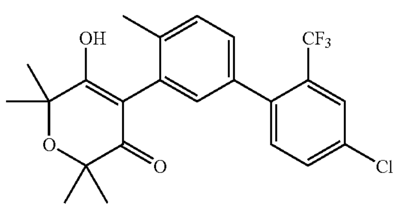 | δ 7.72 (d, 1H), 7.53 (d, 1H), 7.37 (d, 1H), 7.33 (d, 1H), 7.26 (d, 1H), 7.04 (d, 1H), 5.71 (br. s, 1H), 2.20 (s, 3H), 1.61 (app. d, 6H), 1.50 (app. d, 6H). |
| A-56 | 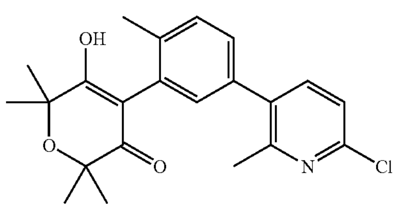 [SMILES: Cc1ccc(-c2ccc(Cl)nc2C)cc1C1=C(O)C(C)(C)OC(C)(C)C1=O] | δ 7.52 (dd, 1H), 7.40 (d, 1H), 7.28 (d, 1H), 7.22 (d, 1H), 7.05 (s, 1H), 5.53 (br. s, 1H), 2.52 (s, 3H), 2.21 (s, 3H), 1.63 (app. d, 6H), 1.51 (app. d, 6H). |
| A-57 | 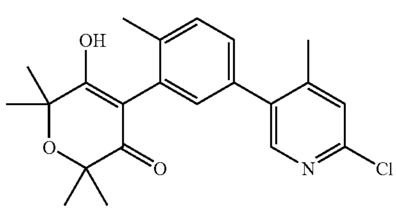 [SMILES: Cc1ccc(-c2cnc(Cl)cc2C)cc1C1=C(O)C(C)(C)OC(C)(C)C1=O] | δ 7.52 (s, 1H), 7.18 (s, 1H), 7.15 (d, 1H), 7.03, (s, 1H), 6.97 (d, 1H), 5.53 (br. s, 1H), 2.30 (s, 3H), 2.25 (s, 3H), 1.65 (d, 6H), 1.51 (d, 6H). |

TABLE A-continued

| Compound Number | Structure | ¹H nmr (CDCl₃ unless stated) or other physical data |
|---|---|---|
| A-58 | 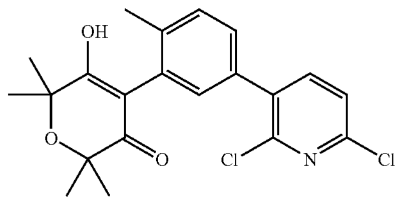 [SMILES: Cc1ccc(-c2ccc(Cl)nc2Cl)cc1C1=C(O)C(C)(C)OC(C)(C)C1=O] | δ 7.67 (dd, 1H), 7.42 (d, 1H), 7.37 (d, 1H), 7.35 (d, 1H), 7.18 (d, 1H), 5.75 (br. s, 1H), 2.22 (s, 3H), 1.62 (app. d, 6H), 1.50 (app. d, 6H). |
| A-59 | 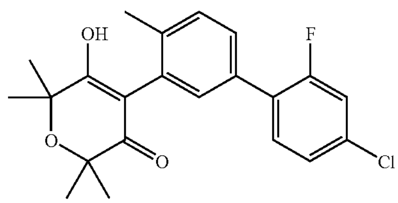 | δ 7.47 (dd, 1H), 7.46 (d, 1H), 7.39 (d, 1H), 7.22 (dd, 1H), 7.20 (d, 1H), 7.17 (d, 1H), 5.75 (br. s, 1H), 2.18 (s, 3H), 1.62 (s, 6H), 1.51 (d, 6H). |
| A-60 | 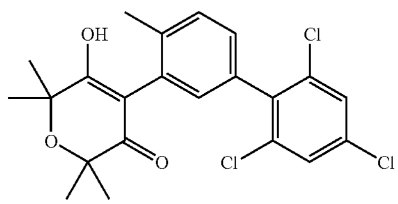 [SMILES: Cc1ccc(-c2c(Cl)cc(Cl)cc2Cl)cc1C1=C(O)C(C)(C)OC(C)(C)C1=O] | δ 7.42 (app. dd, 2H), 7.26 (m, 1H), 7.21 (dd, 1H), 6.99 (d, 1H), 5.74 (br. s, 1H), 2.23 (s, 3H), 1.59 (app. d, 6H), 1.51 (app. d, 6H). |
| A-61 | 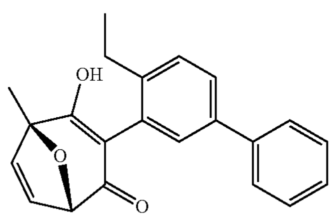 [SMILES: CCc1ccc(-c2ccccc2)cc1C1=C(O)[C@@]2(C)C=C[C@H](O2)C1=O] | δ 7.5-7.28 (m, 8H), 6.4 (dd, 1H), 6.2 (dd, 1H), 5.44 (s, 1H), 5.39 (dd, 1H), 2.5 (m, 2H), 1.73 (s, 3H), 1.17 (t, 3H). |
| A-62 | 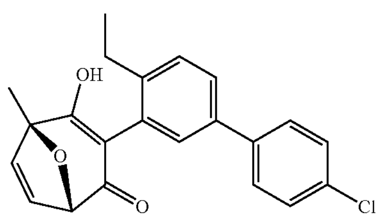 [SMILES: CCc1ccc(-c2ccc(Cl)cc2)cc1C1=C(O)[C@@]2(C)C=C[C@H](O2)C1=O] | δ 746-7.3 (m, 7H), 6.43 (dd, 1H), 6.25 (d, 1H), 5.45 (s, 1H), 5.39 (d, 1H), 2.47 (m, 2H), 1.73 (s, 3H), 1.14 (t, 3H). |
| A-63 | 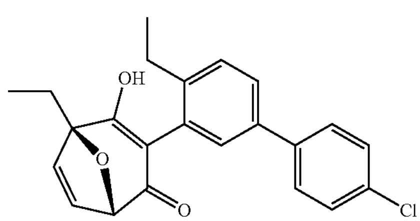 [SMILES: CCc1ccc(-c2ccc(Cl)cc2)cc1C1=C(O)[C@@]2(CC)C=C[C@H](O2)C1=O] | δ 7.46-7.3 (m, 7H), 6.4 (dd, 1H), 6.2 (d, 1H), 5.43 (s, 1H), 5.4 (m, 1H), 2.45 (m, 2H), 2.1 (q, 2H), 1.15 (t, 3H), 1.05 (t, 3H). |
| A-64 | 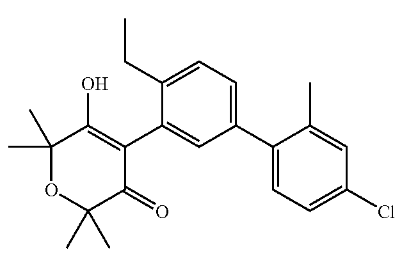 | δ 7.40 (d, 1H), 7.30 (dd, 1H), 7.26 (m, 1H), 7.20 (dd, 1H), 7.16 (d, 1H), 6.99 (d, 1H), 5.69 (br. s, 1H), 2.55-2.43 (m, 2H), 2.27 (s, 3H), 1.60 (app. d, 6H), 1.49 (app. d, 6H), 1.17 (t, 3H). |

TABLE A-continued

| Compound Number | Structure | $^1$H nmr (CDCl$_3$ unless stated) or other physical data |
|---|---|---|
| A-65 | 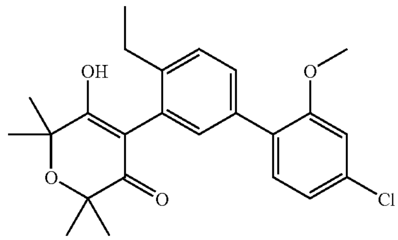 [SMILES: CCc1ccc(-c2ccc(Cl)cc2OC)cc1C1=C(O)C(C)(C)OC(C)(C)C1=O] | δ 7.49 (dd, 1H), 7.39 (d, 1H), 7.24 (d, 1H), 7.15 (s, 1H), 7.02 (dd, 1H), 6.95 (s, 1H), 3.82 (s, 3H), 2.45 (br., 2H), 1.56 (br., 12H), 1.15 (t, 3H). |
| A-66 | 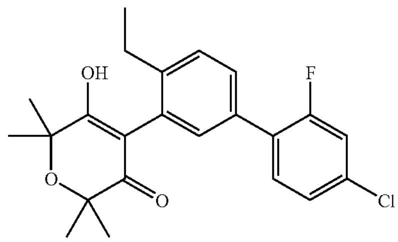 | δ 7.52 (dd, 1H), 7.44-7.36 (m, 2H), 7.21-7.16 (m, 3H), 5.77 (br. s, 1H), 2.54-2.43 (m, 2H), 1.61 (s, 6H), 1.49 (app. d, 6H), 1.15 (t, 3H). |
| A-67 | 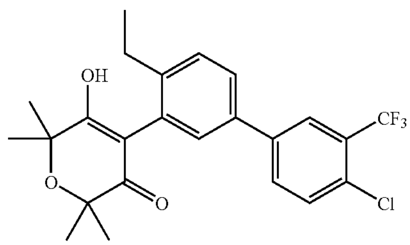 [SMILES: CCc1ccc(-c2ccc(Cl)c(C(F)(F)F)c2)cc1C1=C(O)C(C)(C)OC(C)(C)C1=O] | δ 7.86 (d, 1H), 7.67 (dd, 1H), 7.57 (m, 2H), 7.46 (d, 1H), 7.25 (m, 1H), 5.60 (br. s, 1H), 2.55-2.43 (m, 2H), 1.62 (s, 6H), 1.51 (s, 6H), 1.16 (t, 3H). |
| A-68 | 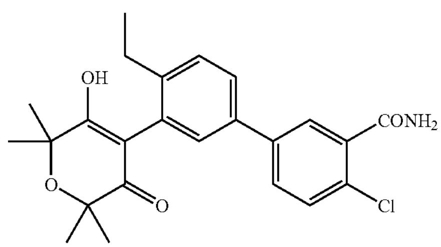 [SMILES: CCc1ccc(-c2ccc(Cl)c(C(N)=O)c2)cc1C1=C(O)C(C)(C)OC(C)(C)C1=O] | δ 8.02 (s, 1H), 7.62 (dd, 1H), 7.57 (dd, 1H), 7.48 (d, 1H), 7.43 (d, 1H), 7.27 (s, 1H), 6.61 (br. s, 2H), 2.48 (m, 2H), 1.56 (br., 12H), 1.15 (t, 3H). |
| A-69 | 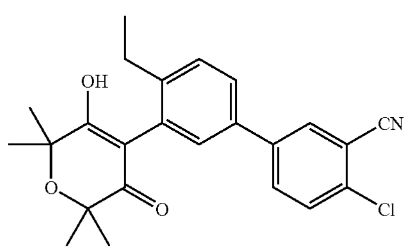 [SMILES: CCc1ccc(-c2ccc(Cl)c(C#N)c2)cc1C1=C(O)C(C)(C)OC(C)(C)C1=O] | δ 7.84 (s, 1H), 7.73 (dd, 1H), 7.54 (m, 2H), 7.46 (d, 1H), 7.23 (s, 1H), 5.68 (br. s, 1H), 2.49 (m, 2H), 1.62 (s, 6H), 1.52 (s, 6H), 1.16 (t, 3H). |
| A-70 | 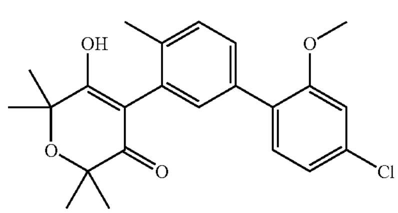 | δ 7.46 (dd, 1H), 7.36 (d, 1H), 7.24 (d, 1H), 7.18 (d, 1H), 7.01 (dd, 1H), 6.94 (d, 1H), 3.80 (s, 3H), 2.18 (s, 3H), 1.62 (s, 6H), 1.51 (app. d, 6H). |

TABLE A-continued

| Compound Number | Structure | $^1$H nmr (CDCl$_3$ unless stated) or other physical data |
|---|---|---|
| A-71 | 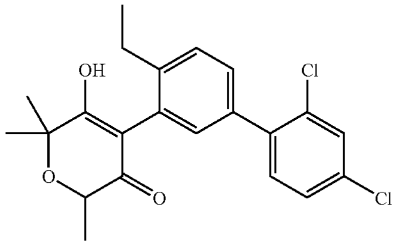 [SMILES: CCc1ccc(-c2ccc(Cl)cc2Cl)cc1C1=C(O)C(C)(C)OC(C)C1=O] | δ 7.48 (app. d, 1H), 7.44-7.40 (m, 2H, isomers A and B), 7.29 (m, 2H, isomers A and B), 7.15-7.10 (m, 1H, isomers A and B), 5.80 (app. d, 0.5H, isomer A or B), 5.66 (app. d, 0.5H, isomer A or B), 5.76 (m, 0.5H, isomer A or B), 4.44 (m, 0.5H, isomer A or B), 2.58-2.36 (m, 2H, isomers A and B), 1.62-1.44 (m, 9H, isomers A and B), 1.19-1.14 (m, 3H, isomers A and B). |
| A-72 | 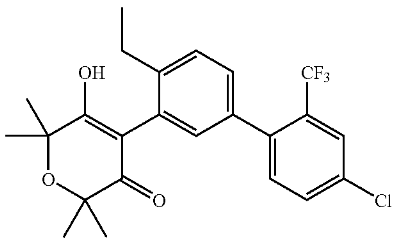 | δ 7.76 (s, 1H), 7.57 (dd, 1H), 7.44 (d, 1H), 7.35 (m, 2H), 7.05 (s, 1H), 5.82 (br. s, 1H), 2.54 (m, 2H), 1.66 (br., 12H), 1.22 (t, 3H). |
| A-73 | 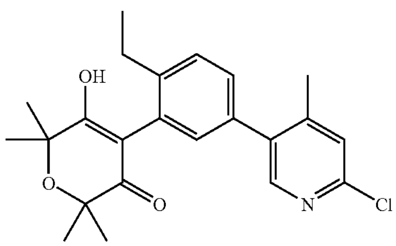 | δ 7.82 (s, 1H), 7.58 (br., 1H), 7.33 (d, 1H), 7.24 (s, 1H), 7.17 (dd, 1H), 7.04 (s, 1H), 2.59 (m, 2H), 2.34 (s, 3H), 1.63 (br., 6H), 1.53 (br., 6H), 1.21 (t, 3H). |
| A-74 | 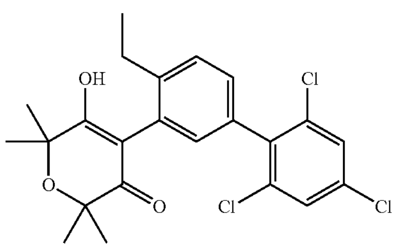 | δ 7.52-7.45 (m, 3H), 7.30 (dd, 1H), 7.02 (s, 1H), 5.86 (br. s, 1H), 2.57 (m, 2H), 1.62 (d, 6H), 1.53 (d, 6H), 1.23 (t, 3H). |
| A-75 | 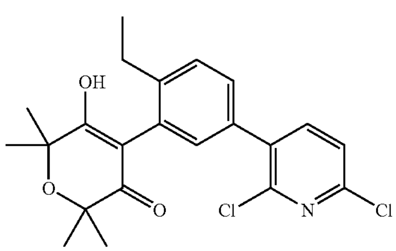 [SMILES: CCc1ccc(-c2ccc(Cl)nc2Cl)cc1C1=C(O)C(C)(C)OC(C)(C)C1=O] | δ 7.68 (d, 1H), 7.43 (s, 2H), 7.33 (d, 1H), 7.14 (s, 1H), 5.81 (br. s, 1H), 2.51 (m, 2H), 1.58 (br., 6H), 1.48 (br., 6H), 1.17 (t, 3H). |
| A-76 | 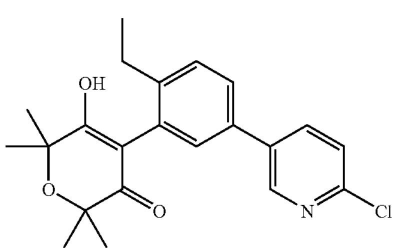 | δ 8.52 (s, 1H), 7.84 (dd, 1H), 7.46 (dd, 1H), 7.38 (d, 1H), 7.35 (d, 1H), 7.23 (s, 1H), 2.48 (t, 2H), 1.58 (br., 6H), 1.47 (br., 6H), 1.14 (t, 3H). |

TABLE A-continued

| Compound Number | Structure | $^1$H nmr (CDCl$_3$ unless stated) or other physical data |
|---|---|---|
| A-77 | 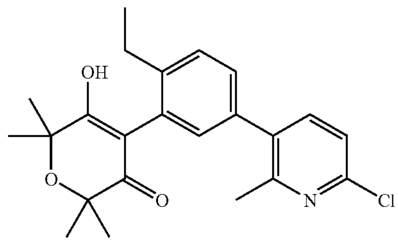 [SMILES: CCc1ccc(-c2ccc(Cl)nc2C)cc1C1=C(O)C(C)(C)OC(C)(C)C1=O] | δ 7.51 (d, 1H), 7.42 (d, 1H), 7.32 (dd, 1H), 7.20 (d, 1H), 7.01 (s, 1H), 5.61 (br. s, 1H), 2.52 (s, 3H), 2.50 (m, 2H), 1.61 (d, 6H), 1.48 (d, 6H), 1.17 (t, 3H). |
| A-78 | 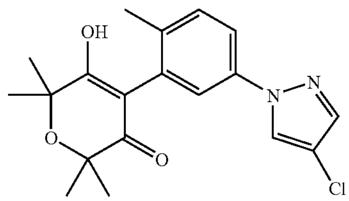 [SMILES: Cc1ccc(-n2cc(Cl)cn2)cc1C1=C(O)C(C)(C)OC(C)(C)C1=O] | δ 7.81 (s, 1H), 7.54 (s, 1H), 7.44 (dd, 1H), 7.32-7.30 (m, 2H), 2.10 (s, 3H), 1.54 (s, 6H), 1.42 (s, 6H). |
| A-79 | 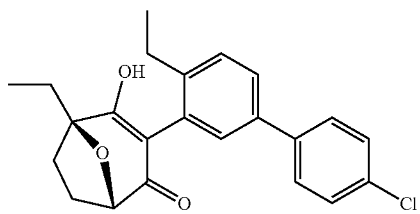 [SMILES: CCc1ccc(-c2ccc(Cl)cc2)cc1C1=C(O)[C@@]2(CC)CC[C@H](O2)C1=O] | δ 7.6-7.1 (m, 7H), 4.7 (br. s, 1H), 1.8-2.5 (m, 8H), 1.2 (t, 3H), 1.1 (t, 3H). |
| A-80 | 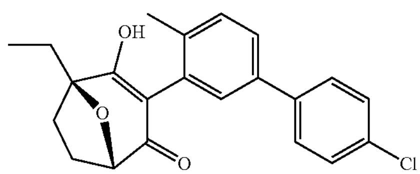 [SMILES: CC[C@]12CC[C@H](O1)C(=O)C(c1cc(-c3ccc(Cl)cc3)ccc1C)=C2O] | δ 7.47-7.17 (m, 7H, isomers A and B), 5.9 (br. s, 1H, isomer A), 5.8 (br. s, 1H, isomer B), 4.8 (dd, 1H, isomer A), 4.7 (d, 1H, isomer B), 2.1 (s, 3H, isomers A and B), 1.8-2.5 (m, 6H, isomers A and B), 1.1 (t, 3H, isomer B), 1.0 (t, 3H, isomer A). |
| A-81 | 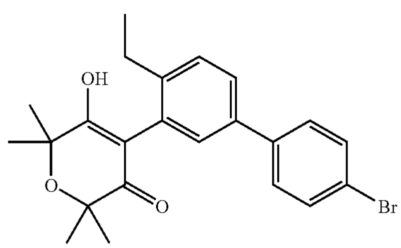 [SMILES: CCc1ccc(-c2ccc(Br)cc2)cc1C1=C(O)C(C)(C)OC(C)(C)C1=O] | δ 7.54 (m, 3H), 7.42 (m, 3H), 7.24 (s, 1H), 5.63 (s, 1H), 2.47 (m, 2H), 1.62 (s, 6H), 1.50 (s, 6H), 1.15 (t, 3H). |
| A-82 | 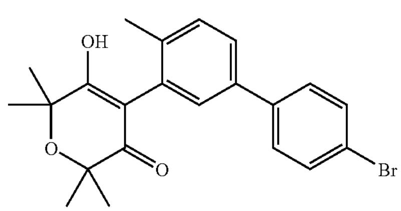 [SMILES: Cc1ccc(-c2ccc(Br)cc2)cc1C1=C(O)C(C)(C)OC(C)(C)C1=O] | δ 7.55 (d, 2H), 7.50 (d, 1H), 7.38 (d, 1H), 7.35 (d, 2H), 7.27 (s, 1H), 5.60 (br. s, 1H), 2.18 (s, 3H), 1.63 (s, 6H), 1.51 (app. d, 6H). |
| A-83 | 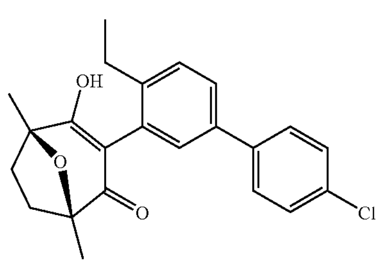 [SMILES: CCc1ccc(-c2ccc(Cl)cc2)cc1C1=C(O)[C@@]2(C)CC[C@](C)(O2)C1=O] | δ 7.55-7.14 (m, 7H, isomers A and B), 5.7 (br. s, 1H, isomer B), 5.6 (br. s, isomer A), 2.6-2.1 (m, 6H, isomers A and B), 1.62 (s, 6H, isomers A and B), 1.2 (m, 3H, isomer B), 1.1 (m, 3H, isomer A). |

TABLE A-continued

| Compound Number | Structure | $^1$H nmr (CDCl$_3$ unless stated) or other physical data |
|---|---|---|
| A-84 | 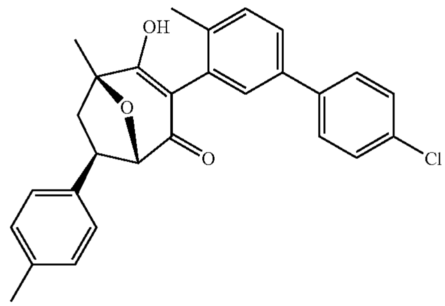 [SMILES: Cc1ccc([C@H]2C[C@@]3(C)O[C@@H]2C(=O)C(c2cc(-c4ccc(Cl)cc4)ccc2C)=C3O)cc1] | δ 7.51-7.46 (m, 4H), 7.40-7.37 (m, 4H), 7.1 (m, 3H), 6.25 (br. s, 1H), 4.7 (s, 1H), 3.57-3.47 (m, 1H), 2.9-2.6 (m, 2H), 2.35 (s, 3H), 2.16 (s, 3H), 1.68 (s, 3H). |
| A-85 | 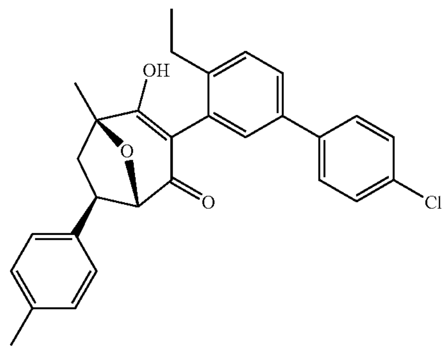 [SMILES: CCc1ccc(-c2ccc(Cl)cc2)cc1C1=C(O)[C@@]2(C)C[C@H](c3ccc(C)cc3)[C@H](O2)C1=O] | δ 7.55-7.16 (m, 11H), 5.8 (br. s, 1H), 4.7 (d, 1H), 3.6-3.4 (m, 1H), 2.66-2.4 (m, 4H), 2.35 (s, 3H), 1.7 (s, 3H), 1.12 (m, 3H). |
| A-86 | 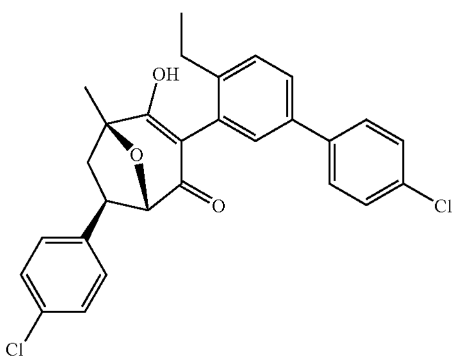 [SMILES: CCc1ccc(-c2ccc(Cl)cc2)cc1C1=C(O)[C@@]2(C)C[C@H](c3ccc(Cl)cc3)[C@H](O2)C1=O] | δ 7.55-7.25 (m, 11H), 5.95 (br., 1H), 4.7 (d, 1H), 3.6-3.35 (m, 1H), 2.85-2.4 (m, 4H), 1.66 (d, 3H), 1.15 (m, 3H). |
| A-87 | 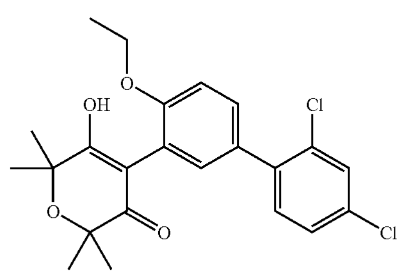 | Methanol-d$_4$ δ 7.50 (m, 1H), 7.40 (m, 3H), 7.10 (m, 1H), 7.05 (d, 1H), 4.05 (q, 2H), 1.50 (s, 12H), 1.32 (t, 3H). |
| A-88 | 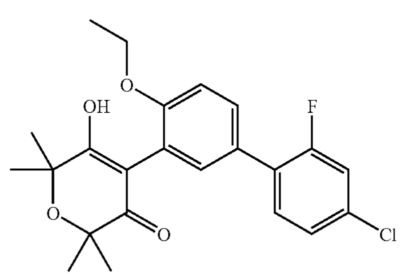 | Methanol-d$_4$ δ 7.50 (m, 2H), 7.25 (m, 2H), 7.20 (m, 1H), 7.05 (d, 1H), 4.05 (q, 2H), 1.50 (s, 12H), 1.32 (t, 3H). |

TABLE A-continued

| Compound Number | Structure | $^1$H nmr (CDCl$_3$ unless stated) or other physical data |
|---|---|---|
| A-89 | 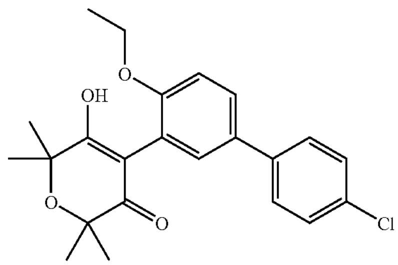 [SMILES: CCOc1ccc(-c2ccc(Cl)cc2)cc1C1=C(O)C(C)(C)OC(C)(C)C1=O] | Methanol-d$_4$ δ 7.55 (m, 3H), 7.38 (m, 2H), 7.28 (m, 1H), 7.05 (d, 1H), 4.05 (q, 2H), 1.50 (s, 12H), 1.30 (t, 3H). |
| A-90 | 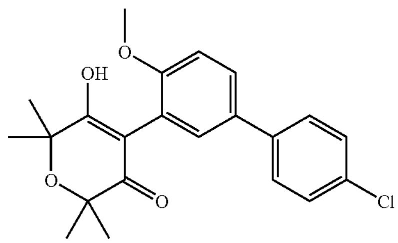 | δ 7.57-7.53 (d, 1H), 7.5-7.46 (dd, 2H), 7.39-7.36 (dd, 2H), 7.28-7.26 (d, 1H), 7.09-6.9 (d, 1H), 3.9 (s, 3H), 1.5-1.7 (m, 12H). |
| A-91 | 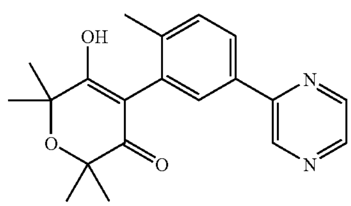 [SMILES: Cc1ccc(-c2cnccn2)cc1C1=C(O)C(C)(C)OC(C)(C)C1=O] | Methanol-d$_4$ δ 9.10 (s, 1H), 8.65 (m, 1H), 8.50 (d, 1H), 7.95 (dd, 1H), 7.72 (d, 1H), 7.42 (d, 1H), 2.20 (s, 3H), 1.52 (s, 12H). |
| A-92 | 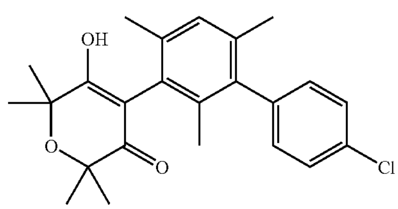 [SMILES: Cc1cc(C)c(-c2ccc(Cl)cc2)c(C)c1C1=C(O)C(C)(C)OC(C)(C)C1=O] | δ 7.39 (m, 2H), 7.11 (dd, 1H), 7.06 (s, 1H), 7.04 (dd, 1H), 5.51 (br. s, 1H), 2.11 (s, 3H), 1.99 (s, 3H), 1.76 (s, 3H), 1.60 (d, 6H), 1.49 (d, 6H). |
| A-93 | 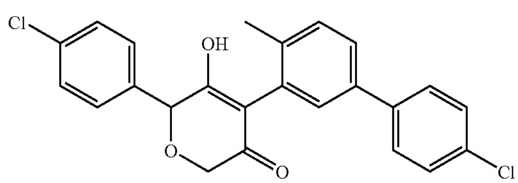 [SMILES: Cc1ccc(-c2ccc(Cl)cc2)cc1C1=C(O)C(c2ccc(Cl)cc2)OCC1=O] | δ 7.52-7.22 (m, 11H, isomers A and B), 5.28 and 5.26 (br. s each, 1H together, isomers A and B), 4.36 (m, 2H, isomers A and B), 2.19 and 2.16 (s each, 3H together, isomers A and B). |
| A-94 | 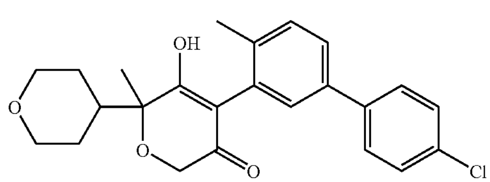 [SMILES: Cc1ccc(-c2ccc(Cl)cc2)cc1C1=C(O)C(C)(C2CCOCC2)OCC1=O] | δ 7.49-7.16 (m, 7H), 4.38 (m, 2H), 3.91 (m, 2H), 3.30 (m, 2H), 2.18-2.08 (m, 1H), 2.14 and 2.11 (s each, 3H together), 1.75 (m, 1H), 1.55 (m, 3H), 1.37 (br. s, 3H). |
| A-95 | 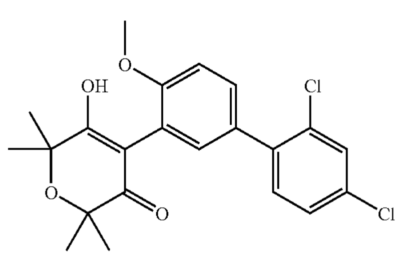 | δ 7.5-7.4 (m, 2H), 7.35-7.25 (m, 3H), 7.05-6.95 (2xd, 1H), 3.9 (2 x s, 3H), 1.55-1.45 (m, 12H). |

TABLE A-continued

| Compound Number | Structure | ¹H nmr (CDCl₃ unless stated) or other physical data |
|---|---|---|
| A-96 | 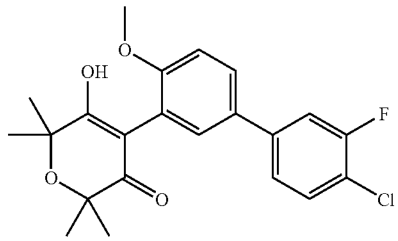 [SMILES: COc1ccc(-c2ccc(Cl)c(F)c2)cc1C1=C(O)C(C)(C)OC(C)(C)C1=O] | δ 7.55-7.6 (d, 1H), 7.5-7.3 (m, 3H), 7.1-7.0 (dd, 2H), 3.9-3.8 (2x s, 3H), 1.6-1.5 (m, 12H). |
| A-97 | 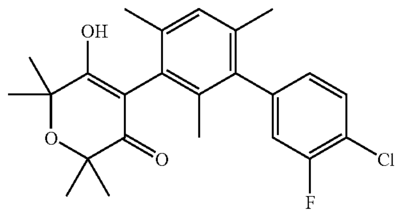 [SMILES: Cc1cc(C)c(-c2ccc(Cl)c(F)c2)c(C)c1C1=C(O)C(C)(C)OC(C)(C)C1=O] | δ 7.44 (m, 1H), 7.07 (s, 1H), 6.99 (m, 0.5H), 6.91 (m, 1H), 6.84 (m, 0.5H), 5.50 (br. d, 1H), 2.11 (s, 3H), 2.00 (s, 3H), 1.78 (s, 3H), 1.61 (d, 6H), 1.49 (d, 6H). |
| A-98 | 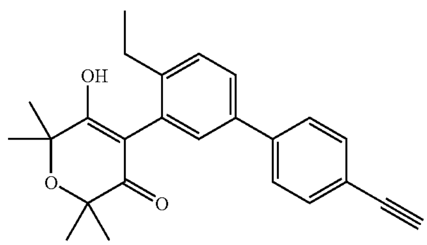 [SMILES: C#Cc1ccc(-c2ccc(CC)c(C3=C(O)C(C)(C)OC(C)(C)C3=O)c2)cc1] | δ 7.58 (dd, 1H), 7.55 (s, 4H), 7.43 (d, 1H), 7.28 (s, 1H), 5.62 (br. s, 1H), 3.13 (s, 1H), 2.48 (m, 2H), 1.62 (s, 6H), 1.51 (s, 6H), 1.16 (t, 3H). |
| A-99 | 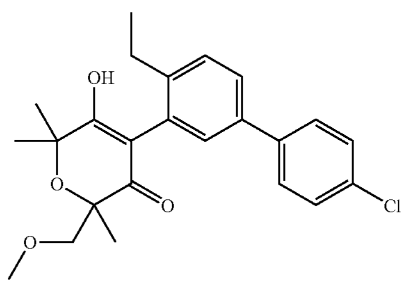 [SMILES: CCc1ccc(-c2ccc(Cl)cc2)cc1C1=C(O)C(C)(C)OC(C)(COC)C1=O] | m.p. 123-124° C.; LC-MS (ES⁺): 415, 417 (M + H)⁺ |
| A-100 | 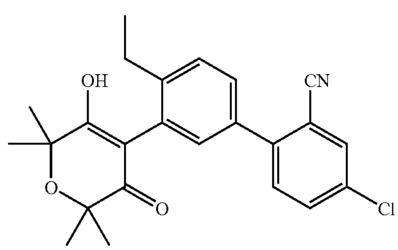 | δ 7.77 (s, 1H), 7.66 (d, 1H), 7.53 (m, 3H), 7.29 (s, 1H), 6.00 (s, 1H), 2.55 (m, 2H), 1.68 (d, 6H), 1.54 (d, 6H), 1.22 (t, 3H). |
| A-101 | 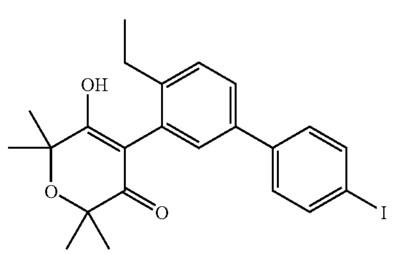 [SMILES: CCc1ccc(-c2ccc(I)cc2)cc1C1=C(O)C(C)(C)OC(C)(C)C1=O] | δ 7.74 (d, 2H), 7.53 (dd, 1H), 7.41 (d, 1H), 7.31 (d, 2H), 7.23 (s, 1H), 5.59 (br. s, 1H), 2.47 (m, 2H), 1.61 (s, 6H), 1.49 (s, 6H), 1.15 (t, 3H). |

TABLE A-continued

| Compound Number | Structure | ¹H nmr (CDCl₃ unless stated) or other physical data |
|---|---|---|
| A-102 | 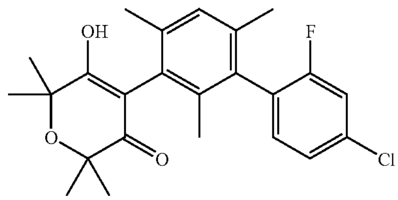 | δ 7.24-7.00 (m, 4H), 5.80 (br. s, 0.75H), 5.51 (br. s, 0.25H), 2.12 (s, 3H), 2.02 (s, 3H), 1.79 (s, 3H), 1.61 (d, 6H), 1.49 (d, 6H). |
| A-103 | 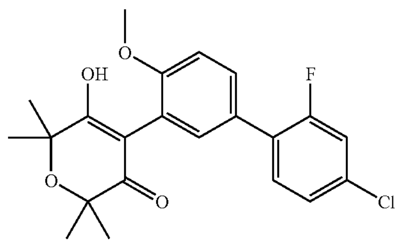 | δ 7.55-7.5 (m, 1H); 7.4-7.35 (m, 1H); 7.33-7.34 (m, 1H); 7.2-7.14 (m, 2H); 7.14-6.96 (2xd, 1H); 3.86-3.75 (2xs, 3H); 1.63-1.45 (m, 12H). |
| A-104 | 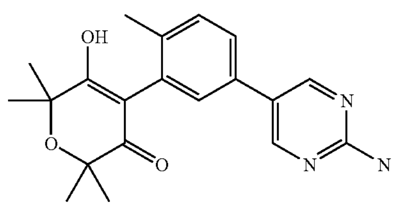 [SMILES: Cc1ccc(-c2cnc(N)nc2)cc1C1=C(O)C(C)(C)OC(C)(C)C1=O] | DMSO-d₆ δ 8.46 (s, 2H), 7.39 (dd, 1H), 7.22 (d, 1H), 7.12 (s, 1H), 6.66 (s, 2H), 1.98 (s, 3H), 1.44 (br. s, 6H), 1.31 (br. s, 6H). |
| A-105 | 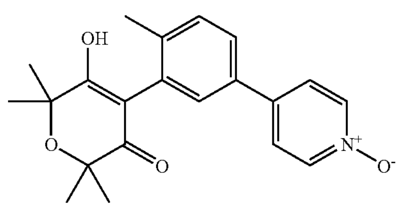 | DMSO-d₆ δ 8.19 (d, 2H), 7.71 (d, 2H), 7.60 (dd, 1H), 7.31 (s, 2H), 2.03 (s, 3H), 1.50 (br. s, 6H), 1.32 (br. s, 6H). |
| A-106 | 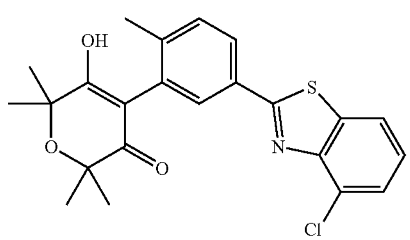 [SMILES: Cc1ccc(-c2nc3c(Cl)cccc3s2)cc1C1=C(O)C(C)(C)OC(C)(C)C1=O] | DMSO-d₆ δ 8.00 (d, 1H), 7.82 (dd, 1H), 7.60 (d 1H), 7.52 (d, 1H), 7.35 (m, 2H), 2.03 (s, 3H), 1.38 (br. s, 12H). |
| A-107 | 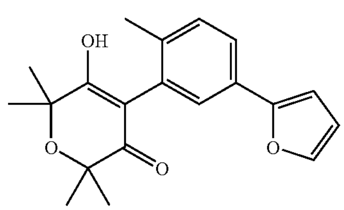 [SMILES: Cc1ccc(-c2ccco2)cc1C1=C(O)C(C)(C)OC(C)(C)C1=O] | DMSO-d₆ δ 7.60 (s, 1H), 7.43 (dd, 1H), 7.17 (m, 2H), 6.78 (d, 1H), 6.47 (m, 1H), 1.95 (s, 3H), 1.40 (br. s, 12H). |
| A-108 | 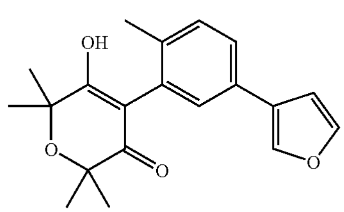 [SMILES: Cc1ccc(-c2ccoc2)cc1C1=C(O)C(C)(C)OC(C)(C)C1=O] | DMSO-d₆ δ 8.10 (s, 1H). 7.67 (m, 1H), 7.40 (dd, 1H), 7.19 (d, 1H), 7.12 (d, 1H), 6.89 (m, 1H), 1.98 (s, 3H), 1.47 (br. s, 6H), 1.33 (br. s, 6H). |

TABLE A-continued

| Compound Number | Structure | ¹H nmr (CDCl₃ unless stated) or other physical data |
| --- | --- | --- |
| A-109 | 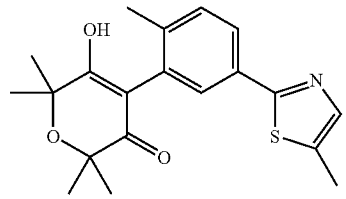 [SMILES: Cc1cnc(-c2ccc(C)c(C3=C(O)C(C)(C)OC(C)(C)C3=O)c2)s1] | DMSO-d$_6$ δ 7.63 (dd, 1H), 7.51 (s, 1H), 7.40 (s, 1H), 7.27 (d, 1H), 2.44 (app. d, 3H), 2.03 (s, 3H), 1.40 (br. s, 12H). |
| A-110 | 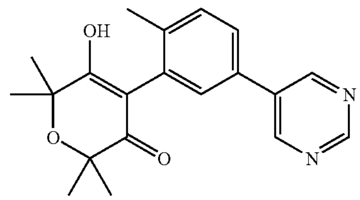 [SMILES: Cc1ccc(-c2cncnc2)cc1C1=C(O)C(C)(C)OC(C)(C)C1=O] | DMSO-d$_6$ δ 9.09 (s, 1H), 9.04 (s, 2H), 7.60 (dd, 1H), 7.33 (m, 2H), 2.03 (s, 3H), 1.38 (br. s, 12H). |
| A-111 | 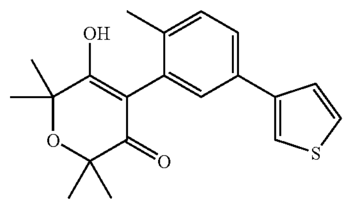 [SMILES: Cc1ccc(-c2ccsc2)cc1C1=C(O)C(C)(C)OC(C)(C)C1=O] | DMSO-d$_6$ δ 7.70 (m, 1H), 7.50 (m, 1H), 7.42 (m, 2H), 7.17 (m, 2H), 1.94 (s, 3H), 1.35 (br. s, 12H). |
| A-112 | 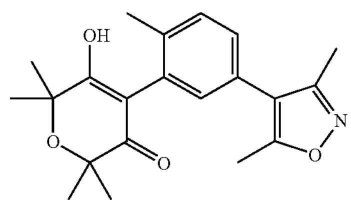 [SMILES: Cc1ccc(-c2c(C)noc2C)cc1C1=C(O)C(C)(C)OC(C)(C)C1=O] | DMSO-d$_6$ δ 7.27 (d, 1H), 7.17 (dd, 1H), 6.89 (d, 1H), 2.35 (s, 3H), 2.18 (s, 3H), 2.04 (s, 3H), 1.40 (br. s, 12H). |
| A-113 | 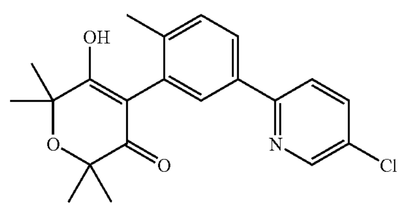 | DMSO-d$_6$ δ 8.63 (s, 1H), 7.93 (s, 2H), 7.86 (dd, 1H), 7.63 (d, 1H), 7.30 (d, 1H), 2.04 (s, 3H), 1.41 (br. s, 12H). |
| A-114 | 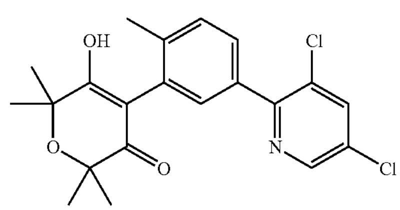 | DMSO-d$_6$ δ 8.65 (d, 1H), 8.28 (d, 1H), 7.56 (dd, 1H), 7.30 (d, 1H), 7.23 (d, 1H), 2.06 (s, 3H), 1.41 (br. d, 12H). |
| A-115 | 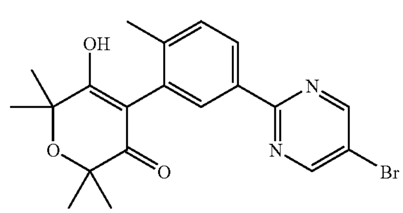 | DMSO-d$_6$ δ 9.00 (s, 2H), 8.15 (dd, 1H), 7.91 (d, 1H), 7.34 (d, 1H), 2.06 (s, 3H), 1.40 (br.s, 12H). |

TABLE A-continued

| Compound Number | Structure | ¹H nmr (CDCl₃ unless stated) or other physical data |
|---|---|---|
| A-116 | 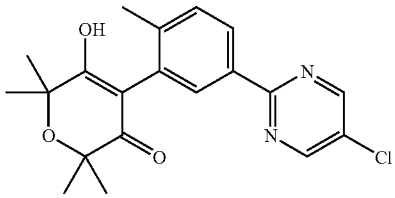 | DMSO-d₆ δ 8.98 (s, 2H), 8.20 (dd, 1H), 7.95 (d, 1H), 7.38 (d, 1H), 2.11 (s, 3H), 1.45 (br. s, 12H). |
| A-117 | 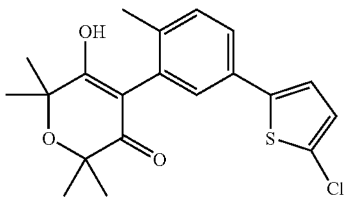 [SMILES: Cc1ccc(-c2ccc(Cl)s2)cc1C1=C(O)C(C)(C)OC(C)(C)C1=O] | DMSO-d₆ δ 7.44 (dd, 1H), 7.33 (d, 1H), 7.26 (d, 1H), 7.15 (d, 1H), 7.12 (d, 1H), 2.03 (s, 3H), 1.45 (br. s, 12H). |
| A-118 | 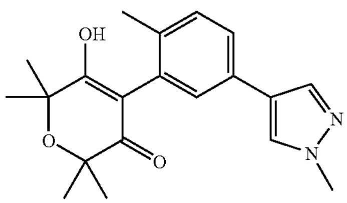 [SMILES: Cc1ccc(-c2cnn(C)c2)cc1C1=C(O)C(C)(C)OC(C)(C)C1=O] | DMSO-d₆ δ 8.03 (s, 1H), 7.73 (s, 1H), 7.34 (dd, 1H), 7.13 (d, 1H), 7.05 (d, 1H), 3.78 (s, 3H), 1.94 (s, 3H), 1.44 (br. s 6H), 1.32 (br. s, 6H). |
| A-119 | 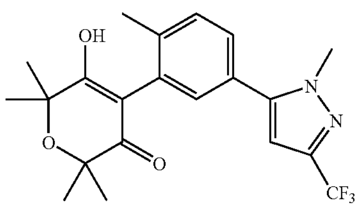 [SMILES: Cc1ccc(-c2cc(C(F)(F)F)nn2C)cc1C1=C(O)C(C)(C)OC(C)(C)C1=O] | DMSO-d₆ δ 7.42 (app. dd, 1H), 7.38 (app. d, 1H) 7.16 (d, 1H), 6.84 (s, 1H), 3.92 (s, 3H), 2.10 (s, 3H), 1.45 (br. s, 12H). |
| A-120 | 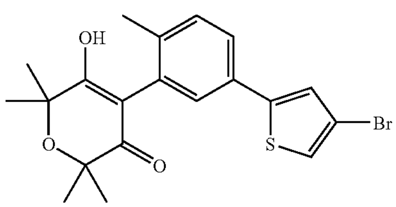 [SMILES: Cc1ccc(-c2cc(Br)cs2)cc1C1=C(O)C(C)(C)OC(C)(C)C1=O] | DMSO-d₆ δ 7.62 (d, 1H), 7.52 (d, 1H), 7.50 (d, 1H) 7.27 (d, 1H), 7.23 (d, 1H), 2.04 (s, 3H), 1.39 (br. s, 6H), 1.51 (br. s, 6H). |
| A-121 | 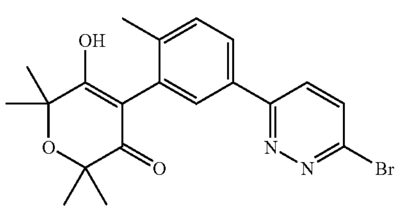 [SMILES: Cc1ccc(-c2ccc(Br)nn2)cc1C1=C(O)C(C)(C)OC(C)(C)C1=O] | DMSO-d₆ δ 8.20 (d, 1H), 8.08 (d, 1H), 7.98 (dd, 1H), 7.74 (d, 1H), 7.42 (d, 1H), 2.11 (s, 3H), 1.45 (br. s, 12H). |
| A-122 | 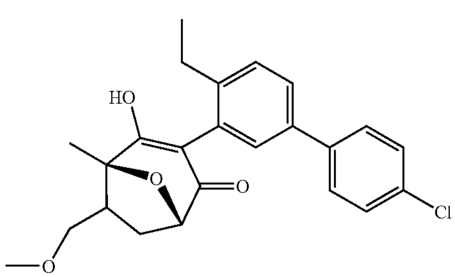 [SMILES: CCc1ccc(-c2ccc(Cl)cc2)cc1C1=C(O)[C@]2(C)O[C@@H](CC2COC)C1=O] | δ 7.1-7.47 (m, 7H), 6.15 (br. s, 1H), 4.5-4.8 (m, 1H), 3.44 (s, 2H), 3.26 (s, 3H), 2.7-2.25 (m, 5H), 1.65 (s, 3H), 1.14 (m, 3H). |

TABLE A-continued

| Compound Number | Structure | $^1$H nmr (CDCl$_3$ unless stated) or other physical data |
|---|---|---|
| A-123 | 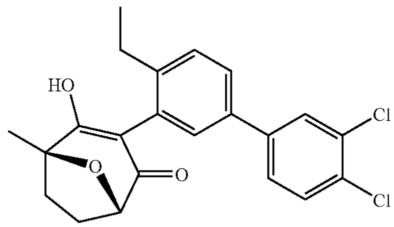 [SMILES: CCc1ccc(-c2ccc(Cl)c(Cl)c2)cc1C1=C(O)[C@@]2(C)CC[C@H](O2)C1=O] | δ 7.64-7.12 (m, 6H, isomers A and B), 5.75 (br. s, 1H, isomers A and B), 4.8 (d, 1H, isomer A), 4.7 (d, 1H, isomer B) 2.6-1.9 (m, 6H, isomers A and B), 1.56 (s, 3H, isomers A and B), 1.2 (t, 3H, isomer A), 1.14 (t, 3H, isomer B). |
| A-124 | 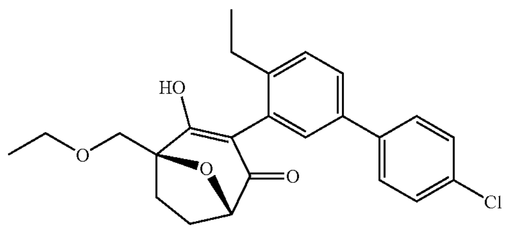 [SMILES: CCOC[C@]12CC[C@H](O1)C(=O)C(c1cc(-c3ccc(Cl)cc3)ccc1CC)=C2O] | δ 8.6 (br. s, 1H, isomer A), 8.4 (br. s, 1H, isomer B), 7.5-7.2 (m, 7H, isomers A and B), 4.9 (m, 1H, isomer B), 4.72 (m, 1H, isomer A), 4.14-3.7 (m, 4H, isomers A and B), 2.4-2.3 (m, 6H, isomers A and B), 1.25 (m, 3H, isomers A and B), 1.2 (m, 3H, isomer B), 1.18 (m, 3H, isomer A) |
| A-125 | 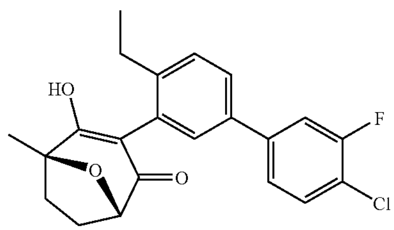 | δ 7.42-7.12 (m, 6H, isomers A and B), 5.9 (br. s, 1H, isomers A and B), 4.85 (d, 1H, isomer A), 4.69 (d, 1H isomer B), 2.5-1.95 (m, 6H, isomers A and B), 1.67 (s, 3H, isomers A and B), 1.16 (t, 3H, isomer A), 1.11 (t, 3H, isomer B). |
| A-126 | 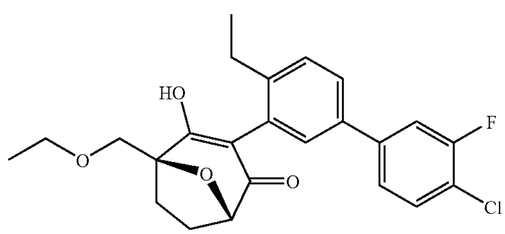 [SMILES: CCOC[C@]12CC[C@H](O1)C(=O)C(c1cc(-c3ccc(Cl)c(F)c3)ccc1CC)=C2O] | δ 8.8 (br. s, 1H isomer A), 8.7 (br. s, 1H, isomer B), 7.51-7.15 (m, 6H, isomers A and B), 4.9 (m, 1H, isomer B), 4.7 (m, 1H, isomer A), 4.2 (m, 1H, isomers A and B), 3.77-3.6 (m, 2H, isomers A and B), 3.46 (s, 1H, isomers A and B), 2.47-1.86 (m, 6H, isomers A and B), 1.3 (m, 3H, isomers A and B), 1.2 (m, 3H, isomer B), 1.1 (m, 3H, isomer A). |
| A-127 | 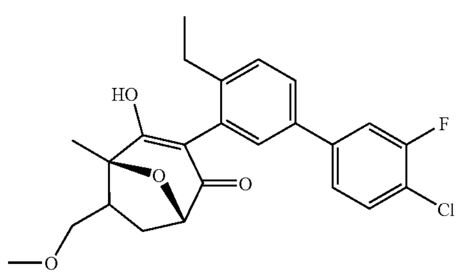 [SMILES: CCc1ccc(-c2ccc(Cl)c(F)c2)cc1C1=C(O)[C@]2(C)O[C@@H](CC2COC)C1=O] | δ 7.5-7.14 (m, 6H), 6.0 (br. s, 1H), 4.8-4.62 (m, 1H), 3.5 (s, 3H), 3.2 (m, 2H), 2.8-2.3 (m, 5H), 1.6 (s, 3H), 1.2 (t, 3H). |
| A-128 | 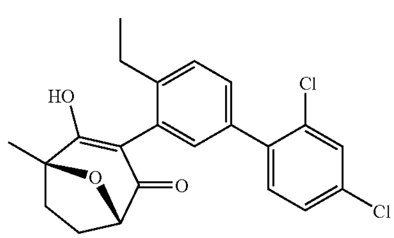 [SMILES: CCc1ccc(-c2ccc(Cl)cc2Cl)cc1C1=C(O)[C@@]2(C)CC[C@H](O2)C1=O] | δ 7.47-7.25 (m, 6H, isomers A and B), 6.1 (br. s, 1H isomers A and B), 4.8 (d, 1H, isomer A), 4.7 (m, 1H, isomer B) 2.5-1.9 (m, 6H, isomers A and B), 1.66 (s, 3H, isomers A and B), 1.2 (t, 3H, isomer A) 1.15 (t, 3H, isomer B). |

TABLE A-continued

| Compound Number | Structure | ¹H nmr (CDCl₃ unless stated) or other physical data |
|---|---|---|
| A-129 | 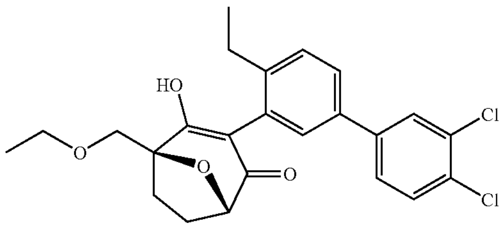 [SMILES: CCOC[C@]12CC[C@H](O1)C(=O)C(c1cc(-c3ccc(Cl)c(Cl)c3)ccc1CC)=C2O] | δ 8.8 (br. s, 1H, isomer A), 8.6 (br. s, 1H, isomer B), 7.7-7.1 (m, 6H, isomers A and B), 4.9 (m, 1H, isomer B), 4.7 (m, 1H, isomer A), 4.2-3.6 (m, 4H, isomers A and B), 2.7-2.3 (m, 6H, isomers A and B), 1.3 (m, 3H, isomers A and B), 1.2 (t, 3H, isomer B), 1.1 (t, 3H, isomer A). |
| A-130 | 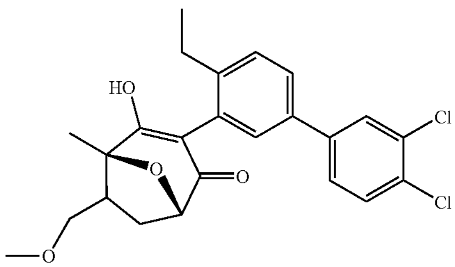 [SMILES: CCc1ccc(-c2ccc(Cl)c(Cl)c2)cc1C1=C(O)[C@]2(C)O[C@@H](CC2COC)C1=O] | δ 7.64-714 (m, 6H), 5.9 (br. s, 1H), 4.6 (m, 1H), 3.48 (s, 3H), 3.3 (m, 2H), 2.8-2.4 (m, 5H), 1.7 (s, 3H), 1.15 (m, 3H). |
| A-131 | 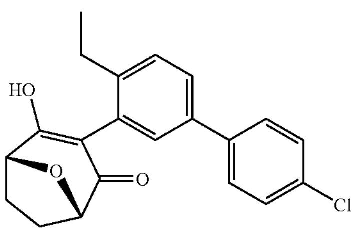 [SMILES: CCc1ccc(-c2ccc(Cl)cc2)cc1C1=C(O)[C@H]2CC[C@H](O2)C1=O] | Gum; LC-MS (ES−) 355, 353 (M − H)⁻ |
| A-132 | 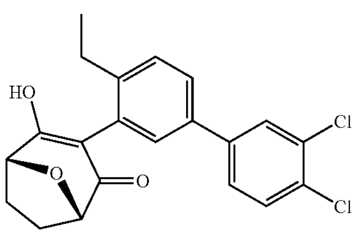 [SMILES: CCc1ccc(-c2ccc(Cl)c(Cl)c2)cc1C1=C(O)[C@H]2CC[C@H](O2)C1=O] | Gum; LC-MS (ES−) 389, 387 (M − H)⁻ |
| A-133 | 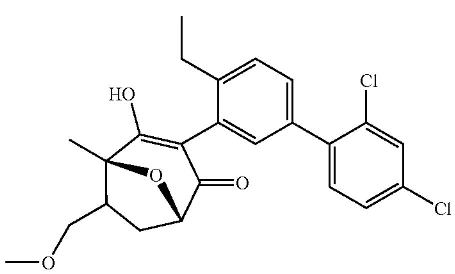 [SMILES: CCc1ccc(-c2ccc(Cl)cc2Cl)cc1C1=C(O)[C@]2(C)O[C@@H](CC2COC)C1=O] | δ 7.04-7.5 (m, 6H), 6.0 (br. s, 1H), 4.7-4.6 (m, 1H), 3.4 (m, 2H), 3.2 (m, 3H), 2.8-2.3 (m, 5H), 1.6 (s, 3H), 1.2 (m, 3H). |
| A-134 | 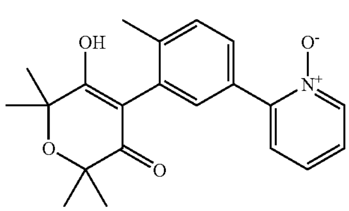 [SMILES: Cc1ccc(-c2cccc[n+]2[O-])cc1C1=C(O)C(C)(C)OC(C)(C)C1=O] | DMSO-d₆ δ 8.27-8.24 (2xd, 1H); 7.72-7.67 (2xd, 1H); 7.54-7.51 (2xd, 1H); 7.37-7.24 (m, 4H); 2.03 (s, 3H); 1.24-1.2 (2xs, 12H). |

TABLE A-continued

| Compound Number | Structure | ¹H nmr (CDCl₃ unless stated) or other physical data |
|---|---|---|
| A-135 | 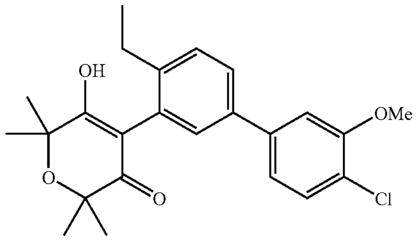 [SMILES: CCc1ccc(-c2ccc(Cl)c(OC)c2)cc1C1=C(O)C(C)(C)OC(C)(C)C1=O] | δ 7.59 (dd, 1H), 7.46 (m, 2H), 7.28 (s, 1H), 7.14 (m, 2H), 5.68 (s, 1H), 4.01 (s, 3H), 2.52 (m, 2H), 1.66 (s, 6H), 1.55 (d, 6H), 1.19 (t, 3H). |
| A-136 | 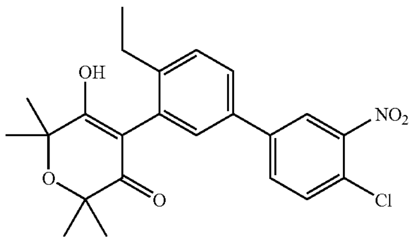 [SMILES: CCc1ccc(-c2ccc(Cl)c([N+](=O)[O-])c2)cc1C1=C(O)C(C)(C)OC(C)(C)C1=O] | δ 8.12 (s, 1H), 7.72 (dd, 1H), 7.58 (m, 2H), 7.47 (d, 1H), 7.28 (s, 1H), 5.56 (s, 1H), 2.49 (m, 2H), 1.62 (d, 6H), 1.51 (s, 6H), 1.16 (t, 3H). |
| A-137 | 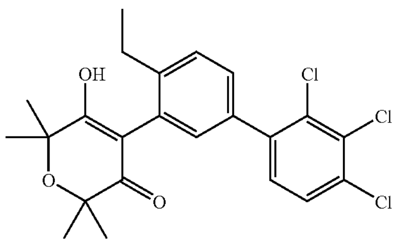 | δ 7.45 (m, 3H), 7.26 (d, 1H), 7.14 (s, 1H), 5.82 (s, 1H), 2.54 (m, 2H), 1.66 (d, 6H), 1.53 (d, 6H), 1.21 (t, 3H). |
| A-138 | 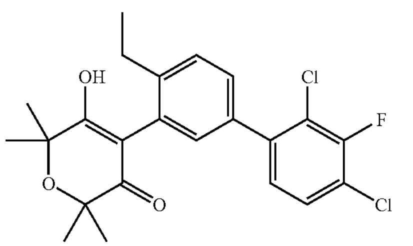 | δ 7.42 (s, 2H), 7.34 (t, 1H), 7.12 (m, 2H), 5.76 (s, 1H), 2.49 (m, 2H), 1.61 (d, 6H), 1.49 (d, 6H), 1.17 (t, 3H). |
| A-139 | 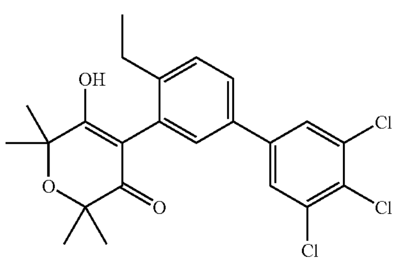 [SMILES: CCc1ccc(-c2cc(Cl)c(Cl)c(Cl)c2)cc1C1=C(O)C(C)(C)OC(C)(C)C1=O] | δ 7.58 (s, 2H), 7.52 (dd, 1H), 7.43 (d, 1H), 7.21 (s, 1H), 5.54 (br. s, 1H), 2.49 (m, 2H), 1.62 (d, 6H), 1.50 (s, 6H), 1.14 (t, 3H). |
| A-140 | 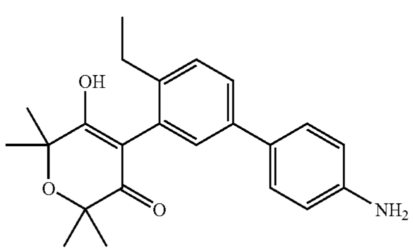 [SMILES: CCc1ccc(-c2ccc(N)cc2)cc1C1=C(O)C(C)(C)OC(C)(C)C1=O] | δ 7.52 (d, 1H), 7.41-7.35 (m, 3H), 7.21 (s, 1H), 6.73 (d, 2H), 5.75 (br., 1H), 3.71 (br., 2H), 2.45 (m, 2H), 1.61 (s, 6H), 1.51 (s, 6H), 1.13 (t, 3H). |

TABLE A-continued

| Compound Number | Structure | ¹H nmr (CDCl₃ unless stated) or other physical data |
|---|---|---|
| A-141 | 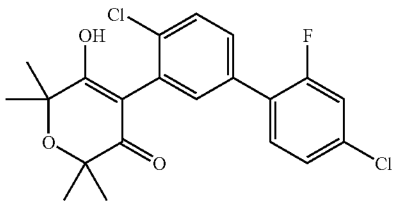 [SMILES: CC1(C)OC(C)(C)C(O)=C(c2cc(-c3ccc(Cl)cc3F)ccc2Cl)C1=O] | δ 7.59 (d, 1H), 7.51 (dt, 1H), 7.41-7.31 (m, 2H), 7.24-7.17 (m, 2H), 5.65 (br. s, 1H), 1.63 (d, 6H), 1.50 (d, 6H). |
| A-142 | 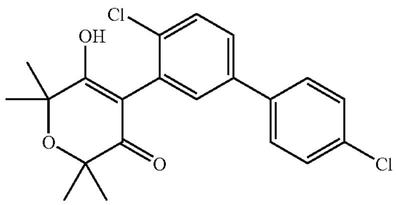 | δ 7.60-7.56 (m, 1H), 7.56-7.51 (m, 1H), 7.50 (d, 2H), 7.41 (d, 2H), 7.38 (d, 1H), 5.59 (br. s, 1H), 1.63 (d, 6H), 1.50 (d, 6H). |
| A-143 | 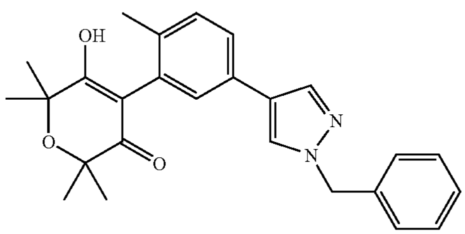 [SMILES: Cc1ccc(-c2cnn(Cc3ccccc3)c2)cc1C1=C(O)C(C)(C)OC(C)(C)C1=O] | δ 7.71 (s, 1H), 7.60 (s, 1H), 7.38 (m, 3H), 7.32 (app. d, 2H), 7.27 (app. d, 2H), 7.17 (s, 1H), 5.31 (s, 2H), 2.17 (s, 3H), 1.65 (br. s, 6H), 1.54 (br. s, 6H). |
| A-144 | 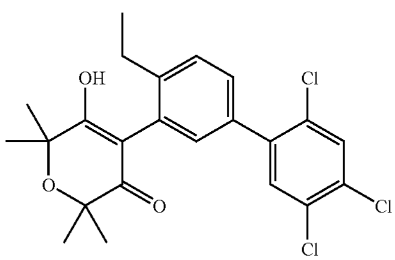 [SMILES: CCc1ccc(-c2cc(Cl)c(Cl)cc2Cl)cc1C1=C(O)C(C)(C)OC(C)(C)C1=O] | δ 7.58 (s, 1H), 7.47 (s, 1H), 7.42 (s, 2H), 7.11 (s, 1H), 5.72 (s, 1H), 2.49 (m, 2H), 1.61 (s, 6H), 1.49 (d, 6H), 1.17 (t, 3H). |
| A-145 | 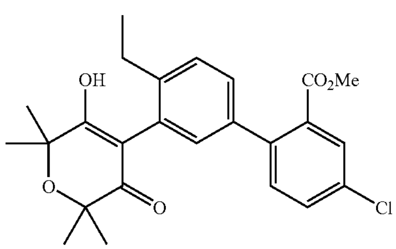 | δ 7.90 (s, 1H), 7.55 (dd, 1H), 7.42 (m, 2H), 7.30 (dd, 1H), 7.01 (s, 1H), 3.82 (s, 3H), 2.52 (m, 2H), 1.63 (d, 6H), 1.62 (d, 6H), 1.22 (t, 3H). |
| A-146 | 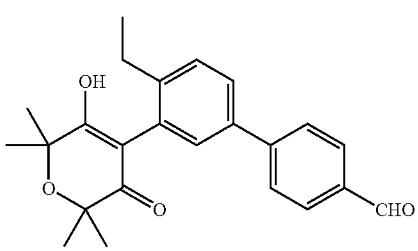 [SMILES: CCc1ccc(-c2ccc(C=O)cc2)cc1C1=C(O)C(C)(C)OC(C)(C)C1=O] | δ 10.04 (s, 1H), 7.94 (app. d, 2H), 7.75 (app. d, 2H), 7.65 (dd, 1H), 7.47 (d, 1H), 7.34 (d, 1H), 5.66 (br. s, 1H), 2.55-2.45 (m, 2H), 1.61-1.51 (m, 12H), 1.16 (t, 3H). |

TABLE A-continued

| Compound Number | Structure | ¹H nmr (CDCl₃ unless stated) or other physical data |
|---|---|---|
| A-147 | 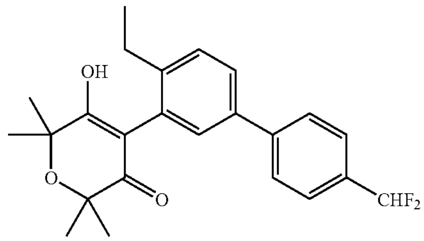 [SMILES: CCc1ccc(-c2ccc(C(F)F)cc2)cc1C1=C(O)C(C)(C)OC(C)(C)C1=O] | δ 7.66 (app. d, 2H), 7.61-7.56 (m, 3H), 7.45 (d, 1H), 7.29 (d, 1H), 6.69 (t, 1H), 5.69 (br. s, 1H), 2.55-2.43 (m, 2H), 1.62 (s, 6H), 1.50 (d, 6H), 1.16 (t, 3H). |
| A-148 | 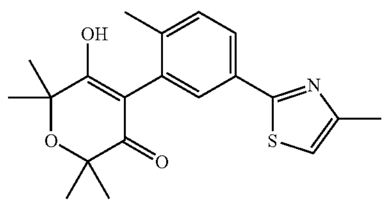 | DMSO-d₆ δ 7.72 (dd, 1H), 7.48 (s, 1H), 7.32 (d, 1H), 7.27 (s, 1H), 2.41 (s, 3H), 2.07 (s, 3H), 1.52 (br. s, 6H), 1.37 (br. s, 6H). |
| A-149 | 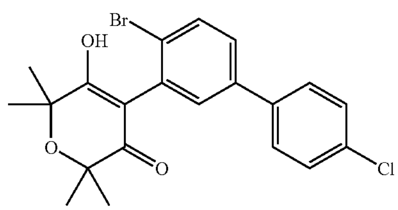 [SMILES: CC1(C)OC(C)(C)C(O)=C(c2cc(-c3ccc(Cl)cc3)ccc2Br)C1=O] | δ 7.76 (d, 1H), 7.51-7.37 (m, 6H), 5.55 (br. s, 1H), 1.66 (s, 3H), 1.60 (s, 3H), 1.54 (s, 3H), 1.48 (s, 3H). |
| A-150 | 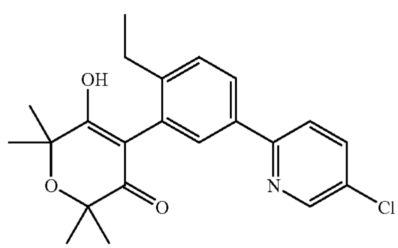 | Methanol-d₄ δ 8.56 (s, 1H), 7.90 (dd, 1H), 7.85 (s, 2H), 7.61 (d 1H), 7.41 (d, 1H), 2.50 (q, 2H), 1.52 (s, 12H), 1.15 (t, 3H). |
| A-151 | 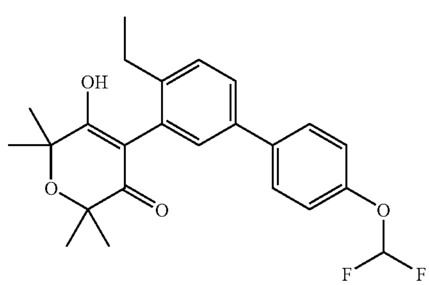 [SMILES: CCc1ccc(-c2ccc(OC(F)F)cc2)cc1C1=C(O)C(C)(C)OC(C)(C)C1=O] | Methanol-d₄ δ 7.64 (d, 2H), 7.52 (dd, 1H), 7.38 (d, 1H), 7.20 (m, 3H), 6.83 (t, 1H), 2.48 (q, 2H), 1.51 (s, 12H), 1.13 (t, 3H). |
| A-152 | 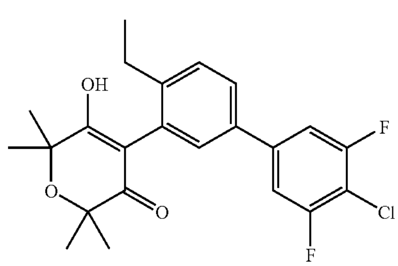 [SMILES: CCc1ccc(-c2cc(F)c(Cl)c(F)c2)cc1C1=C(O)C(C)(C)OC(C)(C)C1=O] | δ 7.58 (dd, 1H), 7.49 (d, 1H), 7.28 (d, 1H), 7.26 (s, 1H), 7.24 (s, 1H), 5.64 (br. s, 1H), 2.59-2.47 (m, 2H), 1.67 (app. d, 6H), 1.55 (s, 6H), 1.20 (t, 3H). |

TABLE A-continued

| Compound Number | Structure | $^1$H nmr (CDCl$_3$ unless stated) or other physical data |
|---|---|---|
| A-153 | 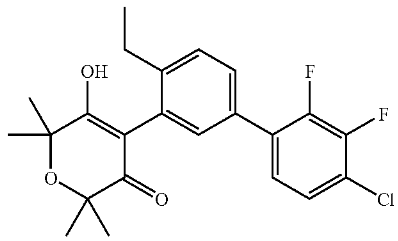 | δ 7.58-7.46 (m, 2H), 7.31-7.19 (m, 3H), 7.57 (br. s, 1H), 2.60-2.45 (m, 2H), 1.66 (s, 6H), 1.55-1.53 (m, 6H), 1.23-1.18 (m, 3H). |
| A-154 | 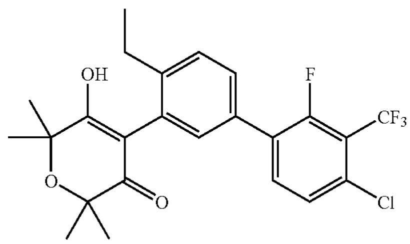 [SMILES: CCc1ccc(-c2ccc(Cl)c(C(F)(F)F)c2F)cc1C1=C(O)C(C)(C)OC(C)(C)C1=O] | δ 7.55-7.44 (m, 3H), 7.36 (d, 1H), 7.19 (s, 1H), 5.70 (br. s, 1H), 2.55-2.44 (m, 2H), 1.62 (s, 6H), 1.49 (app. d, 6H), 1.16 (t, 3H). |
| A-155 | 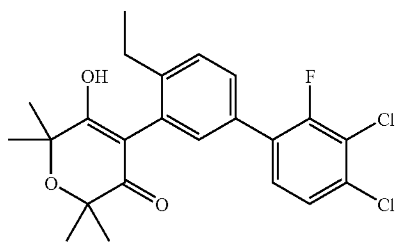 | δ 7.51 (dt, 1H), 7.45 (d, 1H), 7.34-7.27 (m, 2H), 7.21 (t, 1H), 5.74 (br. s, 1H), 2.55-2.44 (m, 2H), 1.61 (s, 6H), 1.49 (app. d, 6H), 1.16 (t, 3H). |
| A-156 | 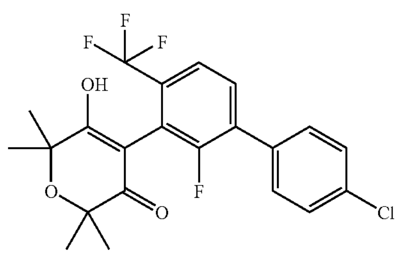 [SMILES: CC1(C)OC(C)(C)C(O)=C(c2c(C(F)(F)F)ccc(-c3ccc(Cl)cc3)c2F)C1=O] | Methanol-d$_4$ δ 7.65 (app. d, 2H), 7.59 (app. d, 1H), 7.56 (app. d, 1H), 7.49 (s, 1H), 7.47 (s, 1H), 1.50 (s, 6H), 1.47 (s, 6H). |
| A-157 | 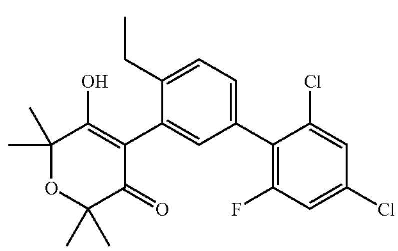 | δ 7.50 (d, 1H), 7.40-7.37 (m, 2H), 7.18-7.15 (dd, 1H), 7.11 (s, 1H), 5.82 (br. s, 1H), 2.63-2.47 (m, 2H), 1.65 (app. d, 6H), 1.54 (s, 3H), 1.52 (s, 3H), 1.22 (t, 3H). |
| A-158 | 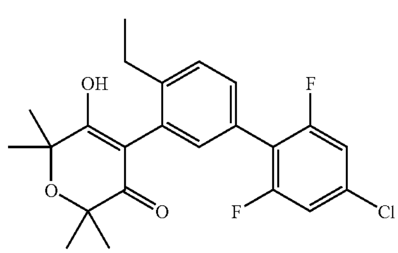 | δ 7.49 (s, 2H), 7.20 (br. s, 1H), 7.09-7.05 (m, 2H), 5.78 (br. s, 1H), 2.60-2.48 (m, 2H), 1.65 (s, 3H), 1.62 (s, 3H), 1.54 (s, 3H), 1.52 (s, 3H), 1.21 (t, 3H). |

TABLE A-continued

| Compound Number | Structure | ¹H nmr (CDCl₃ unless stated) or other physical data |
|---|---|---|
| A-159 | 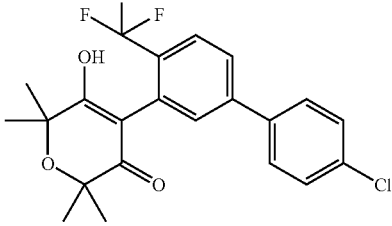 | δ 7.83 (d, 1H), 7.69 (d, 1H), 7.54 (d, 2H), 7.44 (d, 2H), 7.39 (s, 1H), 5.48 (br. s, 1H), 1.60 (app. d, 6H), 1.47 (s, 6H). |
| A-160 | 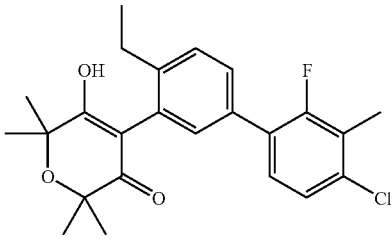 | δ 7.55 (d, 1H), 7.47 (d, 1H), 7.27-7.22 (m, 3H), 5.74 (br. s, 1H), 2.58-2.47 (m, 2H), 2.41 (d, 3H), 1.66 (s, 6H), 1.54 (app. d, 6H), 1.20 (t, 3H). |
| A-161 | 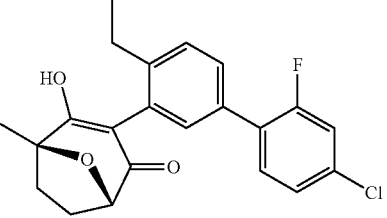 | δ 7.5-6.9 (m, 6H, isomers A and B), 6.1 (d, 1H, isomer A), 5.95 (d, 1H, isomer B), 4.8 (t, 1H, isomer A), 4.7 (t, 1H, isomer B), 2.6-2.3 (m, 3H, isomers A and B), 2.1-1.8 (m, 3H, isomers A and B), 1.6 (s, 3H, isomers A and B), 0.9-0.8 (m, 3H, isomers A and B). |
| A-162 | 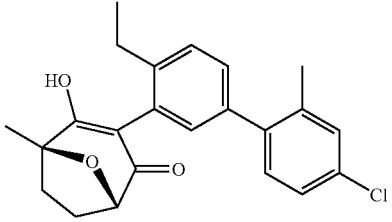 | δ 7.40-6.88 (m, 6H each of isomer I and II), 5.9 (d, 1H, isomer II), 5.8 (s, 1H, isomer I), 4.85 (t, 1H, isomer I), 4.7 (m, 1H, isomer II), 2.6-1.8 (m, 9H each of isomer I and II), 1.5 (s, 3H each of isomer I and II), 1.2 (t, 3H, isomer II), 1.1 (t, 3H, isomer I). |
| A-163 | 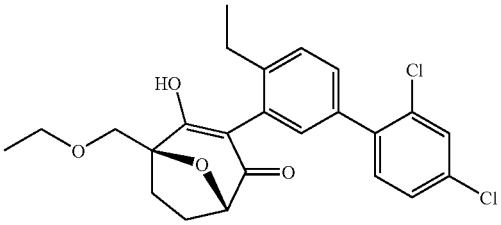 [SMILES: CCOC[C@]12CC[C@H](O1)C(=O)C(c1cc(-c3ccc(Cl)cc3Cl)ccc1CC)=C2O] | δ 8.47 (s, 1H, isomer A), 8.22 (s, 1H, isomer B), 7.5-7.0 (m, 6H, isomers A and B), 4.9 (d, 1H, isomer B), 4.7 (t, 1H, isomer A), 4.2-3.5 (m, 4H, isomers A and B), 2.6-1.9 (m, 6H, isomers A and B), 1.3-1.1 (m, 6H, isomers A and B) |
| A-164 | 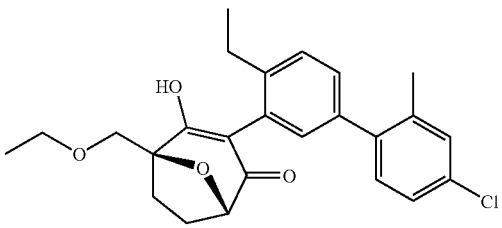 [SMILES: CCOC[C@]12CC[C@H](O1)C(=O)C(c1cc(-c3ccc(Cl)cc3C)ccc1CC)=C2O] | δ 8.08 (s, 1H, isomer A), 8.07 (s, 1H, isomer B), 7.5-6.9 (m, 6H, isomers A and B), 4.9 (m, 1H, isomer B), 4.7 (m, 1H, isomer A), 4.6 (s, 1H, isomers A and B), 4.2-3.5 (m, 3H, isomers A and B), 2.76 (s, 3H, isomers A and B), 2.6-1.9 (m, 6H, isomers A and B), 1.3-1.1 (m, 6H, isomers A and B). |

TABLE A-continued

| Compound Number | Structure | $^1$H nmr (CDCl$_3$ unless stated) or other physical data |
|---|---|---|
| A-165 | 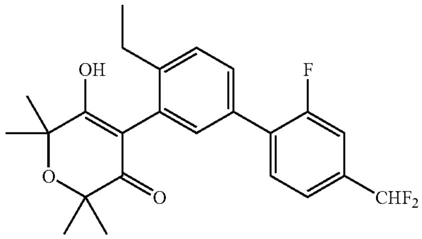 [SMILES: CCc1ccc(-c2ccc(C(F)F)cc2F)cc1C1=C(O)C(C)(C)OC(C)(C)C1=O] | δ 7.62-7.57 (m, 2H), 7.50 (d, 1H), 7.39 (d, 1H), 7.36 (d, 1H), 7.29 (s, 1H), 6.71 (t, 1H), 5.76 (br. s, 1H), 2.60-2.49 (m, 2H), 1.66 (s, 6H), 1.54 (app. d, 6H), 1.21 (t, 3H). |
| A-166 | 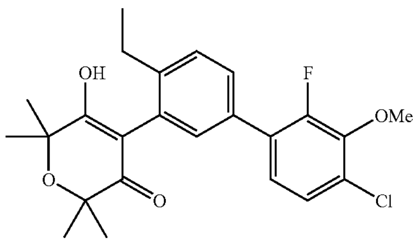 [SMILES: CCc1ccc(-c2ccc(Cl)c(OC)c2F)cc1C1=C(O)C(C)(C)OC(C)(C)C1=O] | δ 7.52 (d, 1H), 7.43 (d, 1H), 7.21-7.19 (m, 2H), 7.10 (t, 1H), 5.69 (br. s, 1H), 3.99 (s, 3H), 2.54-2.43 (m, 2H), 1.61 (s, 6H), 1.50 (app. d, 6H), 1.16 (t, 3H). |
| A-167 | 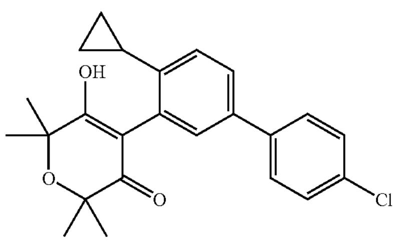 [SMILES: CC1(C)OC(C)(C)C(O)=C(c2cc(-c3ccc(Cl)cc3)ccc2C2CC2)C1=O] | δ 7.58-7.51 (m, 3H), 7.47-7.42 (m, 2H), 7.31 (m, 1H), 7.18 (d, 1H), 5.71 (br. s, 1H), 1.82-1.75 (m, 1H), 1.67 (s, 6H), 1.56 (app. d, 6H), 0.94-0.88 (m, 2H), 0.85-0.79 (m, 1H), 0.63-0.58 (m, 1H). |
| A-168 | 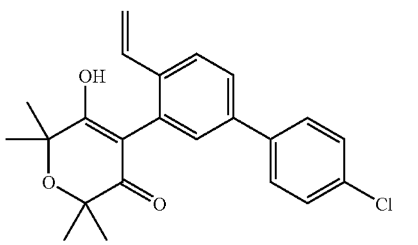 [SMILES: C=Cc1ccc(-c2ccc(Cl)cc2)cc1C1=C(O)C(C)(C)OC(C)(C)C1=O] | δ 7.80 (d, 1H), 7.64 (dd, 1H), 7.57 (app. d, 2H), 7.45 (app. d, 2H), 7.34 (d, 1H), 6.67 (dd, 1H), 5.82 (d, 1H), 5.69 (br. s, 1H), 5.36 (d, 1H), 1.66 (app. d, 6H), 1.55 (s, 6H). |

Example 23

Preparation of 6-(4'-dichloro-4-ethylbiphenyl-3-yl)-2,2,4,4-tetramethyl-cyclohexane-1,3,5-trione

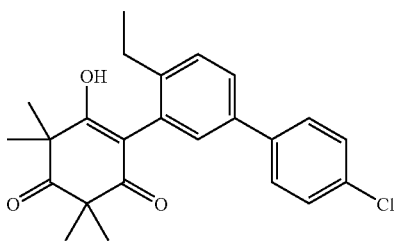

To a mixture of 2,2,4,4-tetramethylcyclohexane-1,3,5-trione (0.100 g, 0.55 mmol) and N,N-dimethylaminopyridine (0.33 g, 2.70 mmol) is added anhydrous chloroform (3.60 ml), followed by stirring at room temperature until dissolution. To this solution is then added anhydrous toluene (1.00 ml), then 4'-chloro-4-ethylbiphenyl-3-yllead triacetate (0.36 g, 0.60 mmol) in one portion. The solution is heated at 80° C. for 1 hour, then cooled to room temperature, followed by addition of dichloromethane (200 ml), then washing with 1M hydrochloric acid (200 ml). The organic phase is separated, dried over anhydrous magnesium sulfate, filtered and the filtrate is concentrated in vacuo. The residue is purified by flash column chromatography on silica gel (hexane/ethyl acetate 5:1 ratio) to afford 6-(4'-dichloro-4-ethylbiphenyl-3-yl)-2,2,4,4-tetra-methylcyclohexane-1,3,5-trione (0.17 g) as a white crystalline solid.

Example 24

Preparation of 6-(2',4'-dichloro-4-ethylbiphenyl-3-yl)-2,2,4,4-tetramethyl-cyclohexane-1,3,5-trione

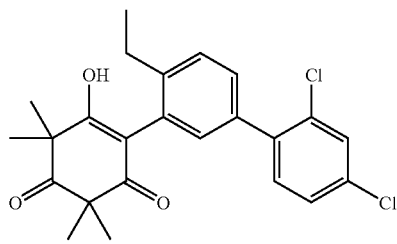 [SMILES: CCc1ccc(-c2ccc(Cl)cc2Cl)cc1C1=C(O)C(C)(C)C(=O)C(C)(C)C1=O]

Step 1 Preparation of 6-(5-bromo-2-ethylphenyl)-2,2,4,4-tetramethylcyclohexane-1,3,5-trione

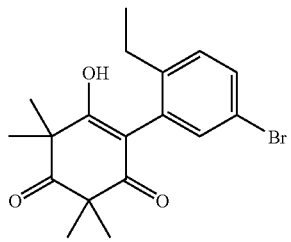 [SMILES: CCc1ccc(Br)cc1C1=C(O)C(C)(C)C(=O)C(C)(C)C1=O]

To a mixture of 2,2,4,4-tetramethylcyclohexane-1,3,5-trione (0.6 g, 3.6 mmol), 5-bromo-2-ethylphenyllead triacetate (2.27 g, 4.00 mmol) and N,N-dimethylaminopyridine (2.22 g, 18 mmol) is added anhydrous chloroform (25 ml) and toluene (6.3 ml), and the reaction mixture is heated at 80° C. for 3 hours. The mixture is diluted with dichloromethane (50 ml) and 2M aqueous hydrochloric acid (100 ml), and filtered through diatomaceous earth to remove inorganic residues. The filter cake is washed with dichloromethane, and all organic fractions are combined, washed with brine, dried over anhydrous magnesium sulphate then filtered. The filtrate is concentrated in vacuo and the residue is purified by flash column chromatography to give 6-(5-bromo-2-ethylphenyl)-2,2,4,4-tetramethylcyclohexane-1,3,5-trione as a white solid (0.84 g).

Step 2: Preparation of 6-(2',4'-dichloro-4-ethylbiphenyl-3-yl)-2,2,4,4-tetramethylcyclohexane-1,3,5-trione

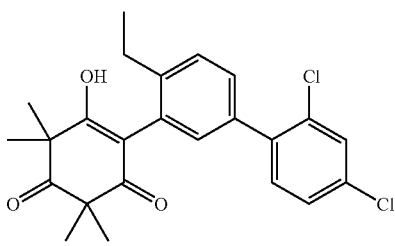

To a microwave vial is added palladium(II) acetate (1.1 mg, 0.0049 mmol), tris(3-sulfophenyl)phosphine trisodium salt (5.1 mg, 0.0099 mmol), 2,4-dichlorophenylboronic acid (0.099 g, 0.5 mmol), 6-(5-bromo-2-ethylphenyl)-2,2,4,4-tetramethylcyclohexane-1,3,5-trione (0.19 g, 0.5 mmol) and potassium phosphate (0.53 g, 2.5 mmol). Degassed water (0.75 ml) is next added (washing-down any solids from the slides of the vial), followed by stirring for 5 minutes and flushing with argon. This mixture is then heated at 160° C. under microwave irradiation for 15 minutes. A further quantity of 2,4-dichlorophenylboronic acid (0.099 g, 0.5 mmol) and potassium phosphate (0.095 g, 0.5 mmol) are added, the reaction mixture again blanketed under an atmosphere of argon, and the mixture is heated at 160° C. for a further 15 minutes. After cooling to room temperature the reaction mixture is diluted with dichloromethane (5 ml) and acidified with 2M aqueous hydrochloric acid. The organic phase is separated, dried over anhydrous magnesium sulfate, and filtered through a plug of silica gel. The filtrate is concentrated under reduced pressure and the residue is dissolved in N,N-dimethylformamide (approximately 1 ml) and purified by preparative reverse phase HPLC to afford 6-(2',4'-dichloro-4-ethylbiphenyl-3-yl)-2,2,4,4-tetramethyl-cyclohexane-1,3,5-trione as a colourless oil (80.6 mg).

Example 25

Preparation of 6-[5-(6-chloro-2-methylpyridin-3-yl)-2-ethylphenyl]-2,2,4,4-tetramethylcyclohexane-1,3,5-trione

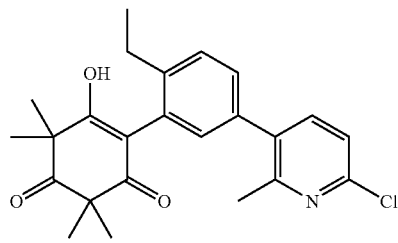 [SMILES: CCc1ccc(-c2ccc(Cl)nc2C)cc1C1=C(O)C(C)(C)C(=O)C(C)(C)C1=O]

A mixture of 6-(5-bromo-2-ethylphenyl)-2,2,4,4-tetramethylcyclohexane-1,3,5-trione (0.19 g, 0.5 mmol), cesium fluoride (0.24 g, 1.6 mmol), 6-chloro-2-methylpyridin-3-ylboronic acid (0.13 g, 0.8 mmol) and degassed 1,2-dimethoxyethane (1.7 ml) is stirred under nitrogen at room temperature for 30 minutes. [1,1'-Bis-(diphenylphosphino)ferrocene]dichloro-palladium(II) (0.034 g, 0.042 mmol) is added and the mixture is stirred at room temperature for 10 minutes and then heated at 80° C. overnight. After cooling to room temperature the reaction mixture is diluted with dichloromethane (5 ml) and water and filtered through diatomaceous earth. The filtrate is acidified with 2M aqueous hydrochloric acid, and the organic phase is separated, dried over anhydrous magnesium sulfate and concentrated in vacuo. The residue is dissolved in N,N-dimethylformamide (approximately 1 ml) and purified by preparative reverse phase HPLC to afford 6-[5-(6-chloro-2-methylpyridin-3-yl)-2-ethylphenyl]-2,2,4,4-tetramethylcyclohexane-1,3,5-trione as a pale brown solid (75.3 mg).

Example 26

Preparation of 3-(4'-dichloro-4-ethylbiphenyl-3-yl)bicyclo[3.2.1]nonane-2,4,9-trione

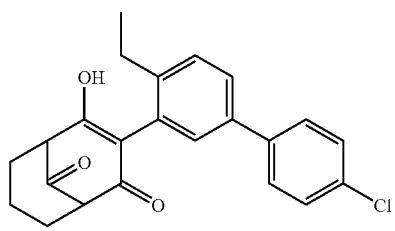 [SMILES: CCc1ccc(-c2ccc(Cl)cc2)cc1C1=C(O)C2CCCC(C1=O)C2=O]

4'-Chloro-4-ethylbiphenyl-3-yllead triacetate (0.94 g, 1.57 mmol) is cautiously added to a solution of bicyclo[3.2.1]nonane-2,4,9-trione (prepared according to the procedure of F. Effenberger et al., Chem Ber. (1986) 119, 3394-3404) (0.237 g, 1.42 mmol) and N,N-dimethylaminopyridine (0.87 g, 7.13 mmol) in a mixture of anhydrous chloroform (10 ml)

and toluene (2.5 ml) at 80° C. The mixture is stirred at 80° C. for 3 hours, then cooled to room temperature, diluted with dichloromethane and 2M aqueous hydrochloric acid is added. The mixture is filtered through diatomaceous earth to remove inorganic residues. The filter cake is washed with dichloromethane and the filtrates are combined, washed with brine, dried over anhydrous magnesium sulfate, and filtered. The filtrate is concentrated in vacuo and the residue is purified by flash column chromatography on silica gel and then further purified by preparative reverse phase HPLC to give 3-(4'-dichloro-4-ethylbiphenyl-3-yl)bicyclo[3.2.1]nonane-2,4,9-trione (0.087 g) as an off-white solid.

Additional compounds in Table B were prepared by analogues procedures, from appropriate starting materials.

TABLE B

| Compound Number | Structure | $^1$H nmr (CDCl$_3$ unless stated) or other physical data |
|---|---|---|
| B-1 | 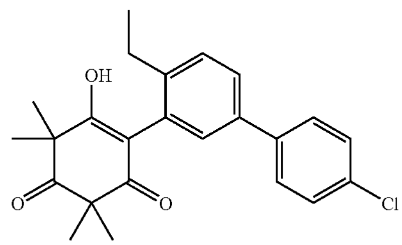 | δ 7.58 (dd, 1H), 7.52-7.59 (m, 2H), 7.45 (d, 1H), 7.41-7.38 (m, 2H), 7.25 (d, 1H), 5.74 (s, 1H), 2.54-2.43 (m, 2H), 1.56 (app. d, 6H), 1.46 (app. d, 6H), 1.15 (t, 3H). |
| B-2 | 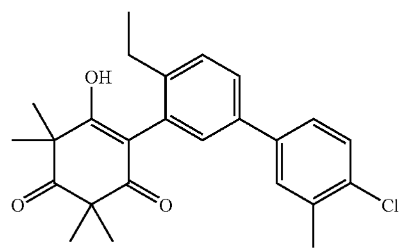 [SMILES: CCc1ccc(-c2ccc(Cl)c(C)c2)cc1C1=C(O)C(C)(C)C(=O)C(C)(C)C1=O] | δ 7.55 (dd, 1H), 7.44-7.29 (m, 4H), 7.22-7.26 (m, 1H), 5.91 (br. s, 1H), 2.52-2.39 (m, 2H), 2.42 (s, 3H), 1.55 (app. d, 6H), 1.45 (app. d, 6H), 1.14 (t, 3H). |
| B-3 | 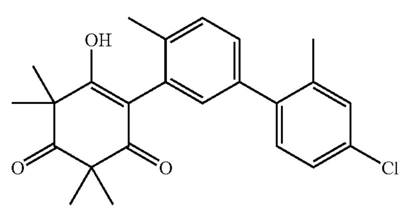 [SMILES: Cc1ccc(-c2ccc(Cl)cc2C)cc1C1=C(O)C(C)(C)C(=O)C(C)(C)C1=O] | δ 7.38 (m, 1H), 7.25 (m, 2H), 7.18 (m, 2H) 7.02 (s, 1H), 5.84 (b, 1H), 2.28 (s, 3H), 2.19 (s, 3H), 1.56 (s, 3H), 1.52 (s, 3H), 1.48 (s, 3H), 1.42 (s, 3H). |
| B-4 | 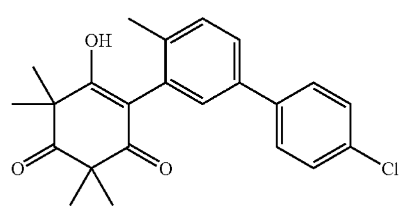 [SMILES: Cc1ccc(-c2ccc(Cl)cc2)cc1C1=C(O)C(C)(C)C(=O)C(C)(C)C1=O] | δ 7.55 (m, 3H), 7.43 (m, 3H), 7.3 (m, 1H), 5.9 (s, 1H), 2.23 (s, 3H), 1.61 (d, 6H), 1.5 (d, 6H). |
| B-5 | 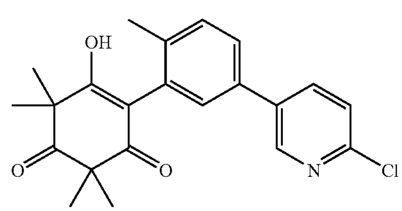 [SMILES: Cc1ccc(-c2ccc(Cl)nc2)cc1C1=C(O)C(C)(C)C(=O)C(C)(C)C1=O] | δ 8.37 (s, 1H), 7.99 (d, 1H), 7.8 (m, 1H), 7.34 (m, 2H), 7.12 (m, 1H), 1.82 (b, 6H), 1.5 (b, 6H). |
| B-6 | 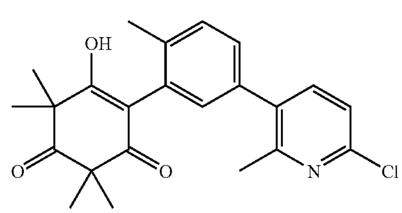 [SMILES: Cc1ccc(-c2ccc(Cl)nc2C)cc1C1=C(O)C(C)(C)C(=O)C(C)(C)C1=O] | δ 7.5 (d, 1H), 7.4 (d, 1H), 7.28 (dd, 1H), 7.2 (d, 1H), 7.04 (d, 1H) 2.5 (s, 3H), 2.2 (s, 3H), 1.56 (bd, 6H), 1.43 (bd, 6H). |

TABLE B-continued

| Compound Number | Structure | $^1$H nmr (CDCl$_3$ unless stated) or other physical data |
|---|---|---|
| B-7 | 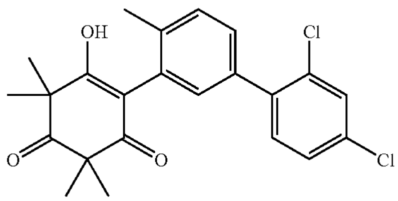 [SMILES: Cc1ccc(-c2ccc(Cl)cc2Cl)cc1C1=C(O)C(C)(C)C(=O)C(C)(C)C1=O] | δ 7.5 (s, 1H), 7.4 (s, 2H), 7.3 (m, 2H), 7.17 (s, 1H), 2.21 (s, 3H), 1.55 (b, 6H), 1.48 (s, 3H), 1.42 (s, 3H). |
| B-8 | 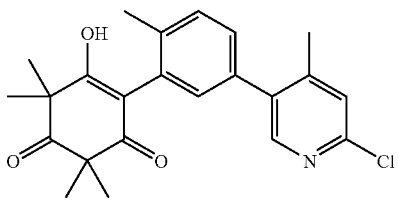 [SMILES: Cc1ccc(-c2cnc(Cl)cc2C)cc1C1=C(O)C(C)(C)C(=O)C(C)(C)C1=O] | δ 7.9 (s, 1H), 7.31 (d, 1H), 7.21 (s, 1H), 7.14 (d, 1H), 7.04 (s, 1H), 2.31 (s, 3H), 2.24 (s, 3H), 1.55 (d, 6H), 1.45 (d, 6H). |
| B-9 | 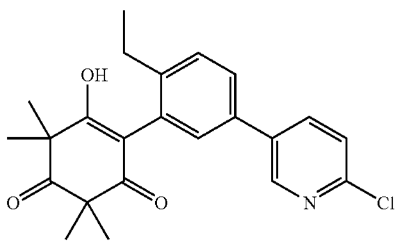 | δ 8.32 (d, 1H), 7.52-7.38 (m, 1H), 7.83 (dd, 1H), 7.34 (d, 1H), 7.29-7.21 (m, 2H), 6.03-5.67 (m, 1H), 2.58-2.35 (m, 2H), 1.65-1.38 (m, 12H), 1.16 (t, 2.3H), 1.10 (t, 0.7H). |
| B-10 | 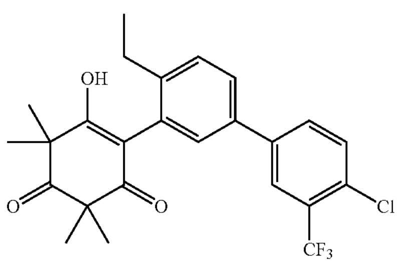 [SMILES: CCc1ccc(-c2ccc(Cl)c(C(F)(F)F)c2)cc1C1=C(O)C(C)(C)C(=O)C(C)(C)C1=O] | δ 7.87 (d, 1H), 7.67 (dd, 1H), 7.61-7.53 (m, 2H), 7.51-7.46 (m, 1H), 7.31-7.23 (m, 1H), 5.73 (s, 1H), 2.50 (m, 2H), 1.62-1.52 (m, 6H), 1.46 (d, 6H), 1.16 (t, 3H). |
| B-11 | 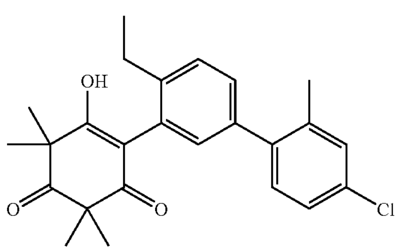 [SMILES: CCc1ccc(-c2ccc(Cl)cc2C)cc1C1=C(O)C(C)(C)C(=O)C(C)(C)C1=O] | δ 7.42 (d, 1H), 7.32 (dd, 1H), 7.29-7.24 (m, 1H), 7.23-7.14 (m, 2H), 7.03-6.99 (m, 1H), 5.84 (br. s, 1H), 2.50 (m, 2H), 2.27 (s, 3H), 1.55 (d, 6H), 1.44 (d, 6H), 1.17 (t, 3H). |
| B-12 | 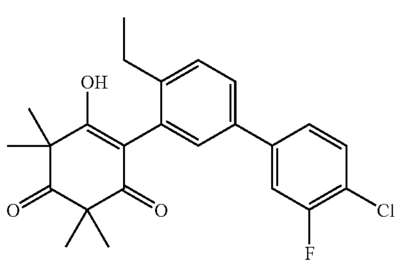 [SMILES: CCc1ccc(-c2ccc(Cl)c(F)c2)cc1C1=C(O)C(C)(C)C(=O)C(C)(C)C1=O] | δ 7.57 (dd, 1H), 7.48-7.41 (m, 2H), 7.38-7.28 (m, 2H), 7.25-7.23 (m, 1H), 5.85 (s, 1H), 2.49 (m, 2H), 1.57 (d, 6H), 1.46 (d, 6H), 1.16 (t, 3H),. |

TABLE B-continued

| Compound Number | Structure | ¹H nmr (CDCl₃ unless stated) or other physical data |
|---|---|---|
| B-13 | 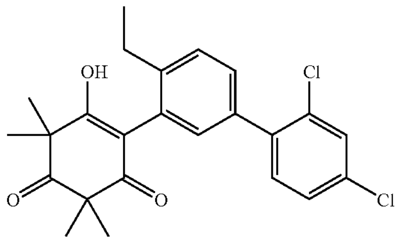 [SMILES: CCc1ccc(-c2ccc(Cl)cc2Cl)cc1C1=C(O)C(C)(C)C(=O)C(C)(C)C1=O] | δ 7.49 (s, 1H), 7.44 (s, 2H), 7.34-7.29 (m, 2H), 7.14 (s, 1H), 6.02-5.91 (m, 1H), 2.50 (m, 2H), 1.55 (d, 6H), 1.45 (d, 6H), 1.17 (t, 3H). |
| B-14 | 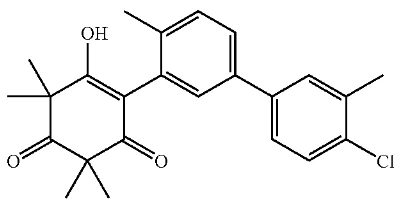 | δ 7.51 (m, 1H), 7.4 (m, 1H), 7.31 (m, 1H), 7.29 (s, 1H), 5.87 (s, 1H), 2.42 (s, 3H), 2.19 (s, 3H), 1.57 (s, 6H), 1.46 (d, 6H). |
| B-15 | 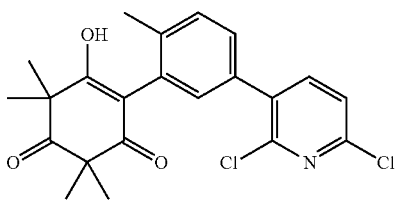 [SMILES: Cc1ccc(-c2ccc(Cl)nc2Cl)cc1C1=C(O)C(C)(C)C(=O)C(C)(C)C1=O] | δ 7.68 (d, 1H), 7.41 (m, 2H), 7.34 (d, 1H), 7.18 (d, 1H), 6.1 (b, 1H), 2.21 (s, 3H) 1.4-1.55 (br, 12H). |
| B-16 | 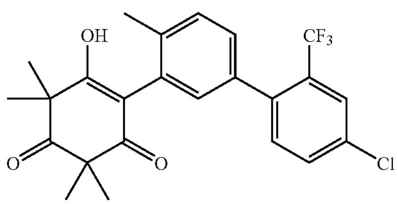 [SMILES: Cc1ccc(-c2ccc(Cl)cc2C(F)(F)F)cc1C1=C(O)C(C)(C)C(=O)C(C)(C)C1=O] | δ 7.72 (d, 1H), 7.53 (dd, 1H), 7.38 (d, 1H), 7.32 (d, 1H), 7.28 (m, 1H), 7.05 (s, 1H), 5.9 (s, 1H), 2.21 (s, 3H), 1.56 s, 3H), 1.52 (s, 3H), 1.47 (s, 3H), 1.4 (s, 3H). |
| B-17 | 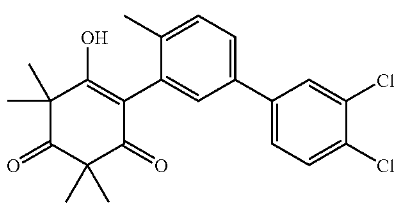 [SMILES: Cc1ccc(-c2ccc(Cl)c(Cl)c2)cc1C1=C(O)C(C)(C)C(=O)C(C)(C)C1=O] | δ 7.69 (s, 1H), 7.51 (m, 2H), 7.42 (m, 2H), 7.3 (s, 1H), 5.89 (s, 1H), 2.25 (s, 3H), 1.6 (br, 6H), 1.51 (br, 6H). |
| B-18 | 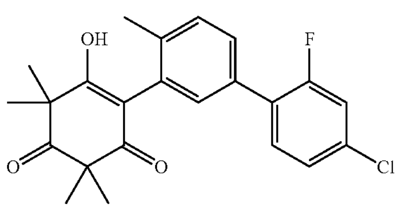 [SMILES: Cc1ccc(-c2ccc(Cl)cc2F)cc1C1=C(O)C(C)(C)C(=O)C(C)(C)C1=O] | δ 7.53 (m, 1H), 7.45 (m, 2H), 7.28 (m, 3H), 6.0 (s, 1H), 2.24 (s, 3H), 1.6 (d, 6H), 1.5 (d, 6H). |
| B-19 | 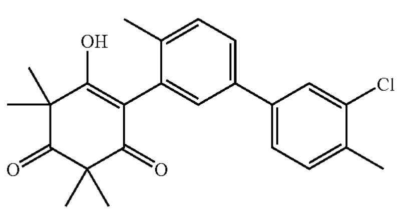 [SMILES: Cc1ccc(-c2ccc(C)c(C3=C(O)C(C)(C)C(=O)C(C)(C)C3=O)c2)cc1Cl] | δ 7.52 (m, 2H), 7.37 (m, 2H), 7.28 (m, 2H), 5.87 (s, 1H), 2.4 (s, 3H), 2.18 (s, 3H), 1.57 (d, 6H), 1.46 (d, 6H). |

TABLE B-continued

| Compound Number | Structure | ¹H nmr (CDCl₃ unless stated) or other physical data |
|---|---|---|
| B-20 | 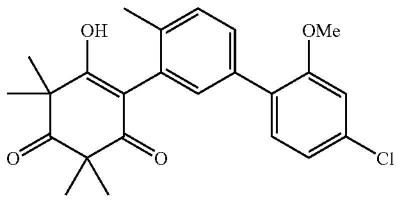 [SMILES: COc1cc(Cl)ccc1-c1ccc(C)c(C2=C(O)C(C)(C)C(=O)C(C)(C)C2=O)c1] | δ 7.48 (m, 1H), 7.4 (m, 1H), 7.29 (m, 1H), 7.22 (s, 1H), 7.03 (d, 1H), 6.99 (s, 1H), 6.29 (s, 1H), 3.86 (s, 3H), 2.22 (s, 3H), 1.61 (d, 6H), 1.51 (s, 3H), 1.48 (s, 3H) |
| B-21 | 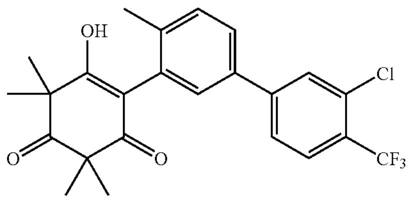 [SMILES: Cc1ccc(-c2ccc(C(F)(F)F)c(Cl)c2)cc1C1=C(O)C(C)(C)C(=O)C(C)(C)C1=O] | δ 7.77 (m, 2H), 7.59 (m, 2H), 7.49 (s, 1H), 7.34 (s, 1H), 5.88 (b, 1H), 2.26 (s, 3H), 1.62 (d, 6H), 1.5 (d, 6H). |
| B-22 | 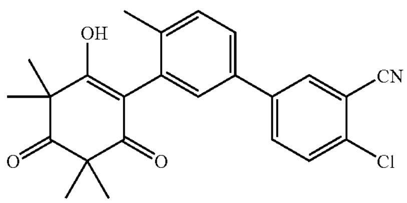 [SMILES: Cc1ccc(-c2ccc(Cl)c(C#N)c2)cc1C1=C(O)C(C)(C)C(=O)C(C)(C)C1=O] | δ 7.85 (s, 1H), 7.71 (dd, 1H), 7.55 (d, 1H), 7.5 (dd, 1H), 7.43 (d, 1H), 7.26 (s, 1H), 5.8 (b, 1H), 2.2 (s, 3H), 1.55 (d, 6H), 1.46 (d, 6H). |
| B-23 | 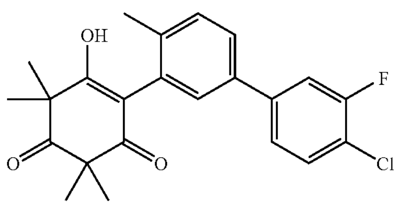 [SMILES: Cc1ccc(-c2ccc(Cl)c(F)c2)cc1C1=C(O)C(C)(C)C(=O)C(C)(C)C1=O] | δ 7.51 (d, 1H), 7.42 (m, 2H), 7.35 (dd, 1H), 7.3 (m, 2H), 5.83 (s, 1H), 2.19 (s, 3H), 1.57 (d, 6H), 1.46 (s, 6H). |
| B-24 | 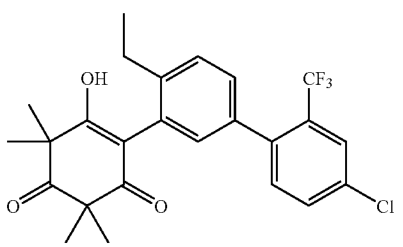 | δ 7.73-7.71 (m, 1H), 7.54 (d, 1H), 7.42 (d, 1H), 7.36-7.30 (m, 2H), 7.03 (s, 1H), 5.80 (br. s, 1H), 2.56-2.44 (m, 2H), 1.54 (d, 6H), 1.44 (d, 6H), 1.18 (t, 3H),. |
| B-25 | 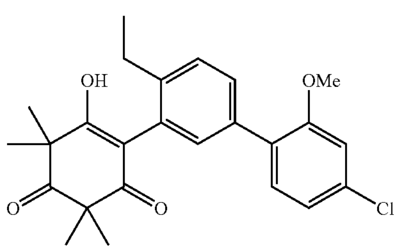 [SMILES: CCc1ccc(-c2ccc(Cl)cc2OC)cc1C1=C(O)C(C)(C)C(=O)C(C)(C)C1=O] | δ 7.50 (d, 1H), 7.40 (d, 1H), 7.27-7.23 (m, 1H), 7.15-7.18 (m, 1H), 7.02-6.98 (m, 1H), 6.96-6.93 (m, 1H), 6.16-6.04 (m, 1H), 3.81 (s, 3H), 2.54-2.41 (m, 2H), 1.55 (d, 6H), 1.45 (d, 6H), 1.15 (t, 3H). |
| B-26 | 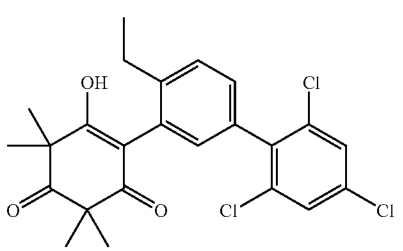 [SMILES: CCc1ccc(-c2c(Cl)cc(Cl)cc2Cl)cc1C1=C(O)C(C)(C)C(=O)C(C)(C)C1=O] | δ 7.47 (d, 1H), 7.45-7.39 (m, 2H), 7.30-7.21 (m, 1H), 6.99-6.95 (m, 1H), 6.01-5.76 (m, 1H), 2.58-2.43 (m, 2H), 1.52-1.60 (m, 6H), 1.44 (d, 6H), 1.19 (t, 3H). |

TABLE B-continued

| Compound Number | Structure | ¹H nmr (CDCl₃ unless stated) or other physical data |
|---|---|---|
| B-27 | 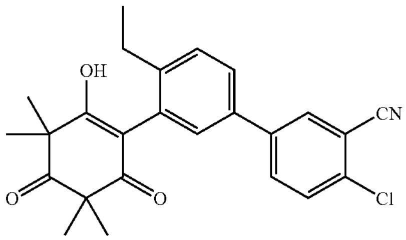 [SMILES: CCc1ccc(-c2ccc(Cl)c(C#N)c2)cc1C1=C(O)C(C)(C)C(=O)C(C)(C)C1=O] | δ 7.86-7.84 (m, 1H), 7.74 (dd, 1H), 7.58-7.53 (m, 2H), 7.50-7.47 (m, 1H), 7.29-7.23 (m, 1H), 5.92 (br. s, 1H), 2.57-2.44 (m, 2H), 1.60-1.55 (m, 6H), 1.47 (d, 6H), 1.16 (t, 3H). |
| B-28 | 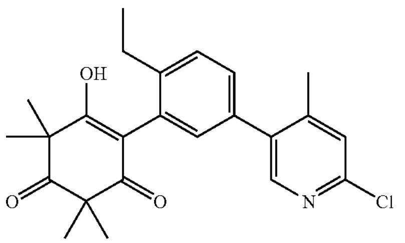 [SMILES: CCc1ccc(-c2cnc(Cl)cc2C)cc1C1=C(O)C(C)(C)C(=O)C(C)(C)C1=O] | δ 8.10-7.94 (m, 1H), 7.50-7.35 (m, 1H), 7.29-7.20 (m, 2H), 7.03-7.00 (m, 1H), 6.58-6.31 (m, 1H), 2.59-2.48 (m, 2H), 2.30 (s, 3H), 1.56 (d, 6H), 1.45 (d, 6H), 1.17 (t, 3H). |
| B-29 | 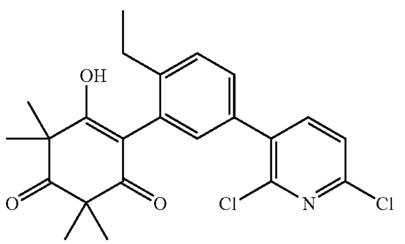 [SMILES: CCc1ccc(-c2ccc(Cl)nc2Cl)cc1C1=C(O)C(C)(C)C(=O)C(C)(C)C1=O] | δ 7.68 (d, 1H), 7.50-7.44 (m, 2H), 7.34 (d, 1H), 7.19-7.15 (m, 1H), 6.01-5.95 (m, 1H), 2.57-2.45 (m, 2H), 1.56 (d, 6H), 1.45 (d, 6H), 1.18 (t, 3H). |
| B-30 | 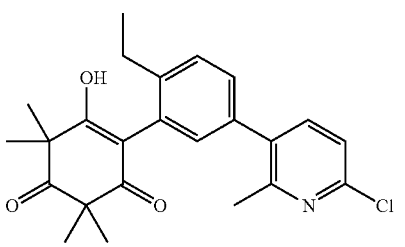 [SMILES: CCc1ccc(-c2ccc(Cl)nc2C)cc1C1=C(O)C(C)(C)C(=O)C(C)(C)C1=O] | δ 7.51 (d, 1H), 7.45 (d, 1H), 7.34 (dd, 1H), 7.22 (d, 1H), 7.04-7.00 (m, 1H), 6.04-5.82 (m, 1H), 2.58-2.44 (m, 2H), 2.52 (s, 3H), 1.56 (d, 6H), 1.45 (d, 6H), 1.18 (t, 3H). |
| B-31 | 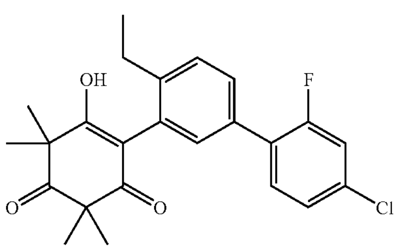 | δ 7.54 (d, 1H), 7.45 (d, 1H), 7.38 (t, 1H), 7.23-7.16 (m, 3H), 5.96-5.84 (m, 1H), 2.56-2.42 (m, 2H), 1.56 (d, 6H), 1.45 (d, 6H), 1.16 (t, 3H), |
| B-32 | 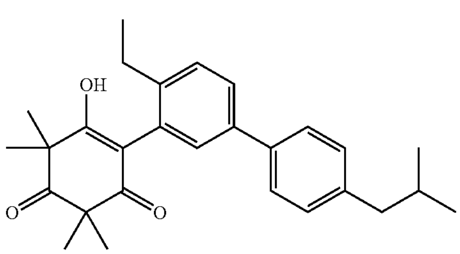 [SMILES: CCc1ccc(-c2ccc(CC(C)C)cc2)cc1C1=C(O)C(C)(C)C(=O)C(C)(C)C1=O] | δ 7.62-7.58 (m, 1H), 7.48 (d, 2H), 7.42 (d, 1H), 7.29-7.25 (m, 1H), 7.20 (d, 2H), 6.03-5.96 (m, 1H), 2.54-2.41 (m, 2H), 2.51 (d, 2H), 1.94-1.83 (m, 1H), 1.56 (d, 6H), 1.46 (d, 6H), 1.15 (t, 3H), 0.93 (d, 6H). |

TABLE B-continued

| Compound Number | Structure | ¹H nmr (CDCl₃ unless stated) or other physical data |
|---|---|---|
| B-33 | 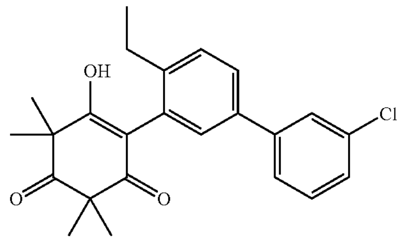 [SMILES: CCc1ccc(-c2cccc(Cl)c2)cc1C1=C(O)C(C)(C)C(=O)C(C)(C)C1=O] | δ 7.61-7.54 (m, 2H), 7.45 (d, 2H), 7.38-7.29 (m, 2H), 7.27-7.25 (m, 1H), 5.91-5.84 (m, 1H), 2.55-2.42 (m, 2H), 1.59-1.54 (m, 6H). 1.46 (d, 6H), 1.16 (t, 3H). |
| B-34 | 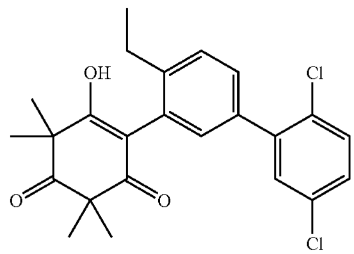 [SMILES: CCc1ccc(-c2cc(Cl)ccc2Cl)cc1C1=C(O)C(C)(C)C(=O)C(C)(C)C1=O] | δ 7.47-7.44 (m, 2H), 7.41-7.36 (m, 2H), 7.26-7.23 (m, 1H), 7.15 (s, 1H), 6.00-5.94 (m, 1H), 2.57-2.44 (m, 2H), 1.55 (d, 6H), 1.45 (d, 6H), 1.17 (t, 3H). |
| B-35 | 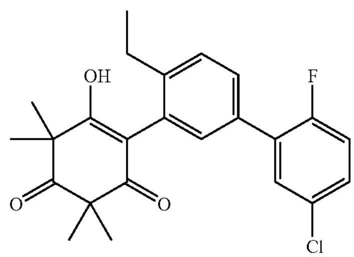 [SMILES: CCc1ccc(-c2cc(Cl)ccc2F)cc1C1=C(O)C(C)(C)C(=O)C(C)(C)C1=O] | δ 7.56 (d, 1H), 7.46 (d, 1H), 7.43 (dd, 1H), 7.29-7.21 (m, 2H), 7.08 (t, 1H), 5.99-5.90 (m, 1H), 2.56-2.41 (m, 2H), 1.57 (d, 6H), 1.46 (d, 6H), 1.16 (t, 3H). |
| B-36 | 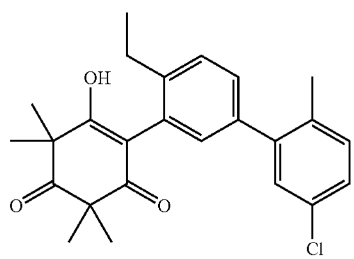 [SMILES: CCc1ccc(-c2cc(Cl)ccc2C)cc1C1=C(O)C(C)(C)C(=O)C(C)(C)C1=O] | δ 7.42 (d, 1H), 7.33 (dd, 1H), 7.25-7.16 (m, 3H), 7.03-7.00 (m, 1H), 5.87 (s, 1H), 2.57-2.42 (m, 2H), 2.25 (s, 3H), 1.55 (d, 6H), 1.45 (d, 6H), 1.17 (t, 3H). |
| B-37 | 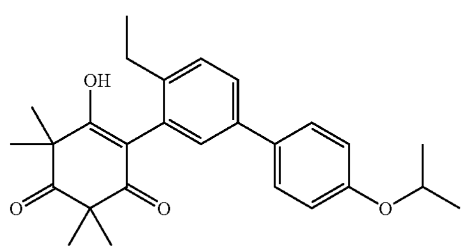 [SMILES: CCc1ccc(-c2ccc(OC(C)C)cc2)cc1C1=C(O)C(C)(C)C(=O)C(C)(C)C1=O] | δ 7.54-7.58 (m, 1H), 7.48 (d, 2H), 7.40 (d, 1H), 7.24-7.22 (m, 1H), 6.94 (d, 2H), 6.03-5.95 (m, 1H), 4.58 (quintet, 1H), 2.52-2.39 (m, 2H), 1.56 (d, 6H), 1.46 (d, 6H), 1.36 (d, 6H), 1.15 (t, 3H). |
| B-38 | 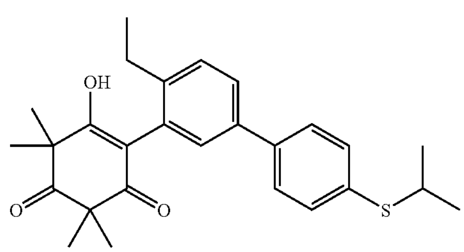 [SMILES: CCc1ccc(-c2ccc(SC(C)C)cc2)cc1C1=C(O)C(C)(C)C(=O)C(C)(C)C1=O] | δ 7.61-7.58 (m, 1H), 7.51 (d, 2H), 7.46-7.42 (m, 3H), 7.28-7.26 (m, 1H), 5.87 (br. s, 1H), 3.41 (quintet, 1H), 2.54-2.41 (m, 2H), 1.56 (d, 6H), 1.46 (d, 6H), 1.32 (d, 6H), 1.15 (t, 3H). |

TABLE B-continued

| Compound Number | Structure | ¹H nmr (CDCl₃ unless stated) or other physical data |
|---|---|---|
| B-39 | 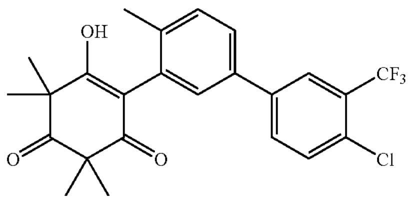 [SMILES: Cc1ccc(-c2ccc(Cl)c(C(F)(F)F)c2)cc1C1=C(O)C(C)(C)C(=O)C(C)(C)C1=O] | δ 7.91 (s, 1H), 7.71 (dd, 1H), 7.6 (m, 2H), 7.49 (d, 1H), 7.32 (s, 1H), 5.89 (s, 1H), 2.26 (s, 3H), 1.59 (d, 6H), 1.56 (d, 6H). |
| B-40 | 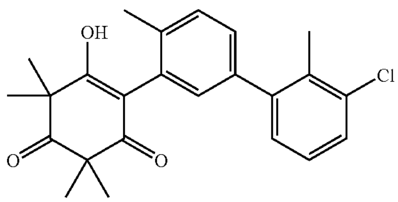 [SMILES: Cc1ccc(-c2cccc(Cl)c2C)cc1C1=C(O)C(C)(C)C(=O)C(C)(C)C1=O] | δ 7.38 (m, 2H), 7.27 (d, 1H), 7.13 (m, 2H), 7.02 (s, 1H), 5.84 (s, 1H), 2.3 (s, 3H), 2.2 (s, 3H), 1.56 (s, 3H), 1.52 (s, 3H), 1.47 (s, 3H), 1.42 (s, 3H). |
| B-41 | 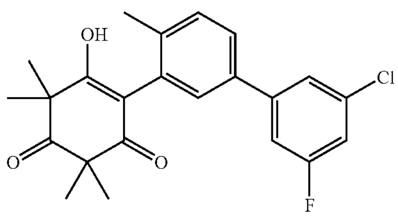 [SMILES: Cc1ccc(-c2cc(F)cc(Cl)c2)cc1C1=C(O)C(C)(C)C(=O)C(C)(C)C1=O] | δ 7.5 (d, 1H), 7.42 (d, 1H), 7.35 (s, 1H), 7.25 (d, 1H), 7.17 (m, 1H), 7.06 (m, 1H), 5.78 (s, 1H), 2.2 (s, 3H), 1.56 (d, 6H), 1.47 (d, 6H). |
| B-42 | 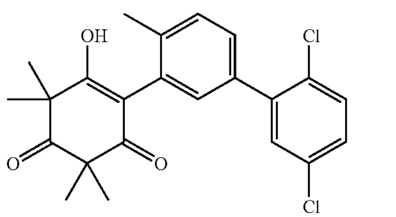 [SMILES: Cc1ccc(-c2cc(Cl)ccc2Cl)cc1C1=C(O)C(C)(C)C(=O)C(C)(C)C1=O] | δ 7.4 (m, 4H), 7.24 (m, 1H), 7.17 (s, 1H), 6.0 (s, 1H), 2.21 (s, 3H), 1.54 (d, 6H), 1.45 (d, 6H). |
| B-43 | 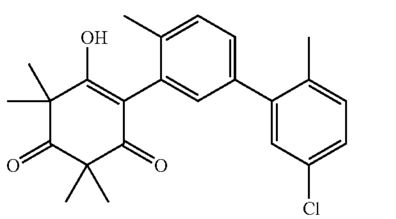 [SMILES: Cc1ccc(-c2cc(Cl)ccc2C)cc1C1=C(O)C(C)(C)C(=O)C(C)(C)C1=O] | δ 7.38 (d, 1H), 7.25 (m, 1H), 7.2 (m, 3H), 7.02 (s, 1H), 5.84 (s, 1H), 2.23 (s, 3H), 2.19 (s, 3H), 1.54 (d, 6H), 1.46 (s, 3H), 1.43 (s, 3H). |
| B-44 | 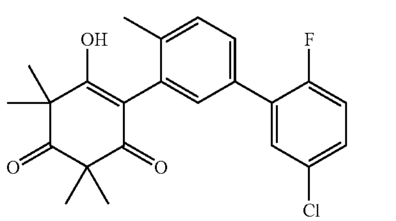 [SMILES: Cc1ccc(-c2cc(Cl)ccc2F)cc1C1=C(O)C(C)(C)C(=O)C(C)(C)C1=O] | δ 7.5 (m, 1H), 7.41 (d, 2H), 7.27 (m, 2H), 7.08 (t, 1H), 5.9 (s, 1H), 2.2 (s, 3H), 1.54 (s, 6H), 1.46 (s, 3H), 1.43 (s, 3H). |
| B-45 | 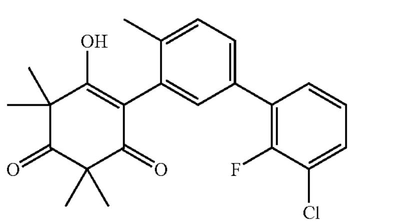 [SMILES: Cc1ccc(-c2cccc(Cl)c2F)cc1C1=C(O)C(C)(C)C(=O)C(C)(C)C1=O] | δ 7.49 (d, 1H), 7.41 (m, 1H), 7.37 (m, 1H), 7.32 (m, 1H), 7.28 (s, 1H), 7.13 (m, 1H), 5.94 (s, 1H), 2.21 (s, 3H), 1.54 (s, 6H), 1.47 (s, 3H), 1.42 (s, 3H). |

TABLE B-continued

| Compound Number | Structure | ¹H nmr (CDCl₃ unless stated) or other physical data |
|---|---|---|
| B-46 | 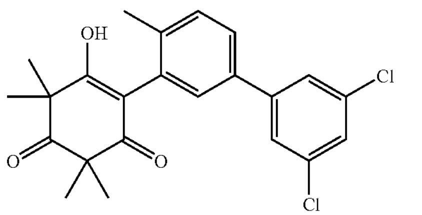 [SMILES: Cc1ccc(-c2cc(Cl)cc(Cl)c2)cc1C1=C(O)C(C)(C)C(=O)C(C)(C)C1=O] | δ 7.51 (d, 1H), 7.42 (m, 3H), 7.32 (s, 1H), 7.27 (s, 1H), 5.8 (s, 1H), 2,2 (s, 3H), 1.56 (s, 6H), 1.47 (d, 6H). |
| B-47 | 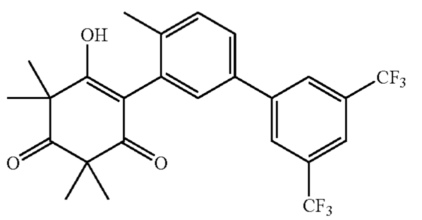 [SMILES: Cc1ccc(-c2cc(C(F)(F)F)cc(C(F)(F)F)c2)cc1C1=C(O)C(C)(C)C(=O)C(C)(C)C1=O] | δ 7.99 (s, 2H), 7.85 (s, 1H), 7.59 (m, 1H), 7.49 (m, 1H), 7.31 (s, 1H), 2.2 (s, 3H), 1.55 (b, 6H), 1.48 (b, 6H). |
| B-48 | 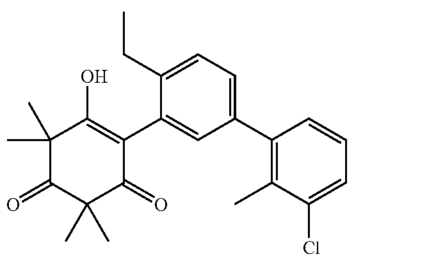 [SMILES: CCc1ccc(-c2cccc(Cl)c2C)cc1C1=C(O)C(C)(C)C(=O)C(C)(C)C1=O] | δ 7.42 (d, 1H), 7.38-7.34 (m, 1H), 7.32 (dd, 1H), 7.16 (d, 1H), 7.15 (s, 1H), 7.01 (d, 1H), 5.86 (br. s, 1H), 2.57-2.43 (m, 2H), 2.31 (s, 3H), 1.55 (d, 6H), 1.44 (d, 6H), 1.18 (t, 3H). |
| B-49 | 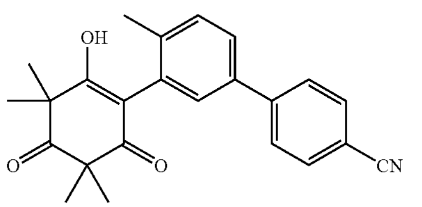 [SMILES: Cc1ccc(-c2ccc(C#N)cc2)cc1C1=C(O)C(C)(C)C(=O)C(C)(C)C1=O] | δ 7.69 (q, 4H), 7.57 (dd, 1H), 7.46 (d, 1H), 7.31 (s, 1H), 5.81 (s, 1H), 2.21 (s, 3H), 1.57 (s, 6H), 1.46 (s, 6H). |
| B-50 | 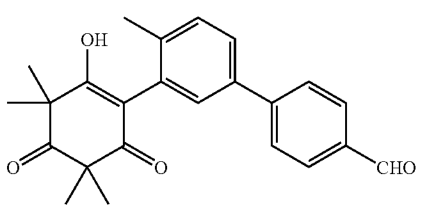 [SMILES: Cc1ccc(-c2ccc(C=O)cc2)cc1C1=C(O)C(C)(C)C(=O)C(C)(C)C1=O] | δ 10.04 (s, 1H), 7.93 (d, 2H), 7.73 (d, 2H), 7.61 (dd, 1H), 7.45 (d, 1H), 7.37 (s, 1H) 5.88 (b, 1H), 2.21 (s, 3H), 1.56 (d, 6H), 1.47 (d, 6H). |
| B-51 | 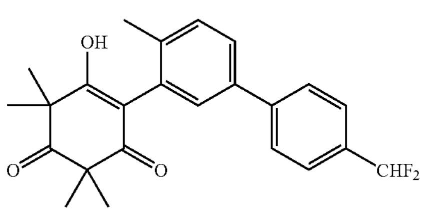 [SMILES: Cc1ccc(-c2ccc(C(F)F)cc2)cc1C1=C(O)C(C)(C)C(=O)C(C)(C)C1=O] | δ 7.65 (m, 2H), 7.58 (m, 3H), 7.43 (d, 1H), 7.31 (s, 1H), 6.82-6.54 (t, 1H), 5.84 (s, 1H), 2.2 (s, 3H), 1.57 (d, 6H), 1.46 (d, 6H) |
| B-52 | 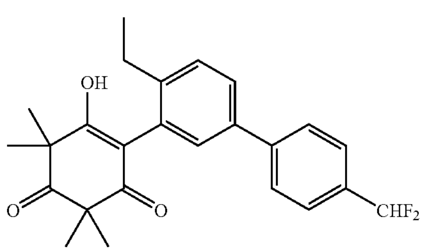 [SMILES: CCc1ccc(-c2ccc(C(F)F)cc2)cc1C1=C(O)C(C)(C)C(=O)C(C)(C)C1=O] | δ 7.66 (app. d, 2H), 7.62 (dd, 1H), 7.57 (app. d, 2H), 7.47 (d, 1H), 7.30 (d, 1H), 6.69 (t, 1H), 5.80 (br. s, 1H), 2.55-2.44 (m, 2H), 1.57 (br. s, 6H), 1.47 (app. d, 6H), 1.16 (t, 3H) |

TABLE B-continued

| Compound Number | Structure | $^1$H nmr (CDCl$_3$ unless stated) or other physical data |
|---|---|---|
| B-53 | 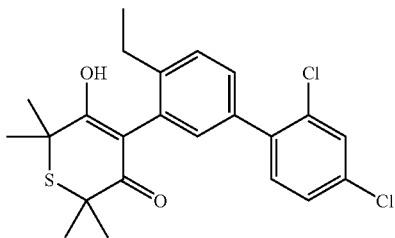 | m.p. 79.5° C.; LC-MS (ES+) 381 (M + H)$^+$ |
| B-54 | 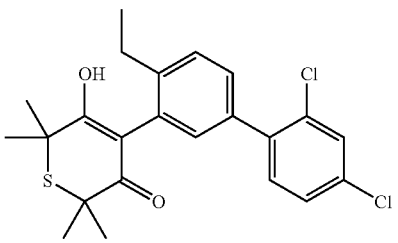 | δ 7.65-7.50 (m, 3H), 7.40-7.29 (m, 3H), 6.71 (t, 1H), 5.93 (br. s, 1H), 2.61-2.48 (m, 2H), 1.61-1.60 (m, 6H), 1.51-1.47 (m, 6H), 1.23-1.18 (m, 3H). |

Example 27

Preparation of 4-(2',4'-dichloro-4-ethylbiphenyl-3-yl)-2,2,6,6-tetramethyl-thiopyran-3,5-dione Step 1: Preparation of 4-(5-bromo-2-ethylphenyl)-2,2,6,6-tetramethylthiopyran-3,5-dione

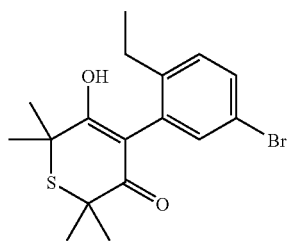

To a solution of 2,2,6,6-tetramethylthiopyran-3,5-dione (prepared according to the procedure of E. Er and P. Margaretha, Helvetica Chimica Acta (1992), 75(7), 2265-69) (1.8 g, 9.9 mmol) and N,N-dimethylaminopyridine (5.3 g, 4.34 mmol) in chloroform (60 ml), is added toluene (18 ml) then 5-bromo-2-ethylphenyllead triacetate (6.2 g, 1.09 mmol) in one portion. The resulting mixture is heated at reflux for 2 hours, then allowed to cool to ambient temperature, diluted with dichloromethane and 1M aqueous hydrochloric acid, and the organic phase is separated. The organic phase is concentrated under reduced pressure, and the residue is purified by flash chromatography on silica gel (hexane/ethyl acetate 95:5 to 7:3 ratio), giving 4-(5-bromo-2-ethylphenyl)-2,2,6,6-tetramethylthiopyran-3,5-dione (2.42 g) as an orange solid.

Step 2: Preparation of 4-(2',4'-dichloro-4-ethylbiphenyl-3-yl)-2,2,6,6-tetramethyl-thiopyran-3,5-dione To a microwave vial is added 4-(5-bromo-2-methylphenyl)-2,2,6,6-tetramethylthiopyran-3,5-dione (500 mg, 1.36 mmol), 2,4-dichlorophenylboronic acid (389 mg, 2.05 mmol), [1,1-bis(diphenyl-phosphino)ferrocene]palladium (II) chloride (111 mg, 0.000136 mol), and cesium fluoride (620 mg, 0.00408 mol), followed by degassed 1,2-dimethoxyethane (3 ml) under an atmosphere of nitrogen. The mixture is then stirred for 5 minutes at ambient temperature, then heated at 160° C. under microwave irradiation for 15 minutes. The reaction mixture is cooled to room temperature, and partitioned between 2M aqueous hydrochloric acid and dichloromethane. The organic phase is separated and concentrated under reduced pressure. The residue is purified by preparative reverse phase HPLC to give 4-(2',4'-dichloro-4-ethylbiphenyl-3-yl)-2,2,6,6-tetramethyl-thiopyran-3,5-dione (264 mg) as a brown gum.

Example 28

Preparation of 4-(2',4'-dichloro-4-ethylbiphenyl-3-yl)-2,2,6,6-tetramethyl-1-oxothiopyran-3,5-dione

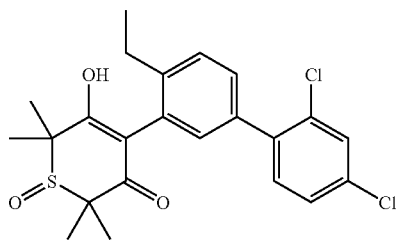

A mixture of 4-(2',4'-dichloro-4-ethylbiphenyl-3-yl)-2,2,6,6-tetramethylthiopyran-3,5-dione (79 mg, 0.1816 mmol), peracetic acid (1.8 g, 7.2 mmol, 36-40% solution in acetic acid) and dichloromethane (0.23 ml) is stirred for 4 hours at ambient temperature. The reaction mixture is partitioned between water and dichloromethane, and the organic phase is separated then concentrated under reduced pressure. The residue is purified by preparative reverse phase HPLC to give 4-(2',4'-dichloro-4-ethylbiphenyl-3-yl)-2,2,6,6-tetramethyl-1-oxothiopyran-3,5-dione (32.9 mg) as a clear gum.

Example 29

Preparation of 4-(2',4'-dichloro-4-ethylbiphenyl-3-yl)-2,2,6,6-tetramethyl-1,1-dioxothiopyran-3,5-dione

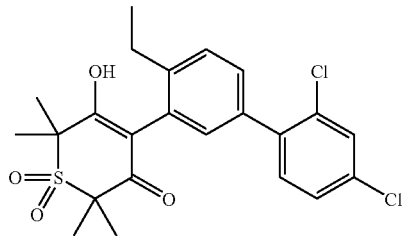 [SMILES: CCc1ccc(-c2ccc(Cl)cc2Cl)cc1C1=C(O)C(C)(C)S(=O)(=O)C(C)(C)C1=O]

A mixture of 4-(2',4'-dichloro-4-ethylbiphenyl-3-yl)-2,2,6,6-tetramethylthiopyran-3,5-dione (79 mg, 0.1816 mmol) and oxone (446 mg, 0.726 mmol) is stirred at ambient temperature for 20 hours as a solution in methanol/water (1 ml, 1:1 ratio). The reaction mixture is then partitioned between water and dichloromethane, the organic phase is separated and concentrated under reduced pressure. The residue is purified by preparative reverse phase HPLC to give 4-(2',4'-dichloro-4-ethylbiphenyl-3-yl)-2,2,6,6-tetramethyl-1,1-di-oxo-thiopyran-3,5-dione (24.6 mg) as a clear gum.

Additional compounds in Table C were prepared by analogues procedures, from appropriate starting materials.

TABLE C

| Compound Number | Structure | $^1$H nmr (CDCl$_3$ unless stated) or other physical data |
|---|---|---|
| C-1 | 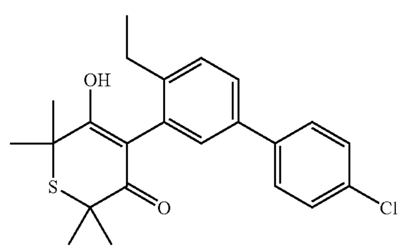 | δ 7.55 (dd, 1H), 7.51-7.48 (m, 2H), 7.43-7.38 (m, 1H), 7.43-7.38 (m, 2H), 7.21 (d, 1H), 5.42 (br. s, 1H), 2.53-2.42 (m, 2H), 1.72 (app. d, 6H), 1.60 (app. d, 6H), 1.15 (t, 3H). |
| C-2 | 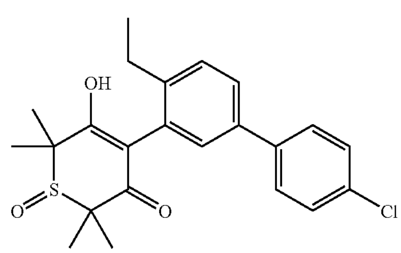 [SMILES: CCc1ccc(-c2ccc(Cl)cc2)cc1C1=C(O)C(C)(C)S(=O)C(C)(C)C1=O] | δ 7.58 (dd, 1H), 7.50 (d, 2H), 7.40 (d, 2H), 7.46 (d, 1H), 7.18 (d, 1H), 2.48 (m, 2H), 1.69 (s, 12H), 1.16 (t, 3H). |
| C-3 | 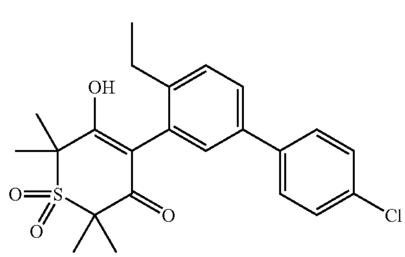 [SMILES: CCc1ccc(-c2ccc(Cl)cc2)cc1C1=C(O)C(C)(C)S(=O)(=O)C(C)(C)C1=O] | δ 7.60 (dd, 1H), 7.49 (d, 2H), 7.46 (d, 1H), 7.40 (d, 2H), 7.23 (d, 1H), 5.78 (s, 1H), 2.44 (m, 2H), 1.86 (s, 6H), 1.74 (s, 6H), 1.15 (t, 3H). |

TABLE C-continued

| Compound Number | Structure | ¹H nmr (CDCl₃ unless stated) or other physical data |
|---|---|---|
| C-4 | 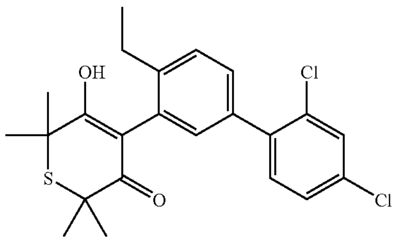 | δ 7.52-7.31 (m, 5H), 7.14 (s, 0.65H, isomer A), 7.08 (s, 0.25H, isomer B), 5.87 (br. s, 0.25H, isomer B), 5.67 (br. s, 0.65H, isomer A), 2.62-2.48 (m, 2H), 1.76-1.59 (m, 12H), 1.28-1.19 (m, 3H) |
| C-5 | 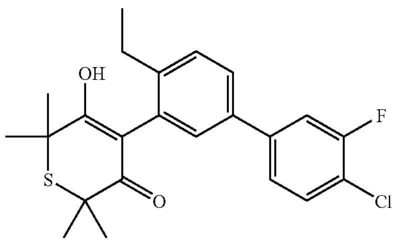 | δ 7.59-7.31 (m, 5H); 7.25 (d, 0.7H, isomer A), 7.19 (d, 0.3H, isomer B), 5.90 (br. s, 0.3H, isomer B), 5.54 (br. s, 0.7H, isomer A), 2.62-2.47 (m, 2H); 1.17-1.61 (m, 12H); 1.26-1.18 (m, 3H) |
| C-6 | 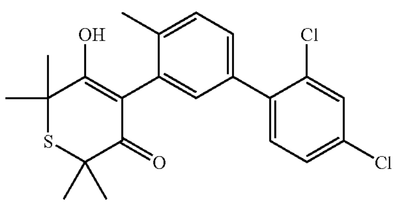 | Methanol-d₄ δ 7.55 (s, 1H); 7.40 (s, 2H); 7.35 (s, 2H); 7.03 (s, 1H); 2.18 (s, 3H); 1.65 (s, 6H), 1.60 (s, 6H) |
| C-7 | 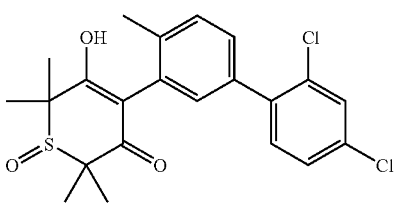 [SMILES: Cc1ccc(-c2ccc(Cl)cc2Cl)cc1C1=C(O)C(C)(C)S(=O)C(C)(C)C1=O] | Methanol-d₄ δ 7.53 (s, 1H), 7.36 (s, 2H), 7.34 (s, 2H), 7.09 (s, 0.5H, isomer A), 7.00 (s, 0.5H, isomer B), 2.16 (s, 1.5H, isomer A or B), 2.13 (s, 1.5H, isomer A or B), 1.69 (s, 3H, isomer A or B), 1.67 (s, 3H, isomer A or B), 1.62 (s, 6H, isomers A and B) |
| C-8 | 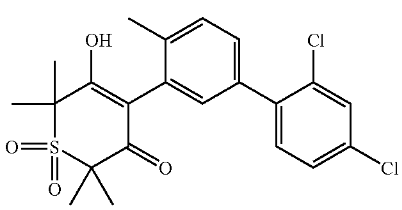 [SMILES: Cc1ccc(-c2ccc(Cl)cc2Cl)cc1C1=C(O)C(C)(C)S(=O)(=O)C(C)(C)C1=O] | Methanol-d₄ δ 7.53 (s, 1H); 7.37 (s, 2H), 7.33 (s, 2H), 7.03 (s, 1H); 2.13 (s, 3H); 1.72 (s, 12H) |
| C-9 | 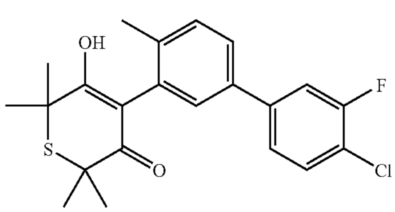 | δ 7.50-7.15 (m, 6H); 5.75 (br. s, 1H), 2.23 (s, 1H, isomer A), 2.18 (s, 2H, isomer B), 1.65 (br. s, 12H) |
| C-10 | 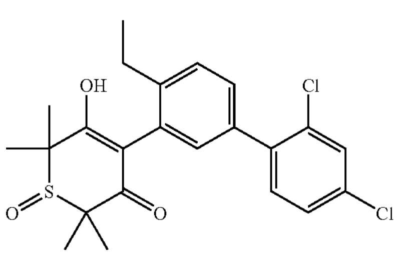 [SMILES: CCc1ccc(-c2ccc(Cl)cc2Cl)cc1C1=C(O)C(C)(C)S(=O)C(C)(C)C1=O] | δ 7.51 (s, 1H); 7.46 (s, 2H); 7.33 (s, 2H), 7.16 (s, 0.5H, isomer A), 7.09 (s, 0.5H, isomer B), 6.16 (br. s, 1H), 2.55-2.45 (m, 2H); 1.76 (app. d, 6H); 1.62 (app. d, 6H); 1.20 (m, 3H) |

TABLE C-continued

| Compound Number | Structure | $^1$H nmr (CDCl$_3$ unless stated) or other physical data |
|---|---|---|
| C-11 | 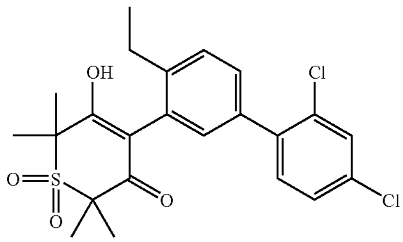 [SMILES: CCc1ccc(-c2ccc(Cl)cc2Cl)cc1C1=C(O)C(C)(C)S(=O)(=O)C(C)(C)C1=O] | δ 7.48 (s, 1H); 7.45 (s, 2H); 7.31 (s, 2H); 7.12 (s, 1H); 6.04 (br. s, 1H); 2.50-2.41 (m, 2H); 1.85 (s, 6H); 1.72 (app. d, 6H); 1.16 (t, 3H) |
| C-12 | 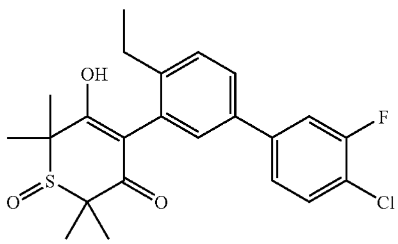 [SMILES: CCc1ccc(-c2ccc(Cl)c(F)c2)cc1C1=C(O)C(C)(C)S(=O)C(C)(C)C1=O] | δ 7.56 (dd, 1H); 7.47-7.41 (m, 2H); 7.37-7.28 (m, 2.5H); 7.16 (d, 0.5H); 2.49-2.39 (m, 2H); 1.68 (app. d, 12H); 1.17-1.12 (m, 3H) |
| C-13 | 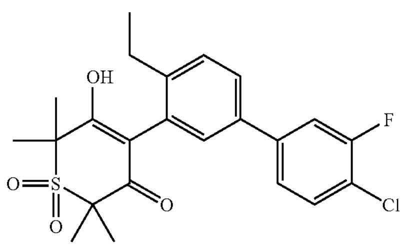 [SMILES: CCc1ccc(-c2ccc(Cl)c(F)c2)cc1C1=C(O)C(C)(C)S(=O)(=O)C(C)(C)C1=O] | δ 7.59 (dd, 1H); 7.47-7.44 (m, 2H); 7.35 (dd, 1H); 7.30 (dd, 1H); 7.22 (d, 1H); 5.84 (br. s, 1H); 2.49-2.40 (m, 2H); 1.87 (app. d, 6H); 1.73 (s, 6H); 1.14 (t, 3H) |

The compounds of the following Tables 1 to 294 may be obtained in an analogous manner.

TABLE 1

This table covers 378 compounds of the following type:

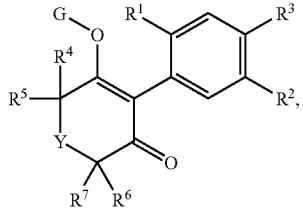

wherein Y is O, R$^1$ is methyl, R$^4$, R$^5$, R$^6$ and R$^7$ are hydrogen, G is hydrogen and R$^2$ and R$^3$ are as defined below:

| Compound Number | R$^2$ | R$^3$ |
|---|---|---|
| 1.001 | Phenyl | H |
| 1.002 | 2-fluorophenyl | H |
| 1.003 | 3-fluorophenyl | H |
| 1.004 | 4-fluorophenyl | H |
| 1.005 | 2-chlorophenyl | H |
| 1.006 | 3-chlorophenyl | H |
| 1.007 | 4-chlorophenyl | H |
| 1.008 | 2-bromophenyl | H |
| 1.009 | 3-bromophenyl | H |
| 1.010 | 4-bromophenyl | H |
| 1.011 | 4-tert-butyl | H |
| 1.012 | 2-iodophenyl | H |
| 1.013 | 3-iodophenyl | H |
| 1.014 | 4-iodophenyl | H |
| 1.015 | 2-methylphenyl | H |

TABLE 1-continued

This table covers 378 compounds of the following type:

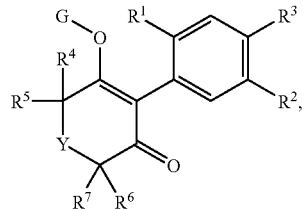

wherein Y is O, R$^1$ is methyl, R$^4$, R$^5$, R$^6$ and R$^7$ are hydrogen, G is hydrogen and R$^2$ and R$^3$ are as defined below:

| Compound Number | R$^2$ | R$^3$ |
|---|---|---|
| 1.016 | 3-methylphenyl | H |
| 1.017 | 4-methylphenyl | H |
| 1.018 | 2-cyanophenyl | H |
| 1.019 | 3-cyanophenyl | H |
| 1.020 | 4-cyanophenyl | H |
| 1.021 | 2-methoxyphenyl | H |
| 1.022 | 3-methoxyphenyl | H |
| 1.023 | 4-methoxyphenyl | H |
| 1.024 | 2-difluoromethoxyphenyl | H |
| 1.025 | 3-difluoromethoxyphenyl | H |
| 1.026 | 4-difluoromethoxyphenyl | H |
| 1.027 | 2-difluoromethylphenyl | H |
| 1.028 | 3-difluoromethylphenyl | H |
| 1.029 | 4-difluoromethylphenyl | H |
| 1.030 | 2-trifluoromethylphenyl | H |
| 1.031 | 3-trifluoromethylphenyl | H |
| 1.032 | 4-trifluoromethylphenyl | H |
| 1.033 | 2-trifluoromethoxyphenyl | H |
| 1.034 | 3-trifluoromethoxyphenyl | H |

TABLE 1-continued

This table covers 378 compounds of the following type:

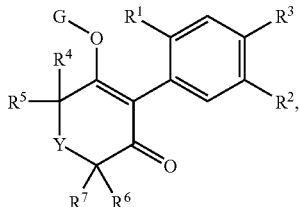

wherein Y is O, $R^1$ is methyl, $R^4$, $R^5$, $R^6$ and $R^7$ are hydrogen, G is hydrogen and $R^2$ and $R^3$ are as defined below:

| Compound Number | $R^2$ | $R^3$ |
|---|---|---|
| 1.035 | 4-trifluoromethoxyphenyl | H |
| 1.036 | 4-methylthiophenyl | H |
| 1.037 | 4-methylsulfinylphenyl | H |
| 1.038 | 4-methylsulfonylphenyl | H |
| 1.039 | 4-trifluoromethylthiophenyl | H |
| 1.040 | 4-trifluoromethylsulfinylphenyl | H |
| 1.041 | 4-trifluoromethylsulfonylphenyl | H |
| 1.042 | 2,3-difluorophenyl | H |
| 1.043 | 2,4-difluorophenyl | H |
| 1.044 | 2,5-difluorophenyl | H |
| 1.045 | 2,6-difluorophenyl | H |
| 1.046 | 3,4-difluorophenyl | H |
| 1.047 | 3,5-difluorophenyl | H |
| 1.048 | 2,3-dichlorophenyl | H |
| 1.049 | 2,4-dichlorophenyl | H |
| 1.050 | 2,5-dichlorophenyl | H |
| 1.051 | 2,6-dichlorophenyl | H |
| 1.052 | 3,4-dichlorophenyl | H |
| 1.053 | 3,5-dichlorophenyl | H |
| 1.054 | 4-chloro-2-cyanophenyl | H |
| 1.055 | 4-chloro-3-cyanophenyl | H |
| 1.056 | 4-chloro-2-fluorophenyl | H |
| 1.057 | 4-chloro-3-fluorophenyl | H |
| 1.058 | 4-chloro-2-methoxyphenyl | H |
| 1.059 | 4-chloro-3-methoxyphenyl | H |
| 1.060 | 4-chloro-2-methylphenyl | H |
| 1.061 | 4-chloro-3-methylphenyl | H |
| 1.062 | 4-chloro-2-difluoromethoxyphenyl | H |
| 1.063 | 4-chloro-3-difluoromethoxyphenyl | H |
| 1.064 | 4-chloro-2-trifluoromethoxyphenyl | H |
| 1.065 | 4-chloro-3-trifluoromethoxyphenyl | H |
| 1.066 | 4-chloro-2-difluoromethylphenyl | H |
| 1.067 | 4-chloro-3-difluoromethylphenyl | H |
| 1.068 | 4-chloro-2-trifluoromethylphenyl | H |
| 1.069 | 4-chloro-3-trifluoromethylphenyl | H |
| 1.070 | 4-chloro-2,3-difluorophenyl | H |
| 1.071 | 4-chloro-2,5-difluorophenyl | H |
| 1.072 | 4,-chloro-2,6-difluorophenyl | H |
| 1.073 | 2,4-dichloro-3-fluorophenyl | H |
| 1.074 | 2,4-dichloro-5-fluorophenyl | H |
| 1.075 | 2,4-dichloro-6-fluorophenyl | H |
| 1.076 | 2,3,4-trichlorophenyl | H |
| 1.077 | 2,3,5-trichlorophenyl | H |
| 1.078 | 2,3,6-trichlorophenyl | H |
| 1.079 | 2,4,5-trichlorophenyl | H |
| 1.080 | 2,4,6-trichlorophenyl | H |
| 1.081 | 2,3,4-trifluorophenyl | H |
| 1.082 | 2,3,5-trifluorophenyl | H |
| 1.083 | 2,3,6-trifluorophenyl | H |
| 1.084 | 2,4,5-trifluorophenyl | H |
| 1.085 | 2,4,6-trifluorophenyl | H |
| 1.086 | 2-fluoro-4-trifluoromethylphenyl | H |
| 1.087 | 3-fluoro-4-trifluoromethylphenyl | H |
| 1.088 | 2-chloropyridin-5-yl | H |
| 1.089 | 3-chloropyridinyl-5-yl | H |
| 1.090 | 2-methylpyridin-5-yl | H |
| 1.091 | 3-methylpyridinyl-5-yl | H |
| 1.092 | 2-trifluoromethylpyridin-5-yl | H |
| 1.093 | 3-trifluoromethylpyridin-5-yl | H |
| 1.094 | 2-chloro-3-methylpyridin-5-yl | H |
| 1.095 | 2-chloro-4-methylpyridin-5-yl | H |
| 1.096 | 6-chloro-2-methylpyridin-3-yl | H |
| 1.097 | 2,3-dichloropyridin-5-yl | H |

TABLE 1-continued

This table covers 378 compounds of the following type:

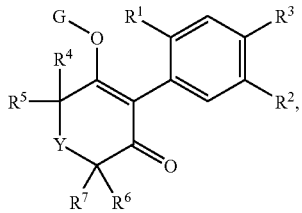

wherein Y is O, $R^1$ is methyl, $R^4$, $R^5$, $R^6$ and $R^7$ are hydrogen, G is hydrogen and $R^2$ and $R^3$ are as defined below:

| Compound Number | $R^2$ | $R^3$ |
|---|---|---|
| 1.098 | 2,4-dichloropyridin-5-yl | H |
| 1.099 | 2,6-dichloropyridin-3-yl | H |
| 1.100 | pyrazin-2-yl | H |
| 1.101 | 2-chloropyrazin-5-yl | H |
| 1.102 | 2-bromopyrazin-5-yl | H |
| 1.103 | pyridazin-3-yl | H |
| 1.104 | 6-bromopyridazin-3-yl | H |
| 1.105 | 6-chloropyridazin-3-yl | H |
| 1.106 | pyrimidin-5-yl | H |
| 1.107 | 2-bromopyrimidin-5-yl | H |
| 1.108 | 5-bromopyrimidin-2-yl | H |
| 1.109 | 2-chloropyrimidin-5-yl | H |
| 1.110 | 5-chloropyrimidin-2-yl | H |
| 1.111 | 2-furyl | H |
| 1.112 | 3-furyl | H |
| 1.113 | 2-thienyl | H |
| 1.114 | 3-thienyl | H |
| 1.115 | 4-bromothien-2-yl | H |
| 1.116 | 5-bromothien-2-yl | H |
| 1.117 | 4-chlorothien-2-yl | H |
| 1.118 | 5-chlorothien-2-yl | H |
| 1.119 | pyrazol-1-yl | H |
| 1.120 | 3-chloropyrazol-1-yl | H |
| 1.121 | 4-chloropyrazol-1-yl | H |
| 1.122 | 1-methylpyrazol-4-yl | H |
| 1.123 | 1-methyl-3-trifluoromethylpyrazol-5-yl | H |
| 1.124 | 2-thiazolyl | H |
| 1.125 | 4-methylthiazol-2-yl | H |
| 1.126 | 5-methylthiazol-2-yl | H |
| 1.127 | phenyl | $CH_3$ |
| 1.128 | 2-fluorophenyl | $CH_3$ |
| 1.129 | 3-fluorophenyl | $CH_3$ |
| 1.130 | 4-fluorophenyl | $CH_3$ |
| 1.131 | 2-chlorophenyl | $CH_3$ |
| 1.132 | 3-chlorophenyl | $CH_3$ |
| 1.133 | 4-chlorophenyl | $CH_3$ |
| 1.134 | 2-bromophenyl | $CH_3$ |
| 1.135 | 3-bromophenyl | $CH_3$ |
| 1.136 | 4-bromophenyl | $CH_3$ |
| 1.137 | 4-tert-butyl | $CH_3$ |
| 1.138 | 2-iodophenyl | $CH_3$ |
| 1.139 | 3-iodophenyl | $CH_3$ |
| 1.140 | 4-iodophenyl | $CH_3$ |
| 1.141 | 2-methylphenyl | $CH_3$ |
| 1.142 | 3-methylphenyl | $CH_3$ |
| 1.143 | 4-methylphenyl | $CH_3$ |
| 1.144 | 2-cyanophenyl | $CH_3$ |
| 1.145 | 3-cyanophenyl | $CH_3$ |
| 1.146 | 4-cyanophenyl | $CH_3$ |
| 1.147 | 2-methoxyphenyl | $CH_3$ |
| 1.148 | 3-methoxyphenyl | $CH_3$ |
| 1.149 | 4-methoxyphenyl | $CH_3$ |
| 1.150 | 2-difluoromethoxyphenyl | $CH_3$ |
| 1.151 | 3-difluoromethoxyphenyl | $CH_3$ |
| 1.152 | 4-difluoromethoxyphenyl | $CH_3$ |
| 1.153 | 2-difluoromethylphenyl | $CH_3$ |
| 1.154 | 3-difluoromethylphenyl | $CH_3$ |
| 1.155 | 4-difluoromethylphenyl | $CH_3$ |
| 1.156 | 2-trifluoromethylphenyl | $CH_3$ |
| 1.157 | 3-trifluoromethylphenyl | $CH_3$ |
| 1.158 | 4-trifluoromethylphenyl | $CH_3$ |
| 1.159 | 2-trifluoromethoxyphenyl | $CH_3$ |
| 1.160 | 3-trifluoromethoxyphenyl | $CH_3$ |

TABLE 1-continued

This table covers 378 compounds of the following type:

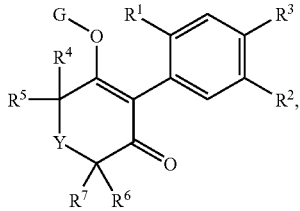

wherein Y is O, $R^1$ is methyl, $R^4$, $R^5$, $R^6$ and $R^7$ are hydrogen, G is hydrogen and $R^2$ and $R^3$ are as defined below:

| Compound Number | $R^2$ | $R^3$ |
|---|---|---|
| 1.161 | 4-trifluoromethoxyphenyl | $CH_3$ |
| 1.162 | 4-methylthiophenyl | $CH_3$ |
| 1.163 | 4-methylsulfinylphenyl | $CH_3$ |
| 1.164 | 4-methylsulfonylphenyl | $CH_3$ |
| 1.165 | 4-trifluoromethylthiophenyl | $CH_3$ |
| 1.166 | 4-trifluoromethylsulfinylphenyl | $CH_3$ |
| 1.167 | 4-trifluoromethylsulfonylphenyl | $CH_3$ |
| 1.168 | 2,3-difluorophenyl | $CH_3$ |
| 1.169 | 2,4-difluorophenyl | $CH_3$ |
| 1.170 | 2,5-difluorophenyl | $CH_3$ |
| 1.171 | 2,6-difluorophenyl | $CH_3$ |
| 1.172 | 3,4-difluorophenyl | $CH_3$ |
| 1.173 | 3,5-difluorophenyl | $CH_3$ |
| 1.174 | 2,3-dichlorophenyl | $CH_3$ |
| 1.175 | 2,4-dichlorophenyl | $CH_3$ |
| 1.176 | 2,5-dichlorophenyl | $CH_3$ |
| 1.177 | 2,6-dichlorophenyl | $CH_3$ |
| 1.178 | 3,4-dichlorophenyl | $CH_3$ |
| 1.179 | 3,5-dichlorophenyl | $CH_3$ |
| 1.180 | 4-chloro-2-cyanophenyl | $CH_3$ |
| 1.181 | 4-chloro-3-cyanophenyl | $CH_3$ |
| 1.182 | 4-chloro-2-fluorophenyl | $CH_3$ |
| 1.183 | 4-chloro-3-fluorophenyl | $CH_3$ |
| 1.184 | 4-chloro-2-methoxyphenyl | $CH_3$ |
| 1.185 | 4-chloro-3-methoxyphenyl | $CH_3$ |
| 1.186 | 4-chloro-2-methylphenyl | $CH_3$ |
| 1.187 | 4-chloro-3-methylphenyl | $CH_3$ |
| 1.188 | 4-chloro-2-difluoromethoxyphenyl | $CH_3$ |
| 1.189 | 4-chloro-3-difluoromethoxyphenyl | $CH_3$ |
| 1.190 | 4-chloro-2-trifluoromethoxyphenyl | $CH_3$ |
| 1.191 | 4-chloro-3-trifluoromethoxyphenyl | $CH_3$ |
| 1.192 | 4-chloro-2-difluoromethylphenyl | $CH_3$ |
| 1.193 | 4-chloro-3-difluoromethylphenyl | $CH_3$ |
| 1.194 | 4-chloro-2-trifluoromethylphenyl | $CH_3$ |
| 1.195 | 4-chloro-3-trifluoromethylphenyl | $CH_3$ |
| 1.196 | 4-chloro-2,3-difluorophenyl | $CH_3$ |
| 1.197 | 4-chloro-2,5-difluorophenyl | $CH_3$ |
| 1.198 | 4,-chloro-2,6-difluorophenyl | $CH_3$ |
| 1.199 | 2,4-dichloro-3-fluorophenyl | $CH_3$ |
| 1.200 | 2,4-dichloro-5-fluorophenyl | $CH_3$ |
| 1.201 | 2,4-dichloro-6-fluorophenyl | $CH_3$ |
| 1.202 | 2,3,4-trichlorophenyl | $CH_3$ |
| 1.203 | 2,3,5-trichlorophenyl | $CH_3$ |
| 1.204 | 2,3,6-trichlorophenyl | $CH_3$ |
| 1.205 | 2,4,5-trichlorophenyl | $CH_3$ |
| 1.206 | 2,4,6-trichlorophenyl | $CH_3$ |
| 1.207 | 2,3,4-trifluorophenyl | $CH_3$ |
| 1.208 | 2,3,5-trifluorophenyl | $CH_3$ |
| 1.209 | 2,3,6-trifluorophenyl | $CH_3$ |
| 1.210 | 2,4,5-trifluorophenyl | $CH_3$ |
| 1.211 | 2,4,6-trifluorophenyl | $CH_3$ |
| 1.212 | 2-fluoro-4-trifluoromethylphenyl | $CH_3$ |
| 1.213 | 3-fluoro-4-trifluoromethylphenyl | $CH_3$ |
| 1.214 | 2-chloropyridin-5-yl | $CH_3$ |
| 1.215 | 3-chloropyridinyl-5-yl | $CH_3$ |
| 1.216 | 2-methylpyridin-5-yl | $CH_3$ |
| 1.217 | 3-methylpyridinyl-5-yl | $CH_3$ |
| 1.218 | 2-trifluoromethylpyridin-5-yl | $CH_3$ |
| 1.219 | 3-trifluoromethylpyridin-5-yl | $CH_3$ |
| 1.220 | 2-chloro-3-methylpyridin-5-yl | $CH_3$ |
| 1.221 | 2-chloro-4-methylpyridin-5-yl | $CH_3$ |
| 1.222 | 6-chloro-2-methylpyridin-3-yl | $CH_3$ |
| 1.223 | 2,3-dichloropyridin-5-yl | $CH_3$ |

TABLE 1-continued

This table covers 378 compounds of the following type:

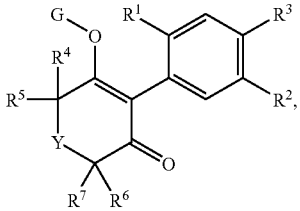

wherein Y is O, $R^1$ is methyl, $R^4$, $R^5$, $R^6$ and $R^7$ are hydrogen, G is hydrogen and $R^2$ and $R^3$ are as defined below:

| Compound Number | $R^2$ | $R^3$ |
|---|---|---|
| 1.224 | 2,4-dichloropyridin-5-yl | $CH_3$ |
| 1.225 | 2,6-dichloropyridin-3-yl | $CH_3$ |
| 1.226 | pyrazin-2-yl | $CH_3$ |
| 1.227 | 2-chloropyrazin-5-yl | $CH_3$ |
| 1.228 | 2-bromopyrazin-5-yl | $CH_3$ |
| 1.229 | pyridazin-3-yl | $CH_3$ |
| 1.230 | 6-bromopyridazin-3-yl | $CH_3$ |
| 1.231 | 6-chloropyridazin-3-yl | $CH_3$ |
| 1.232 | pyrimidin-5-yl | $CH_3$ |
| 1.233 | 2-bromopyrimidin-5-yl | $CH_3$ |
| 1.234 | 5-bromopyrimidin-2-yl | $CH_3$ |
| 1.235 | 2-chloropyrimidin-5-yl | $CH_3$ |
| 1.236 | 5-chloropyrimidin-2-yl | $CH_3$ |
| 1.237 | 2-furyl | $CH_3$ |
| 1.238 | 3-furyl | $CH_3$ |
| 1.239 | 2-thienyl | $CH_3$ |
| 1.240 | 3-thienyl | $CH_3$ |
| 1.241 | 4-bromothien-2-yl | $CH_3$ |
| 1.242 | 5-bromothien-2-yl | $CH_3$ |
| 1.243 | 4-chlorothien-2-yl | $CH_3$ |
| 1.244 | 5-chlorothien-2-yl | $CH_3$ |
| 1.245 | pyrazol-1-yl | $CH_3$ |
| 1.246 | 3-chloropyrazol-1-yl | $CH_3$ |
| 1.247 | 4-chloropyrazol-1-yl | $CH_3$ |
| 1.248 | 1-methylpyrazol-4-yl | $CH_3$ |
| 1.249 | 1-methyl-3-trifluoromethylpyrazol-5-yl | $CH_3$ |
| 1.250 | 2-thiazolyl | $CH_3$ |
| 1.251 | 4-methylthiazol-2-yl | $CH_3$ |
| 1.252 | 5-methylthiazol-2-yl | $CH_3$ |
| 1.253 | phenyl | Cl |
| 1.254 | 2-fluorophenyl | Cl |
| 1.255 | 3-fluorophenyl | Cl |
| 1.256 | 4-fluorophenyl | Cl |
| 1.257 | 2-chlorophenyl | Cl |
| 1.258 | 3-chlorophenyl | Cl |
| 1.259 | 4-chlorophenyl | Cl |
| 1.260 | 2-bromophenyl | Cl |
| 1.261 | 3-bromophenyl | Cl |
| 1.262 | 4-bromophenyl | Cl |
| 1.263 | 4-tert-butyl | Cl |
| 1.264 | 2-iodophenyl | Cl |
| 1.265 | 3-iodophenyl | Cl |
| 1.266 | 4-iodophenyl | Cl |
| 1.267 | 2-methylphenyl | Cl |
| 1.268 | 3-methylphenyl | Cl |
| 1.269 | 4-methylphenyl | Cl |
| 1.270 | 2-cyanophenyl | Cl |
| 1.271 | 3-cyanophenyl | Cl |
| 1.272 | 4-cyanophenyl | Cl |
| 1.273 | 2-methoxyphenyl | Cl |
| 1.274 | 3-methoxyphenyl | Cl |
| 1.275 | 4-methoxyphenyl | Cl |
| 1.276 | 2-difluoromethoxyphenyl | Cl |
| 1.277 | 3-difluoromethoxyphenyl | Cl |
| 1.278 | 4-difluoromethoxyphenyl | Cl |
| 1.279 | 2-difluoromethylphenyl | Cl |
| 1.280 | 3-difluoromethylphenyl | Cl |
| 1.281 | 4-difluoromethylphenyl | Cl |
| 1.282 | 2-trifluoromethylphenyl | Cl |
| 1.283 | 3-trifluoromethylphenyl | Cl |
| 1.284 | 4-trifluoromethylphenyl | Cl |
| 1.285 | 2-trifluoromethoxyphenyl | Cl |
| 1.286 | 3-trifluoromethoxyphenyl | Cl |

TABLE 1-continued

This table covers 378 compounds of the following type:

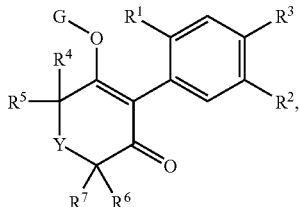

wherein Y is O, R¹ is methyl, R⁴, R⁵, R⁶ and R⁷ are hydrogen,
G is hydrogen and R² and R³ are as defined below:

| Compound Number | R² | R³ |
|---|---|---|
| 1.287 | 4-trifluoromethoxyphenyl | Cl |
| 1.288 | 4-methylthiophenyl | Cl |
| 1.289 | 4-methylsulfinylphenyl | Cl |
| 1.290 | 4-methylsulfonylphenyl | Cl |
| 1.291 | 4-trifluoromethylthiophenyl | Cl |
| 1.292 | 4-trifluoromethylsulfinylphenyl | Cl |
| 1.293 | 4-trifluoromethylsulfonylphenyl | Cl |
| 1.294 | 2,3-difluorophenyl | Cl |
| 1.295 | 2,4-difluorophenyl | Cl |
| 1.296 | 2,5-difluorophenyl | Cl |
| 1.297 | 2,6-difluorophenyl | Cl |
| 1.298 | 3,4-difluorophenyl | Cl |
| 1.299 | 3,5-difluorophenyl | Cl |
| 1.300 | 2,3-dichlorophenyl | Cl |
| 1.301 | 2,4-dichlorophenyl | Cl |
| 1.302 | 2,5-dichlorophenyl | Cl |
| 1.303 | 2,6-dichlorophenyl | Cl |
| 1.304 | 3,4-dichlorophenyl | Cl |
| 1.305 | 3,5-dichlorophenyl | Cl |
| 1.306 | 4-chloro-2-cyanophenyl | Cl |
| 1.307 | 4-chloro-3-cyanophenyl | Cl |
| 1.308 | 4-chloro-2-fluorophenyl | Cl |
| 1.309 | 4-chloro-3-fluorophenyl | Cl |
| 1.310 | 4-chloro-2-methoxyphenyl | Cl |
| 1.311 | 4-chloro-3-methoxyphenyl | Cl |
| 1.312 | 4-chloro-2-methylphenyl | Cl |
| 1.313 | 4-chloro-3-methylphenyl | Cl |
| 1.314 | 4-chloro-2-difluoromethoxyphenyl | Cl |
| 1.315 | 4-chloro-3-difluoromethoxyphenyl | Cl |
| 1.316 | 4-chloro-2-trifluoromethoxyphenyl | Cl |
| 1.317 | 4-chloro-3-trifluoromethoxyphenyl | Cl |
| 1.318 | 4-chloro-2-difluoromethylphenyl | Cl |
| 1.319 | 4-chloro-3-difluoromethylphenyl | Cl |
| 1.320 | 4-chloro-2-trifluoromethylphenyl | Cl |
| 1.321 | 4-chloro-3-trifluoromethylphenyl | Cl |
| 1.322 | 4-chloro-2 3-difluorophenyl | Cl |
| 1.323 | 4-chloro-2,5-difluorophenyl | Cl |
| 1.324 | 4,-chloro-2,6-difluorophenyl | Cl |
| 1.325 | 2,4-dichloro-3-fluorophenyl | Cl |
| 1.326 | 2,4-dichloro-5-fluorophenyl | Cl |
| 1.327 | 2,4-dichloro-6-fluorophenyl | Cl |
| 1.328 | 2,3,4-trichlorophenyl | Cl |
| 1.329 | 2,3,5-trichlorophenyl | Cl |
| 1.330 | 2,3,6-trichlorophenyl | Cl |
| 1.331 | 2,4,5-trichlorophenyl | Cl |
| 1.332 | 2,4,6-trichlorophenyl | Cl |
| 1.333 | 2,3,4-trifluorophenyl | Cl |
| 1.334 | 2,3,5-trifluorophenyl | Cl |
| 1.335 | 2,3,6-trifluorophenyl | Cl |
| 1.336 | 2,4,5-trifluorophenyl | Cl |
| 1.337 | 2,4,6-trifluorophenyl | Cl |
| 1.338 | 2-fluoro-4-trifluoromethylphenyl | Cl |
| 1.339 | 3-fluoro-4-trifluoromethylphenyl | Cl |
| 1.340 | 2-chloropyridin-5-yl | Cl |
| 1.341 | 3-chloropyridinyl-5-yl | Cl |
| 1.342 | 2-methylpyridin-5-yl | Cl |
| 1.343 | 3-methylpyridinyl-5-yl | Cl |
| 1.344 | 2-trifluoromethylpyridin-5-yl | Cl |
| 1.345 | 3-trifluoromethylpyridin-5-yl | Cl |
| 1.346 | 2-chloro-3-methylpyridin-5-yl | Cl |
| 1.347 | 2-chloro-4-methylpyridin-5-yl | Cl |
| 1.348 | 6-chloro-2-methylpyridin-3-yl | Cl |
| 1.349 | 2,3-dichloropyridin-5-yl | Cl |

TABLE 1-continued

This table covers 378 compounds of the following type:

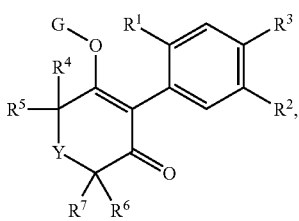

wherein Y is O, R¹ is methyl, R⁴, R⁵, R⁶ and R⁷ are hydrogen,
G is hydrogen and R² and R³ are as defined below:

| Compound Number | R² | R³ |
|---|---|---|
| 1.350 | 2,4-dichloropyridin-5-yl | Cl |
| 1.351 | 2,6-dichloropyridin-3-yl | Cl |
| 1.352 | pyrazin-2-yl | Cl |
| 1.353 | 2-chloropyrazin-5-yl | Cl |
| 1.354 | 2-bromopyrazin-5-yl | Cl |
| 1.355 | pyridazin-3-yl | Cl |
| 1.356 | 6-bromopyridazin-3-yl | Cl |
| 1.357 | 6-chloropyridazin-3-yl | Cl |
| 1.358 | pyrimidin-5-yl | Cl |
| 1.359 | 2-bromopyrimidin-5-yl | Cl |
| 1.360 | 5-bromopyrimidin-2-yl | Cl |
| 1.361 | 2-chloropyrimidin-5-yl | Cl |
| 1.362 | 5-chloropyrimidin-2-yl | Cl |
| 1.363 | 2-furyl | Cl |
| 1.364 | 3-furyl | Cl |
| 1.365 | 2-thienyl | Cl |
| 1.366 | 3-thienyl | Cl |
| 1.367 | 4-bromothien-2-yl | Cl |
| 1.368 | 5-bromothien-2-yl | Cl |
| 1.369 | 4-chlorothien-2-yl | Cl |
| 1.370 | 5-chlorothien-2-yl | Cl |
| 1.371 | pyrazol-1-yl | Cl |
| 1.372 | 3-chloropyrazol-1-yl | Cl |
| 1.373 | 4-chloropyrazol-1-yl | Cl |
| 1.374 | 1-methylpyrazol-4-yl | Cl |
| 1.375 | 1-methyl-3-trifluoromethylpyrazol-5-yl | Cl |
| 1.376 | 2-thiazolyl | Cl |
| 1.377 | 4-methylthiazol-2-yl | Cl |
| 1.378 | 5-methylthiazol-2-yl | Cl |

TABLE 2

This table covers 378 compounds of the following type:

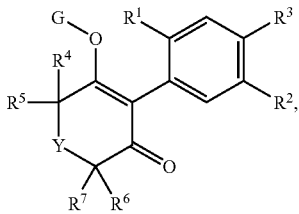

wherein Y is O, R¹ is ethyl, R⁴, R⁵, R⁶ and R⁷ are hydrogen,
G is hydrogen and R² and R³ are as defined in Table 1.

TABLE 3

This table covers 378 compounds of the following type:

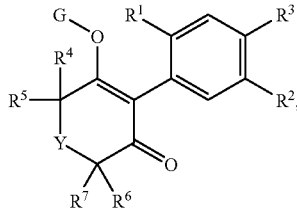

wherein Y is O, $R^1$ is chlorine, $R^4$, $R^5$, $R^6$ and $R^7$ are hydrogen, G is hydrogen and $R^2$ and $R^3$ are as defined in Table 1.

TABLE 4

This table covers 378 compounds of the following type:

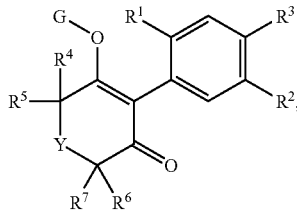

wherein Y is O, $R^1$ is methyl, $R^4$ is methyl, $R^5$, $R^6$ and $R^7$ are hydrogen, G is hydrogen and $R^2$ and $R^3$ are as defined in Table 1.

TABLE 5

This table covers 378 compounds of the following type:

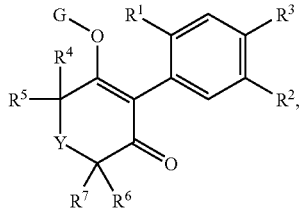

wherein Y is O, $R^1$ is ethyl, $R^4$ is methyl, $R^5$, $R^6$ and $R^7$ are hydrogen, G is hydrogen and $R^2$ and $R^3$ as defined in Table 1.

TABLE 6

This table covers 378 compounds of the following type:

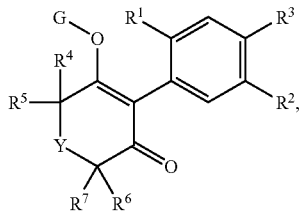

wherein Y is O, $R^1$ is chlorine, $R^4$ is methyl, $R^5$, $R^6$ and $R^7$ are hydrogen, G is hydrogen and $R^2$ and $R^3$ as defined in Table 1.

TABLE 7

This table covers 378 compounds of the following type:

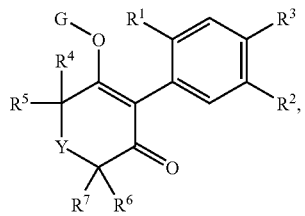

Wherein Y is O, $R^1$ is methyl, $R^4$ and $R^5$ are methyl, $R^6$ and $R^7$ are hydrogen, G is hydrogen and $R^2$ and $R^3$ are as defined in Table 1.

TABLE 8

This table covers 378 compounds of the following type:

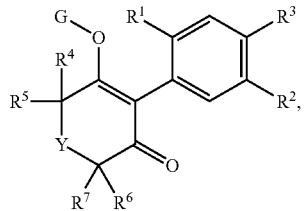

wherein Y is O, $R^1$ is ethyl, $R^4$ and $R^5$ are methyl, $R^6$ and $R^7$ are hydrogen, G is hydrogen and $R^2$ and $R^3$ are as defined in Table 1.

TABLE 9

This table covers 378 compounds of the following type:

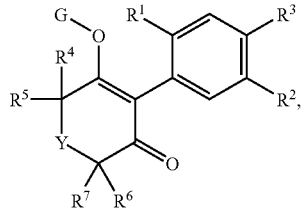

Wherein Y is O, $R^1$ is chlorine, $R^4$ and $R^5$ are methyl, $R^6$ and $R^7$ are hydrogen, G is hydrogen and $R^2$ and $R^3$ are as defined in Table 1.

TABLE 10

This table covers 378 compounds of the following type:

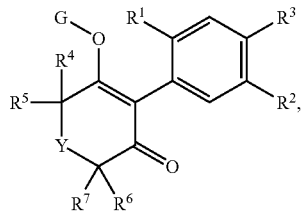

wherein Y is O, $R^1$ is methyl, $R^4$ and $R^6$ are methyl, $R^5$ and $R^7$ are hydrogen, G is hydrogen and $R^2$ and $R^3$ are as defined in Table 1.

TABLE 11

This table covers 378 compounds of the following type:

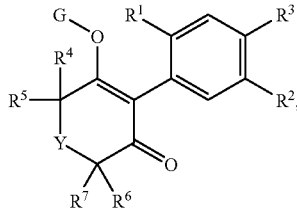

wherein Y is O, $R^1$ is ethyl, $R^4$ and $R^6$ are methyl, $R^5$ and $R^7$ are hydrogen, G is hydrogen and $R^2$ and $R^3$ are as defined in Table 1.

TABLE 12

This table covers 378 compounds of the following type:

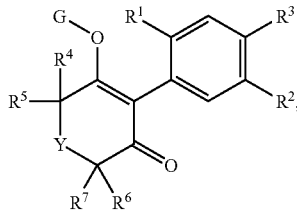

wherein Y is O, $R^1$ is chlorine, $R^4$ and $R^6$ are methyl, $R^5$ and $R^7$ are hydrogen, G is hydrogen and $R^2$ and $R^3$ are as defined in Table 1.

TABLE 13

This table covers 378 compounds of the following type:

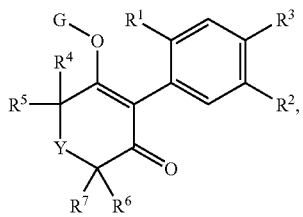

wherein Y is O, $R^1$ is methyl, $R^4$, $R^5$ and $R^6$ are methyl, $R^7$ is hydrogen, G is hydrogen and $R^2$ and $R^3$ are as defined in Table 1.

TABLE 14

This table covers 378 compounds of the following type:

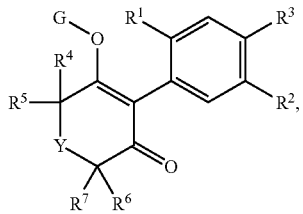

wherein Y is O, $R^1$ is ethyl, $R^4$, $R^5$ and $R^6$ are methyl, $R^7$ is hydrogen, G is hydrogen and $R^2$ and $R^3$ are as defined in Table 1.

TABLE 15

This table covers 378 compounds of the following type:

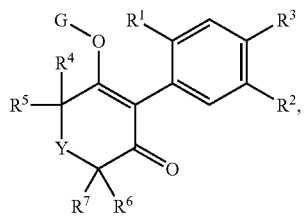

wherein Y is O, $R^1$ is chlorine, $R^4$, $R^5$ and $R^6$ are methyl, $R^7$ is hydrogen, G is hydrogen and $R^2$ and $R^3$ are as defined in Table 1.

TABLE 16

This table covers 378 compounds of the following type:

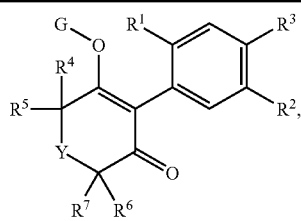

wherein Y is O, $R^1$ is methyl, $R^4$, $R^5$, $R^6$ and $R^7$ are methyl, G is hydrogen and $R^2$ and $R^3$ are as defined in Table 1.

TABLE 17

This table covers 378 compounds of the following type:

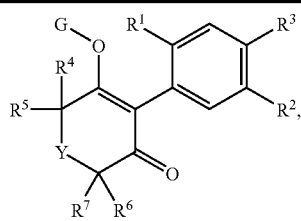

wherein Y is O, $R^1$ is ethyl, $R^4$, $R^5$, $R^6$ and $R^7$ are methyl, G is hydrogen and $R^2$ and $R^3$ are as defined in Table 1.

TABLE 18

This table covers 378 compounds of the following type:

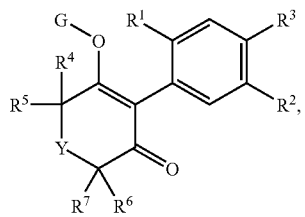

wherein Y is O, $R^1$ is chlorine, $R^4$, $R^5$, $R^6$ and $R^7$ are methyl, G is hydrogen and $R^2$ and $R^3$ are as defined in Table 1.

TABLE 19

This table covers 378 compounds of the following type:

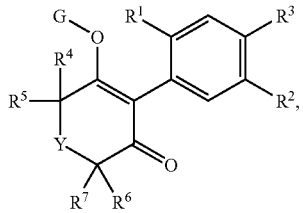

wherein Y is O, R¹ is methyl, R⁴, R⁵ and R⁶ methyl, R⁷ is methoxymethyl, G is hydrogen and R² and R³ are as defined in Table 1.

TABLE 20

This table covers 378 compounds of the following type:

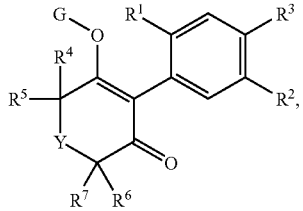

wherein Y is O, R¹ is ethyl, R⁴, R⁵ and R⁶ methyl, R⁷ is methoxymethyl, G is hydrogen and R² and R³ are as defined in Table 1.

TABLE 21

This table covers 378 compounds of the following type:

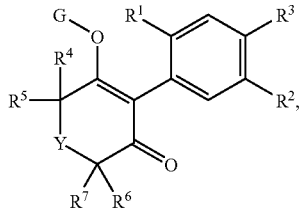

wherein Y is O, R¹ is chlorine, R⁴, R⁵ and R⁶ are methyl, R⁷ is methoxymethyl, G is hydrogen and R² and R³ are as defined in Table 1.

TABLE 22

This table covers 378 compounds of the following type:

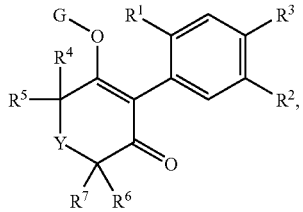

wherein Y is S, R¹ is methyl, R⁴, R⁵, R⁶ and R⁷ are hydrogen, G is hydrogen and R² and R³ are as defined in Table 1.

TABLE 23

This table covers 378 compounds of the following type:

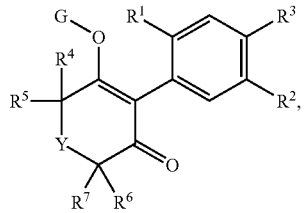

wherein Y is S, R¹ is ethyl, R⁴, R⁵, R⁶ and R⁷ are hydrogen, G is hydrogen and R² and R³ are as defined in Table 1.

TABLE 24

This table covers 378 compounds of the following type:

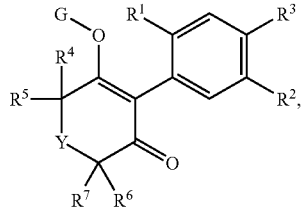

wherein Y is S, R¹ is chlorine, R⁴, R⁵, R⁶ and R⁷ are hydrogen, G is hydrogen and R² and R³ are as defined in Table 1.

TABLE 25

This table covers 378 compounds of the following type:

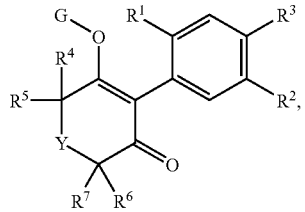

wherein Y is S, R¹ is methyl, R⁴ is methyl, R⁵, R⁶ and R⁷ are hydrogen, G is hydrogen and R² and R³ are as defined in Table 1.

TABLE 26

This table covers 378 compounds of the following type:

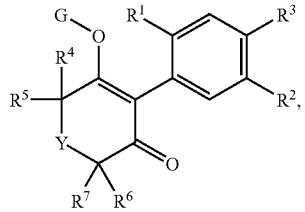

wherein Y is S, R¹ is ethyl, R⁴ is methyl, R⁵, R⁶ and R⁷ are hydrogen, G is hydrogen and R² and R³ as defined in Table 1.

TABLE 27

This table covers 378 compounds of the following type:

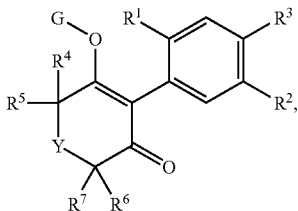

wherein Y is S, $R^1$ is chlorine, $R^4$ is methyl, $R^5$, $R^6$ and $R^7$ are hydrogen, G is hydrogen and $R^2$ and $R^3$ are as defined in Table 1.

TABLE 28

This table covers 378 compounds of the following type:

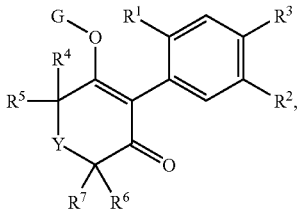

wherein Y is S, $R^1$ is methyl, $R^4$ and $R^5$ are methyl, $R^6$ and $R^7$ are hydrogen, G is hydrogen and $R^2$ and $R^3$ are as defined in Table 1.

TABLE 29

This table covers 378 compounds of the following type:

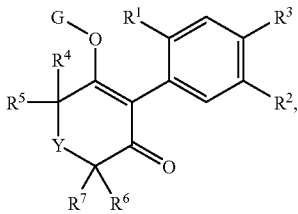

wherein Y is S, $R^1$ is ethyl, $R^4$ and $R^5$ are methyl, $R^6$ and $R^7$ are hydrogen, G is hydrogen and $R^2$ and $R^3$ are as defined in Table 1.

TABLE 30

This table covers 378 compounds of the following type:

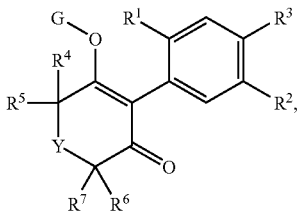

wherein Y is S, $R^1$ is chlorine, $R^4$ and $R^5$ are methyl, $R^6$ and $R^7$ are hydrogen, G is hydrogen and $R^2$ and $R^3$ are as defined in Table 1.

TABLE 31

This table covers 378 compounds of the following type:

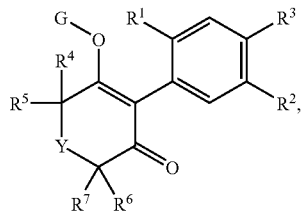

wherein Y is S, $R^1$ is methyl, $R^4$ and $R^6$ are methyl, $R^5$ and $R^7$ are hydrogen, G is hydrogen and $R^2$ and $R^3$ are as defined in Table 1.

TABLE 32

This table covers 378 compounds of the following type:

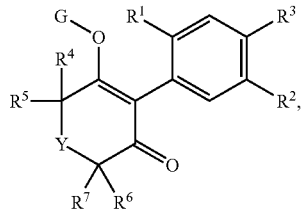

wherein Y is S, $R^1$ is ethyl, $R^4$ and $R^6$ are methyl, $R^5$ and $R^7$ are hydrogen, G is hydrogen and $R^2$ and $R^3$ as defined in Table 1.

TABLE 33

This table covers 378 compounds of the following type:

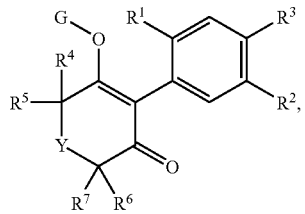

wherein Y is S, $R^1$ is chlorine, $R^4$ and $R^6$ are methyl, $R^5$ and $R^7$ are hydrogen, G is hydrogen and $R^2$ and $R^3$ are as defined in Table 1.

TABLE 34

This table covers 378 compounds of the following type:

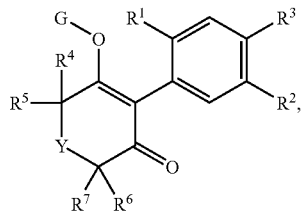

wherein Y is S, $R^1$ is methyl, $R^4$, $R^5$ and $R^6$ are methyl, $R^7$ is hydrogen, G is hydrogen and $R^2$ and $R^3$ are as defined in Table 1.

TABLE 35

This table covers 378 compounds of the following type:

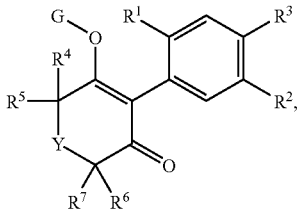

wherein Y is S, R¹ is ethyl, R⁴, R⁵ and R⁶ are methyl, R⁷ is hydrogen, G is hydrogen and R² and R³ as defined in Table 1.

TABLE 36

This table covers 378 compounds of the following type:

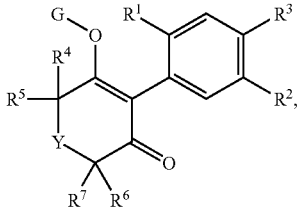

wherein Y is S, R¹ is chlorine, R⁴, R⁵ and R⁶ are methyl, R⁷ is hydrogen, G is hydrogen and R² and R³ are as defined in Table 1.

TABLE 37

This table covers 378 compounds of the following type:

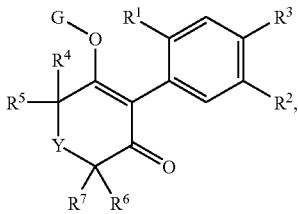

wherein Y is S, R¹ is methyl, R⁴, R⁵, R⁶ and R⁷ are methyl, G is hydrogen and R² and R³ are as defined in Table 1.

TABLE 38

This table covers 378 compounds of the following type:

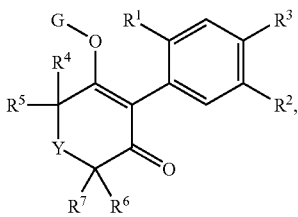

wherein Y is S, R¹ is ethyl, R⁴, R⁵, R⁶ and R⁷ are methyl, G is hydrogen and R² and R³ are as defined in Table 1.

TABLE 39

This table covers 378 compounds of the following type:

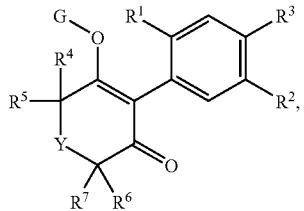

wherein Y is S, R¹ is chlorine, R⁴, R⁵, R⁶ and R⁷ are methyl, G is hydrogen and R² and R³ are as defined in Table 1.

TABLE 40

This table covers 378 compounds of the following type:

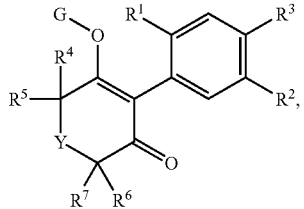

wherein Y is S=O, R¹ is methyl, R⁴, R⁵, R⁶ and R⁷ are hydrogen, G is hydrogen and R² and R³ are as defined in Table 1.

TABLE 41

This table covers 378 compounds of the following type:

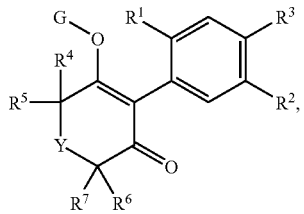

wherein Y is S=O, R¹ is ethyl, R⁴, R⁵, R⁶ and R⁷ are hydrogen, G is hydrogen and R² and R³ are as defined in Table 1.

TABLE 42

This table covers 378 compounds of the following type:

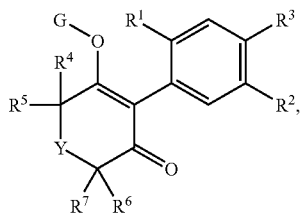

wherein Y is S=O, R¹ is chlorine, R⁴, R⁵, R⁶ and R⁷ are hydrogen, G is hydrogen and R² and R³ as defined in Table 1.

TABLE 43

This table covers 378 compounds of the following type:

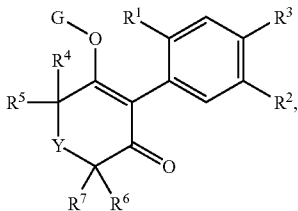

wherein Y is S=O, $R^1$ is methyl, $R^4$ is methyl, $R^5$, $R^6$ and $R^7$ are hydrogen, G is hydrogen and $R^2$ and $R^3$ are as defined in Table 1.

TABLE 44

This table covers 378 compounds of the following type:

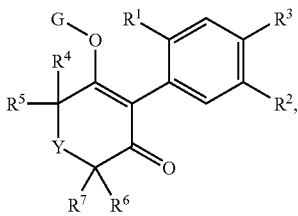

wherein Y is S=O, $R^1$ is ethyl, $R^4$ is methyl, $R^5$, $R^6$ and $R^7$ are hydrogen, G is hydrogen and $R^2$ and $R^3$ are as defined in Table 1.

TABLE 45

This table covers 378 compounds of the following type:

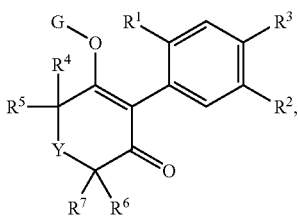

wherein Y is S=O, $R^1$ is chlorine, $R^4$ is methyl, $R^5$, $R^6$ and $R^7$ are hydrogen, G is hydrogen and $R^2$ and $R^3$ are as defined in Table 1.

TABLE 46

This table covers 378 compounds of the following type:

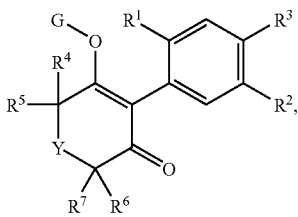

wherein Y is S=O, $R^1$ is methyl, $R^4$ and $R^5$ are methyl, $R^6$ and $R^7$ are hydrogen, G is hydrogen and $R^2$ and $R^3$ are as defined in Table 1.

TABLE 47

This table covers 378 compounds of the following type:

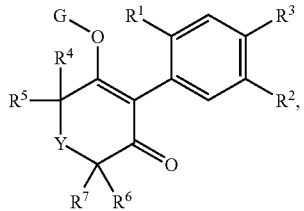

wherein Y is S=O, $R^1$ is ethyl, $R^4$ and $R^5$ are methyl, $R^6$ and $R^7$ are hydrogen, G is hydrogen and $R^2$ and $R^3$ are as defined in Table 1.

TABLE 48

This table covers 378 compounds of the following type:

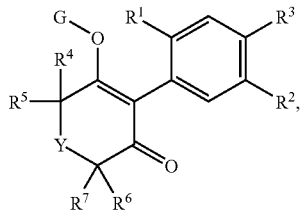

wherein Y is S=O, $R^1$ is chlorine, $R^4$ and $R^5$ are methyl, $R^6$ and $R^7$ are hydrogen, G is hydrogen and $R^2$ and $R^3$ are as defined in Table 1.

TABLE 49

This table covers 378 compounds of the following type:

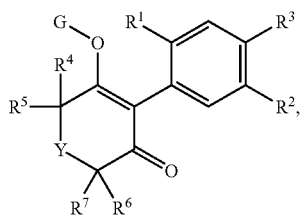

wherein Y is S=O, $R^1$ is methyl, $R^4$ and $R^6$ are methyl, $R^5$ and $R^7$ are hydrogen, G is hydrogen and $R^2$ and $R^3$ are as defined in Table 1.

TABLE 50

This table covers 378 compounds of the following type:

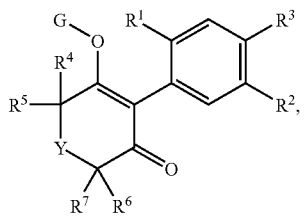

wherein Y is S=O, $R^1$ is ethyl, $R^4$ and $R^6$ are methyl, $R^5$ and $R^7$ are hydrogen, G is hydrogen and $R^2$ and $R^3$ are as defined in Table 1.

TABLE 51

This table covers 378 compounds of the following type:

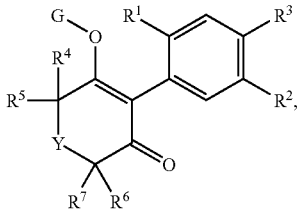

wherein Y is S═O, $R^1$ is chlorine, $R^4$ and $R^6$ are methyl, $R^5$ and $R^7$ are hydrogen, G is hydrogen and $R^2$ and $R^3$ are as defined in Table 1.

TABLE 52

This table covers 378 compounds of the following type:

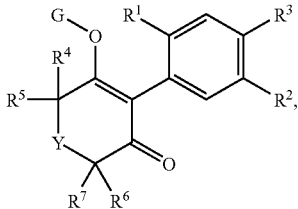

wherein Y is S═O, $R^1$ is methyl, $R^4$, $R^5$ and $R^6$ are methyl, $R^7$ is hydrogen, G is hydrogen and $R^2$ and $R^3$ are as defined in Table 1.

TABLE 53

This table covers 378 compounds of the following type:

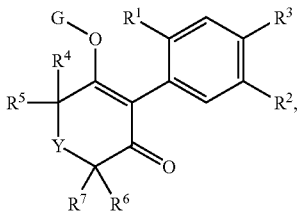

wherein Y is S═O, $R^1$ is ethyl, $R^4$, $R^5$ and $R^6$ are methyl, $R^7$ is hydrogen, G is hydrogen and $R^2$ and $R^3$ are as defined in Table 1.

TABLE 54

This table covers 378 compounds of the following type:

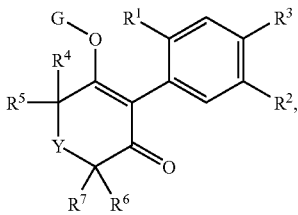

wherein Y is S═O, $R^1$ is chlorine, $R^4$, $R^5$ and $R^6$ are methyl, $R^7$ is hydrogen, G is hydrogen and $R^2$ and $R^3$ are as defined in Table 1.

TABLE 55

This table covers 378 compounds of the following type:

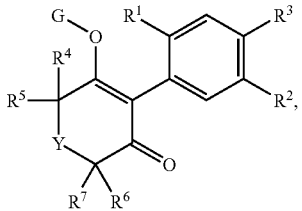

wherein Y is S═O, $R^1$ is methyl, $R^4$, $R^5$, $R^6$ and $R^7$ are methyl, G is hydrogen and $R^2$ and $R^3$ are as defined in Table 1.

TABLE 56

This table covers 378 compounds of the following type:

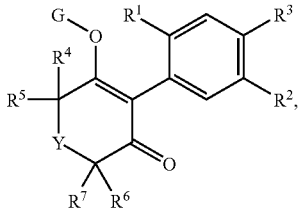

wherein Y is S═O, $R^1$ is ethyl, $R^4$, $R^5$, $R^6$ and $R^7$ are methyl, G is hydrogen and $R^2$ and $R^3$ are as defined in Table 1.

TABLE 57

This table covers 378 compounds of the following type:

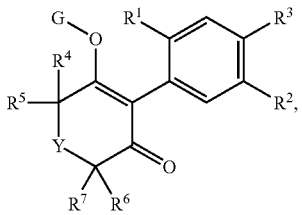

wherein Y is S═O, $R^1$ is chlorine, $R^4$, $R^5$, $R^6$ and $R^7$ are methyl, G is hydrogen and $R^2$ and $R^3$ are as defined in Table 1.

TABLE 58

This table covers 378 compounds of the following type:

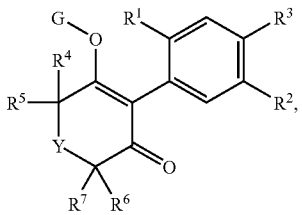

wherein Y is S(═O)$_2$, $R^1$ is methyl, $R^4$, $R^5$, $R^6$ and $R^7$ are hydrogen, G is hydrogen and $R^2$ and $R^3$ are as defined in Table 1.

TABLE 59

This table covers 378 compounds of the following type:

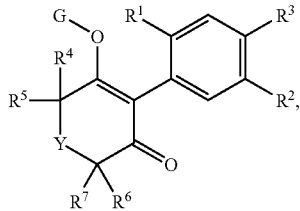

wherein Y is S(=O)$_2$, R$^1$ is ethyl, R$^4$, R$^5$, R$^6$ and R$^7$ are hydrogen, G is hydrogen and R$^2$ and R$^3$ are as defined in Table 1.

TABLE 60

This table covers 378 compounds of the following type:

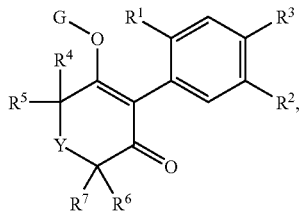

wherein Y is S(=O)$_2$, R$^1$ is chlorine, R$^4$, R$^5$, R$^6$ and R$^7$ are hydrogen, G is hydrogen and R$^2$ and R$^3$ as defined in Table 1.

TABLE 61

This table covers 378 compounds of the following type:

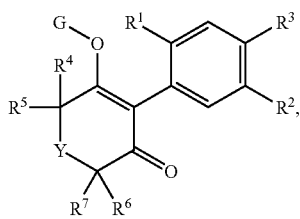

wherein Y is S(=O)$_2$, R$^1$ is methyl, R$^4$ is methyl, R$^5$, R$^6$ and R$^7$ are hydrogen, G is hydrogen and R$^2$ and R$^3$ are as defined in Table 1.

TABLE 62

This table covers 378 compounds of the following type:

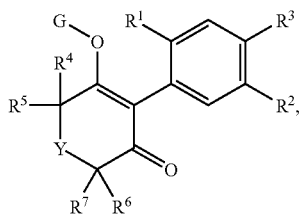

wherein Y is S(=O)$_2$, R$^1$ is ethyl, R$^4$ is methyl, R$^5$, R$^6$ and R$^7$ are hydrogen, G is hydrogen and R$^2$ and R$^3$ are as defined in Table 1.

TABLE 63

This table covers 378 compounds of the following type:

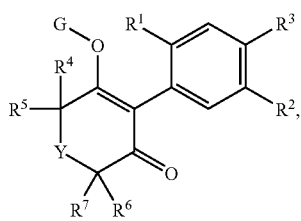

wherein Y is S(=O)$_2$, R is chlorine, R$^4$ is methyl, R$^5$, R$^6$ and R$^7$ are hydrogen, G is hydrogen and R$^2$ and R$^3$ are as defined in Table 1.

TABLE 64

This table covers 378 compounds of the following type:

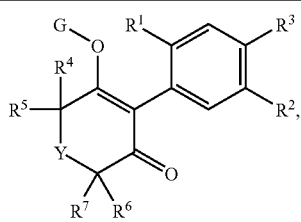

wherein Y is S(=O)$_2$, R$^1$ is methyl, R$^4$ and R$^5$ are methyl, R$^6$ and R$^7$ are hydrogen, G is hydrogen and R$^2$ and R$^3$ are as defined in Table 1.

TABLE 65

This table covers 378 compounds of the following type:

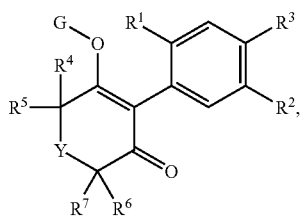

wherein Y is S(=O)$_2$, R$^1$ is ethyl, R$^4$ and R$^5$ are methyl, R$^6$ and R$^7$ are hydrogen, G is hydrogen and R$^2$ and R$^3$ are as defined in Table 1.

TABLE 66

This table covers 378 compounds of the following type:

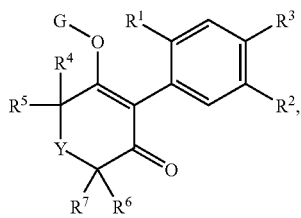

wherein Y is S(=O)$_2$, R$^1$ is chlorine, R$^4$ and R$^5$ are methyl, R$^6$ and R$^7$ are hydrogen, G is hydrogen and R$^2$ and R$^3$ are as defined in Table 1.

TABLE 67

This table covers 378 compounds of the following type:

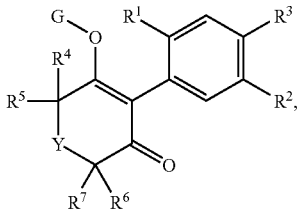

wherein Y is S(=O)$_2$, R$^1$ is methyl, R$^4$ and R$^6$ are methyl, R$^5$ and R$^7$ are hydrogen, G is hydrogen and R$^2$ and R$^3$ are as defined in Table 1.

TABLE 68

This table covers 378 compounds of the following type:

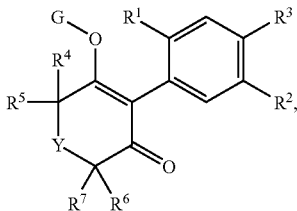

wherein Y is S(=O)$_2$, R$^1$ is ethyl, R$^4$ and R$^6$ are methyl, R$^5$ and R$^7$ are hydrogen, G is hydrogen and R$^2$ and R$^3$ are as defined in Table 1.

TABLE 69

This table covers 378 compounds of the following type:

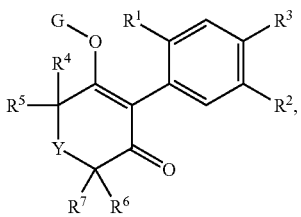

wherein Y is S(=O)$_2$, R$^1$ is chlorine, R$^4$ and R$^6$ are methyl, R$^5$ and R$^7$ are hydrogen, G is hydrogen and R$^2$ and R$^3$ are as defined in Table 1.

TABLE 70

This table covers 378 compounds of the following type:

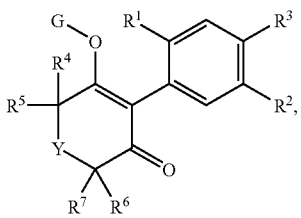

wherein Y is S(=O)$_2$, R$^1$ is methyl, R$^4$, R$^5$ and R$^6$ are methyl, R$^7$ is hydrogen, G is hydrogen and R$^2$ and R$^3$ are as defined in Table 1.

TABLE 71

This table covers 378 compounds of the following type:

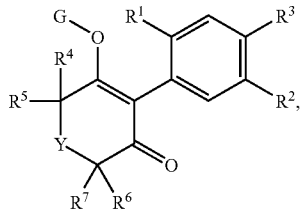

wherein Y is S(=O)$_2$, R$^1$ is ethyl, R$^4$, R$^5$ and R$^6$ methyl, R$^7$ is hydrogen, G is hydrogen and R$^2$ and R$^3$ are as defined in Table 1.

TABLE 72

This table covers 378 compounds of the following type:

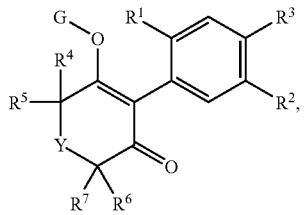

wherein Y is S(=O)$_2$, R$^1$ is chlorine, R$^4$, R$^5$ and R$^6$ are methyl, R$^7$ is hydrogen, G is hydrogen and R$^2$ and R$^3$ are as defined in Table 1.

TABLE 73

This table covers 378 compounds of the following type:

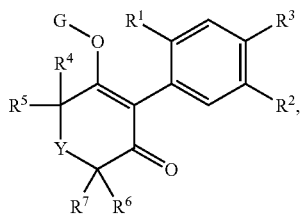

wherein Y is S(=O)$_2$, R$^1$ is methyl, R$^4$, R$^5$, R$^6$ and R$^7$ are methyl, G is hydrogen and R$^2$ and R$^3$ are as defined in Table 1.

TABLE 74

This table covers 378 compounds of the following type:

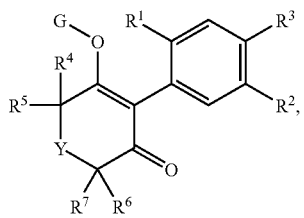

wherein Y is S(=O)$_2$, R$^1$ is ethyl, R$^4$, R$^5$, R$^6$ and R$^7$ are methyl, G is hydrogen and R$^2$ and R$^3$ are as defined in Table 1.

TABLE 75

This table covers 378 compounds of the following type:

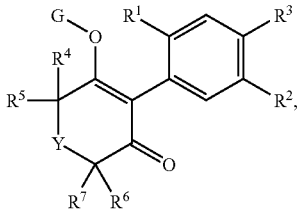

wherein Y is S(=O)$_2$, R$^1$ is chlorine, R$^4$, R$^5$, R$^6$ and R$^7$ are methyl, G is hydrogen and R$^2$ and R$^3$ as defined in Table 1.

TABLE 76

This table covers 378 compounds of the following type:

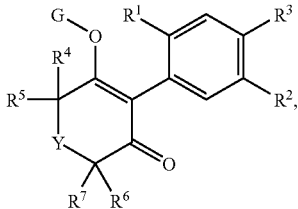

Wherein Y is C=O, R$^1$ is methyl, R$^4$ and R$^5$ are methyl, R$^6$ and R$^7$ are hydrogen, G is hydrogen and R$^2$ and R$^3$ are as defined in Table 1.

TABLE 77

This table covers 378 compounds of the following type:

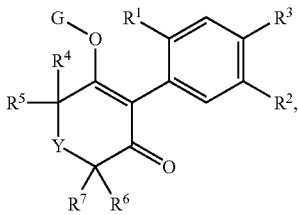

wherein Y is C=O, R$^1$ is ethyl, R$^4$ and R$^5$ are methyl, R$^6$ and R$^7$ are hydrogen, G is hydrogen and R$^2$ and R$^3$ are as defined in Table 1.

TABLE 78

This table covers 378 compounds of the following type:

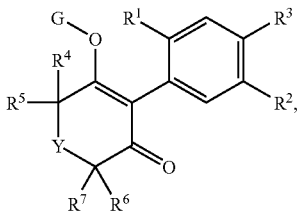

wherein Y is C=O, R$^1$ is ethyl, R$^4$ and R$^5$ are methyl, R$^6$ and R$^7$ are hydrogen, G is hydrogen and R$^2$ and R$^3$ are as defined in Table 1.

TABLE 79

This table covers 378 compounds of the following type:

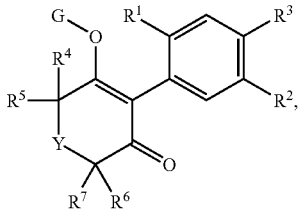

wherein Y is C=O, R$^1$ is methyl, R$^4$, R$^5$ and R$^6$ are methyl, R$^7$ is hydrogen, G is hydrogen and R$^2$ and R$^3$ are as defined in Table 1.

TABLE 80

This table covers 378 compounds of the following type:

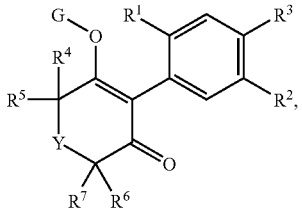

wherein Y is C=O, R$^1$ is ethyl, R$^4$, R$^5$ and R$^6$ are methyl, R$^7$ is hydrogen, G is hydrogen and R$^2$ and R$^3$ are as defined in Table 1.

TABLE 81

This table covers 378 compounds of the following type:

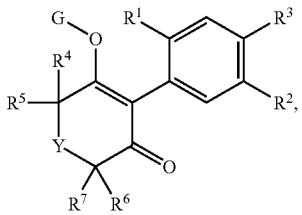

wherein Y is C=O, R$^1$ is chlorine, R$^4$, R$^5$ and R$^6$ are methyl, R$^7$ is hydrogen, G is hydrogen and R$^2$ and R$^3$ are as defined in Table 1.

TABLE 82

This table covers 378 compounds of the following type:

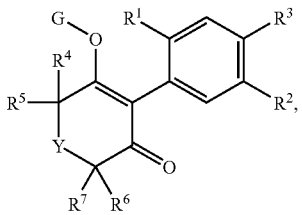

wherein Y is C=O, R$^1$ is methyl, R$^4$, R$^5$, R$^6$ and R$^7$ are methyl, G is hydrogen and R$^2$ and R$^3$ are as defined in Table 1.

TABLE 83

This table covers 378 compounds of the following type:

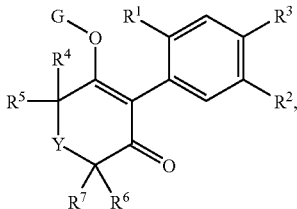

wherein Y is C=O, $R^1$ is ethyl, $R^4$, $R^5$, $R^6$ and $R^7$ are methyl, G is hydrogen and $R^2$ and $R^3$ are as defined in Table 1.

TABLE 84

This table covers 378 compounds of the following type:

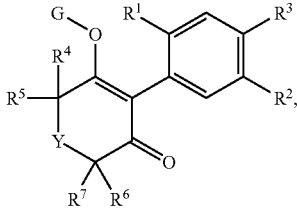

wherein Y is C=O, $R^1$ is chlorine, $R^4$, $R^5$, $R^6$ and $R^7$ are methyl, G is hydrogen and $R^2$ and $R^3$ are as defined in Table 1.

TABLE 85

This table covers 126 compounds of the following type:

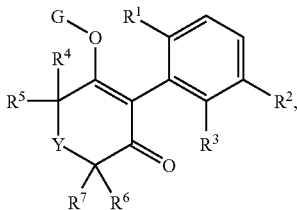

wherein Y is O, $R^1$ is methyl, $R^4$, $R^5$, $R^6$ and $R^7$ are hydrogen, G is hydrogen and $R^2$ and $R^{3'}$ are as defined below:

| Compound Number | $R^2$ | $R^3$ |
|---|---|---|
| 85.001 | phenyl | $CH_3$ |
| 85.002 | 2-fluorophenyl | $CH_3$ |
| 85.003 | 3-fluorophenyl | $CH_3$ |
| 85.004 | 4-fluorophenyl | $CH_3$ |
| 85.005 | 2-chlorophenyl | $CH_3$ |
| 85.006 | 3-chlorophenyl | $CH_3$ |
| 85.007 | 4-chlorophenyl | $CH_3$ |
| 85.008 | 2-bromophenyl | $CH_3$ |
| 85.009 | 3-bromophenyl | $CH_3$ |
| 85.010 | 4-bromophenyl | $CH_3$ |
| 85.011 | 4-tert-butyl | $CH_3$ |
| 85.012 | 2-iodophenyl | $CH_3$ |
| 85.013 | 3-iodophenyl | $CH_3$ |
| 85.014 | 4-iodophenyl | $CH_3$ |
| 85.015 | 2-methylphenyl | $CH_3$ |
| 85.016 | 3-methylphenyl | $CH_3$ |
| 85.017 | 4-methylphenyl | $CH_3$ |
| 85.018 | 2-cyanophenyl | $CH_3$ |
| 85.019 | 3-cyanophenyl | $CH_3$ |
| 85.020 | 4-cyanophenyl | $CH_3$ |
| 85.021 | 2-methoxyphenyl | $CH_3$ |
| 85.022 | 3-methoxyphenyl | $CH_3$ |

TABLE 85-continued

This table covers 126 compounds of the following type:

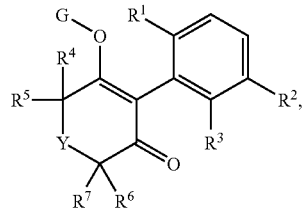

wherein Y is O, $R^1$ is methyl, $R^4$, $R^5$, $R^6$ and $R^7$ are hydrogen, G is hydrogen and $R^2$ and $R^{3'}$ are as defined below:

| Compound Number | $R^2$ | $R^3$ |
|---|---|---|
| 85.023 | 4-methoxyphenyl | $CH_3$ |
| 85.024 | 2-difluoromethoxyphenyl | $CH_3$ |
| 85.025 | 3-difluoromethoxyphenyl | $CH_3$ |
| 85.026 | 4-difluoromethoxyphenyl | $CH_3$ |
| 85.027 | 2-difluoromethylphenyl | $CH_3$ |
| 85.028 | 3-difluoromethylphenyl | $CH_3$ |
| 85.029 | 4-difluoromethylphenyl | $CH_3$ |
| 85.030 | 2-trifluoromethylphenyl | $CH_3$ |
| 85.031 | 3-trifluoromethylphenyl | $CH_3$ |
| 85.032 | 4-trifluoromethylphenyl | $CH_3$ |
| 85.033 | 2-trifluoromethoxyphenyl | $CH_3$ |
| 85.034 | 3-trifluoromethoxyphenyl | $CH_3$ |
| 85.035 | 4-trifluoromethoxyphenyl | $CH_3$ |
| 85.036 | 4-methylthiophenyl | $CH_3$ |
| 85.037 | 4-methylsulfinylphenyl | $CH_3$ |
| 85.038 | 4-methylsulfonylphenyl | $CH_3$ |
| 85.039 | 4-trifluoromethylthiophenyl | $CH_3$ |
| 85.040 | 4-trifluoromethylsulfinylphenyl | $CH_3$ |
| 85.041 | 4-trifluoromethylsulfonylphenyl | $CH_3$ |
| 85.042 | 2,3-difluorophenyl | $CH_3$ |
| 85.043 | 2,4-difluorophenyl | $CH_3$ |
| 85.044 | 2,5-difluorophenyl | $CH_3$ |
| 85.045 | 2,6-difluorophenyl | $CH_3$ |
| 85.046 | 3,4-difluorophenyl | $CH_3$ |
| 85.047 | 3,5-difluorophenyl | $CH_3$ |
| 85.048 | 2,3-dichlorophenyl | $CH_3$ |
| 85.049 | 2,4-dichlorophenyl | $CH_3$ |
| 85.050 | 2,5-dichlorophenyl | $CH_3$ |
| 85.051 | 2,6-dichlorophenyl | $CH_3$ |
| 85.052 | 3,4-dichlorophenyl | $CH_3$ |
| 85.053 | 3,5-dichlorophenyl | $CH_3$ |
| 85.054 | 4-chloro-2-cyanophenyl | $CH_3$ |
| 85.055 | 4-chloro-3-cyanophenyi | $CH_3$ |
| 85.056 | 4-chloro-2-fluorophenyl | $CH_3$ |
| 85.057 | 4-chloro-3-fluorophenyl | $CH_3$ |
| 85.058 | 4-chloro-2-methoxyphenyl | $CH_3$ |
| 85.059 | 4-chloro-3-methoxyphenyl | $CH_3$ |
| 85.060 | 4-chloro-2-methylphenyl | $CH_3$ |
| 85.061 | 4-chloro-3-methylphenyl | $CH_3$ |
| 85.062 | 4-chloro-2-difuoromethoxyphenyl | $CH_3$ |
| 85.063 | 4-chloro-3-difluoromethoxyphenyl | $CH_3$ |
| 85.064 | 4-chloro-2-trifluoromethoxyphenyl | $CH_3$ |
| 85.065 | 4-chloro-3-trifluoromethoxyphenyl | $CH_3$ |
| 85.066 | 4-chloro-2-difluoromethylphenyl | $CH_3$ |
| 85.067 | 4-chloro-3-difluoromethylphenyl | $CH_3$ |
| 85.068 | 4-chloro-2-trifluoromethylphenyl | $CH_3$ |
| 85.069 | 4-chloro-3-trifluoromethylphenyl | $CH_3$ |
| 85.070 | 4-chloro-2,3-difluorophenyl | $CH_3$ |
| 85.071 | 4-chloro-2,5-difluorophenyl | $CH_3$ |
| 85.072 | 4,-chloro-2,6-difluorophenyl | $CH_3$ |
| 85.073 | 2,4-dichloro-3-fluorophenyl | $CH_3$ |
| 85.074 | 2,4-dichloro-5-fluorophenyl | $CH_3$ |
| 85.075 | 2,4-dichloro-6-fluorophenyl | $CH_3$ |
| 85.076 | 2,3,4-trichlorophenyl | $CH_3$ |
| 85.077 | 2,3,5-trichlorophenyl | $CH_3$ |
| 85.078 | 2,3,6-trichlorophenyl | $CH_3$ |
| 85.079 | 2,4,5-trichlorophenyl | $CH_3$ |
| 85.080 | 2,4,6-trichlorophenyl | $CH_3$ |
| 85.081 | 2,3,4-trifluorophenyl | $CH_3$ |
| 85.082 | 2,3,5-trifluorophenyl | $CH_3$ |
| 85.083 | 2,3,6-trifluorophenyl | $CH_3$ |
| 85.084 | 2,4,5-trifluorophenyl | $CH_3$ |
| 85.085 | 2,4,6-trifluorophenyl | $CH_3$ |

TABLE 85-continued

This table covers 126 compounds of the following type:

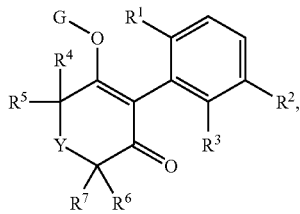

wherein Y is O, R¹ is methyl, R⁴, R⁵, R⁶ and R⁷ are hydrogen,
G is hydrogen and R² and R³' are as defined below:

| Compound Number | R² | R³ |
|---|---|---|
| 85.086 | 2-fluoro-4-trifluoromethylphenyl | CH₃ |
| 85.087 | 3-fluoro-4-trifluoromethylphenyl | CH₃ |
| 85.088 | 2-chloropyridin-5-yl | CH₃ |
| 85.089 | 3-chloropyridinyl-5-yl | CH₃ |
| 85.090 | 2-methylpyridin-5-yl | CH₃ |
| 85.091 | 3-methylpyridinyl-5-yl | CH₃ |
| 85.092 | 2-trifluoromethylpyridin-5-yl | CH₃ |
| 85.093 | 3-trifluoromethylpyridin-5-yl | CH₃ |
| 85.094 | 2-chloro-3-methylpyridin-5-yl | CH₃ |
| 85.095 | 2-chloro-4-methylpyridin-5-yl | CH₃ |
| 85.096 | 6-chloro-2-methylpyridin-3-yl | CH₃ |
| 85.097 | 2,3-dichloropyridin-5-yl | CH₃ |
| 85.098 | 2,4-dichloropyridin-5-yl | CH₃ |
| 85.099 | 2,6-dichloropyridin-3-yl | CH₃ |
| 85.100 | pyrazin-2-yl | CH₃ |
| 85.101 | 2-chloropyrazin-5-yl | CH₃ |
| 85.102 | 2-bromopyrazin-5-yl | CH₃ |
| 85.103 | pyridazin-3-yl | CH₃ |
| 85.104 | 6-bromopyridazin-3-yl | CH₃ |
| 85.105 | 6-chloropyridazin-3-yl | CH₃ |
| 85.106 | pyrimidin-5-yl | CH₃ |
| 85.107 | 2-bromopyrimidin-5-yl | CH₃ |
| 85.108 | 5-bromopyrimidin-2-yl | CH₃ |
| 85.109 | 2-chloropyrimidin-5-yl | CH₃ |
| 85.110 | 5-chloropyrimidin-2-yl | CH₃ |
| 85.111 | 2-furyl | CH₃ |
| 85.112 | 3-furyl | CH₃ |
| 85.113 | 2-thienyl | CH₃ |
| 85.114 | 3-thienyl | CH₃ |
| 85.115 | 4-bromothien-2-yl | CH₃ |
| 85.116 | 5-bromothien-2-yl | CH₃ |
| 85.117 | 4-chlorothien-2-yl | CH₃ |
| 85.118 | 5-chlorothien-2-yl | CH₃ |
| 85.119 | pyrazol-1-yl | CH₃ |
| 85.120 | 3-chloropyrazol-1-yl | CH₃ |
| 85.121 | 4-chloropyrazol-1-yl | CH₃ |
| 85.122 | 1-methylpyrazol-4-yl | CH₃ |
| 85.123 | 1-methyl-3-trifluoromethylpyrazol-5-yl | CH₃ |
| 85.124 | 2-thiazolyl | CH₃ |
| 85.125 | 4-methylthiazol-2-yl | CH₃ |
| 85.126 | 5-methylthiazol-2-yl | CH₃ |

TABLE 86

This table covers 126 compounds of the following type:

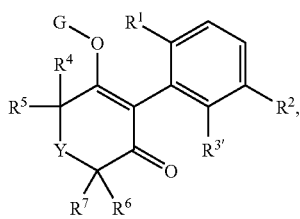

wherein Y is O, R¹ is ethyl, R⁴, R⁵, R⁶ and R⁷ are hydrogen,
G is hydrogen and R² and R³ are as defined in Table 85.

TABLE 87

This table covers 126 compounds of the following type:

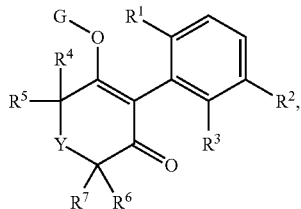

wherein Y is O, R¹ is methyl, R⁴ is methyl, R⁵, R⁶ and R⁷ are hydrogen,
G is hydrogen and R² and R³ are as defined in Table 85.

TABLE 88

This table covers 126 compounds of the following type:

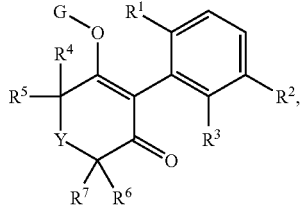

wherein Y is O, R¹ is ethyl, R⁴ is methyl, R⁵, R⁶ and R⁷ are hydrogen,
G is hydrogen and R² and R³ are as defined in Table 85.

TABLE 89

This table covers 126 compounds of the following type:

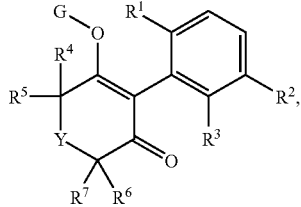

wherein Y is O, R¹ is methyl, R⁴ and R⁵ are methyl, R⁶ and R⁷ are hydrogen,
G is hydrogen and R² and R³ are as defined in Table 85.

TABLE 90

This table covers 126 compounds of the following type:

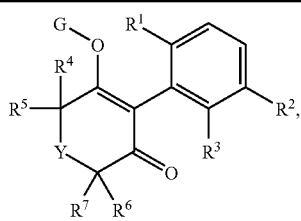

wherein Y is O, R¹ is ethyl, R⁴ and R⁵ are methyl, R⁶ and R⁷ are
hydrogen, G is hydrogen and R² and R³ are as defined in Table 85.

TABLE 91

This table covers 126 compounds of the following type:

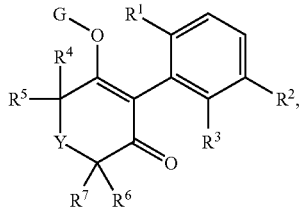

wherein Y is O, $R^1$ is methyl, $R^4$ and $R^6$ are methyl, $R^5$ and $R^7$ are hydrogen, G is hydrogen and $R^2$ and $R^3$ are as defined in Table 85.

TABLE 92

This table covers 126 compounds of the following type:

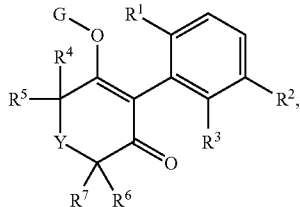

wherein Y is O, $R^1$ is ethyl, $R^4$ and $R^6$ are methyl, $R^5$ and $R^7$ are hydrogen, G is hydrogen and $R^2$ and $R^3$ are as defined in Table 85.

TABLE 93

This table covers 126 compounds of the following type:

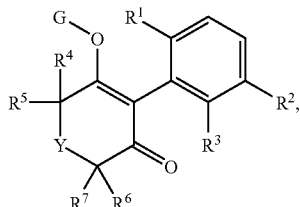

wherein Y is O, $R^1$ is methyl, $R^4$, $R^5$ and $R^6$ are methyl, $R^7$ is hydrogen, G is hydrogen and $R^2$ and $R^3$ are as defined in Table 85.

TABLE 94

This table covers 126 compounds of the following type:

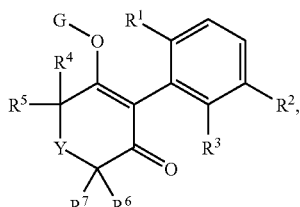

wherein Y is O, $R^1$ is ethyl, $R^4$, $R^5$ and $R^6$ are methyl, $R^7$ is hydrogen, G is hydrogen and $R^2$ and $R^3$ are as defined in Table 85.

TABLE 95

This table covers 126 compounds of the following type:

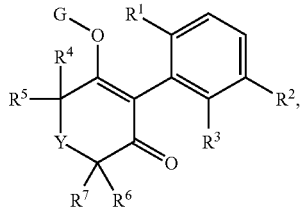

wherein Y is O, $R^1$ is methyl, $R^4$, $R^5$, $R^6$ and $R^7$ are methyl, G is hydrogen and $R^2$ and $R^3$ are as defined in Table 85.

TABLE 96

This table covers 126 compounds of the following type:

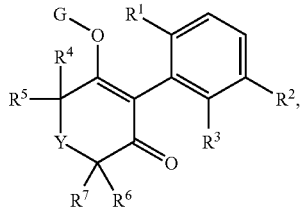

wherein Y is O, $R^1$ is ethyl, $R^4$, $R^5$, $R^6$ and $R^7$ are methyl, G is hydrogen and $R^2$ and $R^3$ are as defined in Table 85.

TABLE 97

This table covers 126 compounds of the following type:

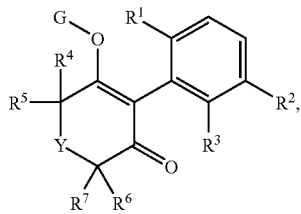

wherein Y is O, $R^1$ is methyl, $R^4$, $R^5$, $R^6$ are methyl, $R^7$ is methoxymethyl, G is hydrogen and $R^2$ and $R^3$ are as defined in Table 85.

TABLE 98

This table covers 126 compounds of the following type:

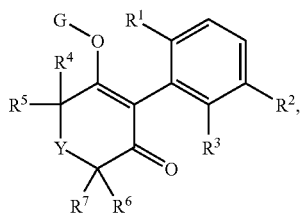

wherein Y is O, $R^1$ is ethyl, $R^4$, $R^5$, $R^6$ are methyl, $R^7$ is methoxymethyl, G is hydrogen and $R^2$ and $R^3$ are as defined in Table 85.

TABLE 99

This table covers 126 compounds of the following type:

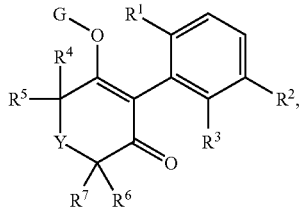

wherein Y is S, $R^1$ is methyl, $R^4$, $R^5$, $R^6$ and $R^7$ are hydrogen, G is hydrogen and $R^2$ and $R^3$ are as defined in Table 85.

TABLE 100

This table covers 126 compounds of the following type:

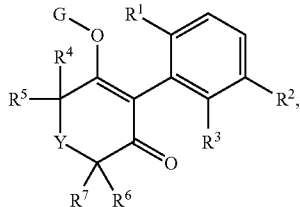

wherein Y is S, $R^1$ is ethyl, $R^4$, $R^5$, $R^6$ and $R^7$ are hydrogen, G is hydrogen and $R^2$ and $R^3$ are as defined in Table 85.

TABLE 101

This table covers 126 compounds of the following type:

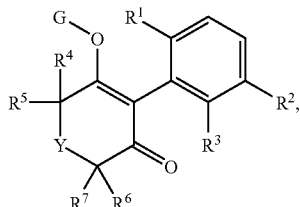

wherein Y is S, $R^1$ is methyl, $R^4$ is methyl, $R^5$, $R^6$ and $R^7$ are hydrogen, G is hydrogen and $R^2$ and $R^3$ are as defined in Table 85.

TABLE 102

This table covers 126 compounds of the following type:

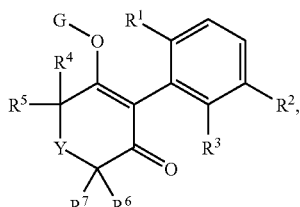

wherein Y is S, $R^1$ is ethyl, $R^4$ is methyl, $R^5$, $R^6$ and $R^7$ are hydrogen, G is hydrogen and $R^2$ and $R^3$ are as defined in Table 85.

TABLE 103

This table covers 126 compounds of the following type:

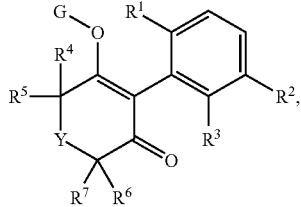

wherein Y is S, $R^1$ is methyl, $R^4$ and $R^5$ are methyl, $R^6$ and $R^7$ are hydrogen, G is hydrogen and $R^2$ and $R^3$ are as defined in Table 85.

TABLE 104

This table covers 126 compounds of the following type:

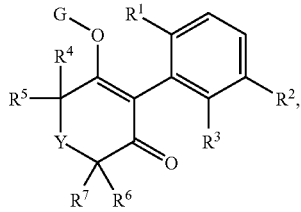

wherein Y is S, $R^1$ is ethyl, $R^4$ and $R^5$ are methyl, $R^6$ and $R^7$ are hydrogen, G is hydrogen and $R^2$ and $R^3$ are as defined in Table 85.

TABLE 105

This table covers 126 compounds of the following type:

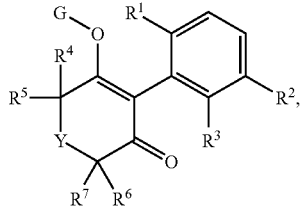

wherein Y is S, $R^1$ is methyl, $R^4$ and $R^6$ are methyl, $R^5$ and $R^7$ are hydrogen, G is hydrogen and $R^2$ and $R^3$ are as defined in Table 85.

TABLE 106

This table covers 126 compounds of the following type:

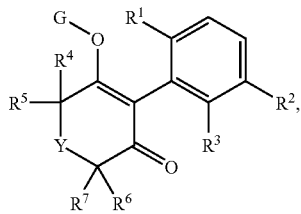

wherein Y is S, $R^1$ is ethyl, $R^4$ and $R^6$ are methyl, $R^5$ and $R^7$ are hydrogen, G is hydrogen and $R^2$ and $R^3$ are as defined in Table 85.

TABLE 107

This table covers 126 compounds of the following type:

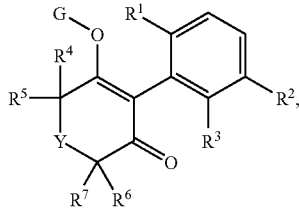

wherein Y is S, $R^1$ is methyl, $R^4$, $R^5$ and $R^6$ are methyl, $R^7$ is hydrogen, G is hydrogen and $R^2$ and $R^3$ are as defined in Table 85.

TABLE 108

This table covers 126 compounds of the following type:

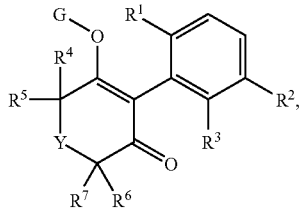

wherein Y is S, $R^1$ is ethyl, $R^4$, $R^5$ and $R^6$ are methyl, $R^7$ is hydrogen, G is hydrogen and $R^2$ and $R^3$ are as defined in Table 85.

TABLE 109

This table covers 126 compounds of the following type:

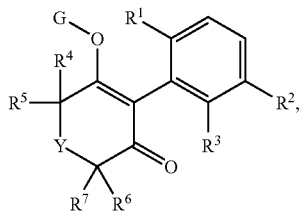

wherein Y is S, $R^1$ is methyl, $R^4$, $R^5$, $R^6$ and $R^7$ are methyl, G is hydrogen and $R^2$ and $R^3$ are as defined in Table 85.

TABLE 110

This table covers 126 compounds of the following type:

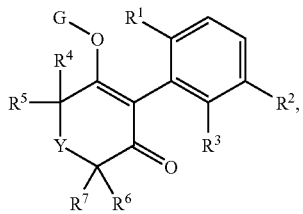

wherein Y is S, $R^1$ is ethyl, $R^4$, $R^5$, $R^6$ and $R^7$ are methyl, G is hydrogen and $R^2$ and $R^3$ are as defined in Table 85.

TABLE 111

This table covers 126 compounds of the following type:

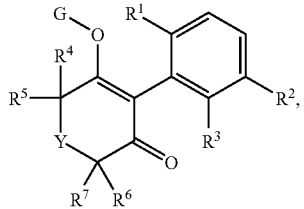

wherein Y is S=O, $R^1$ is methyl, $R^4$, $R^5$, $R^6$ and $R^7$ are hydrogen, G is hydrogen and $R^2$ and $R^3$ are as defined in Table 85.

TABLE 112

This table covers 126 compounds of the following type:

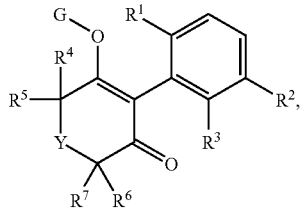

wherein Y is S=O, $R^1$ is ethyl, $R^4$, $R^5$, $R^6$ and $R^7$ are hydrogen, G is hydrogen and $R^2$ and $R^3$ are as defined in Table 85.

TABLE 113

This table covers 126 compounds of the following type:

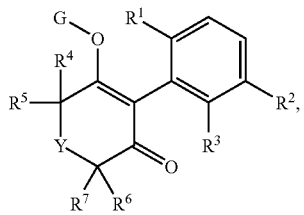

wherein Y is S=O, $R^1$ is methyl, $R^4$ is methyl, $R^5$, $R^6$ and $R^7$ are hydrogen, G is hydrogen and $R^2$ and $R^3$ are as defined in Table 85.

TABLE 114

This table covers 126 compounds of the following type:

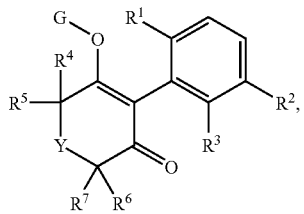

wherein Y is S=O, $R^1$ is ethyl, $R^4$ is methyl, $R^5$, $R^6$ and $R^7$ are hydrogen, G is hydrogen and $R^2$ and $R^3$ are as defined in Table 85.

TABLE 115

This table covers 126 compounds of the following type:

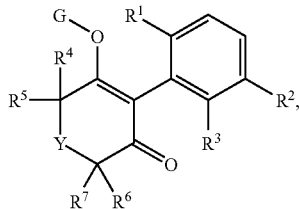

wherein Y is S=O, R¹ is methyl, R⁴ and R⁵ are methyl, R⁶ and R⁷ are hydrogen, G is hydrogen and R² and R³ are as defined in Table 85.

TABLE 116

This table covers 126 compounds of the following type:

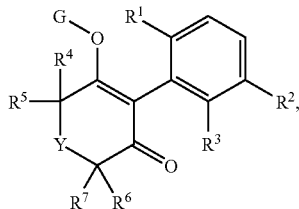

wherein Y is S=O, R¹ is ethyl, R⁴ and R⁵ are methyl, R⁶ and R⁷ are hydrogen, G is hydrogen and R² and R³ are as defined in Table 85.

TABLE 117

This table covers 126 compounds of the following type:

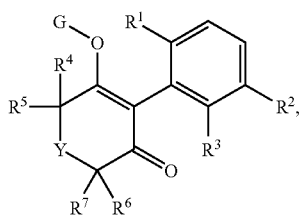

wherein Y is S=O, R¹ is methyl, R⁴ and R⁶ are methyl, R⁵ and R⁷ are hydrogen, G is hydrogen and R² and R³ are as defined in Table 85.

TABLE 118

This table covers 126 compounds of the following type:

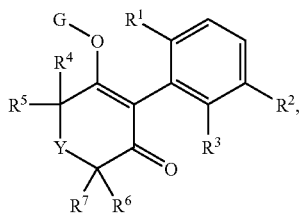

wherein Y is S=O, R¹ is ethyl, R⁴ and R⁶ are methyl, R⁵ and R⁷ are hydrogen, G is hydrogen and R² and R³ are as defined in Table 85.

TABLE 119

This table covers 126 compounds of the following type:

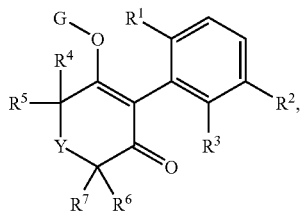

wherein Y is S=O, R¹ is methyl, R⁴, R⁵ and R⁶ methyl, R⁷ is hydrogen, G is hydrogen and R² and R³ are as defined in Table 85.

TABLE 120

This table covers 126 compounds of the following type:

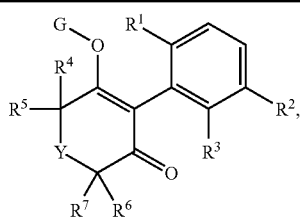

wherein Y is S=O, R¹ is ethyl, R⁴, R⁵ and R⁶ are methyl, R⁷ is hydrogen, G is hydrogen and R² and R³ are as defined in Table 85.

TABLE 121

This table covers 126 compounds of the following type:

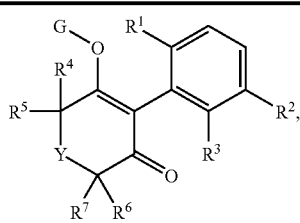

wherein Y is S=O, R¹ is methyl, R⁴, R⁵, R⁶ and R⁷ are methyl, G is hydrogen and R² and R³ are as defined in Table 85.

TABLE 122

This table covers 126 compounds of the following type:

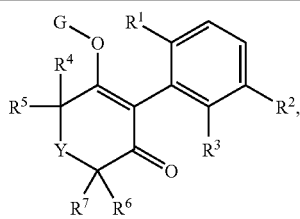

wherein Y is S=O, R¹ is ethyl, R⁴, R⁵, R⁶ and R⁷ are methyl, G is hydrogen and R² and R³ are as defined in Table 85.

TABLE 123

This table covers 126 compounds of the following type:

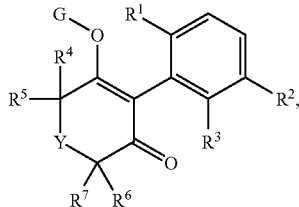

wherein Y is $S(=O)_2$, $R^1$ is methyl, $R^4$, $R^5$, $R^6$ and $R^7$ are hydrogen, G is hydrogen and $R^2$ and $R^3$ are as defined in Table 85.

TABLE 124

This table covers 126 compounds of the following type:

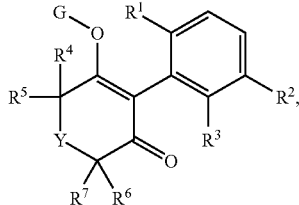

wherein Y is $S(=O)_2$, $R^1$ is ethyl, $R^4$, $R^5$, $R^6$ and $R^7$ are hydrogen, G is hydrogen and $R^2$ and $R^3$ are as defined in Table 85.

TABLE 125

This table covers 126 compounds of the following type:

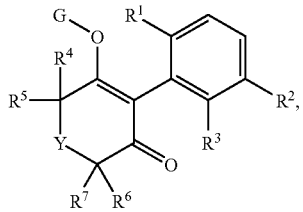

wherein Y is $S(=O)_2$, $R^1$ is methyl, $R^4$ is methyl, $R^5$, $R^6$ and $R^7$ are hydrogen, G is hydrogen and $R^2$ and $R^3$ are as defined in Table 85.

TABLE 126

This table covers 126 compounds of the following type:

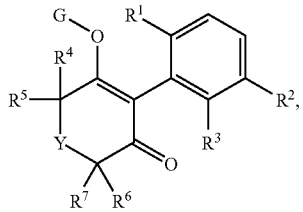

wherein Y is $S(=O)_2$, $R^1$ is ethyl, $R^4$ is methyl, $R^5$, $R^6$ and $R^7$ are hydrogen, G is hydrogen and $R^2$ and $R^3$ are as defined in Table 85.

TABLE 127

This table covers 126 compounds of the following type:

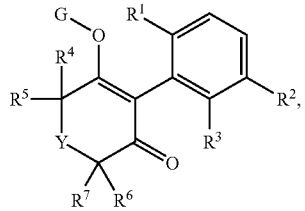

wherein Y is $S(=O)_2$, $R^1$ is methyl, $R^4$ and $R^5$ are methyl, $R^6$ and $R^7$ are hydrogen, G is hydrogen and $R^2$ and $R^3$ are as defined in Table 85.

TABLE 128

This table covers 126 compounds of the following type:

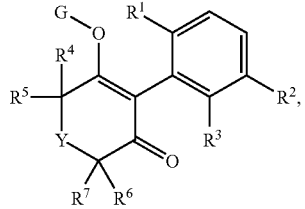

wherein Y is $S(=O)_2$, $R^1$ is ethyl, $R^4$ and $R^5$ are methyl, $R^6$ and $R^7$ are hydrogen, G is hydrogen and $R^2$ and $R^3$ are as defined in Table 85.

TABLE 129

This table covers 126 compounds of the following type:

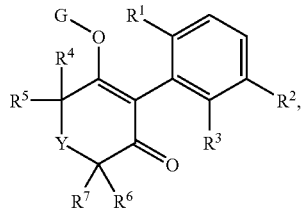

wherein Y is $S(=O)_2$, $R^1$ is methyl, $R^4$ and $R^6$ are methyl, $R^5$ and $R^7$ are hydrogen, G is hydrogen and $R^2$ and $R^3$ are as defined in Table 85.

TABLE 130

This table covers 126 compounds of the following type:

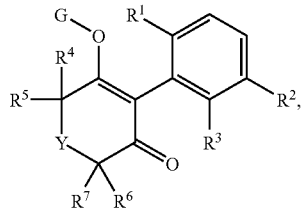

wherein Y is $S(=O)_2$, $R^1$ is ethyl, $R^4$ and $R^6$ are methyl, $R^5$ and $R^7$ are hydrogen, G is hydrogen and $R^2$ and $R^3$ are as defined in Table 85.

TABLE 131

This table covers 126 compounds of the following type:

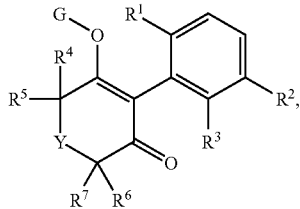

wherein Y is S(=O)$_2$, R$^1$ is methyl, R$^4$, R$^5$ and R$^6$ are methyl, R$^7$ is hydrogen, G is hydrogen and R$^2$ and R$^3$ are as defined in Table 85.

TABLE 132

This table covers 126 compounds of the following type:

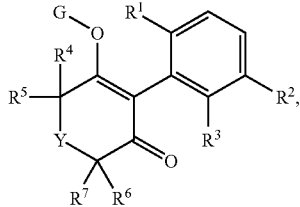

wherein Y is S(=O)$_2$, R$^1$ is ethyl, R$^4$, R$^5$ and R$^6$ are methyl, R$^7$ is hydrogen, G is hydrogen and R$^2$ and R$^3$ are as defined in Table 85.

TABLE 133

This table covers 126 compounds of the following type:

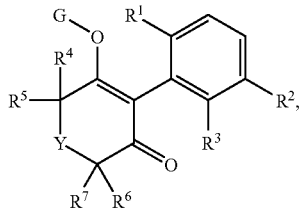

wherein Y is S(=O)$_2$, R$^1$ is methyl, R$^4$, R$^5$, R$^6$ and R$^7$ are methyl, G is hydrogen and R$^2$ and R$^3$ are as defined in Table 85.

TABLE 134

This table covers 126 compounds of the following type:

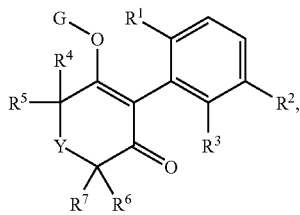

wherein Y is S(=O)$_2$, R$^1$ is ethyl, R$^4$, R$^5$, R$^6$ and R$^7$ are methyl, G is hydrogen and R$^2$ and R$^3$ are as defined in Table 85.

TABLE 135

This table covers 126 compounds of the following type:

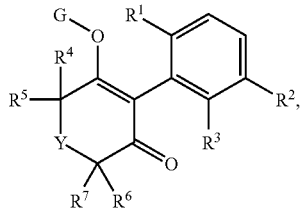

wherein Y is C=O, R$^1$ is methyl, R$^4$ and R$^5$ are methyl, R$^6$ and R$^7$ are hydrogen, G is hydrogen and R$^2$ and R$^3$ are as defined in Table 85.

TABLE 136

This table covers 126 compounds of the following type:

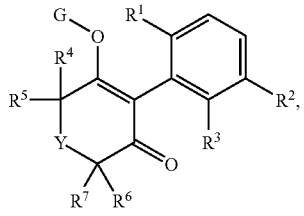

wherein Y is C=O, R$^1$ is ethyl, R$^4$ and R$^5$ are methyl, R$^6$ and R$^7$ are hydrogen, G is hydrogen and R$^2$ and R$^3$ are as defined in Table 85.

TABLE 137

This table covers 126 compounds of the following type:

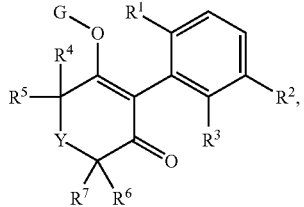

wherein Y is C=O, R$^1$ is methyl, R$^4$, R$^5$ and R$^6$ are methyl, R$^7$ is hydrogen, G is hydrogen and R$^2$ and R$^3$ are as defined in Table 85.

TABLE 138

This table covers 126 compounds of the following type:

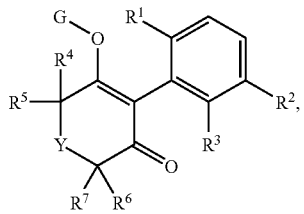

wherein Y is C=O, R$^1$ is ethyl, R$^4$, R$^5$ and R$^6$ methyl, R$^7$ is hydrogen, G is hydrogen and R$^2$ and R$^3$ are as defined in Table 85.

TABLE 139

This table covers 126 compounds of the following type:

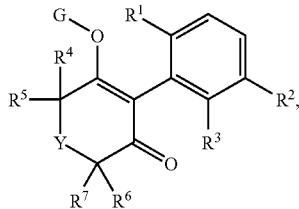

wherein Y is C=O, R$^1$ is methyl, R$^4$, R$^5$, R$^6$ and R$^7$ are methyl, G is hydrogen and R$^2$ and R$^3$ are as defined in Table 85.

TABLE 140

This table covers 126 compounds of the following type:

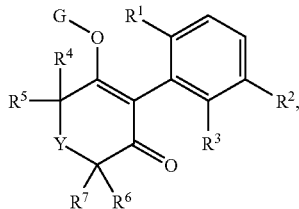

wherein Y is C=O, R$^1$ is ethyl, R$^4$, R$^5$, R$^6$ and R$^7$ are methyl, G is hydrogen and R$^2$ and R$^3$ are as defined in Table 85.

TABLE 141

This table covers 126 compounds of the following type:

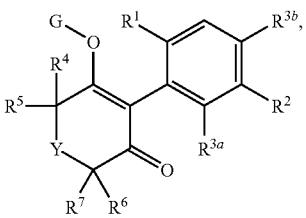

wherein Y is O and R$^1$ and R$^{3a}$ are methyl, R$^4$, R$^5$, R$^6$ and R$^7$ are methyl, R$^{3b}$ is methyl, and G is hydrogen and R$^2$ is as defined in Table 85.

TABLE 142

This table covers 126 compounds of the following type:

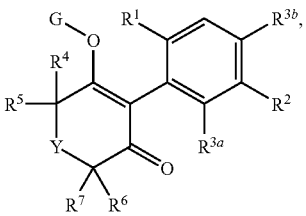

wherein Y is S and R$^1$ and R$^{3a}$ are methyl, R$^4$, R$^5$, R$^6$ and R$^7$ are methyl, R$^{3b}$ is methyl, and G is hydrogen and R$^2$ is as defined in the Table 85.

TABLE 143

This table covers 126 compounds of the following type:

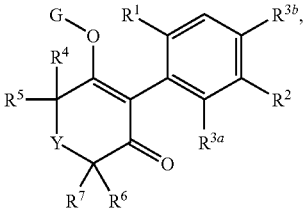

wherein Y is S=O and R$^1$ and R$^{3a}$ are methyl, R$^4$, R$^5$, R$^6$ and R$^7$ are methyl, R$^{3b}$ is methyl, and G is hydrogen and R$^2$ is as defined in the Table 85.

TABLE 144

This table covers 126 compounds of the following type:

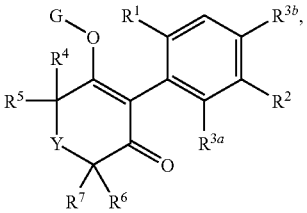

wherein Y is S(=O)$_2$ and R$^1$ and R$^{3a}$ are methyl, R$^4$, R$^5$, R$^6$ and R$^7$ are methyl, R$^{3b}$ is methyl, and G is hydrogen and R$^2$ is as defined in the Table 85.

TABLE 145

This table covers 126 compounds of the following type:

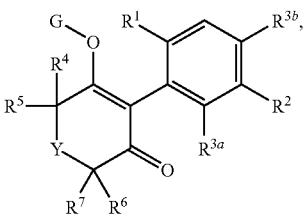

wherein Y is C=O and R$^1$ and R$^{3a}$ are methyl, R$^4$, R$^5$, R$^6$ and R$^7$ are methyl, R$^{3b}$ is methyl, and G is hydrogen and R$^2$ is as defined in the Table 85.

TABLE 146

This table covers 126 compounds of the following type:

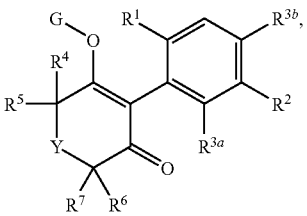

wherein Y is O and R$^1$ is ethyl and R$^{3a}$ is methyl, R$^4$, R$^5$, R$^6$ and R$^7$ are methyl, R$^{3b}$ is methyl, and G is hydrogen and R$^2$ is as defined in Table 85.

TABLE 147

This table covers 126 compounds of the following type:

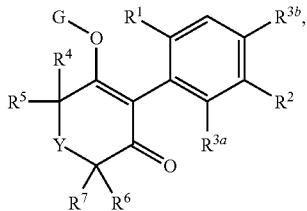

wherein Y is S and R¹ is ethyl and R$^{3a}$ is methyl, R⁴, R⁵, R⁶ and R⁷ are methyl, R$^{3b}$ is methyl, and G is hydrogen and R² is as defined in Table 85.

TABLE 148

This table covers 126 compounds of the following type:

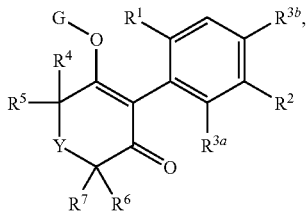

wherein Y is S=O and R¹ is ethyl and R$^{3a}$ is methyl, R⁴, R⁵, R⁶ and R⁷ are methyl, R$^{3b}$ is methyl, and G is hydrogen and R² is as defined in Table 85.

TABLE 149

This table covers 126 compounds of the following type:

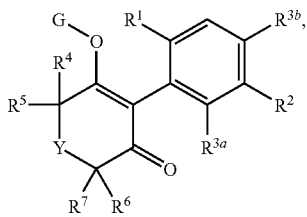

wherein Y is S(=O)₂ and R¹ is ethyl and R$^{3a}$ is methyl, R⁴, R⁵, R⁶ and R⁷ are methyl, R$^{3b}$ is methyl, and G is hydrogen and R² is as defined in Table 85.

TABLE 150

This table covers 126 compounds of the following type:

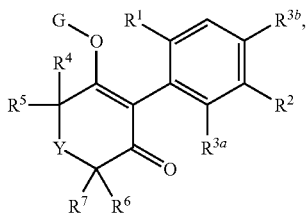

wherein Y is C=O and R¹ is ethyl and R$^{3a}$ is methyl, R⁴, R⁵, R⁶ and R⁷ are methyl, R$^{3b}$ is methyl, and G is hydrogen and R² is as defined in Table 85.

TABLE 151

This table covers 126 compounds of the following type:

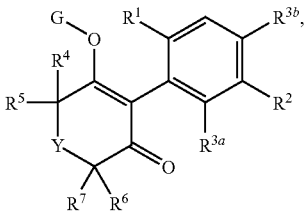

wherein Y is O and R¹ and R$^{3a}$ are ethyl, R⁴, R⁵, R⁶ and R⁷ are methyl, R$^{3b}$ is methyl, and G is hydrogen and R² is as defined in Table 85.

TABLE 152

This table covers 126 compounds of the following type:

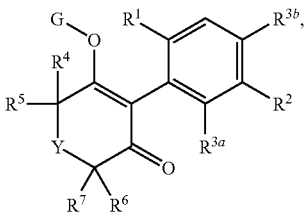

wherein Y is S and R¹ and R$^{3a}$ are ethyl, R⁴, R⁵, R⁶ and R⁷ are methyl, R$^{3b}$ is methyl, and G is hydrogen and R² is as defined in Table 85.

TABLE 153

This table covers 126 compounds of the following type:

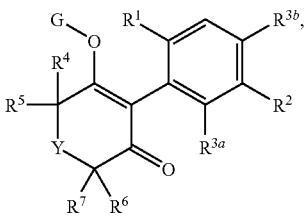

wherein Y is S=O and R¹ and R$^{3a}$ are ethyl, R⁴, R⁵, R⁶ and R⁷ are methyl, R$^{3b}$ is methyl, and G is hydrogen and R² is as defined in Table 85.

TABLE 154

This table covers 126 compounds of the following type:

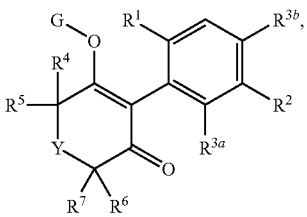

wherein Y is S(=O)₂ and R¹ and R$^{3a}$ are ethyl, R⁴, R⁵, R⁶ and R⁷ are methyl, R$^{3b}$ is methyl, and G is hydrogen and R² is as defined in Table 85.

TABLE 155

This table covers 126 compounds of the following type:

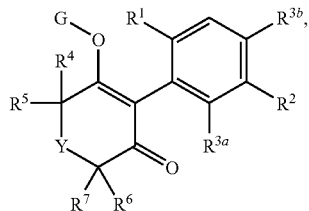

wherein Y is C=O and R¹ and R³ᵃ are ethyl, R⁴, R⁵, R⁶ and R⁷ are methyl, R³ᵇ is methyl, and G is hydrogen and R² is as defined in Table 85.

TABLE 156

This table covers 378 compounds of the following type:

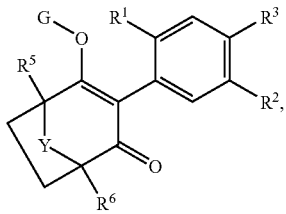

wherein Y is O, R¹ is methyl, R⁵ and R⁶ are hydrogen, G is hydrogen and R² and R³ are as defined in Table 1.

TABLE 157

This table covers 378 compounds of the following type:

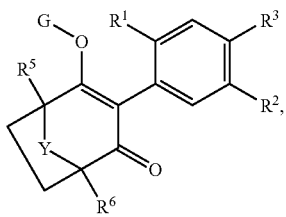

wherein Y is O, R¹ is ethyl, R⁵ and R⁶ are hydrogen, G is hydrogen and R² and R³ are as defined in Table 1.

TABLE 158

This table covers 378 compounds of the following type:

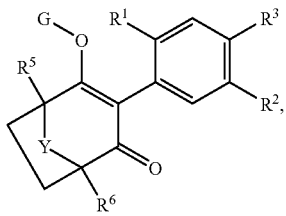

wherein Y is O, R¹ is chlorine, R⁵ and R⁶ are hydrogen, G is hydrogen and R² and R³ are as defined in Table 1.

TABLE 159

This table covers 378 compounds of the following type:

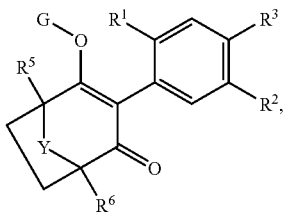

wherein Y is O, R¹ is methyl, R⁵ is hydrogen and R⁶ is methyl, G is hydrogen and R² and R³ are as defined in Table 1.

TABLE 160

This table covers 378 compounds of the following type:

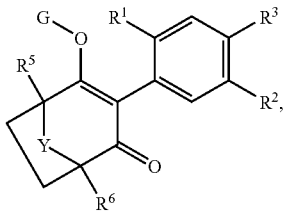

wherein Y is O, R¹ is ethyl, R⁵ is hydrogen and R⁶ is methyl, G is hydrogen and R² and R³ are as defined in Table 1.

TABLE 161

This table covers 378 compounds of the following type:

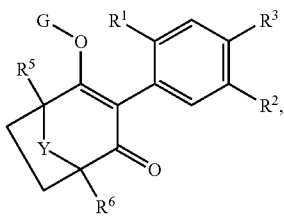

wherein Y is O, R¹ is chlorine, R⁵ is hydrogen and R⁶ is methyl, G is hydrogen and R² and R³ are as defined in Table 1.

TABLE 162

This table covers 378 compounds of the following type:

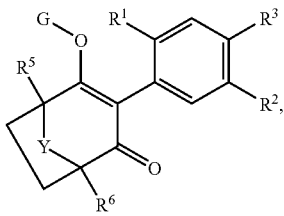

wherein Y is O, R¹ is methyl, R⁵ and R⁶ are methyl, G is hydrogen and R² and R³ are as defined in Table 1.

TABLE 163

This table covers 378 compounds of the following type:

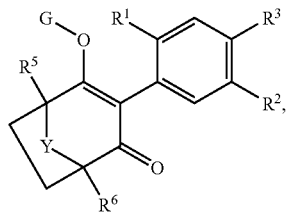

wherein Y is O, R¹ is ethyl, R⁵ and R⁶ methyl, G is hydrogen and R² and R³ are as defined in Table 1.

TABLE 164

This table covers 378 compounds of the following type:

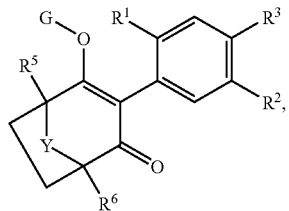

wherein Y is O, R¹ is chlorine, R⁵ and R⁶ are methyl, G is hydrogen and R² and R³ are as defined in Table 1.

TABLE 165

This table covers 378 compounds of the following type:

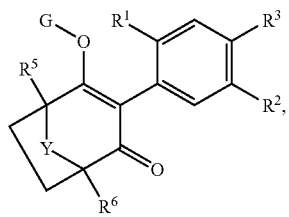

wherein Y is O, R¹ is methyl, R⁵ is hydrogen and R⁶ is methoxymethyl, G is hydrogen and R² and R³ are as defined in Table 1.

TABLE 166

This table covers 378 compounds of the following type:

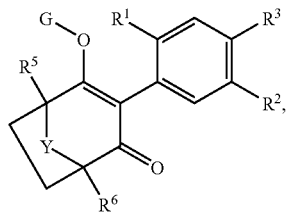

wherein Y is O, R¹ is ethyl, R⁵ is hydrogen and R⁶ is methoxymethyl, G is hydrogen and R² and R³ are as defined in Table 1.

TABLE 167

This table covers 378 compounds of the following type:

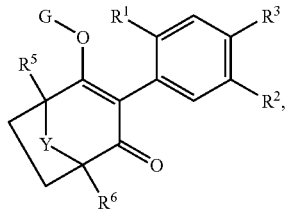

wherein Y is O, R¹ is chlorine, R⁵ is hydrogen and R⁶ is methoxymethyl, G is hydrogen and R² and R³ are as defined in Table 1.

TABLE 168

This table covers 378 compounds of the following type:

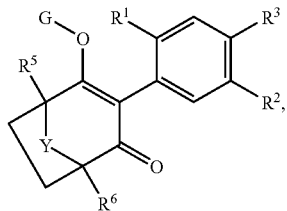

wherein Y is O, R¹ is methyl, R⁵ is hydrogen and R⁶ is ethoxymethyl, G is hydrogen and R² and R³ are as defined in Table 1.

TABLE 169

This table covers 378 compounds of the following type:

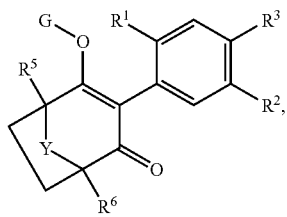

wherein Y is O, R¹ is ethyl, R⁵ is hydrogen and R⁶ is ethoxymethyl, G is hydrogen and R² and R³ are as defined in Table 1.

TABLE 170

This table covers 378 compounds of the following type:

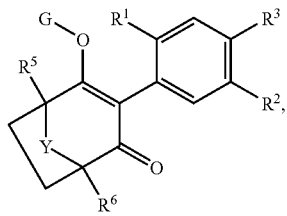

wherein Y is O, R¹ is chlorine, R⁵ is hydrogen and R⁶ is ethoxymethyl, G is hydrogen and R² and R3 are as defined in Table 1.

TABLE 171

This table covers 378 compounds of the following type:

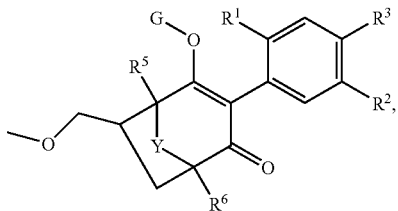

wherein Y is O, R¹ is methyl, R⁵ and R⁶ are hydrogen, G is hydrogen and R² and R³ are as defined in Table 1.

TABLE 172

This table covers 378 compounds of the following type:

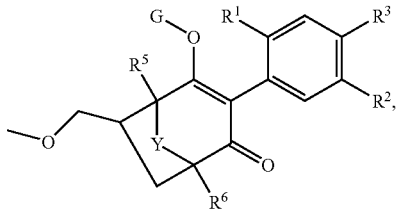

wherein Y is O, R¹ is ethyl, R⁵ and R⁶ are hydrogen, G is hydrogen and R² and R³ are as defined in Table 1.

TABLE 173

This table covers 378 compounds of the following type:

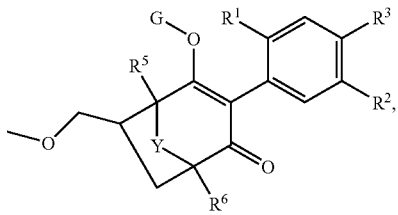

wherein Y is O, R¹ is chlorine, R⁵ and R⁶ are hydrogen, G is hydrogen and R² and R³ are as defined in Table 1.

TABLE 174

This table covers 378 compounds of the following type:

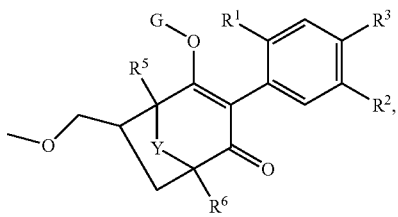

wherein Y is O, R¹ is methyl, R⁵ is methyl, R⁶ is hydrogen, G is hydrogen and R² and R³ are as defined in Table 1.

TABLE 175

This table covers 378 compounds of the following type:

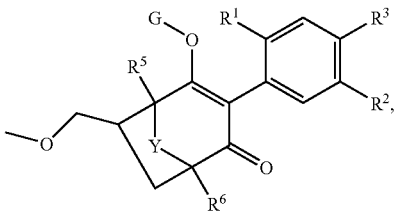

wherein Y is O, R¹ is ethyl, R⁵ is methyl, R⁶ is hydrogen, G is hydrogen and R² and R³ are as defined in Table 1.

TABLE 176

This table covers 378 compounds of the following type:

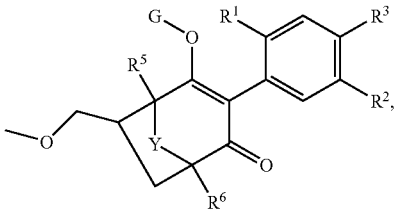

wherein Y is O, R¹ is chlorine, R⁵ is methyl, R⁶ is hydrogen, G is hydrogen and R² and R³ are as defined in Table 1.

TABLE 177

This table covers 126 compounds of the following type:

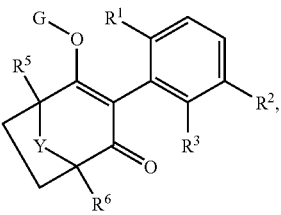

wherein Y is O, R¹ is methyl, R⁵ and R⁶ are hydrogen, G is hydrogen and R² and R³ are as defined in Table 85.

TABLE 178

This table covers 126 compounds of the following type:

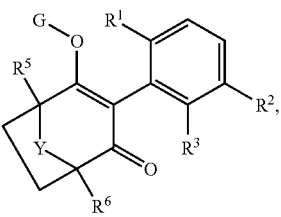

wherein Y is O, R¹ is ethyl, R⁵ and R⁶ are hydrogen, G is hydrogen and R² and R³ are as defined in Table 85.

TABLE 179

This table covers 126 compounds of the following type:

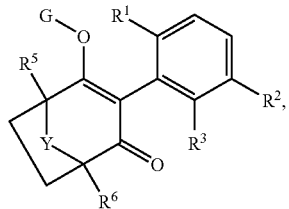

wherein Y is O, $R^1$ is methyl, $R^5$ is hydrogen and $R^6$ is methyl, G is hydrogen and $R^2$ and $R^3$ are as defined in Table 85.

TABLE 180

This table covers 126 compounds of the following type:

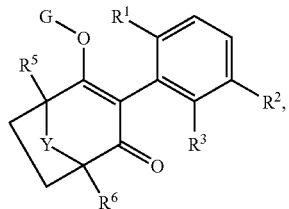

wherein Y is O, $R^1$ is ethyl, $R^5$ is hydrogen and $R^6$ is methyl, G is hydrogen and $R^2$ and $R^3$ are as defined in Table 85.

TABLE 181

This table covers 126 compounds of the following type:

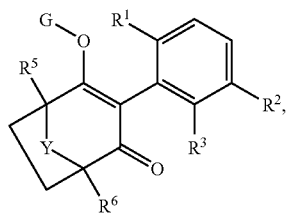

wherein Y is O, $R^1$ is methyl, $R^5$ and $R^6$ are methyl, G is hydrogen and $R^2$ and $R^3$ are as defined in Table 85.

TABLE 182

This table covers 126 compounds of the following type:

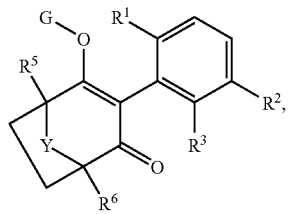

wherein Y is O, $R^1$ is ethyl, $R^5$ and $R^6$ are methyl, G is hydrogen and $R^2$ and $R^3$ are as defined in Table 85.

TABLE 183

This table covers 126 compounds of the following type:

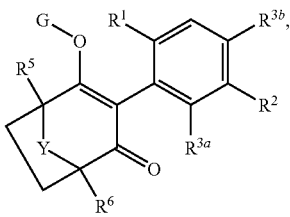

wherein Y is O, $R^1$ and $R^{3a}$ are methyl, $R^5$ and $R^6$ are hydrogen, $R^{3b}$ is methyl, and G is hydrogen and $R^2$ is as defined in Table 85.

TABLE 184

This table covers 126 compounds of the following type:

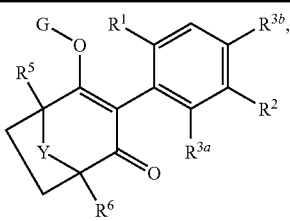

wherein Y is O, $R^1$ is ethyl and $R^{3a}$ is methyl, $R^5$ and $R^6$ are hydrogen, $R^{3b}$ is methyl, and G is hydrogen and $R^2$ is as defined in Table 85.

TABLE 185

This table covers 126 compounds of the following type:

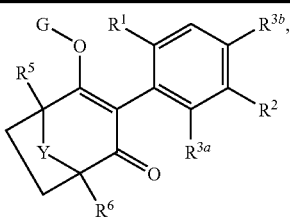

wherein Y is O, $R^1$ and $R^{3a}$ are ethyl, $R^5$ and $R^6$ are hydrogen, $R^{3b}$ is methyl, and G is hydrogen and $R^2$ is as defined in Table 85.

TABLE 186

This table covers 126 compounds of the following type:

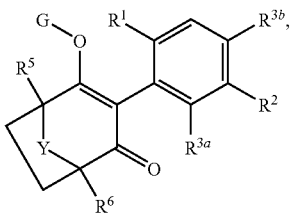

wherein Y is O, $R^1$ and $R^{3a}$ are methyl, $R^5$ is hydrogen and $R^6$ is methyl, $R^{3b}$ is methyl, and G is hydrogen and $R^2$ is as defined in Table 85.

TABLE 187

This table covers 126 compounds of the following type:

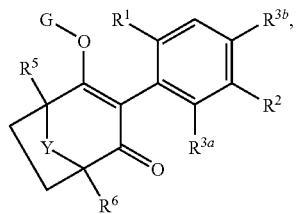

wherein Y is O, R¹ is ethyl and R³ᵃ is methyl, R⁵ is hydrogen and R⁶ is methyl, R³ᵇ is methyl, and G is hydrogen and R² is as defined in Table 85.

TABLE 188

This table covers 126 compounds of the following type:

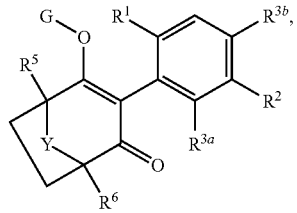

wherein Y is O, R¹ and R³ᵃ are ethyl, R⁵ is hydrogen and R⁶ is methyl, R³ᵇ is methyl, and G is hydrogen and R² is as defined in Table 85.

TABLE 189

This table covers 126 compounds of the following type:

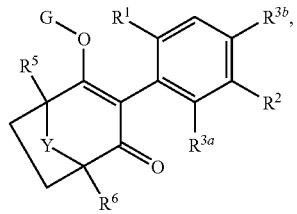

wherein Y is O, R¹ and R³ᵃ are methyl, R⁵ are R⁶ are methyl, R³ᵇ is methyl, and G is hydrogen and R² is as defined in Table 85.

TABLE 190

This table covers 126 compounds of the following type:

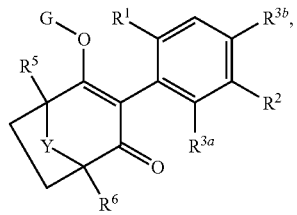

wherein Y is O, R¹ is ethyl and R³ᵃ is methyl, R⁵ are R⁶ are methyl, R³ᵇ is methyl, and G is hydrogen and R² is as defined in Table 85.

TABLE 191

This table covers 126 compounds of the following type:

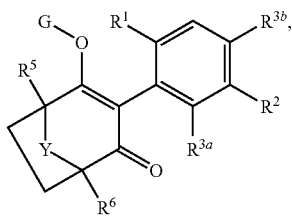

wherein Y is O, R¹ and R³ᵃ are ethyl, R⁵ are R⁶ are methyl, R³ᵇ is methyl, and G is hydrogen and R² is as defined in Table 85.

TABLE 192

This table covers 378 compounds of the following type:

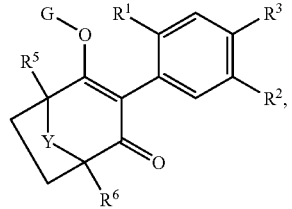

wherein Y is S, R¹ is methyl, R⁵ and R⁶ are hydrogen, G is hydrogen and R² and R³ are as defined in Table 1.

TABLE 193

This table covers 378 compounds of the following type:

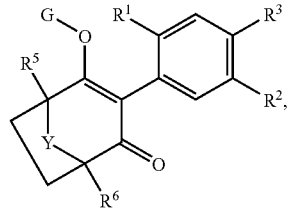

wherein Y is S, R¹ is ethyl, R⁵ and R⁶ are hydrogen, G is hydrogen and R² and R³ are as defined in Table 1.

TABLE 194

This table covers 378 compounds of the following type:

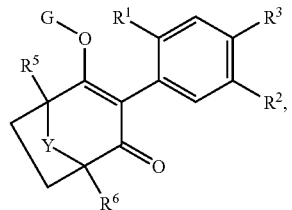

wherein Y is S, R¹ is chlorine, R⁵ and R⁶ are hydrogen, G is hydrogen and R² and R³ are as defined in Table 1.

TABLE 195

This table covers 378 compounds of the following type:

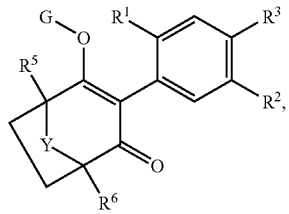

wherein Y is S, R$^1$ is methyl, R$^5$ is hydrogen and R$^6$ is methyl, G is hydrogen and R$^2$ and R$^3$ are as defined in Table 1.

TABLE 196

This table covers 378 compounds of the following type:

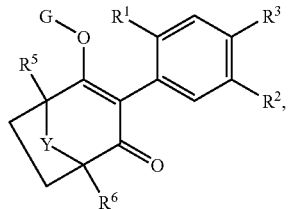

wherein Y is S, R$^1$ is ethyl, R$^5$ is hydrogen and R$^6$ is methyl, G is hydrogen and R$^2$ and R$^3$ are as defined in Table 1.

TABLE 197

This table covers 378 compounds of the following type:

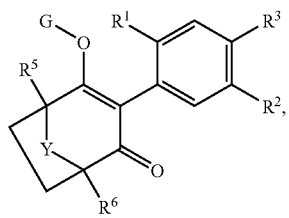

wherein Y is S, R$^1$ is chlorine, R$^5$ is hydrogen and R$^6$ is methyl, G is hydrogen and R$^2$ and R$^3$ are as defined in Table 1.

TABLE 198

This table covers 378 compounds of the following type:

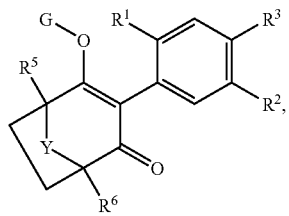

wherein Y is S, R$^1$ is methyl, R$^5$ and R$^6$ are methyl, G is hydrogen and R$^2$ and R$^3$ are as defined in Table 1.

TABLE 199

This table covers 378 compounds of the following type:

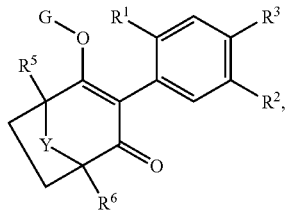

wherein Y is S, R$^1$ is ethyl, R$^5$ and R$^6$ are methyl, G is hydrogen and R$^2$ and R$^3$ are as defined in Table 1.

TABLE 200

This table covers 378 compounds of the following type:

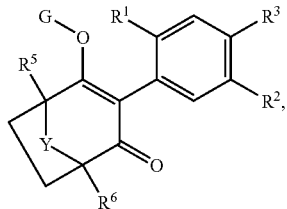

wherein Y is S, R$^1$ is chlorine, R$^5$ and R$^6$ are methyl, G is hydrogen and R$^2$ and R$^3$ are as defined in Table 1.

TABLE 201

This table covers 126 compounds of the following type:

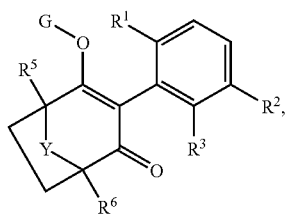

wherein Y is S, R$^1$ is methyl, R$^5$ and R$^6$ are hydrogen, G is hydrogen and R$^2$ and R$^3$ are as defined in Table 85.

TABLE 202

This table covers 126 compounds of the following type:

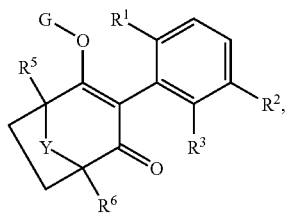

wherein Y is S, R$^1$ is ethyl, R$^5$ and R$^6$ are hydrogen, G is hydrogen and R$^2$ and R$^3$ are as defined in Table 85.

TABLE 203

This table covers 126 compounds of the following type:

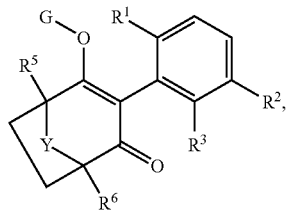

wherein Y is S, R$^1$ is methyl, R$^5$ is hydrogen and R$^6$ is methyl, G is hydrogen and R$^2$ and R$^3$ are as defined in Table 85.

TABLE 204

This table covers 126 compounds of the following type:

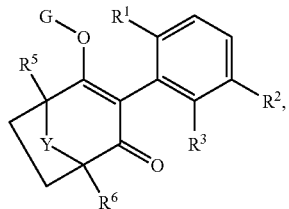

wherein Y is S, R$^1$ is ethyl, R$^5$ is hydrogen and R$^6$ is methyl, G is hydrogen and R$^2$ and R$^3$ are as defined in Table 85.

TABLE 205

This table covers 126 compounds of the following type:

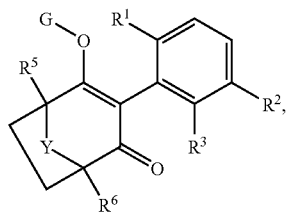

wherein Y is S, R$^1$ is methyl, R$^5$ and R$^6$ are methyl, G is hydrogen and R$^2$ and R$^3$ are as defined in Table 85.

TABLE 206

This table covers 126 compounds of the following type:

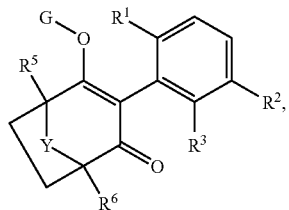

wherein Y is S, R$^1$ is ethyl, R$^5$ and R$^6$ are methyl, G is hydrogen and R$^2$ and R$^3$ are as defined in Table 85.

TABLE 207

This table covers 126 compounds of the following type:

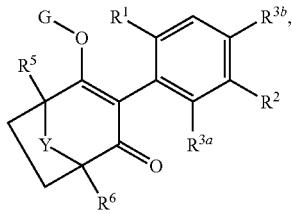

wherein Y is S, R$^1$ and R$^{3a}$ are methyl, R$^5$ and R$^6$ are hydrogen, R$^{3b}$ is methyl, and G is hydrogen and R$^2$ is as defined in Table 85.

TABLE 208

This table covers 126 compounds of the following type:

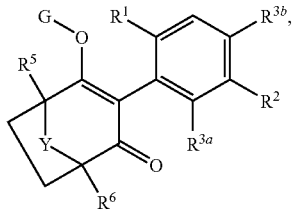

wherein Y is S, R$^1$ is ethyl and R$^{3a}$ is methyl, R$^5$ and R$^6$ are hydrogen, R$^{3b}$ is methyl, and G is hydrogen and R$^2$ is as defined in Table 85.

TABLE 209

This table covers 126 compounds of the following type:

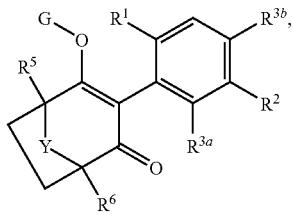

wherein Y is S, R$^1$ and R$^{3a}$ are ethyl, R$^5$ and R$^6$ are hydrogen, R$^{3b}$ is methyl, and G is hydrogen and R$^2$ is as defined in Table 85.

TABLE 210

This table covers 126 compounds of the following type:

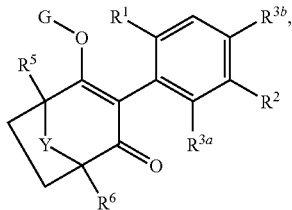

wherein Y is S, R$^1$ and R$^{3a}$ are methyl, R$^5$ is hydrogen and R$^6$ is methyl, R$^{3b}$ is methyl, and G is hydrogen and R$^2$ is as defined in Table 85.

TABLE 211

This table covers 126 compounds of the following type:

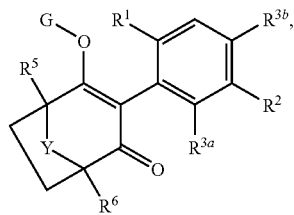

wherein Y is S, R¹ is ethyl and R³ᵃ is methyl, R⁵ is hydrogen and R⁶ is methyl, R³ᵇ is methyl, and G is hydrogen and R² is as defined in Table 85.

TABLE 212

This table covers 126 compounds of the following type:

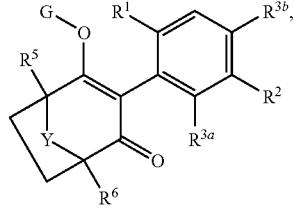

wherein Y is S, R¹ and R³ᵃ are ethyl, R⁵ is hydrogen and R⁶ is methyl, R³ᵇ is methyl, and G is hydrogen and R² is as defined in Table 85.

TABLE 213

This table covers 126 compounds of the following type:

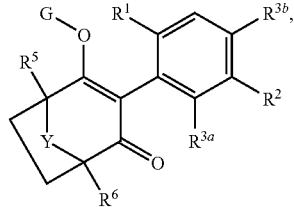

wherein Y is S, R¹ and R³ᵃ are methyl, R⁵ are R⁶ are methyl, R³ᵇ is methyl, and G is hydrogen and R² is as defined in Table 85.

TABLE 214

This table covers 126 compounds of the following type:

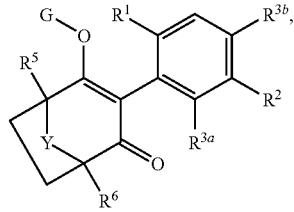

wherein Y is S, R¹ is ethyl and R³ᵃ is methyl, R⁵ are R⁶ are methyl, R³ᵇ is methyl, and G is hydrogen and R² is as defined in Table 85.

TABLE 215

This table covers 126 compounds of the following type:

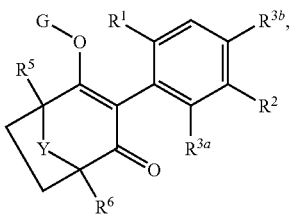

wherein Y is S, R¹ and R³ᵃ are ethyl, R⁵ are R⁶ are methyl, R³ᵇ is methyl, and G is hydrogen and R² is as defined in Table 85.

TABLE 216

This table covers 378 compounds of the following type:

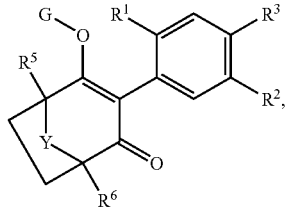

wherein Y is S=O, R¹ is methyl, R⁵ and R⁶ are hydrogen, G is hydrogen and R² and R³ are as defined in Table 1.

TABLE 217

This table covers 378 compounds of the following type:

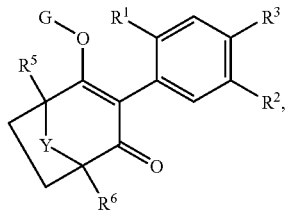

wherein Y is S=O, R¹ is ethyl, R⁵ and R⁶ are hydrogen, G is hydrogen and R² and R³ are as defined in Table 1.

TABLE 218

This table covers 378 compounds of the following type:

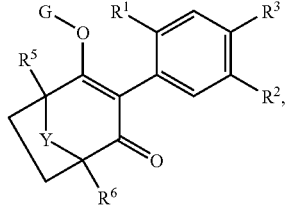

wherein Y is S=O, R¹ is chlorine, R⁵ and R⁶ are hydrogen, G is hydrogen and R² and R³ are as defined in Table 1.

TABLE 219

This table covers 378 compounds of the following type:

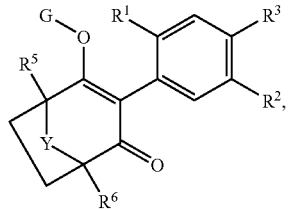

wherein Y is S=O, $R^1$ is methyl, $R^5$ is hydrogen and $R^6$ is methyl, G is hydrogen and $R^2$ and $R^3$ are as defined in Table 1.

TABLE 220

This table covers 378 compounds of the following type:

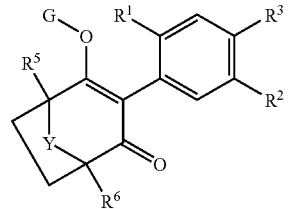

wherein Y is S=O, $R^1$ is ethyl, $R^5$ is hydrogen and $R^6$ is methyl, G is hydrogen and $R^2$ and $R^3$ are as defined in Table 1.

TABLE 221

This table covers 378 compounds of the following type:

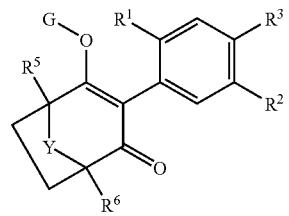

wherein Y is S=O, $R^1$ is chlorine, $R^5$ is hydrogen and $R^6$ is methyl, G is hydrogen and $R^2$ and $R^3$ are as defined in Table 1.

TABLE 222

This table covers 378 compounds of the following type:

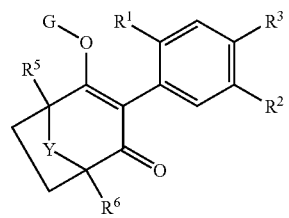

wherein Y is S=O, $R^1$ is methyl, $R^5$ and $R^6$ are methyl, G is hydrogen and $R^2$ and $R^3$ are as defined in Table 1.

TABLE 223

This table covers 378 compounds of the following type:

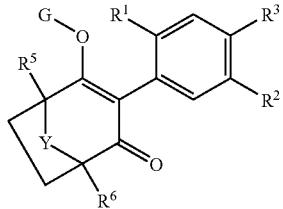

wherein Y is S=O, $R^1$ is ethyl, $R^5$ and $R^6$ are methyl, G is hydrogen and $R^2$ and $R^3$ are as defined in Table 1.

TABLE 224

This table covers 378 compounds of the following type:

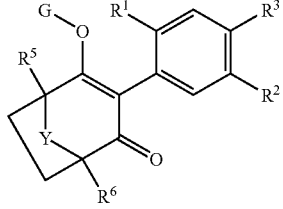

wherein Y is S=O, $R^1$ is chlorine, $R^5$ and $R^6$ are methyl, G is hydrogen and $R^2$ and $R^3$ are as defined in Table 1.

TABLE 225

This table covers 126 compounds of the following type:

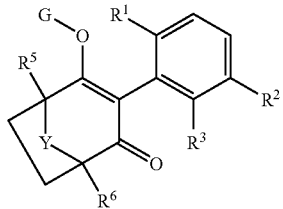

wherein Y is S=O, $R^1$ is methyl, $R^5$ and $R^6$ are hydrogen, G is hydrogen and $R^2$ and $R^3$ are as defined in Table 85.

TABLE 226

This table covers 126 compounds of the following type:

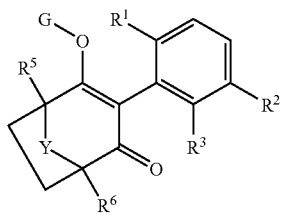

wherein Y is S=O, $R^1$ is ethyl, $R^5$ and $R^6$ are hydrogen, G is hydrogen and $R^2$ and $R^3$ are as defined in Table 85.

TABLE 227

This table covers 126 compounds of the following type:

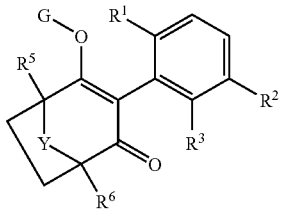

wherein Y is S=O, $R^1$ is methyl, $R^5$ is hydrogen and $R^6$ is methyl, G is hydrogen and $R^2$ and $R^3$ are as defined in Table 85.

TABLE 228

This table covers 126 compounds of the following type:

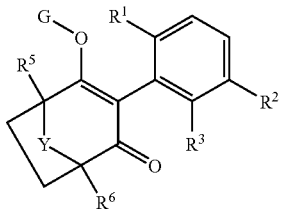

wherein Y is S=O, $R^1$ is ethyl, $R^5$ is hydrogen and $R^6$ is methyl, G is hydrogen and $R^2$ and $R^3$ are as defined in Table 85.

TABLE 229

This table covers 126 compounds of the following type:

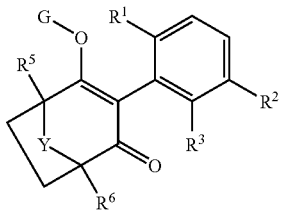

wherein Y is S=O, $R^1$ is methyl, $R^5$ and $R^6$ are methyl, G is hydrogen and $R^2$ and $R^3$ are as defined in Table 85.

TABLE 230

This table covers 126 compounds of the following type:

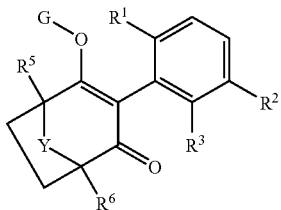

wherein Y is S=O, $R^1$ is ethyl, $R^5$ and $R^6$ are methyl, G is hydrogen and $R^2$ and $R^3$ are as defined in Table 85.

TABLE 231

This table covers 378 compounds of the following type:

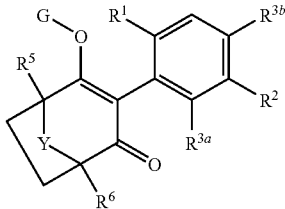

wherein Y is S=O, $R^1$ and $R^{3a}$ are methyl, $R^5$ and $R^6$ are hydrogen, $R^{3b}$ is methyl, and G is hydrogen and $R^2$ is as defined in Table 85.

TABLE 232

This table covers 126 compounds of the following type:

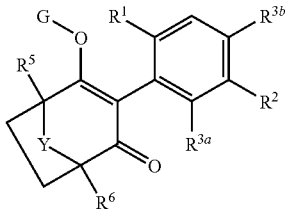

wherein Y is S=O, $R^1$ is ethyl and $R^{3a}$ is methyl, $R^5$ and $R^6$ are hydrogen, $R^{3b}$ is methyl, and G is hydrogen and $R^2$ is as defined in Table 85.

TABLE 233

This table covers 126 compounds of the following type:

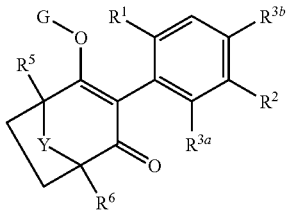

wherein Y is S=O, $R^1$ and $R^{3a}$ are ethyl $R^5$ and $R^6$ are hydrogen, $R^{3b}$ is methyl, and G is hydrogen and $R^2$ is as defined in Table 85.

TABLE 234

This table covers 126 compounds of the following type:

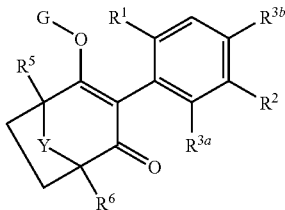

wherein Y is S=O, $R^1$ and $R^{3a}$ are methyl, $R^5$ is hydrogen and $R^6$ is methyl, $R^{3b}$ is methyl, and G is hydrogen and $R^2$ is as defined in Table 85.

TABLE 235

This table covers 126 compounds of the following type:

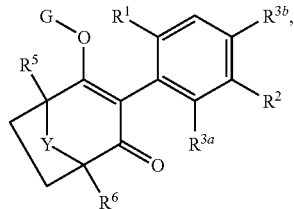

wherein Y is S=O, $R^1$ is ethyl and $R^{3a}$ is methyl, $R^5$ is hydrogen and $R^6$ is methyl, $R^{3b}$ is methyl, and G is hydrogen and $R^2$ is as defined in Table 85.

TABLE 236

This table covers 126 compounds of the following type:

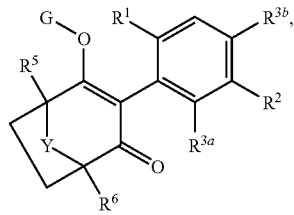

wherein Y is S=O, $R^1$ and $R^{3a}$ are ethyl, $R^5$ is hydrogen and $R^6$ is methyl, $R^{3b}$ is methyl, and G is hydrogen and $R^2$ is as defined in Table 85.

TABLE 237

This table covers 126 compounds of the following type:

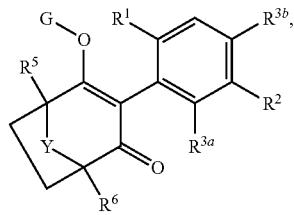

wherein Y is S=O, $R^1$ and $R^{3a}$ are methyl, $R^5$ are $R^6$ are methyl, $R^{3b}$ is methyl, and G is hydrogen and $R^2$ is as defined in Table 85.

TABLE 238

This table covers 126 compounds of the following type:

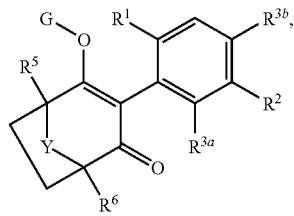

wherein Y is S=O, $R^1$ is ethyl and $R^{3a}$ is methyl, $R^5$ are $R^6$ are methyl, $R^{3b}$ is methyl, and G is hydrogen and $R^2$ is as defined in Table 85.

TABLE 239

This table covers 126 compounds of the following type:

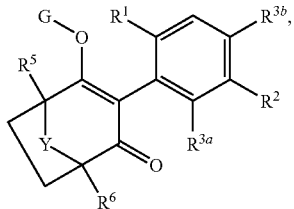

wherein Y is S=O, $R^1$ and $R^{3a}$ are ethyl, $R^5$ are $R^6$ are methyl, $R^{3b}$ is methyl, and G is hydrogen and $R^2$ is as defined in Table 85.

TABLE 240

This table covers 378 compounds of the following type:

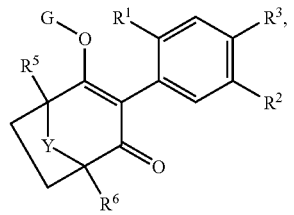

wherein Y is $S(=O)_2$, $R^1$ is methyl, $R^5$ and $R^6$ are hydrogen, G is hydrogen and $R^2$ and $R^3$ are as defined in Table 1.

TABLE 241

This table covers 378 compounds of the following type:

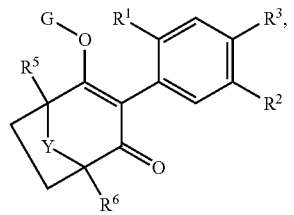

wherein Y is $S(=O)_2$, $R^1$ is ethyl, $R^5$ and $R^6$ are hydrogen, G is hydrogen and $R^2$ and $R^3$ are as defined in Table 1.

TABLE 242

This table covers 378 compounds of the following type:

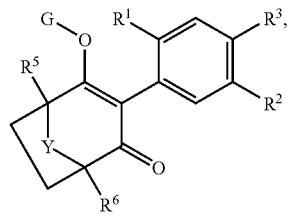

wherein Y is $S(=O)_2$, $R^1$ is chlorine, $R^5$ and $R^6$ are hydrogen, G is hydrogen and $R^2$ and $R^3$ are as defined in Table 1.

TABLE 243

This table covers 378 compounds of the following type:

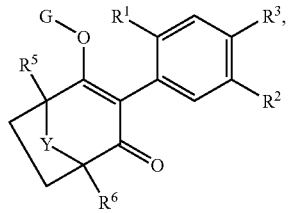

wherein Y is S(=O)$_2$, R$^1$ is methyl, R$^5$ is hydrogen and R$^6$ is methyl, G is hydrogen and R$^2$ and R$^3$ are as defined in Table 1.

TABLE 244

This table covers 378 compounds of the following type:

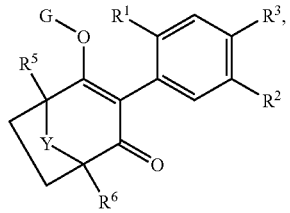

wherein Y is S(=O)$_2$, R$^1$ is ethyl, R$^5$ is hydrogen and R$^6$ is methyl, G is hydrogen and R$^2$ and R$^3$ are as defined in Table 1.

TABLE 245

This table covers 378 compounds of the following type:

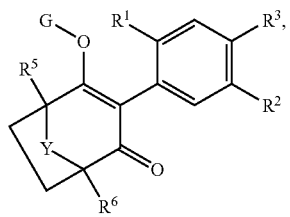

wherein Y is S(=O)$_2$, R$^1$ is chlorine, R$^5$ is hydrogen and R$^6$ is methyl, G is hydrogen and R$^2$ and R$^3$ are as defined in Table 1.

TABLE 246

This table covers 378 compounds of the following type:

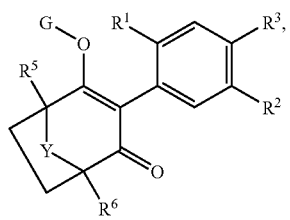

wherein Y is S(=O)$_2$, R$^1$ is methyl, R$^5$ and R$^6$ are methyl, G is hydrogen and R$^2$ and R$^3$ are as defined in Table 1.

TABLE 247

This table covers 378 compounds of the following type:

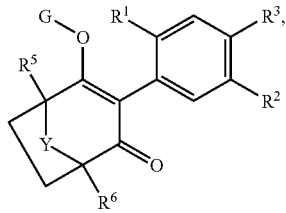

wherein Y is S(=O)$_2$, R$^1$ is ethyl, R$^5$ and R$^6$ are methyl, G is hydrogen and R$^2$ and R$^3$ are as defined in Table 1.

TABLE 248

This table covers 378 compounds of the following type:

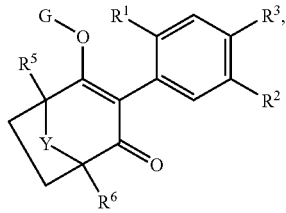

wherein Y is S(=O)$_2$, R$^1$ is chlorine, R$^5$ and R$^6$ are methyl, G is hydrogen and R$^2$ and R$^3$ are as defined in Table 1.

TABLE 249

This table covers 126 compounds of the following type:

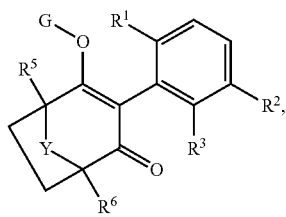

wherein Y is S(=O)$_2$, R$^1$ is methyl, R$^5$ and R$^6$ are hydrogen, G is hydrogen and R$^2$ and R$^3$ are as defined in Table 85.

TABLE 250

This table covers 126 compounds of the following type:

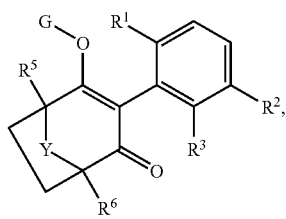

wherein Y is S(=O)$_2$, R$^1$ is ethyl, R$^5$ and R$^6$ are hydrogen, G is hydrogen and R$^2$ and R$^3$ are as defined in Table 85.

TABLE 251

This table covers 126 compounds of the following type:

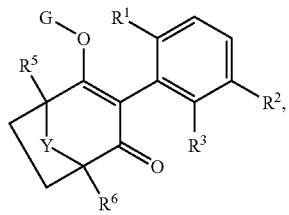

wherein Y is S(=O)$_2$, R$^1$ is methyl, R$^5$ is hydrogen and R$^6$ is methyl, G is hydrogen and R$^2$ and R$^3$ are as defined in Table 85.

TABLE 252

This table covers 126 compounds of the following type:

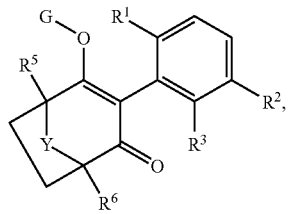

wherein Y is S(=O)$_2$, R$^1$ is ethyl, R$^5$ is hydrogen and R$^6$ is methyl, G is hydrogen and R$^2$ and R$^3$ are as defined in Table 85.

TABLE 253

This table covers 126 compounds of the following type:

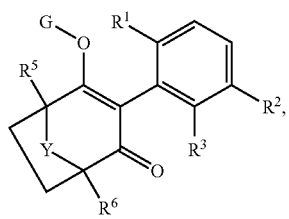

wherein Y is S(=O)$_2$, R$^1$ is methyl, R$^5$ and R$^6$ are methyl, G is hydrogen and R$^2$ and R$^3$ are as defined in Table 85.

TABLE 254

This table covers 126 compounds of the following type:

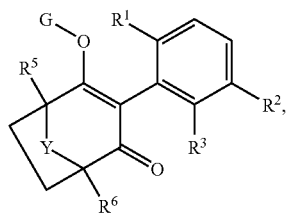

wherein Y is S(=O)$_2$, R$^1$ is ethyl, R$^5$ and R$^6$ are methyl, G is hydrogen and R$^2$ and R$^3$ are as defined in Table 85.

TABLE 255

This table covers 126 compounds of the following type:

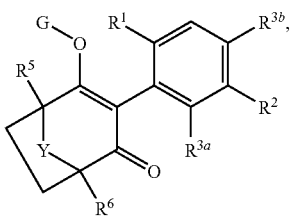

wherein Y is S(=O)$_2$, R$^1$ and R$^{3a}$ are methyl, R$^5$ and R$^6$ are hydrogen, R$^{3b}$ is methyl, and G is hydrogen and R$^2$ is as defined in Table 85.

TABLE 256

This table covers 126 compounds of the following type:

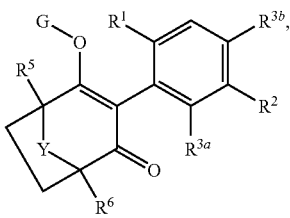

wherein Y is S(=O)$_2$, R$^1$ is ethyl and R$^{3a}$ is methyl, R$^5$ and R$^6$ are hydrogen, R$^{3b}$ is methyl, and G is hydrogen and R$^2$ is as defined in Table 85.

TABLE 257

This table covers 126 compounds of the following type:

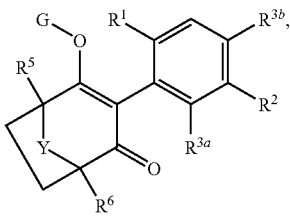

wherein Y is S(=O)$_2$, R$^1$ and R$^{3a}$ are ethyl, R$^5$ and R$^6$ are hydrogen, R$^{3b}$ is methyl, and G is hydrogen and R$^2$ is as defined in Table 85.

TABLE 258

This table covers 126 compounds of the following type:

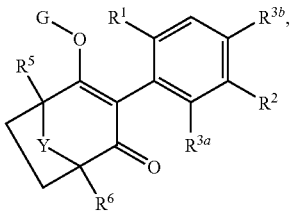

wherein Y is S(=O)$_2$, R$^1$ and R$^{3a}$ are methyl, R$^5$ is hydrogen and R$^6$ is methyl, R$^{3b}$ is methyl, and G is hydrogen and R$^2$ is as defined in Table 85.

TABLE 259

This table covers 126 compounds of the following type:

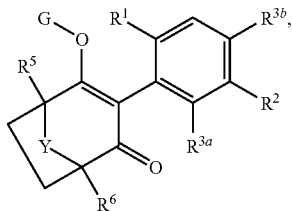

wherein Y is S(=O)$_2$, R$^1$ is ethyl and R$^{3a}$ is methyl, R$^5$ is hydrogen and R$^6$ is methyl, R$^{3b}$ is methyl, and G is hydrogen and R$^2$ is as defined in Table 85.

TABLE 260

This table covers 126 compounds of the following type:

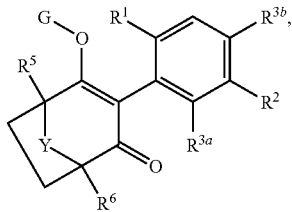

wherein Y is S(=O)$_2$, R$^1$ and R$^{3a}$ are ethyl, R$^5$ is hydrogen and R$^6$ is methyl, R$^{3b}$ is methyl, and G is hydrogen and R$^2$ is as defined in Table 85.

TABLE 261

This table covers 126 compounds of the following type:

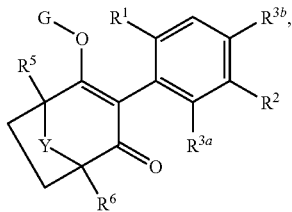

wherein Y is S(=O)$_2$, R$^1$ and R$^{3a}$ are methyl, R$^5$ are R$^6$ are methyl, R$^{3b}$ is methyl, and G is hydrogen and R$^2$ is as defined in Table 85.

TABLE 262

This table covers 126 compounds of the following type:

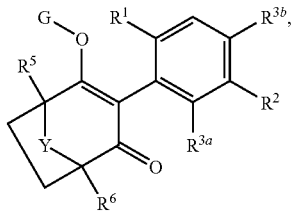

wherein Y is S(=O)$_2$, R$^1$ is ethyl and R$^{3a}$ is methyl, R$^5$ are R$^6$ are methyl, R$^{3b}$ is methyl, and G is hydrogen and R$^2$ is as defined in Table 85.

TABLE 263

This table covers 126 compounds of the following type:

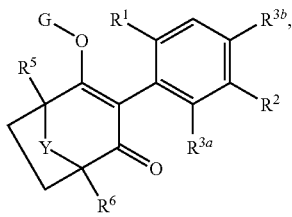

wherein Y is S(=O)$_2$, R$^1$ and R$^{3a}$ are ethyl, R$^5$ are R$^6$ are methyl, R$^{3b}$ is methyl, and G is hydrogen and R$^2$ is as defined in Table 85.

TABLE 264

This table covers 378 compounds of the following type:

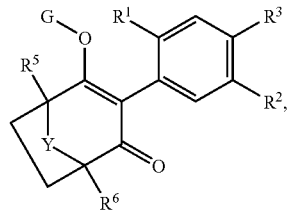

wherein Y is C=O, R$^1$ is methyl, R$^5$ and R$^6$ are hydrogen, G is hydrogen and R$^2$ and R$^3$ are as defined in Table 1.

TABLE 265

This table covers 378 compounds of the following type:

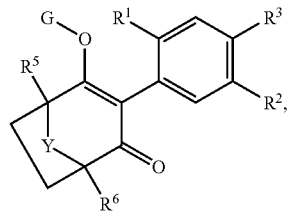

wherein Y is C=O, R$^1$ is ethyl, R$^5$ and R$^6$ are hydrogen, G is hydrogen and R$^2$ and R$^3$ are as defined in Table 1.

TABLE 266

This table covers 378 compounds of the following type:

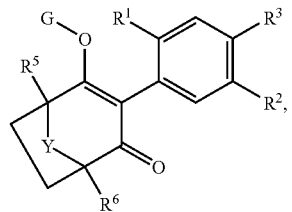

wherein Y is C=O, R$^1$ is chlorine, R$^5$ and R$^6$ are hydrogen, G is hydrogen and R$^2$ and R$^3$ are as defined in Table 1.

TABLE 267

This table covers 378 compounds of the following type:

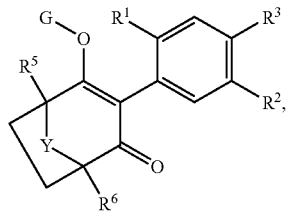

wherein Y is C=O, $R^1$ is methyl, $R^5$ is hydrogen and $R^6$ is methyl, G is hydrogen and $R^2$ and $R^3$ are as defined in Table 1.

TABLE 268

This table covers 378 compounds of the following type:

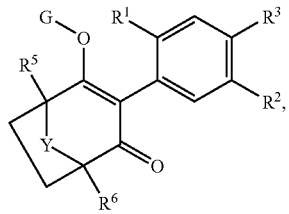

wherein Y is C=O, $R^1$ is ethyl, $R^5$ is hydrogen and $R^6$ is methyl, G is hydrogen and $R^2$ and $R^3$ are as defined in Table 1.

TABLE 269

This table covers 378 compounds of the following type:

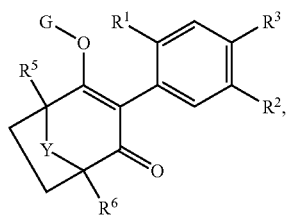

wherein Y is C=O, $R^1$ is chlorine, $R^5$ is hydrogen and $R^6$ is methyl, G is hydrogen and $R^2$ and $R^3$ are as defined in Table 1.

TABLE 270

This table covers 378 compounds of the following type:

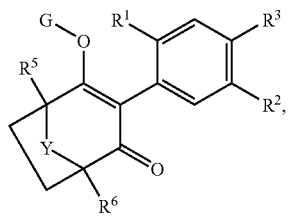

wherein Y is C=O, $R^1$ is methyl, $R^5$ and $R^6$ are methyl, G is hydrogen and $R^2$ and $R^3$ are as defined in Table 1.

TABLE 271

This table covers 378 compounds of the following type:

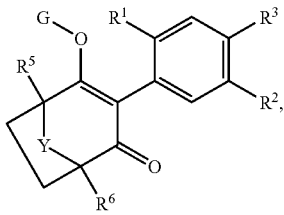

wherein Y is C=O, $R^1$ is ethyl, $R^5$ and $R^6$ are methyl, G is hydrogen and $R^2$ and $R^3$ are as defined in Table 1.

TABLE 272

This table covers 378 compounds of the following type:

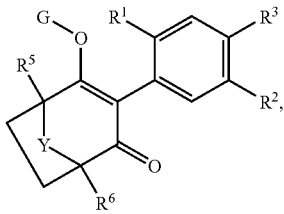

wherein Y is C=O, $R^1$ is chlorine, $R^5$ and $R^6$ are methyl, G is hydrogen and $R^2$ and $R^3$ are as defined in Table 1.

TABLE 273

This table covers 378 compounds of the following type:

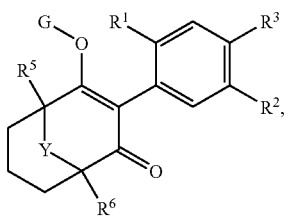

wherein Y is C=O, $R^1$ is methyl, $R^5$ and $R^6$ are hydrogen, G is hydrogen and $R^2$ and $R^3$ are as defined in Table 1.

TABLE 274

This table covers 378 compounds of the following type:

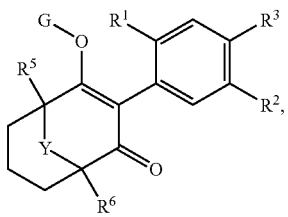

wherein Y is C=O, $R^1$ is ethyl, $R^5$ and $R^6$ are hydrogen, G is hydrogen and $R^2$ and $R^3$ are as defined in Table 1.

TABLE 275

This table covers 378 compounds of the following type:

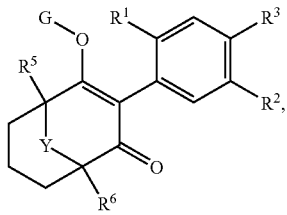

wherein Y is C=O, $R^1$ is chlorine, $R^5$ and $R^6$ are hydrogen,
G is hydrogen and $R^2$ and $R^3$ are as defined in Table 1.

TABLE 276

This table covers 126 compounds of the following type:

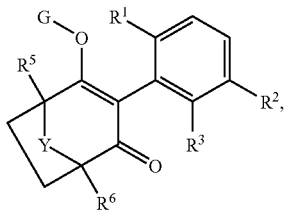

wherein Y is C=O, $R^1$ is methyl, $R^5$ and $R^6$ are hydrogen,
G is hydrogen and $R^2$ and $R^3$ are as defined in Table 85.

TABLE 277

This table covers 126 compounds of the following type:

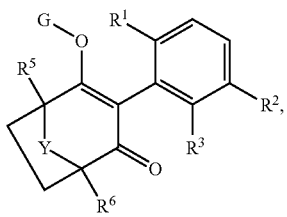

wherein Y is C=O, $R^1$ is ethyl, $R^5$ and $R^6$ are hydrogen,
G is hydrogen and $R^2$ and $R^3$ are as defined in Table 85.

TABLE 278

This table covers 126 compounds of the following type:

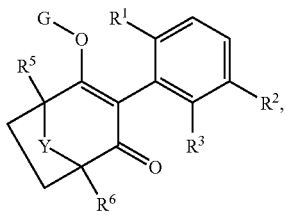

wherein Y is C=O, $R^1$ is methyl, $R^5$ is hydrogen and $R^6$ is methyl,
G is hydrogen and $R^2$ and $R^3$ are as defined in Table 85.

TABLE 279

This table covers 126 compounds of the following type:

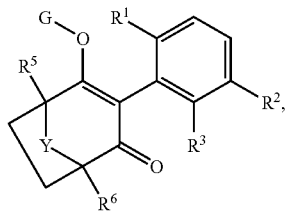

wherein Y is C=O, $R^1$ is ethyl, $R^5$ is hydrogen and $R^6$ is methyl,
G is hydrogen and $R^2$ and $R^3$ are as defined in Table 85.

TABLE 280

This table covers 126 compounds of the following type:

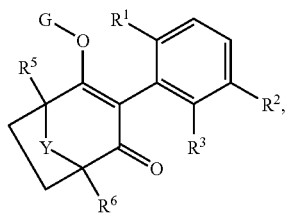

wherein Y is C=O, $R^1$ is methyl, $R^5$ and $R^6$ are methyl,
G is hydrogen and $R^2$ and $R^3$ are as defined in Table 85.

TABLE 281

This table covers 126 compounds of the following type:

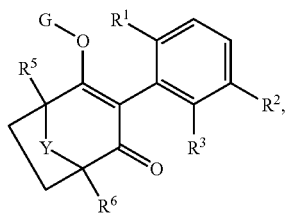

wherein Y is C=O, $R^1$ is ethyl, $R^5$ and $R^6$ are methyl,
G is hydrogen and $R^2$ and $R^3$ are as defined in Table 85.

TABLE 282

This table covers 126 compounds of the following type:

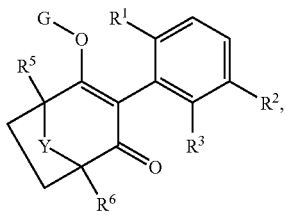

wherein Y is C=O, $R^1$ is methyl, $R^5$ and $R^6$ are hydrogen,
G is hydrogen and $R^2$ and $R^3$ are as defined in Table 85.

TABLE 283

This table covers 126 compounds of the following type:

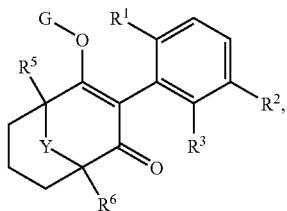

wherein Y is C=O, R¹ is ethyl, R⁵ and R⁶ are hydrogen,
G is hydrogen and R² and R³ are as defined in Table 85.

TABLE 284

This table covers 126 compounds of the following type:

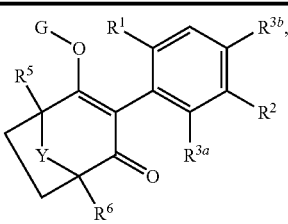

wherein Y is C=O, R¹ and R³ᵃ are methyl, R⁵ and R⁶ are hydrogen,
R³ᵇ is methyl, and G is hydrogen and R² is as defined in Table 85.

TABLE 285

This table covers 126 compounds of the following type:

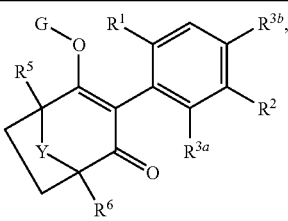

wherein Y is C=O, R¹ is ethyl and R³ᵃ is methyl, R⁵ and R⁶ are
hydrogen, R³ᵇ is methyl, and G is hydrogen and R² is as defined
in Table 85.

TABLE 286

This table covers 126 compounds of the following type:

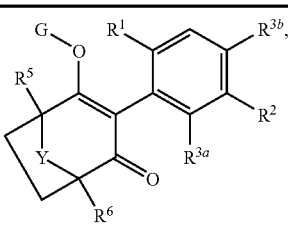

wherein Y is C=O, R¹ and R³ᵃ are ethyl, R⁵ and R⁶ are hydrogen,
R³ᵇ is methyl, and G is hydrogen and R² is as defined in Table 85.

TABLE 287

This table covers 126 compounds of the following type:

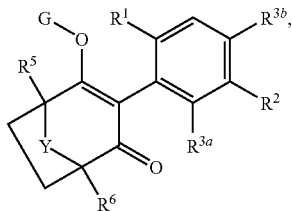

wherein Y is C=O, R¹ and R³ᵃ are methyl, R⁵ is hydrogen and R⁶
is methyl, R³ᵇ is methyl, and G is hydrogen and R² is as defined
in Table 85.

TABLE 288

This table covers 126 compounds of the following type:

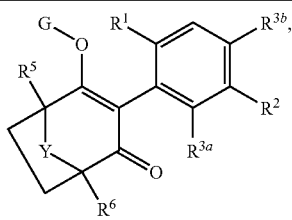

wherein Y is C=O, R¹ is ethyl and R³ᵃ is methyl, R⁵ is hydrogen
and R⁶ is methyl, R³ᵇ is methyl, and G is hydrogen and R² is as
defined in Table 85.

TABLE 289

This table covers 126 compounds of the following type:

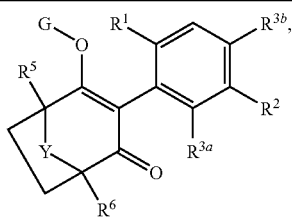

wherein Y is C=O, R¹ and R³ᵃ are ethyl, R⁵ is hydrogen and R⁶
is methyl, R³ᵇ is methyl, and G is hydrogen and R² is as defined
in Table 85.

TABLE 290

This table covers 126 compounds of the following type:

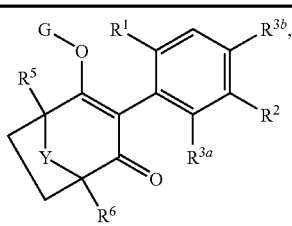

wherein Y is C=O, R¹ and R³ᵃ are methyl, R⁵ are R⁶ are methyl,
R³ᵇ is methyl, and G is hydrogen and R² is as defined in Table 85.

TABLE 291

This table covers 126 compounds of the following type:

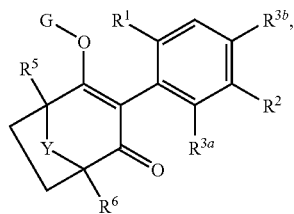

wherein Y is C=O, $R^1$ is ethyl and $R^{3a}$ is methyl, $R^5$ are $R^6$ are methyl, $R^{3b}$ is methyl, and G is hydrogen and $R^2$ is as defined in Table 85.

TABLE 292

This table covers 126 compounds of the following type:

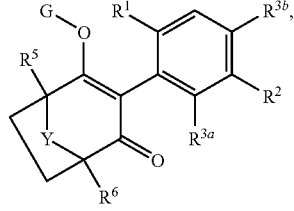

wherein Y is C=O, $R^1$ and $R^{3a}$ are ethyl, $R^5$ are $R^6$ are methyl, $R^{3b}$ is methyl, and G is hydrogen and $R^2$ is as defined in Table 85.

TABLE 293

This table covers 126 compounds of the following type:

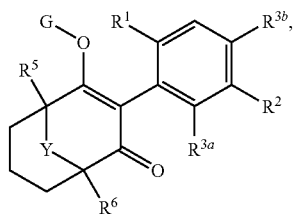

wherein Y is C=O, $R^1$ and $R^{3a}$ are methyl, $R^5$ and $R^6$ are hydrogen, $R^{3b}$ is methyl, and G is hydrogen and $R^2$ is as defined in Table 85.

TABLE 294

This table covers 126 compounds of the following type:

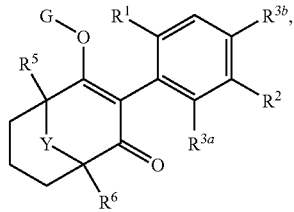

wherein Y is C=O, $R^1$ is ethyl and $R^{3a}$ is methyl, $R^5$ and $R^6$ are hydrogen, $R^{3b}$ is methyl, and G is hydrogen and $R^2$ is as defined in Table 85.

Example 30

Preparation of 2,2-dimethylpropionic acid 4-(4'-chloro-4-ethylbiphenyl-3-yl)-2,2,6,6-tetramethyl-5-oxo-5,6-dihydro-2H-pyran-3-yl ester

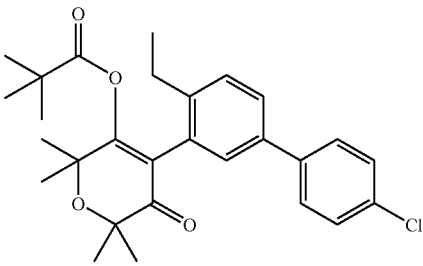 [SMILES: CCc1ccc(-c2ccc(Cl)cc2)cc1C1=C(OC(=O)C(C)(C)C)C(C)(C)OC(C)(C)C1=O]

To a solution of 4-(4'-chloro-4-ethylbiphenyl-3-yl)-2,2,6,6-tetramethylpyran-3,5-dione (0.077 g, 0.20 mmol) dissolved in anhydrous dichloromethane (3 ml) is added triethylamine (0.031 ml, 0.22 mmol) then pivaloyl chloride (0.027 ml, 0.22 mmol). This mixture is stirred at room temperature for 3 hours, then diluted with dichloromethane (15 ml) and washed with distilled water (2×10 ml). Organic fractions are combined, dried over magnesium sulphate, then concentrated to give a crude oil which is purified by flash chromatography (100% hexane to hexane/ethyl acetate 9:1 ratio) to afford 2,2-dimethylpropionic acid 4-(4'-chloro-4-ethylbiphenyl-3-yl)-2,2,6,6-tetramethyl-5-oxo-5,6-dihydro-2H-pyran-3-yl ester (0.090 g) as a colourless gum.

Example 31

Preparation of carbonic acid 4-(4'-chloro-4-ethylbiphenyl-3-yl)-2,2,6,6-tetramethyl-5-oxo-5,6-dihydro-2H-pyran-3-yl ester methyl ester

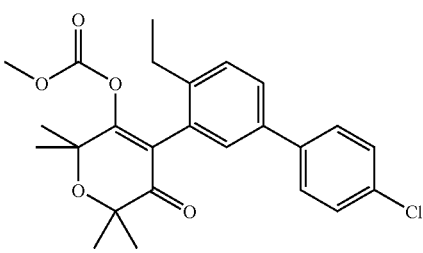 [SMILES: CCc1ccc(-c2ccc(Cl)cc2)cc1C1=C(OC(=O)OC)C(C)(C)OC(C)(C)C1=O]

To a solution of 4-(4'-chloro-4-ethylbiphenyl-3-yl)-2,2,6,6-tetramethylpyran-3,5-dione (0.141 g, 0.366 mmol) in dry chloroform (3 ml) is added triethylamine (0.152 ml, 1.09 mmol), and methyl chloroformate (0.084 ml, 1.09 mmol) and the mixture is stirred at room temperature for 2 hours. Solvents are removed, and the residue is purified directly by column chromatography (hexane/ethyl acetate 5:1 ratio) to afford carbonic acid 4-(4'-chloro-4-ethylbiphenyl-3-yl)-2,2,6,6-tetramethyl-5-oxo-5,6-dihydro-2H-pyran-3-yl ester methyl ester (0.150 g) as a white solid.

Example 32

Preparation of carbonic acid 4-[5-(4-chloropyrazol-1-yl)-2-ethylphenyl]-2,2,6,6-tetramethyl-5-oxo-5,6-dihydro-2H-pyran-3-yl ester methyl ester

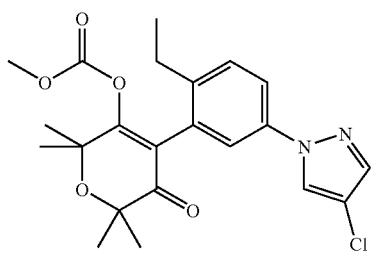 [SMILES: CCc1ccc(-n2cc(Cl)cn2)cc1C1=C(OC(=O)OC)C(C)(C)OC(C)(C)C1=O]

To a mixture of 4-(5-bromo-2-ethylphenyl)-2,2,6,6-tetramethylpyran-3,5-dione (0.15 g, 0.42 mmol), 4-chloropyrazole (0.065 g, 0.63 mmol), L-proline (0.049 g, 0.42 mmol), copper(I) iodide (0.080 g, 0.42 mmol) and anhydrous powdered potassium phosphate (0.36 g, 1.68 mmol) is added degassed anhydrous dimethylsulfoxide (1.5 ml). This mixture is then heated at 160° C. under microwave irradiation for 30 minutes, followed by cooling to room temperature, dilution with dichloromethane (150 ml) and washing with 1M aqueous hydrochloric acid (2×50 ml). The organic fractions are combined, dried over anhydrous magnesium sulfate, then concentrated in vacuo. Diethyl ether is then added to the crude oil to precipitate the product, which is filtered and re-dissolved in dichloromethane (20 ml). To this solution is then added triethylamine (0.16 ml, 1.16 mmol) followed by methyl chloroformate (0.090 ml, 1.16 mmol) and stirring at room temperature for 3 hours. The solvents are removed under reduced pressure, and the residue is purified directly by column chromatography on silica gel (hexane/ethyl acetate 3:1 ratio) to afford carbonic acid 4-[5-(4-chloropyrazol-1-yl)-2-ethylphenyl]-2,2,6,6-tetramethyl-5-oxo-5,6-dihydro-2H-pyran-3-yl ester methyl ester (0.075 g) as a colourless oil.

Additional compounds in Table D below were prepared by similar methods using appropriate starting materials.

TABLE D

| Compound Number | Structure | $^1$H nmr (CDCl$_3$ unless stated) or other physical data |
|---|---|---|
| D-1 | 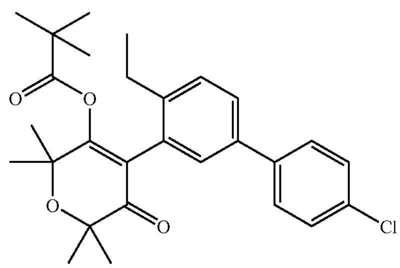 [SMILES: CCc1ccc(-c2ccc(Cl)cc2)cc1C1=C(OC(=O)C(C)(C)C)C(C)(C)OC(C)(C)C1=O] | δ 7.49 (m, 2H), 7.45 (dd, 1H), 7.38 (m, 2H), 7.30 (d, 1H), 7.16 (d, 1H), 2.49 (m, 2H), 1.54 (d, 12H), 1.20 (t, 3H), 0.85 (s, 9H). |
| D-2 | 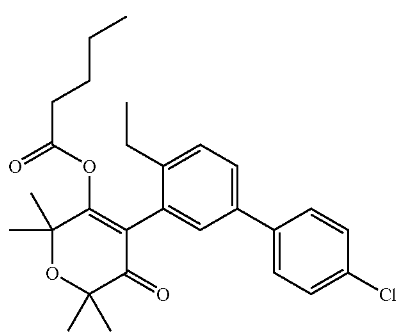 [SMILES: CCCCC(=O)OC1=C(c2cc(-c3ccc(Cl)cc3)ccc2CC)C(=O)C(C)(C)OC1(C)C] | δ 7.49 (m, 2H), 7.47 (dd, 1H), 7.39 (m, 2H), 7.31 (d, 1H), 7.14 (d, 1H), 2.49 (m, 2H), 2.05 (t, 2H), 1.54 (d, 12H), 1.20 (t, 3H), 1.18 (m, 2H), 0.92 (m, 2H), 0.69 (t, 3H). |
| D-3 | 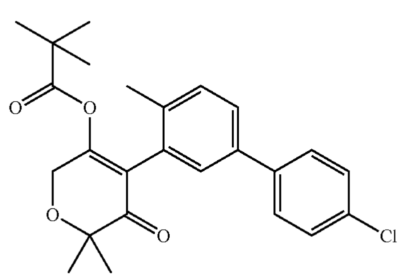 [SMILES: Cc1ccc(-c2ccc(Cl)cc2)cc1C1=C(OC(=O)C(C)(C)C)COC(C)(C)C1=O] | δ 7.46 (m, 2H), 7.41 (dd, 1H), 7.37 (m, 2H), 7.26 (d, 1H), 7.17 (d, 1H), 4.58 (s, 2H), 2.14 (s, 3H), 1.52 (s, 3H), 1.50 (s, 3H), 0.89 (s, 9H). |

TABLE D-continued

| Compound Number | Structure | ¹H nmr (CDCl₃ unless stated) or other physical data |
|---|---|---|
| D-4 | 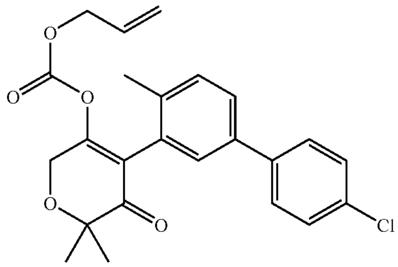 [SMILES: C=CCOC(=O)OC1=C(c2cc(-c3ccc(Cl)cc3)ccc2C)C(=O)C(C)(C)OC1] | Oil, LC-MS (ES+): 429, 427 (M + H)⁺ |
| D-5 | 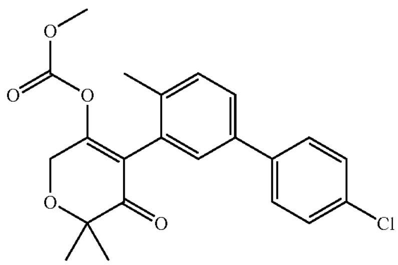 [SMILES: COC(=O)OC1=C(c2cc(-c3ccc(Cl)cc3)ccc2C)C(=O)C(C)(C)OC1] | Foam, LC-MS (ES+): 403, 401 (M + H)⁺ |
| D-6 | 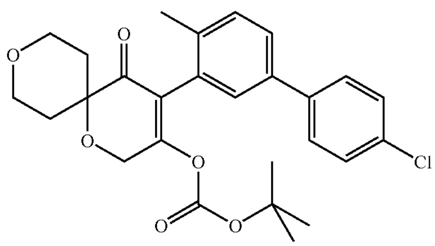 [SMILES: Cc1ccc(-c2ccc(Cl)cc2)cc1C1=C(OC(=O)OC(C)(C)C)COC2(CCOCC2)C1=O] | δ 7.45 (m, 2H), 7.42 (dd, 1H), 7.37 (m, 2H), 7.26 (d, 1H), 7.16 (d, 1H), 4.59 (s, 2H), 3.90 (m, 2H), 3.79 (m, 2H), 2.15 (m, 2H), 2.13 (s, 3H), 1.97 (m, 1H), 1.85 (m, 1H), 0.90 (s, 9H). |
| D-7 | 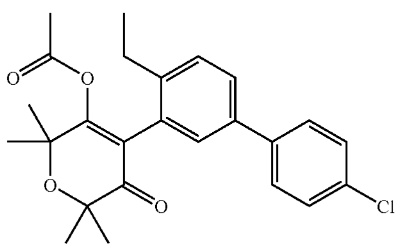 [SMILES: CCc1ccc(-c2ccc(Cl)cc2)cc1C1=C(OC(C)=O)C(C)(C)OC(C)(C)C1=O] | δ 7.50-7.45 (m, 3H), 7.37 (dd, 2H), 7.32 (d, 1H), 7.16 (s, 1H), 2.48 (q, 2H), 1.76 (s, 3H), 1.53 (s, 6H), 1.56 (s, 6H), 1.19 (t, 3H) |
| D-8 | 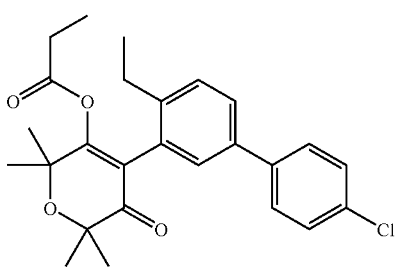 [SMILES: CCC(=O)OC1=C(c2cc(-c3ccc(Cl)cc3)ccc2CC)C(=O)C(C)(C)OC1(C)C] | δ 7.50-7.44 (m, 3H), 7.37 (d, 2H), 7.31 (d, 1H), 7.14 (s, 1H), 2.48 (q, 2H), 2.02 (m, 2H), 1.54 (d, 12H), 1.18 (t, 3H), 0.72 (t, 3H). |
| D-9 | 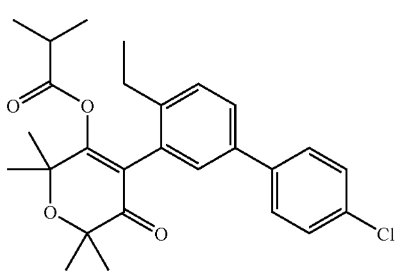 [SMILES: CCc1ccc(-c2ccc(Cl)cc2)cc1C1=C(OC(=O)C(C)C)C(C)(C)OC(C)(C)C1=O] | δ 7.49-7.42 (m, 3H), 7.36 (d, 2H), 7.30 (d, 1H), 7.14 (s, 1H), 2.48 (q, 2H), 2.32 (m, 1H), 1.53 (s, 12H), 1.18 (t, 3H), 0.78 (d, 3H), 0.73 (d, 3H). |

TABLE D-continued

| Compound Number | Structure | ¹H nmr (CDCl₃ unless stated) or other physical data |
|---|---|---|
| D-10 | 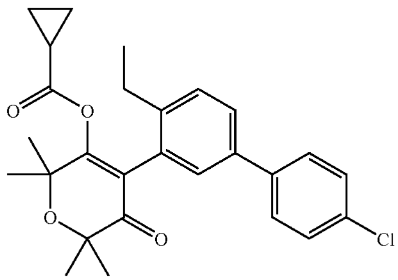 [SMILES: CCc1ccc(-c2ccc(Cl)cc2)cc1C1=C(OC(=O)C2CC2)C(C)(C)OC(C)(C)C1=O] | δ 7.49-7.44 (m, 3H), 7.36 (d, 2H), 7.31 (d, 1H), 7.13 (s, 1H), 2.45 (q, 2H), 1.56 (s, 6H), 1.52 (s, 6H), 1.38 (m, 1H), 1.18 (t, 3H), 0.65-0.60 (m, 2H), 0.60-0.47 (m, 2H). |
| D-11 | 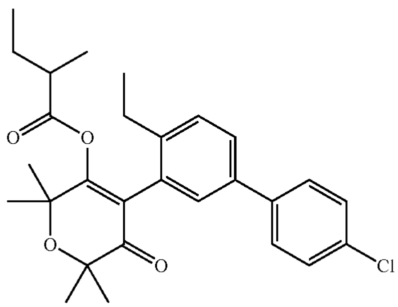 | δ 7.47-7.43 (m, 3H), 7.38-7.36 (m, 2H), 7.30 (d, 1H), 7.15 (m, 1H), 2.51-2.45 (m, 2H), 2.18-2.10 (m, 1H), 1.55-1.53 (m, 12H), 1.41-1.28 (m, 1H), 1.22-1.10 (m, 4H), 0.72 (app. dd, 3H), 0.58 (q, 3H). |
| D-12 | 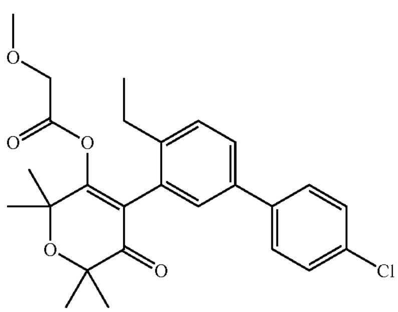 [SMILES: CCc1ccc(-c2ccc(Cl)cc2)cc1C1=C(OC(=O)COC)C(C)(C)OC(C)(C)C1=O] | δ 7.50-7.44 (m, 3H), 7.37 (d, 2H), 7.33 (d, 1H), 7.15 (s, 1H), 3.67 (dd, 2H), 2.98 (s, 3H), 2.48 (q, 2H), 1.53 (s, 6H), 1.56 (s, 6H), 1.19 (t, 3H). |
| D-13 | 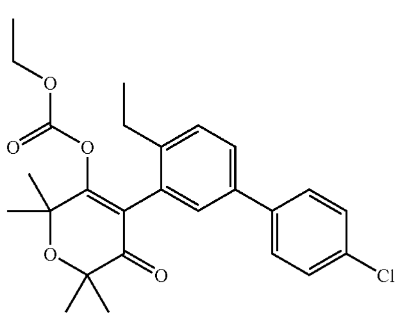 | δ 7.50-7.44 (m, 3H), 7.37 (d, 2H), 7.32 (d, 1H), 7.19 (s, 1H), 3.86 (q, 2H), 2.48 (q, 2H), 1.59 (s, 6H), 1.53 (s, 6H), 1.19 (t, 3H), 0.88 (t, 3H). |

TABLE D-continued

| Compound Number | Structure | $^1$H nmr (CDCl$_3$ unless stated) or other physical data |
|---|---|---|
| D-14 | 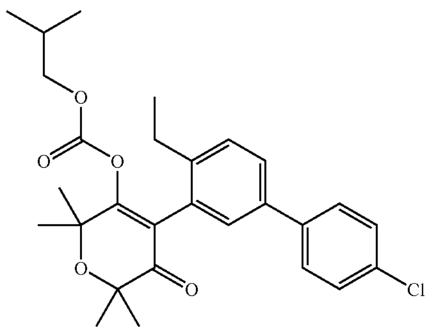 [SMILES: CCc1ccc(-c2ccc(Cl)cc2)cc1C1=C(OC(=O)OCC(C)C)C(C)(C)OC(C)(C)C1=O] | δ 7.49-7.43 (m, 3H), 7.36 (d, 2H), 7.32 (d, 1H), 7.18 (s, 1H), 3.61 (m, 2H), 2.48 (q, 2H), 1.61-1.51 (m, 13H), 1.19 (t, 3H), 0.62 (d, 6H). |
| D-15 | 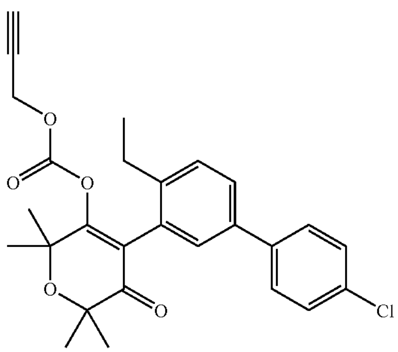 [SMILES: C#CCOC(=O)OC1=C(c2cc(-c3ccc(Cl)cc3)ccc2CC)C(=O)C(C)(C)OC1(C)C] | δ 7.50-7.44 (m, 3H), 7.36 (d, 2H), 7.32 (d, 1H), 7.18 (s, 1H), 4.38 (s, 2H), 2.47 (q, 2H), 2.29 (s, 1H), 1.59 (s, 6H), 1.53 (s, 6H), 1.18 (t, 3H). |
| D-16 | 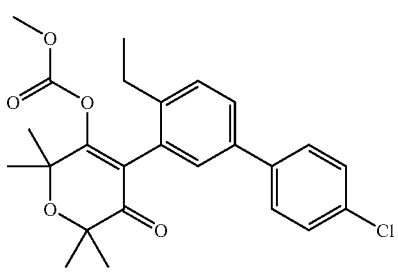 [SMILES: CCc1ccc(-c2ccc(Cl)cc2)cc1C1=C(OC(=O)OC)C(C)(C)OC(C)(C)C1=O] | δ 7.50-7.45 (m, 3H), 7.37 (d, 2H), 7.33 (d, 1H), 7.19 (s, 1H), 3.46 (s, 3H), 2.47 (q, 2H), 1.59 (s, 6H), 1.53 (s, 6H), 1.19 (t, 3H). |
| D-17 | 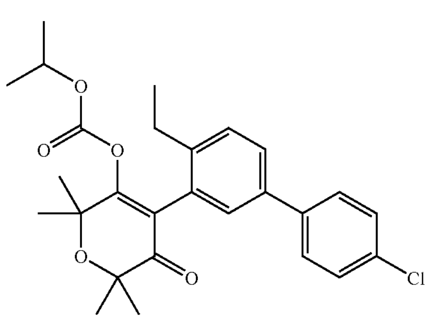 [SMILES: CCc1ccc(-c2ccc(Cl)cc2)cc1C1=C(OC(=O)OC(C)C)C(C)(C)OC(C)(C)C1=O] | δ 7.48-7.43 (m, 3H), 7.36 (d, 2H), 7.33 (d, 1H), 7.19 (s, 1H), 4.49 (m, 1H), 2.48 (q, 2H), 1.60 (s, 6H), 1.53 (d, 6H), 1.19 (t, 3H), 0.91 (app. dd, 6H). |

TABLE D-continued
| Compound Number | Structure | $^1$H nmr (CDCl$_3$ unless stated) or other physical data |
|---|---|---|
| D-18 | mixture of 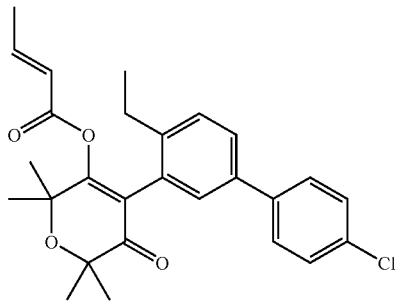 Isomer A 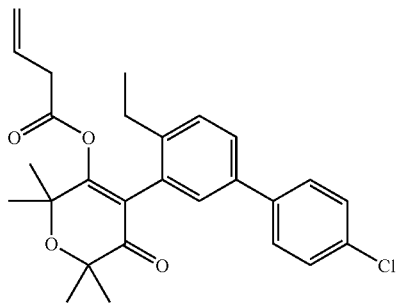 Isomer B | δ 7.48-7.13 (m, 7H, isomers A and B), 6.83-6.74 (m, 0.66H, isomer A), 5.58 (dd, 0.66H, isomer A), 5.42-5.32 (m, 0.33H, isomer B), 4.95-4.86 (m, 0.66H, isomer B), 2.77 (dd, 0.66H, isomer B), 2.50-2.43 (m, 2H, isomers A and B), 1.74 (ddd, 2H, isomer A), 1.57-1.53 (m, 12H, isomers A and B), 1.2 (m, 3H, isomers A and B) |
| D-19 | 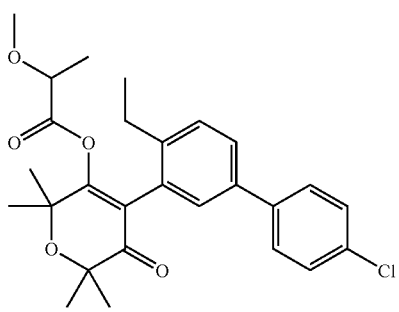 | δ 7.48-7.42 (m, 3H), 7.39-7.36 (m, 2H), 7.32 (d, 1H), 7.15 (s, 1H), 3.59 (m, 1H), 2.94 (s, 3H), 2.48 (m, 2H), 1.55 (m, 12H), 1.19 (m, 3H), 0.96 (app. dd, 3H). |
| D-20 | 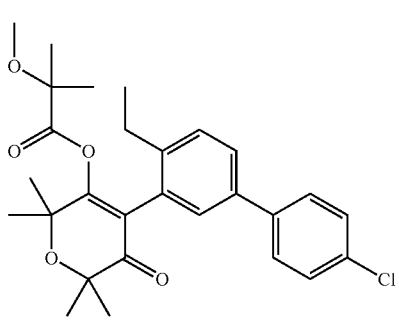 [SMILES: CCc1ccc(-c2ccc(Cl)cc2)cc1C1=C(OC(=O)C(C)(C)OC)C(C)(C)OC(C)(C)C1=O] | δ 7.47-7.43 (m, 3H), 7.36 (d, 2H), 7.31 (d, 1H), 7.17 (s, 1H), 2.83 (s, 3H), 2.49 (q, 2H), 1.59-1.52 (m, 12H), 1.07 (app. d. 6H). |

TABLE D-continued

| Compound Number | Structure | ¹H nmr (CDCl₃ unless stated) or other physical data |
|---|---|---|
| D-21 | 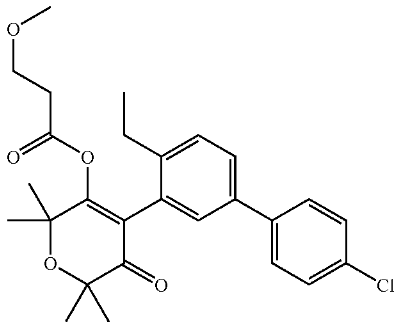 [SMILES: CCc1ccc(-c2ccc(Cl)cc2)cc1C1=C(OC(=O)CCOC)C(C)(C)OC(C)(C)C1=O] | δ 7.49-7.44 (m, 3H), 7.36 (d, 2H), 7.31 (d, 1H), 7.15 (s, 1H), 3.27 (t, 2H), 3.14 (s, 3H), 2.48 (q, 2H), 2.27 (m, 2H), 1.56 (s, 6H), 1.53 (s, 6H), 1.18 (t, 3H). |
| D-22 | 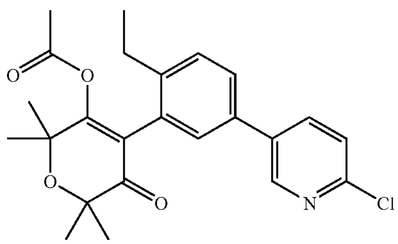 [SMILES: CCc1ccc(-c2ccc(Cl)nc2)cc1C1=C(OC(C)=O)C(C)(C)OC(C)(C)C1=O] | δ 8.57 (s, 1H), 7.81 (dd, 1H), 7.48 (d, 1H), 7.37 (m, 2H), 7.16 (s, 1H), 2.49 (q, 2H), 1.78 (s, 3H), 1.66 (s, 6H), 1.53 (s, 6H), 1.19 (t, 3H). |
| D-23 | 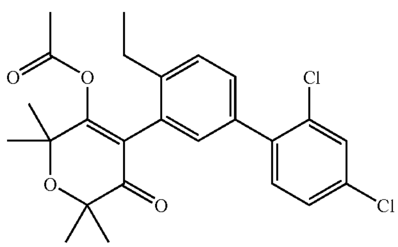 | δ 7.46 (s, 1H), 7.33 (m, 2H), 7.27 (m, 2H), 6.98 (s, 1H), 2.48 (q, 2H), 1.55 (app. d, 6H), 1.50 (s, 6H), 1.21 (t, 3H). |
| D-24 | 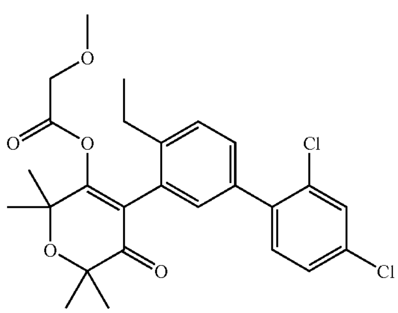 [SMILES: CCc1ccc(-c2ccc(Cl)cc2Cl)cc1C1=C(OC(=O)COC)C(C)(C)OC(C)(C)C1=O] | δ 7.46 (s, 1H), 7.35 (m, 2H), 7.27 (m, 2H), 7.0 (d, 1H), 3.72 (m, 2H), 3.08 (s, 3H), 2.50 (m, 2H), 1.54 (m, 12H), 1.21 (t, 3H). |
| D-25 | 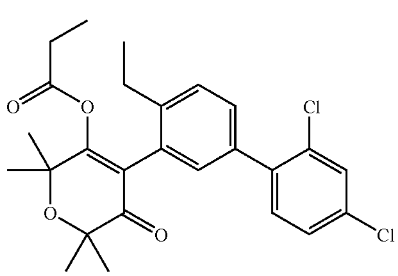 | δ 7.46 (s, 1H), 7.32 (m, 2H), 7.26 (m, 2H), 6.98 (d, 1H), 2.49 (q, 2H), 2.07 (q, 2H), 1.53 (m, 12H), 1.20 (t, 3H), 0.80 (t, 3H). |

TABLE D-continued

| Compound Number | Structure | ¹H nmr (CDCl₃ unless stated) or other physical data |
|---|---|---|
| D-26 | 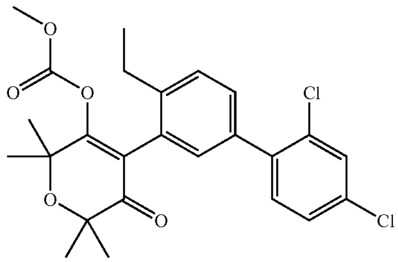 [SMILES: CCc1ccc(-c2ccc(Cl)cc2Cl)cc1C1=C(OC(=O)OC)C(C)(C)OC(C)(C)C1=O] | δ 7.46 (s, 1H), 7.34 (m, 2H), 7.27 (m, 2H), 7.0 (d, 1H), 3.50 (s, 3H), 2.50 (q, 2H), 1.58 (app. d, 6H), 1.52 (app. d, 6H), 1.20 (3H). |
| D-27 | 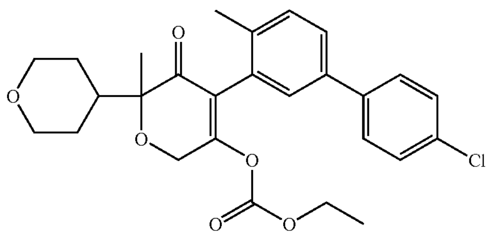 [SMILES: CCOC(=O)OC1=C(c2cc(-c3ccc(Cl)cc3)ccc2C)C(=O)C(C)(C2CCOCC2)OC1] | δ 7.50-7.15 (m, 7H), 4.73 (app. dd, 1H), 4.58 (app. dd, 1H), 4.06 (q, 2H), 4.03 (m, 2H), 3.40 (m, 2H), 2.27 (m, 1H), 2.16 and 2.14 (s each, 3H together), 1.80 (m, 1H), 1.59 (m, 3H), 1.44 and 1.41 (s each, 3H together), 1.10 (t, 3H). |
| D-28 | 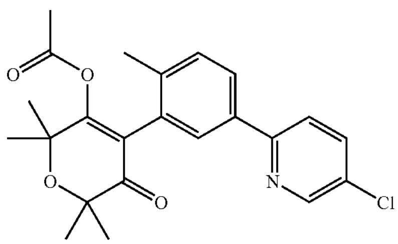 | Methanol-d₄ δ 8.58 (1H, m), 7.90-7.80 (3H, m), 7.62 (1H, m), 7.32 (1H, d), 2.15 (3H, s), 1.75 (3H, s), 1.58 (3H, s), 1.54 (3H, s), 1.51 (3H, s), 1.47 (3H, s). |
| D-29 | 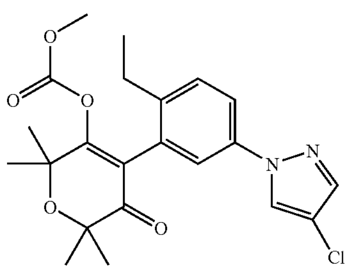 [SMILES: CCc1ccc(-n2cc(Cl)cn2)cc1C1=C(OC(=O)OC)C(C)(C)OC(C)(C)C1=O] | δ 7.88 (s, 1H), 7.60 (m, 2H), 7.36 (d, 1H), 7.25 (m, 1H), 3.51 (s, 3H), 2.47 (m, 2H), 1.60 (s, 6H), 1.52 (s, 6H), 1.19 (t, 3H). |
| D-30 | 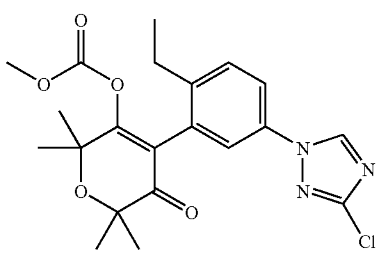 [SMILES: CCc1ccc(-n2cnc(Cl)n2)cc1C1=C(OC(=O)OC)C(C)(C)OC(C)(C)C1=O] | δ 8.40 (s, 1H), 7.60 (dd, 1H), 7.40 (d, 1H), 7.28 (m, 1H), 3.53 (s, 3H), 2.50 (m, 2H), 2.60 (s, 6H), 2.53 (app. d, 6H), 1.20 (t, 3H). |
| D-31 | 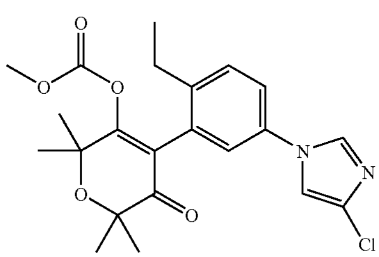 [SMILES: CCc1ccc(-n2cnc(Cl)c2)cc1C1=C(OC(=O)OC)C(C)(C)OC(C)(C)C1=O] | δ 7.65 (s, 1H), 7.39 (d, 1H), 7.30 (dd, 1H), 7.17 (s, 1H), 7.20 (d, 1H), 3.53 (s, 3H), 2.49 (m, 2H), 1.60 (d, 6H), 1.53 (d, 6H), 1.20 (m, 3H). |

TABLE D-continued

| Compound Number | Structure | $^1$H nmr (CDCl$_3$ unless stated) or other physical data |
|---|---|---|
| D-32 | 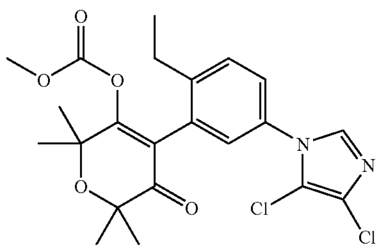 [SMILES: CCc1ccc(-n2cnc(Cl)c2Cl)cc1C1=C(OC(=O)OC)C(C)(C)OC(C)(C)C1=O] | δ 7.51 (s, 1H), 7.42 (d, 1H), 7.30 (dd, 1H), 7.0 (d, 1H), 3.52 (s, 3H), 2.52 (m, 2H), 1.58 (m, 6H), 1.51 (m, 6H), 1.20 (t, 3H). |
| D-33 | 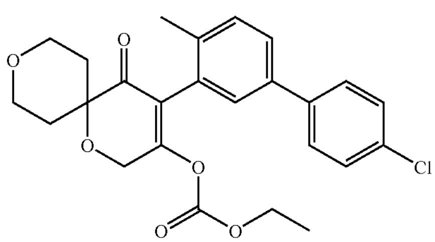 [SMILES: CCOC(=O)OC1=C(c2cc(-c3ccc(Cl)cc3)ccc2C)C(=O)C2(CCOCC2)OC1] | δ 7.47 (m, 2H), 7.45 (dd, 1H), 7.37 (m, 2H), 7.29 (d, 1H), 7.20 (d, 1H), 4.67 (s, 2H), 4.05 (q, 2H), 3.89 (m, 2H), 3.79 (m, 2H), 2.15 (m, 2H), 2.13 (s, 3H), 1.95 (m, 1H), 1.83 (m, 1H), 1.09 (t, 3H). |
| D-34 | 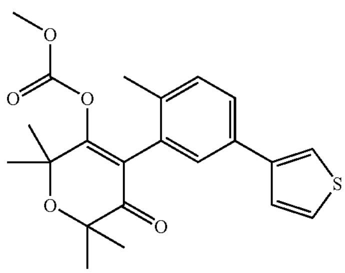 [SMILES: COC(=O)OC1=C(c2cc(-c3ccsc3)ccc2C)C(=O)C(C)(C)OC1(C)C] | DMSO-d$_6$ δ 7.81 (m, 1H), 7.63 (m, 2H), 7.51 (dd, 1H), 7.31 (d, 1H), 7.27 (d, 1H), 3.43 (s, 3H), 2.05 (s, 3H), 1.55 (s, 3H), 1.52 (s, 3H), 1.47 (s, 3H), 1.42 (s, 3H). |
| D-35 | 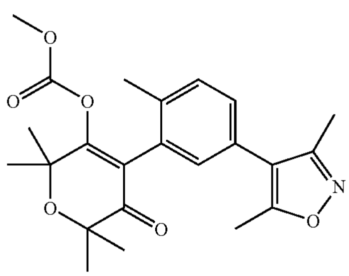 [SMILES: COC(=O)OC1=C(c2cc(-c3c(C)noc3C)ccc2C)C(=O)C(C)(C)OC1(C)C] | DMSO-d$_6$ δ 7.34 (d, 1H), 7.28 (dd, 1H), 6.97 (d, 1H), 3.44 (s, 3H), 2.38 (s, 3H), 2.20 (s, 3H), 2.08 (s, 3H), 1.53 (app. d, 6H), 1.46 (s, 3H), 1.41 (s, 3H). |
| D-36 | 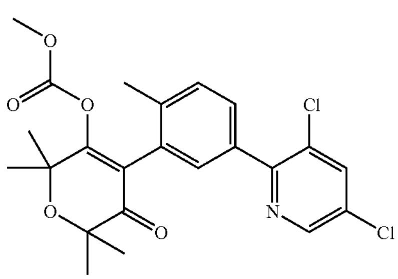 [SMILES: COC(=O)OC1=C(c2cc(-c3ncc(Cl)cc3Cl)ccc2C)C(=O)C(C)(C)OC1(C)C] | DMSO-d$_6$ δ 8.70 (d, 1H), 8.33 (d, 1H), 7.58 (dd, 1H), 7.38 (d, 1H), 7.25 (d, 1H), 3.47 (s, 3H), 2.12 (s, 3H), 1.52 (app. d, 6H), 1.46 (s, 3H), 1.41 (s, 3H). |
| D-37 | 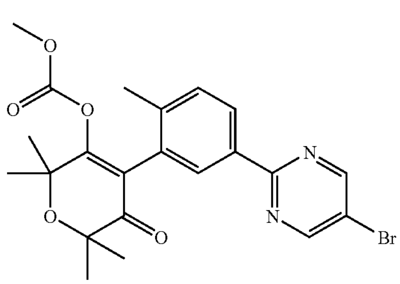 [SMILES: COC(=O)OC1=C(c2cc(-c3ncc(Br)cn3)ccc2C)C(=O)C(C)(C)OC1(C)C] | DMSO-d$_6$ δ 9.02 (s, 2H), 8.20 (dd, 1H), 7.93 (d, 1H), 7.37 (d, 1H), 3.38 (s, 3H), 2.08 (s, 3H), 1.52 (s, 3H), 1.48 (s, 3H), 1.42 (s, 3H), 1.40 (s, 3H). |

TABLE D-continued

| Compound Number | Structure | $^1$H nmr (CDCl$_3$ unless stated) or other physical data |
|---|---|---|
| D-38 | 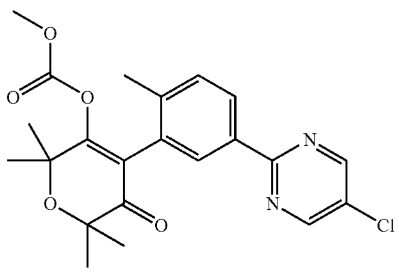 [SMILES: COC(=O)OC1=C(c2cc(-c3ncc(Cl)cn3)ccc2C)C(=O)C(C)(C)OC1(C)C] | DMSO-d$_6$ δ 9.00 (s, 2H), 8.26 (dd, 1H), 7.98 (d, 1H), 7.42 (d, 1H), 3.42 (s, 3H), 2.13 (s, 3H), 1.56 (s, 3H), 1.53 (s, 3H), 1.47 (s, 3H), 1.44 (s, 3H). |
| D-39 | 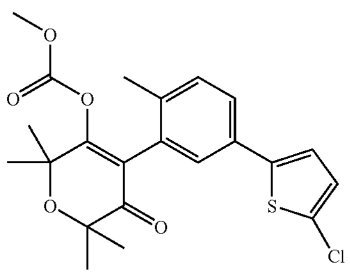 [SMILES: COC(=O)OC1=C(c2cc(-c3ccc(Cl)s3)ccc2C)C(=O)C(C)(C)OC1(C)C] | DMSO-d$_6$ δ 7.52 (dd, 1H), 7.36 (d, 1H), 7.28 (d, 1H), 7.20 (d, 1H), 7.14 (d, 1H), 3.45 (s, 3H), 2.05 (s, 3H), 1.55 (s, 3H), 1.51 (s, 3H), 1.46 (s, 3H), 1.42 (s, 3H). |
| D-40 | 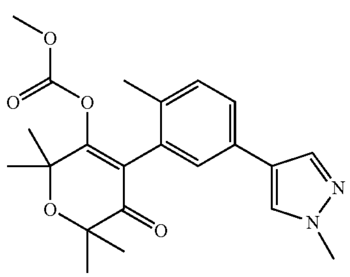 [SMILES: COC(=O)OC1=C(c2cc(-c3cnn(C)c3)ccc2C)C(=O)C(C)(C)OC1(C)C] | (DMSO-d$_6$ δ 8.05 (s, 1H), 7.76 (s, 1H), 7.41 (dd, 1H), 7.17 (d, 1H), 7.10 (d, 1H), 3.81 (s, 3H), 3.39 (s, 3H), 1.97 (s, 3H), 1.51 (3H, s), 1.47 (3H, s), 1.42 (3H, s), 1.38 (3H, s). |
| D-41 | 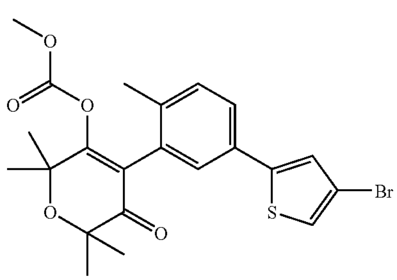 [SMILES: COC(=O)OC1=C(c2cc(-c3cc(Br)cs3)ccc2C)C(=O)C(C)(C)OC1(C)C] | DMSO-d$_6$ δ 7.62 (d, 1H), 7.52 (dd, 1H), 7.50 (d, 1H), 7.25 (m, 2H), 3.40 (s, 3H), 2.01 (s, 3H), 1.52 (s, 3H), 1.47 (s, 3H), 1.42 (s, 3H), 1.38 (s, 3H). |
| D-42 | 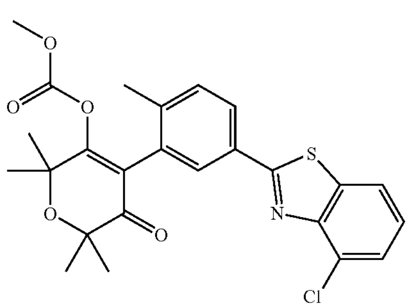 [SMILES: COC(=O)OC1=C(c2cc(-c3nc4c(Cl)cccc4s3)ccc2C)C(=O)C(C)(C)OC1(C)C] | DMSO-d$_6$ δ 8.10 (dd, 1H), 7.98 (dd, 1H), 7.67 (d, 1H), 7.60 (dd, 1H), 7.44 (m, 2H), 3.43 (s, 3H), 2.11 (s, 3H), 1.54 (s, 3H), 1.50 (s, 3H), 1.44 (s, 3H), 1.42 (s, 3H). |

TABLE D-continued

| Compound Number | Structure | $^1$H nmr (CDCl$_3$ unless stated) or other physical data |
|---|---|---|
| D-43 | 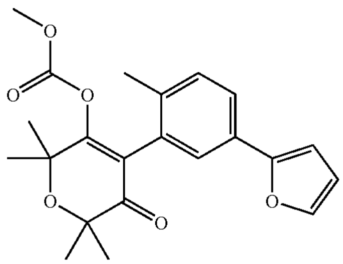 [SMILES: COC(=O)OC1=C(c2cc(-c3ccco3)ccc2C)C(=O)C(C)(C)OC1(C)C] | DMSO-d$_6$ δ 7.69 (d, 1H), 7.55 (dd, 1H), 7.25 (app. d, 2H), 6.86 (d, 1H), 6.54 (m, 1H), 3.40 (s, 3H), 2.01 (s, 3H), 1.51 (s, 3H), 1.48 (s, 3H), 1.42 (s, 3H), 1.38 (s, 3H). |

BIOLOGICAL EXAMPLES

Example A

Seeds of a variety of test species were sown in standard soil in pots. After cultivation for one day (pre-emergence) or after 10 days cultivation (post-emergence) under controlled conditions in a glasshouse, the plants were sprayed with an aqueous spray solution derived from the formulation of the technical active ingredient in 0.6 ml acetone and 45 ml formulation solution containing 10.6% Emulsogen EL (Registry number 61791-12-6), 42.2% N-methylpyrrolidone, 42.2% dipropylene glycol monomethyl ether (Registry number 34590-94-8) and 0.2% X-77 (Registry number 11097-66-8). The test plants were then grown in a greenhouse under optimum conditions until, 15 days later for post-emergence and 20 days for pre-emergence, the test was evaluated (100=total damage to plant; 0=no damage to plant).

Test Plants:
Alopecurus myosuroides (ALOMY), Avena fatua (AVEFA), Lolium perenne (LOLPE), Setaria faberi (SETFA), Digitaria sanguinalis (DIGSA), Echinochloa crus-galli (ECHCG)

Pre-Emergence Activity

| Compound Number | Rate g/ha | ALOMY | AVEFA | LOLPE | SETFA | DIGSA | ECHCG |
|---|---|---|---|---|---|---|---|
| A-1 | 500 | 40 | 10 | 10 | 70 | 70 | 50 |
| A-2 | 500 | 50 | 50 | 60 | 70 | 10 | 100 |
| A-3 | 500 | 30 | 20 | 20 | 50 | 70 | 70 |
| A-5 | 500 | 60 | 50 | 50 | 100 | 100 | 100 |
| A-9 | 500 | 20 | 30 | 20 | 60 | 50 | 50 |
| A-10 | 250 | 40 | 50 | 60 | 100 | 100 | 100 |
| A-34 | 250 | 60 | 50 | 100 | 100 | 100 | 100 |
| A-35 | 250 | 70 | 70 | 80 | 100 | 80 | 100 |
| A-36 | 250 | 60 | 60 | 80 | 90 | 100 | 100 |
| A-38 | 250 | 50 | 10 | 60 | 90 | 30 | 70 |
| A-40 | 250 | 30 | 10 | 20 | 70 | 70 | 70 |
| A-42 | 250 | 100 | 30 | 50 | 100 | 100 | 80 |
| A-43 | 250 | 80 | 90 | 80 | 100 | 100 | 100 |
| A-44 | 250 | 60 | 20 | 80 | 50 | 100 | 70 |
| A-45 | 250 | 50 | 50 | 80 | 90 | 100 | 70 |
| A-47 | 250 | 30 | 20 | 30 | 60 | 70 | 70 |
| A-48 | 250 | 30 | 10 | 0 | 60 | 60 | 100 |
| A-49 | 250 | 0 | 20 | 20 | 50 | 50 | 100 |
| A-51 | 250 | 0 | 0 | 40 | 10 | 50 | 50 |
| A-52 | 250 | 0 | 0 | 10 | 80 | 100 | 70 |
| A-53 | 250 | 10 | 0 | 0 | 10 | 60 | 10 |
| B-1 | 500 | 40 | 60 | 60 | 100 | 100 | 100 |
| C-1 | 500 | 20 | 20 | 30 | 30 | 30 | 50 |
| C-2 | 250 | 10 | 10 | 10 | 70 | 100 | 100 |
| C-3 | 250 | 60 | 80 | 10 | 60 | 90 | 70 |
| D-2 | 500 | 30 | 60 | 80 | 100 | 100 | 80 |
| D-5 | 500 | 0 | 20 | 0 | 20 | 60 | 50 |

Post-Emergence Activity

| Compound Number | Rate g/ha | ALOMY | AVEFA | LOLPE | SETFA | DIGSA | ECHCG |
|---|---|---|---|---|---|---|---|
| A-1 | 125 | 10 | 0 | 80 | 50 | 0 | 70 |
| A-2 | 125 | 20 | 20 | 0 | 80 | 50 | 80 |
| A-3 | 125 | 0 | 0 | 0 | 60 | 40 | 70 |
| A-5 | 125 | 70 | 70 | 70 | 80 | 100 | 100 |
| A-9 | 125 | 50 | 0 | 30 | 80 | 80 | 80 |

-continued

| Compound Number | Rate g/ha | ALOMY | AVEFA | LOLPE | SETFA | DIGSA | ECHCG |
|---|---|---|---|---|---|---|---|
| A-10 | 125 | 30 | 20 | 0 | 50 | 100 | 100 |
| A-34 | 125 | 70 | 20 | 80 | 90 | 90 | 100 |
| A-35 | 125 | 80 | 50 | 70 | 80 | 80 | 100 |
| A-36 | 125 | 40 | 0 | 70 | 60 | 70 | 70 |
| A-38 | 125 | 50 | 60 | 0 | 80 | 70 | 90 |
| A-40 | 125 | 70 | 60 | 60 | 70 | 70 | 100 |
| A-42 | 125 | 80 | 90 | 70 | 100 | 100 | 100 |
| A-43 | 125 | 80 | 90 | 80 | 100 | 100 | 100 |
| A-44 | 125 | 40 | 60 | 60 | 30 | 70 | 100 |
| A-45 | 125 | 20 | 70 | 70 | 80 | 100 | 100 |
| A-47 | 125 | 90 | 90 | 70 | 50 | 80 | 100 |
| A-48 | 125 | 70 | 40 | 0 | 40 | 40 | 40 |
| A-49 | 125 | 50 | 70 | 80 | 50 | 70 | 80 |
| A-51 | 125 | 10 | 20 | 0 | 40 | 60 | 80 |
| A-52 | 125 | 90 | 70 | 30 | 60 | 70 | 90 |
| A-53 | 125 | 30 | 10 | 10 | 0 | 50 | 90 |
| B-1 | 125 | 30 | 30 | 80 | 90 | 100 | 100 |
| C-1 | 125 | 50 | 70 | 30 | 80 | 100 | 100 |
| C-2 | 125 | 70 | 70 | 60 | 90 | 90 | 100 |
| C-3 | 125 | 70 | 80 | 50 | 90 | 100 | 100 |
| D-2 | 125 | 20 | 10 | 20 | 90 | 90 | 90 |
| D-5 | 125 | 10 | 40 | 40 | 70 | 20 | 60 |

Example B

Seeds of a variety of test species were sown in standard soil in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). The test plants were then grown in a glasshouse under controlled conditions in a glasshouse (at 24/16° C., day/night; 14 hours light; 65% humidity) and watered twice daily. After 13 days for pre and post-emergence, the test was evaluated (100=total damage to plant; 0=no damage to plant).

Test Plants:

*Alopecurus myosuroides* (ALOMY), *Avena fatua* (AVEFA), *Setaria faberi* (SETFA), *Echinochloa crus-galli* (ECHCG), *Solanum nigrum* (SOLNI) and *Amaranthus retroflexus* (AMARE)

Pre-Emergence Activity

| Compound Number | Rate g/ha | SOLNI | AMARE | SETFA | ALOMY | ECHCG | AVEFA |
|---|---|---|---|---|---|---|---|
| A-4 | 250 | — | 20 | 100 | 70 | 100 | 70 |
| A-15 | 1000 | 100 | 100 | 50 | 50 | 100 | 50 |
| A-16 | 1000 | 0 | 0 | 100 | 30 | 100 | 20 |
| A-20 | 1000 | 40 | 0 | 100 | 90 | 100 | 60 |
| A-21 | 1000 | 50 | 60 | 100 | 100 | 90 | 50 |
| A-22 | 1000 | 60 | 30 | 40 | 40 | 90 | 20 |
| A-24 | 1000 | 20 | 20 | 90 | 80 | 100 | 60 |
| A-25 | 1000 | 0 | 0 | 20 | 70 | 80 | 30 |
| A-26 | 1000 | 0 | 0 | 100 | 80 | 100 | 80 |
| A-27 | 1000 | 20 | 10 | 90 | 80 | 100 | 60 |
| A-29 | 1000 | 0 | 0 | 100 | 90 | 100 | 80 |
| A-30 | 1000 | 0 | 0 | 100 | 80 | 100 | 70 |
| A-31 | 1000 | 0 | 0 | 100 | 50 | 100 | 0 |
| A-37 | 1000 | 0 | 0 | 20 | 40 | 30 | 20 |
| A-54 | 1000 | 0 | 20 | 90 | 70 | 100 | 80 |
| A-56 | 1000 | 20 | 0 | 0 | 10 | 30 | 40 |
| A-58 | 1000 | 20 | 20 | 100 | 80 | 100 | 60 |
| A-59 | 250 | — | 0 | 40 | 30 | 90 | 40 |
| A-60 | 250 | — | 0 | 20 | 0 | 20 | 0 |
| A-62 | 250 | — | 0 | 60 | 20 | 0 | 20 |
| A-63 | 250 | — | 0 | 30 | 0 | 0 | 0 |
| A-64 | 250 | — | 0 | 40 | 0 | 40 | 20 |
| A-65 | 250 | — | 0 | 0 | 0 | 90 | 0 |
| A-66 | 250 | — | 0 | 50 | 0 | 60 | 40 |
| A-67 | 250 | — | 0 | 90 | 40 | 60 | 0 |
| A-69 | 250 | — | 0 | 80 | 0 | 60 | 0 |
| A-71 | 250 | — | 0 | 100 | 40 | 80 | 20 |
| A-72 | 250 | — | 0 | 0 | 0 | 40 | 0 |
| A-73 | 250 | — | 0 | 20 | 0 | 10 | 0 |
| A-74 | 250 | — | 10 | 50 | 20 | 80 | 0 |
| A-75 | 250 | — | 0 | 90 | 30 | 90 | 30 |
| A-76 | 250 | — | 0 | 100 | 60 | 70 | 50 |

-continued

| Compound Number | Rate g/ha | SOLNI | AMARE | SETFA | ALOMY | ECHCG | AVEFA |
|---|---|---|---|---|---|---|---|
| A-77 | 250 | — | 0 | 20 | 10 | 0 | 0 |
| A-79 | 250 | — | 0 | 100 | 40 | 80 | 40 |
| A-80 | 250 | — | 0 | 70 | 30 | 40 | 0 |
| A-81 | 250 | — | 0 | 100 | 80 | 100 | 90 |
| A-82 | 250 | — | 20 | 90 | 80 | 100 | 90 |
| A-83 | 250 | — | 0 | 100 | 50 | 90 | 40 |
| A-87 | 250 | — | 0 | 0 | 0 | 0 | 0 |
| A-88 | 250 | — | 0 | 0 | 0 | 0 | 10 |
| A-89 | 250 | — | 0 | 50 | 0 | 0 | 0 |
| A-90 | 250 | — | 0 | 0 | 0 | 0 | 0 |
| A-92 | 250 | — | 0 | 60 | 10 | 50 | 0 |
| A-96 | 250 | — | 0 | 0 | 0 | 0 | 0 |
| A-97 | 250 | — | 0 | 60 | 0 | 50 | 0 |
| A-98 | 250 | — | 50 | 90 | 0 | 90 | 0 |
| A-99 | 250 | — | 20 | 100 | 80 | 100 | 50 |
| A-100 | 250 | — | 60 | 100 | 20 | 80 | 90 |
| A-101 | 250 | — | 0 | 100 | 70 | 100 | 100 |
| A-102 | 250 | — | 0 | 90 | 30 | 90 | 0 |
| A-103 | 250 | — | 0 | 0 | 0 | 0 | 0 |
| A-104 | 250 | — | 0 | 0 | 0 | 0 | 0 |
| A-105 | 250 | — | 0 | 0 | 0 | 0 | 0 |
| A-122 | 250 | — | 0 | 100 | 40 | 90 | 100 |
| A-123 | 250 | — | 0 | 100 | 50 | 70 | 80 |
| A-124 | 250 | — | 0 | 100 | 50 | 70 | 60 |
| A-125 | 250 | — | 0 | 100 | 70 | 90 | 80 |
| A-126 | 250 | — | 0 | 100 | 30 | 80 | 90 |
| A-127 | 250 | — | 0 | 90 | 30 | 50 | 70 |
| A-128 | 250 | — | 0 | 90 | 40 | 70 | 80 |
| A-129 | 250 | — | 0 | 90 | 20 | 40 | 30 |
| A-130 | 250 | — | 0 | 90 | 20 | 40 | 20 |
| A-132 | 250 | — | 0 | 0 | 0 | 0 | 0 |
| A-133 | 250 | — | 0 | 80 | 10 | 0 | 70 |
| A-135 | 250 | — | 0 | 100 | 80 | 100 | 100 |
| A-136 | 250 | — | 0 | 30 | 20 | 90 | 80 |
| A-137 | 250 | — | 0 | 100 | 70 | 100 | 90 |
| A-138 | 250 | — | 20 | 100 | 90 | 100 | 90 |
| A-139 | 250 | — | 0 | 70 | 0 | 30 | 0 |
| A-141 | 250 | — | 0 | 80 | 20 | 100 | 30 |
| A-142 | 250 | — | 0 | 100 | 60 | 70 | 70 |
| A-143 | 250 | — | 0 | 70 | 20 | 0 | 0 |
| A-144 | 250 | — | 30 | 100 | 100 | 90 | 80 |
| A-147 | 250 | — | 0 | 70 | 100 | 100 | 60 |
| A-149 | 250 | — | 0 | 90 | 60 | 100 | 30 |
| A-150 | 250 | — | 0 | 100 | 90 | 100 | 40 |
| A-151 | 250 | — | 0 | 100 | 100 | 100 | 100 |
| A-152 | 250 | — | 0 | 100 | 70 | 100 | 90 |
| A-153 | 250 | — | 0 | 100 | 60 | 100 | 50 |
| A-154 | 250 | — | 0 | 90 | 50 | 100 | 20 |
| A-155 | 250 | — | 0 | 100 | 50 | 100 | 0 |
| B-2 | 1000 | 30 | 90 | 0 | 0 | 70 | 20 |
| B-4 | 1000 | 0 | 0 | 0 | 0 | 30 | 0 |
| B-6 | 1000 | 90 | 100 | 0 | 0 | 0 | 0 |
| B-7 | 1000 | 20 | 0 | 60 | 0 | 50 | 0 |
| B-9 | 250 | 0 | 0 | 0 | 0 | 0 | 0 |
| B-10 | 250 | 20 | 0 | 50 | 0 | 30 | 0 |
| B-12 | 250 | 0 | 0 | 50 | 0 | 30 | 0 |
| B-13 | 250 | 0 | 0 | 20 | 0 | 30 | 20 |
| B-18 | 250 | 0 | 0 | 20 | 40 | 0 | 0 |
| B-23 | 250 | 0 | 0 | 0 | 0 | 10 | 0 |
| B-25 | 250 | 0 | 0 | 0 | 0 | 0 | 0 |
| B-27 | 250 | 0 | 0 | 0 | 0 | 0 | 0 |
| B-28 | 250 | 0 | 0 | 0 | 0 | 0 | 0 |
| B-29 | 250 | 0 | 0 | 30 | 0 | 20 | 0 |
| B-30 | 250 | 0 | 0 | 0 | 0 | 0 | 0 |
| B-31 | 250 | 0 | 0 | 50 | 0 | 50 | 20 |
| C-4 | 250 | — | 0 | 0 | 0 | 0 | 0 |
| C-5 | 250 | — | 0 | 0 | 0 | 0 | 0 |
| C-6 | 250 | — | 0 | 0 | 0 | 0 | 0 |
| C-7 | 250 | — | 0 | 0 | 0 | 0 | 0 |
| C-8 | 250 | — | 0 | 0 | 0 | 0 | 0 |
| C-9 | 250 | — | 0 | 0 | 0 | 0 | 0 |
| C-10 | 250 | — | 0 | 0 | 20 | 40 | 20 |
| C-11 | 250 | — | 0 | 0 | 0 | 0 | 80 |
| C-12 | 250 | — | 0 | 90 | 0 | 20 | 90 |
| C-13 | 250 | — | 0 | 80 | 20 | 30 | 90 |
| D-7 | 1000 | 0 | 0 | 100 | 60 | 90 | 30 |
| D-8 | 1000 | 0 | 0 | 90 | 40 | 90 | 0 |

| Compound Number | Rate g/ha | SOLNI | AMARE | SETFA | ALOMY | ECHCG | AVEFA |
|---|---|---|---|---|---|---|---|
| D-9 | 1000 | 0 | 0 | 90 | 20 | 70 | 0 |
| D-10 | 1000 | 0 | 0 | 100 | 50 | 100 | 0 |
| D-11 | 1000 | 0 | 0 | 90 | 20 | 20 | 0 |
| D-12 | 1000 | 0 | 0 | 100 | 90 | 100 | 60 |
| D-13 | 1000 | 0 | 0 | 90 | 50 | 90 | 20 |
| D-14 | 1000 | 0 | 0 | 90 | 50 | 60 | 20 |
| D-15 | 1000 | 0 | 0 | 100 | 80 | 100 | 60 |
| D-16 | 1000 | 0 | 0 | 100 | 50 | 90 | 0 |
| D-17 | 1000 | 0 | 0 | 90 | 20 | 80 | 0 |
| D-18 | 1000 | 0 | 0 | 100 | 70 | 100 | 50 |
| D-19 | 1000 | 0 | 0 | 100 | 70 | 100 | 20 |
| D-20 | 1000 | 0 | 0 | 90 | 30 | 60 | 0 |
| D-21 | 1000 | 0 | 0 | 100 | 90 | 100 | 50 |
| D-22 | 250 | — | 0 | 100 | 60 | 100 | 50 |
| D-23 | 250 | — | 0 | 90 | 0 | 100 | 0 |
| D-24 | 250 | — | 20 | 90 | 0 | 100 | 0 |
| D-25 | 250 | — | 0 | 90 | 20 | 90 | 0 |
| D-28 | 250 | — | 0 | 80 | 30 | 20 | 40 |
| D-32 | 250 | — | 0 | 80 | 20 | 60 | 80 |

Post-Emergence Activity

| Compound Number | Rate g/ha | SOLNI | AMARE | SETFA | ALOMY | ECHCG | AVEFA |
|---|---|---|---|---|---|---|---|
| A-4 | 250 | — | 20 | 100 | 90 | 100 | 80 |
| A-15 | 1000 | 10 | 90 | 10 | 10 | 50 | 20 |
| A-16 | 1000 | 10 | 40 | 100 | 30 | 100 | 30 |
| A-20 | 1000 | 80 | 20 | 100 | 90 | 100 | 90 |
| A-21 | 1000 | 20 | 20 | 60 | 40 | 90 | 60 |
| A-22 | 1000 | 90 | 0 | 20 | 30 | 80 | 0 |
| A-24 | 1000 | 70 | 90 | 100 | 100 | 100 | 80 |
| A-25 | 1000 | 70 | 100 | 70 | 70 | 90 | 0 |
| A-26 | 1000 | 50 | 100 | 100 | 100 | 100 | 100 |
| A-27 | 1000 | 50 | 100 | 100 | 80 | 100 | 80 |
| A-29 | 1000 | 60 | 40 | 100 | 100 | 100 | 100 |
| A-30 | 1000 | 70 | 70 | 100 | 90 | 100 | 100 |
| A-31 | 1000 | 60 | 0 | 100 | 100 | 100 | 90 |
| A-37 | 1000 | 70 | 0 | 80 | 70 | 90 | 30 |
| A-54 | 1000 | 0 | 0 | 80 | 80 | 90 | 50 |
| A-56 | 1000 | 20 | 20 | 80 | 80 | 80 | 50 |
| A-58 | 1000 | 30 | 70 | 90 | 90 | 100 | 90 |
| A-59 | 250 | — | 0 | 90 | 30 | 100 | 50 |
| A-60 | 250 | — | 60 | 80 | 20 | 80 | 0 |
| A-62 | 250 | — | 0 | 100 | 70 | 100 | 70 |
| A-63 | 250 | — | 0 | 100 | 90 | 100 | 60 |
| A-64 | 250 | — | 20 | 90 | 20 | 100 | 0 |
| A-65 | 250 | — | 10 | 70 | 20 | 90 | 0 |
| A-66 | 250 | — | 10 | 100 | 20 | 100 | 30 |
| A-67 | 250 | — | 100 | 30 | 80 | 100 | 80 |
| A-69 | 250 | — | 90 | 100 | 70 | 100 | 90 |
| A-71 | 250 | — | 100 | 100 | 30 | 100 | 30 |
| A-72 | 250 | — | 60 | 80 | 20 | 80 | 0 |
| A-73 | 250 | — | 0 | 90 | 20 | 90 | 0 |
| A-74 | 250 | — | 70 | 90 | 0 | 90 | 0 |
| A-75 | 250 | — | 0 | 100 | 90 | 100 | 90 |
| A-76 | 250 | — | 0 | 100 | 90 | 100 | 70 |
| A-77 | 250 | — | 0 | 90 | 70 | 100 | 60 |
| A-79 | 250 | — | 0 | 100 | 80 | 100 | 50 |
| A-80 | 250 | — | 0 | 90 | 30 | 100 | 0 |
| A-81 | 250 | — | 0 | 100 | 100 | 100 | 100 |
| A-82 | 250 | — | 0 | 100 | 100 | 100 | 100 |
| A-83 | 250 | — | 0 | 100 | 80 | 100 | 80 |
| A-87 | 250 | — | 0 | 80 | 10 | 80 | 0 |
| A-88 | 250 | — | 0 | 90 | 50 | 90 | 10 |
| A-89 | 250 | — | 0 | 80 | 80 | 90 | 50 |
| A-90 | 250 | — | 0 | 90 | 40 | 90 | 20 |
| A-92 | 250 | — | 0 | 90 | 50 | 100 | 0 |
| A-96 | 250 | — | 0 | 90 | 50 | 100 | 30 |
| A-97 | 250 | — | 0 | 70 | 40 | 90 | 30 |
| A-98 | 250 | — | 30 | 100 | 50 | 100 | 70 |
| A-99 | 250 | — | 0 | 100 | 90 | 100 | 90 |
| A-100 | 250 | — | 0 | 100 | 90 | 100 | 90 |

-continued

| Compound Number | Rate g/ha | SOLNI | AMARE | SETFA | ALOMY | ECHCG | AVEFA |
|---|---|---|---|---|---|---|---|
| A-101 | 250 | — | 0 | 100 | 100 | 100 | 100 |
| A-102 | 250 | — | 0 | 30 | 20 | 70 | 0 |
| A-103 | 250 | — | 0 | 100 | 10 | 100 | 0 |
| A-122 | 250 | — | 40 | 100 | 80 | 100 | 50 |
| A-123 | 250 | — | 0 | 100 | 90 | 100 | 70 |
| A-124 | 250 | — | 20 | 100 | 80 | 100 | 90 |
| A-125 | 250 | — | 0 | 100 | 100 | 100 | 90 |
| A-126 | 250 | — | 0 | 100 | 70 | 100 | 90 |
| A-127 | 250 | — | 0 | 100 | 80 | 100 | 40 |
| A-128 | 250 | — | 0 | 100 | 80 | 100 | 90 |
| A-129 | 250 | — | 0 | 80 | 70 | 90 | 80 |
| A-130 | 250 | — | 0 | 100 | 40 | 100 | 40 |
| A-132 | 250 | — | 0 | 90 | 20 | 70 | 30 |
| A-133 | 250 | — | 70 | 100 | 20 | 100 | 80 |
| A-135 | 250 | — | 0 | 100 | 100 | 100 | 100 |
| A-136 | 250 | — | 0 | 70 | 80 | 100 | 100 |
| A-137 | 250 | — | 30 | 100 | 90 | 100 | 90 |
| A-138 | 250 | — | 60 | 100 | 100 | 100 | 100 |
| A-139 | 250 | — | 50 | 80 | 30 | 100 | 50 |
| A-141 | 250 | — | 0 | 80 | 50 | 100 | 50 |
| A-142 | 250 | — | 0 | 80 | 100 | 100 | 80 |
| A-143 | 250 | — | 0 | 90 | 90 | 100 | 80 |
| A-144 | 250 | — | 40 | 100 | 100 | 100 | 100 |
| A-147 | 250 | — | 0 | 70 | 100 | 100 | 90 |
| A-149 | 250 | — | 20 | 100 | 90 | 100 | 70 |
| A-150 | 250 | — | 0 | 100 | 90 | 100 | 80 |
| A-151 | 250 | — | 0 | 100 | 100 | 100 | 100 |
| A-152 | 250 | — | 0 | 100 | 100 | 100 | 100 |
| A-153 | 250 | — | 30 | 100 | 100 | 100 | 100 |
| A-154 | 250 | — | 0 | 100 | 100 | 100 | 70 |
| A-155 | 250 | — | 40 | 100 | 100 | 100 | 90 |
| B-2 | 1000 | 40 | 70 | 20 | 0 | 80 | 0 |
| B-4 | 1000 | 40 | 70 | 90 | 80 | 90 | 30 |
| B-6 | 1000 | 0 | 0 | 30 | 20 | 50 | 0 |
| B-7 | 1000 | 70 | 70 | 70 | 20 | 60 | 20 |
| B-9 | 250 | 20 | 40 | 70 | 40 | 80 | 0 |
| B-10 | 250 | 0 | 40 | 80 | 40 | 90 | 20 |
| B-12 | 250 | 0 | 30 | 90 | 60 | 100 | 0 |
| B-13 | 250 | 0 | 20 | 90 | 0 | 80 | 30 |
| B-18 | 250 | 0 | 0 | 70 | 10 | 60 | 0 |
| B-23 | 250 | 0 | 0 | 70 | 30 | 60 | 0 |
| B-25 | 250 | 0 | 0 | 20 | 20 | 70 | 0 |
| B-27 | 250 | 0 | 0 | 60 | 70 | 80 | 0 |
| B-28 | 250 | 0 | 0 | 70 | 0 | 70 | 0 |
| B-29 | 250 | 30 | 20 | 80 | 30 | 100 | 0 |
| B-30 | 250 | 10 | 0 | 70 | 20 | 70 | 0 |
| B-31 | 250 | 0 | 0 | 90 | 10 | 90 | 0 |
| C-4 | 250 | — | 20 | 70 | 60 | 70 | 30 |
| C-5 | 250 | — | 0 | 90 | 70 | 100 | 70 |
| C-6 | 250 | — | 40 | 30 | 20 | 60 | 0 |
| C-7 | 250 | — | 0 | 30 | 20 | 60 | 0 |
| C-8 | 250 | — | 0 | 40 | 20 | 60 | 0 |
| C-9 | 250 | — | 0 | 10 | 50 | 70 | 40 |
| C-10 | 250 | — | 0 | 20 | 20 | 70 | 50 |
| C-11 | 250 | — | 20 | 30 | 70 | 80 | 60 |
| C-12 | 250 | — | 0 | 90 | 80 | 90 | 90 |
| C-13 | 250 | — | 20 | 100 | 80 | 100 | 90 |
| D-7 | 1000 | 0 | 0 | 100 | 90 | 100 | 70 |
| D-8 | 1000 | 0 | 0 | 100 | 60 | 100 | 10 |
| D-9 | 1000 | 0 | 0 | 90 | 30 | 100 | 0 |
| D-10 | 1000 | 0 | 20 | 100 | 90 | 100 | 20 |
| D-11 | 1000 | 0 | 0 | 90 | 40 | 100 | 0 |
| D-12 | 1000 | 0 | 0 | 100 | 90 | 100 | 90 |
| D-13 | 1000 | 0 | 0 | 100 | 60 | 100 | 0 |
| D-14 | 1000 | 0 | 0 | 100 | 20 | 100 | 10 |
| D-15 | 1000 | 0 | 0 | 100 | 80 | 100 | 60 |
| D-16 | 1000 | 0 | 0 | 100 | 90 | 100 | 20 |
| D-17 | 1000 | 0 | 10 | 100 | 60 | 100 | 20 |
| D-18 | 1000 | 0 | 20 | 100 | 100 | 100 | 90 |
| D-19 | 1000 | 0 | 0 | 100 | 90 | 100 | 80 |
| D-20 | 1000 | 0 | 20 | 100 | 100 | 100 | 90 |
| D-21 | 1000 | 30 | 10 | 100 | 100 | 100 | 90 |
| D-22 | 250 | — | 0 | 100 | 90 | 100 | 100 |
| D-23 | 250 | — | 0 | 90 | 0 | 100 | 0 |
| D-24 | 250 | — | 0 | 100 | 0 | 100 | 20 |
| D-25 | 250 | — | 0 | 90 | 0 | 90 | 20 |
| D-28 | 250 | — | 0 | 80 | 80 | 90 | 50 |

| Compound Number | Rate g/ha | SOLNI | AMARE | SETFA | ALOMY | ECHCG | AVEFA |
|---|---|---|---|---|---|---|---|
| D-32 | 250 | — | 0 | 80 | 50 | 90 | 70 |

What is claimed is:

1. A compound of formula (I)

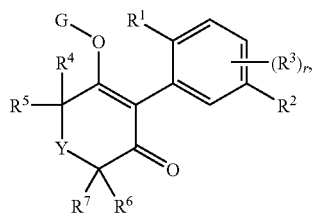

wherein:

$R^1$ is halogen, $C_1$-$C_4$alkyl, $C_1$-$C_4$haloalkyl, $C_3$-$C_6$cycloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, nitro or cyano;

$R^2$ is aryl or heteroaryl; or aryl or heteroaryl both substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, phenoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_3$-$C_6$cycloalkyl, $C_1$-$C_4$alkylsulfonyloxy, $C_1$-$C_4$haloalkylsulfonyloxy, $C_1$-$C_4$alkoxy $C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl, nitro, cyano, thiocyano, hydroxy, amino, $C_1$-$C_6$alkylamino, $C_1$-$C_6$dialkylamino, $C_3$-$C_6$cycloalkylamino, morpholino, thiomorpholino, $C_1$-$C_6$alkylcarbonylamino, $C_1$-$C_6$alkoxycarbonylamino, $C_3$-$C_6$alkenyloxycarbonylamino, $C_3$-$C_6$alkynyloxycarbonylamino, $C_1$-$C_6$alkylaminocarbonylamino, di($C_{1\text{-}6}$alkyl)aminocarbonylamino, formyl, $C_1$-$C_6$alkylcarbonyl, $C_2$-$C_6$alkenylcarbonyl, $C_2$-$C_6$alkynylcarbonyl, carboxy, $C_1$-$C_6$alkoxycarbonyl, $C_3$-$C_6$alkenyloxycarbonyl, $C_3$-$C_6$alkynyloxycarbonyl, carboxamido, $C_1$-$C_6$alkylaminocarbonyl, di($C_1$-$C_6$alkyl)aminocarbonyl, $C_1$-$C_6$alkylcarbonyloxy, $C_1$-$C_6$alkylaminocarbonyloxy, di($C_1$-$C_6$alkyl)aminocarbonyloxy or $C_1$-$C_6$alkylthiocarbonylamino; and wherein, when $R^2$ is heteroaryl or substituted heteroaryl, then the $R^2$ heteroaryl is thienyl, pyrazolyl, imidazolyl, pyridyl, pyrimidinyl, pyrazinyl, or pyridazinyl, or, where appropriate, an N-oxide or a salt thereof; and r is 0, 1, 2 or 3;

$R^3$, if r is 1, is halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylthio, $C_1$-$C_6$alkylsulfinyl, $C_1$-$C_6$alkylsulfonyl, cyano or nitro; or the substituents $R^3$, if r is 2 or 3, independently of each other, are halogen, $C_1$-$C_6$alkyl, $C_1$-$C_6$haloalkyl, $C_1$-$C_6$alkoxy, $C_1$-$C_6$haloalkoxy, $C_2$-$C_6$alkenyl, $C_2$-$C_6$alkynyl, $C_1$-$C_6$alkylthio, $C_1$-$C_6$alkylsulfinyl, $C_1$-$C_6$alkylsulfonyl, cyano or nitro;

$R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl; cyclopropyl or cyclopropyl substituted by $C_1$- or $C_2$alkyl, $C_1$- or $C_2$haloalkyl or halogen; cyclobutyl or cyclobutyl substituted by $C_1$- or $C_2$alkyl; oxetanyl or oxetanyl substituted by $C_1$- or $C_2$alkyl; $C_5$-$C_7$cycloalkyl or $C_5$-$C_7$cycloalkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl or $C_4$-$C_7$cycloalkenyl substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; cyclopropyl$C_1$-$C_5$alkyl or cyclopropyl$C_1$-$C_5$alkyl substituted by $C_1$- or $C_2$alkyl, $C_1$- or $C_2$haloalkyl or halogen; cyclobutyl$C_1$-$C_5$alkyl or cyclobutyl$C_1$-$C_5$alkyl substituted by $C_1$-$C_2$alkyl; oxetanyl$C_1$-$C_5$alkyl or oxetanyl$C_1$-$C_5$alkyl substituted by $C_1$- or $C_2$alkyl; $C_5$-$C_7$ cycloalkyl$C_1$-$C_5$alkyl or $C_5$-$C_7$cycloalkyl$C_1$-$C_5$alkyl substituted by $C_1$- or $C_2$alkyl or $C_1$- or $C_2$haloalkyl, where a methylene group of the cycloalkyl moiety is optionally replaced by an oxygen or sulfur atom or a sulfinyl or sulfonyl group; $C_4$-$C_7$cycloalkenyl$C_1$-$C_5$ alkyl or $C_4$-$C_7$cycloalkenyl$C_1$-$C_5$alkyl which is substituted by $C_1$- or $C_2$alkyl or $C_1$- or $C_2$haloalkyl, where a methylene group of the cycloalkenyl moiety is optionally replaced by an oxygen or sulfur atom or a sulfinyl or sulfonyl group; phenyl or phenyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; benzyl or benzyl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; or heteroaryl or heteroaryl substituted by $C_1$-$C_4$alkyl, $C_1$-$C_4$alkoxy, $C_1$-$C_4$haloalkyl, halogen, nitro, cyano, $C_1$-$C_4$alkylthio, $C_1$-$C_4$alkylsulfinyl, $C_1$-$C_4$alkylsulfonyl or $C_1$-$C_4$alkylcarbonyl; or $R^4$ and $R^5$, or $R^6$ and $R^7$, are joined to form a 5-7 membered saturated or unsaturated ring in which a methylene group is optionally replaced by an oxygen or sulfur atom, or a 5-7 membered saturated or unsaturated ring substituted by $C_1$- or $C_2$alkyl, where a methylene group of the ring is optionally replaced by an oxygen or sulfur atom; or $R^4$ and $R^7$ are joined to form a 5-7 membered saturated or unsaturated ring unsubstituted or substituted by $C_1$- or $C_2$alkyl, or $C_1$- or $C_2$alkoxy; and Y is O, C=O, S(O)$_m$ or S(O)$_n$NR$^8$; provided that when Y is C=O, $R^6$ and $R^7$ are different from hydrogen when either $R^4$ or $R^5$ is hydrogen, and $R^4$ and $R^5$ are different from hydrogen when either $R^6$ or $R^7$ is hydrogen;

m is 0 or 1 or 2 and n is 0 or 1;

$R^8$ is hydrogen, $C_1$-$C_6$alkyl, $C_3$-$C_6$cycloalkyl, $C_1$-$C_6$alkoxycarbonyl, tri($C_1$-$C_6$alkyl)silyl-ethyloxycarbonyl, $C_1$-$C_6$haloalkoxycarbonyl, cyano, $C_1$-$C_6$haloalkyl, $C_1$-$C_6$hydroxyalkyl, $C_2$-$C_6$alkenyl, $C_2$-$C_6$alkynyl, $C_2$-$C_6$haloalkenyl, $C_1$-$C_6$alkylcarbonyl, $C_1$-$C_6$haloalkyl-carbonyl, $C_1$-$C_6$cycloalkylcarbonyl; phenylcarbonyl or phenylcarbonyl substituted by $R^9$; benzylcarbonyl or benzylcarbonyl substituted by $R^9$; pyridylcarbonyl or pyridylcarbonyl substituted by $R^9$; phenoxycarbonyl or phenoxycarbonyl substituted by $R^9$; or benzyloxycarbonyl or benzyloxycarbonyl substituted by $R^9$;

$R^9$ is $C_1$-$C_6$haloalkyl, $C_1$-$C_6$alkoxycarbonyl, nitro, cyano, formyl, carboxyl or halogen; and G is hydrogen, an agriculturally acceptable cation or a latentiating group;

and wherein, when G is a latentiating group then G is selected from the groups $C_1$-$C_8$alkyl, $C_2$-$C_8$haloalkyl, phenyl$C_1$-$C_8$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_8$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_8$ alkenyl, $C_3$-$C_8$ haloalkenyl, $C_3$-$C_8$ alkynyl, $C(X^a)$—$R^a$, $C(X^b)$—$X^c$—$R^b$, $C(X^d)$—$N(R^c)$—$R^d$, —$SO_2$—$R^e$, —$P(X^e)(R^f)$—$R^g$ and $CH_2$—$X^f$—$R^h$;

wherein $X^a$, $X^b$, $X^c$, $X^d$, $X^e$ and $X^f$ are independently of each other oxygen or sulfur;

and wherein $R^a$ is H, $C_1$-$C_{18}$alkyl, $C_2$-$C_{18}$alkenyl, $C_2$-$C_{18}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_8$alkyl)silyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $O_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, $C_3$-$C_8$-trialkylsilyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$ alkyl, $C_1$-$C_3$haloalkyl, $C_1$-$C_3$alkoxy, $C_1$-$C_3$haloalkoxy, halogen, cyano or nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; amino; $C_1$-$C_3$alkylamino; di($C_1$-$C_3$alkyl)amino; $C_1$-$C_3$alkoxy; $C_3$-$C_7$cycloalkylamino; di($C_3$-$C_7$cycloalkyl)amino or $C_3$-$C_7$cycloalkoxy;

or $R^c$ and $R^d$ may join together to form a 3-7 membered ring, optionally containing one heteroatom selected from O or S and optionally substituted by 1 or 2 $C_1$-$C_3$alkyl groups;

and $R^e$ is $C_1$-$C_{10}$alkyl, $C_2$-$C_{10}$alkenyl, $C_2$-$C_{10}$alkynyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_8$alkyl)silyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano, amino or by nitro; heteroarylamino or heteroarylamino substituted by $C_1$-$C_3$alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; amino; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino; di($C_3$-$C_7$cycloalkyl)amino; $C_3$-$C_7$cycloalkoxy; $C_1$-$C_{10}$alkoxy; $C_1$-$C_{10}$haloalkoxy; $C_1$-$C_5$alkylamino or di($C_2$-$C_8$alkyl)amino;

$R^f$ and $R^g$ are each independently of each other $C_1$-$C_{10}$alkyl, $C_2$-$C_{10}$alkenyl, $O_2$-$C_{10}$alkynyl, $C_1$-$C_{10}$alkoxy, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino$C_1$-$C_5$alkyl, di($C_2$-$C_8$alkyl)amino$C_5$alkyl, $O_3$—$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $O_3$—$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_2$-$C_5$alkylaminoalkyl, tri($C_3$-$C_6$alkyl)silyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$alkylsulfonyl, halogen, cyano, or by nitro), $C_2$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen, cyano or nitro; heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro; heteroarylamino or heteroarylamino substituted by $C_1$-$C_3$ alkyl, $C_1$-$C_3$haloalkyl, $C_1$-$C_3$alkoxy, $C_1$-$C_3$haloalkoxy, halogen, cyano or by nitro; diheteroarylamino or diheteroarylamino substituted by $C_1$-$C_3$alkyl, $C_1$-$C_3$haloalkyl, $C_1$-$C_3$alkoxy, $C_1$-$C_3$haloalkoxy, halogen, cyano or nitro; phenylamino or phenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; amino; hydroxy; diphenylamino or diphenylamino substituted by $C_1$-$C_3$alkyl, $C_1$-$C_3$haloalkyl, $C_1$-$C_3$alkoxy, $C_1$-$C_3$haloalkoxy, halogen, cyano or nitro; or $C_3$-$C_7$cycloalkylamino; di($C_3$-$C_7$cycloalkyl)amino; $C_3$-$C_7$cycloalkoxy; $C_1$-$C_{10}$haloalkoxy; $C_1$-$C_5$alkylamino or di($C_2$-$C_8$alkyl)amino; or benzyloxy or phenoxy, wherein the benzyl and phenyl groups may in turn be substituted by $C_1$-$C_3$alkyl, $C_1$-$C_3$haloalkyl, $C_1$-$C_3$alkoxy, $C_1$-$C_3$haloalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$haloalkyl, $C_1$-$C_{10}$cyanoalkyl, $C_1$-$C_{10}$nitroalkyl, $C_2$-$C_{10}$aminoalkyl, $C_1$-$C_5$alkylamino$C_1$-$C_5$alkyl, di($C_2$-$C_8$alkyl)amino$C_1$-$C_5$alkyl, $C_3$-$C_7$cycloalkyl$C_1$-$C_5$alkyl, $C_1$-$C_5$alkoxy$C_1$-$C_5$alkyl, $C_3$-$C_5$alkenyloxy$C_1$-$C_5$alkyl, $C_3$-$C_5$alkynyloxy$C_1$-$C_5$alkyl, $C_1$-$C_5$alkylthio$C_1$-$C_5$alkyl, $C_1$-$C_5$alkylsulfinyl$C_1$-$C_5$alkyl, $C_1$-$C_5$alkylsulfonyl$C_1$-$C_5$alkyl, $C_2$-$C_8$alkylideneaminoxy$C_1$-$C_5$alkyl, $C_1$-$C_5$alkylcarbonyl$C_1$-$C_5$alkyl, $C_1$-$C_5$alkoxycarbonyl$C_1$-$C_5$alkyl, aminocarbonyl$C_1$-$C_5$alkyl, $C_1$-$C_5$alkylaminocarbonyl$C_1$-$C_5$alkyl, di($C_2$-$C_8$alkyl)aminocarbonyl$C_1$-$C_5$alkyl, $C_1$-$C_5$alkylcarbonylamino$C_1$-$C_5$alkyl, N—$C_1$-$C_5$alkylcarbonyl-N—$C_1$-$C_5$alkylamino$C_1$-$C_5$alkyl, tri($C_3$-$C_6$alkyl)silyl$C_1$-$C_5$alkyl, phenyl$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryl$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), phenoxy$C_1$-$C_5$alkyl (wherein the phenyl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), heteroaryloxy$C_1$-$C_5$alkyl (wherein the heteroaryl is optionally substituted by $C_1$-$C_3$alkyl, $C_1$-$C_3$haloalkyl, $C_1$-$C_3$alkoxy, $C_1$-$C_3$haloalkoxy, $C_1$-$C_3$alkylthio, $C_1$-$C_3$alkylsulfinyl, $C_1$-$C_3$ alkylsulfonyl, halogen, cyano or by nitro), $C_3$-$C_5$haloalkenyl, $C_3$-$C_8$cycloalkyl; phenyl or phenyl substituted by $C_1$-$C_3$alkyl, $C_1$-$C_3$haloalkyl, $C_1$-$C_3$alkoxy, $C_1$-$C_3$haloalkoxy, halogen or by nitro; or heteroaryl or heteroaryl substituted by $C_1$-$C_3$alkyl, $C_1$-$C_3$haloalkyl, $C_1$-$C_3$alkoxy, $C_1$-$C_3$haloalkoxy, halogen, cyano or by nitro;

and wherein:

aryl means phenyl or naphthyl; and except for any heteroaryl or substituted heteroaryl within $R^2$, heteroaryl means thienyl, furyl, pyrrolyl, isoxazolyl, oxazolyl, isothiazolyl, thiazolyl, pyrazolyl, imidazolyl, triazolyl, tetrazolyl, pyridyl, pyrimidinyl, pyrazinyl, triazinyl, oxadiazolyl, thiadiazolyl or pyridazinyl, or an N-oxide or a salt thereof.

2. A compound according to claim 1, wherein $R^1$ is halogen, $C_1$-$C_4$alkyl, $C_1$-$C_4$haloalkyl, $C_2$-$C_4$alkenyl or $C_2$-$C_4$alkynyl.

3. A compound according to claim 1, wherein $R^2$ is aryl or heteroaryl; or aryl or heteroaryl both substituted by halogen, $C_1$-$C_4$alkyl, $C_1$-$C_4$haloalkyl, phenoxy, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

4. A compound according to claim 3, wherein $R^2$ is phenyl, thienyl, pyrazolyl, imidazolyl, pyridyl, pyrimidinyl, pyrazinyl, or pyridazinyl, or an N-oxide or a salt thereof, where these rings are unsubstituted or substituted by halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, nitro or cyano.

5. A compound according to claim 1, wherein $R^2$ is phenyl or pyridyl; or phenyl or pyridyl both substituted by halogen, nitro, cyano, $C_1$-$C_2$alkyl, $C_1$-$C_2$haloalkyl, $C_1$-$C_2$alkoxy or $C_1$-$C_2$haloalkoxy.

6. A compound according to claim 1, wherein $R^3$ is hydrogen, which means that r is 0, or $R^3$ is halogen or $C_1$-$C_6$alkyl.

7. A compound according to claim 1, wherein $R^4$, $R^5$, $R^6$ and $R^7$, independently of each other, are hydrogen, $C_1$-$C_4$alkyl, $C_1$-$C_4$haloalkyl, $C_1$-$C_4$alkoxy$C_1$-$C_4$ alkyl, $C_1$-$C_4$alkylthio$C_1$-$C_4$alkyl, $C_1$-$C_4$alkylsulfinyl$C_1$-$C_4$alkyl, $C_1$-$C_4$alkylsulfonyl$C_1$-$C_4$alkyl; $C_5$-$C_7$cycloalkyl or $C_5$-$C_7$cycloalkyl substituted by $C_1$- or $C_2$alkyl or $C_1$- or $C_2$haloalkyl and in which a methylene group is optionally replaced by an oxygen or sulfur atom or a sulfinyl or sulfonyl group; $C_5$-$C_7$cycloalkyl$C_1$-$C_5$alkyl or $C_5$-$C_7$cycloalkyl$C_1$-$C_5$alkyl substituted by $C_1$-$C_2$alkyl or $C_1$- or $C_2$haloalkyl and in which a methylene group is optionally replaced by an oxygen or sulfur atom or a sulfinyl or sulfonyl group.

8. A compound according to claim 1, wherein $R^4$, $R^5$, $R^6$ and $R^7$, independently of each other, are hydrogen, $C_1$-$C_2$alkyl, $C_1$-$C_2$haloalkyl or $C_1$-$C_2$-alkoxy-$C_1$-$C_2$alkyl.

9. A compound according to claim 1, wherein Y is O, S or C=O.

10. A compound according to claim 1, wherein the latentiating group G is $C(X^a)$—$R^a$ or $C(X^b)$—$X^c$—$R^b$, wherein $X^a$, $X^b$ and $X^c$ are oxygen, $R^a$ is $C_1$-$C_6$alkyl, $C_2$-$C_6$alkenyl, $C_2$-$C_6$alkynyl, $C_3$-$C_6$cycloalkyl or $C_1$-$C_4$alkoxy$C_1$-$C_4$alkyl, and $R^b$ is $C_1$-$C_6$alkyl, $C_3$-$C_6$alkenyl, $C_3$-$C_6$alkynyl, $C_3$-$C_6$cycloalkyl or $C_1$-$C_4$alkoxy$C_1$-$C_4$alkyl.

11. A compound according to claim 1, wherein G is hydrogen, or an alkali metal or alkaline earth metal cation as an agriculturally acceptable cation.

12. A compound according to claim 11, wherein G is hydrogen.

13. A compound according to claim 1, wherein $R^1$ is $C_1$-$C_4$alkyl, $R^2$ is phenyl or phenyl substituted by halogen or $C_1$-$C_2$alkyl, $R^3$ is hydrogen, which means that r is 0, $R^4$, $R^5$, $R^6$ and $R^7$, independently of each other, are $C_1$-$C_2$alkyl, Y is O and G is hydrogen.

14. A process for the preparation of a compound of formula (I) according to claim 1, wherein G is hydrogen, which comprises cyclization of the compound of the formula (B)

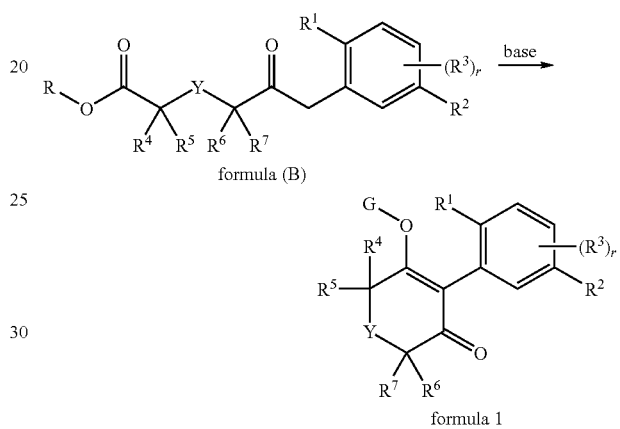

wherein $R^1$, $R^2$, $R^3$, $R^4$, $R^5$, $R^6$, $R^7$ and Y have the meanings assigned to them in claim 1 and R is alkyl, under basic conditions.

15. A process for the preparation of a compound of formula (I) according to claim 1, wherein G is hydrogen, which comprises cyclization of the compound of the formula (B)

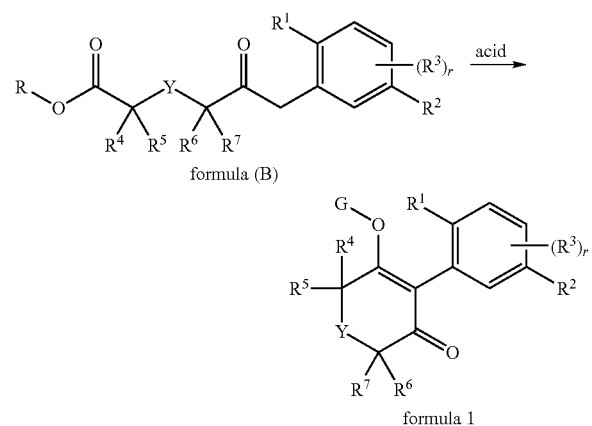

wherein $R^1$, $R^2$, $R^3$, $R^4$, $R^5$, $R^6$, $R^7$ and Y have the meanings assigned to them in claim 1 and R is hydrogen, under acidic conditions.

16. A process for the preparation of a compound of formula (I) according to claim 1, wherein G is hydrogen, which comprises rearrangement of the compound of the formula (Q)

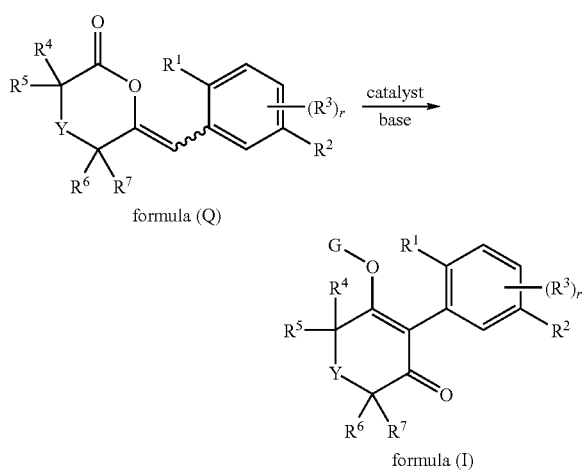

formula (Q)

formula (I)

wherein $R^1$, $R^2$, $R^3$, $R^4$, $R^5$, $R^6$, $R^7$ and Y have the meanings assigned to them in claim 1, in the presence of a base and in the presence or absence of a catalyst, wherein the catalyst is selected from at least one of a palladium(II) dichloride catalyst, a gold(I) chloride catalyst, and a silver carbonate catalyst.

17. A process for the preparation of a compound of formula (I) according to claim 1, which comprises reacting a compound of the formula (H)

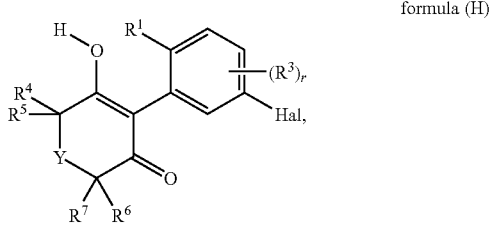

formula (H)

wherein $R^1$, $R^3$, $R^4$, $R^5$, $R^6$, $R^7$, Y and r have the meanings assigned to them in claim 1 and Hal is chlorine, bromine, iodine or trifluoromethanesulfonyloxy, with an aryl- or heteroaryl boronic acid of formula $R^2B(OH)_2$, wherein $R^2$ has the meaning assigned to it in claim 1, or a salt or ester thereof, in the presence of a suitable palladium catalyst, a ligand and a base, and in a suitable solvent.

18. A process for the preparation of a compound of formula (I) according to claim 1, which comprises reacting an aryl boronic acid of the formula (X)

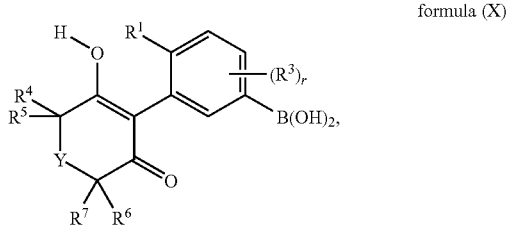

formula (X)

wherein $R^1$, $R^3$, $R^4$, $R^5$, $R^6$, $R^7$, Y and r have the meanings assigned to them in claim 1, or a salt or ester thereof, with a compound of formula $R^2$-Hal, wherein $R^2$ has the meaning assigned to it in claim 1, and Hal is chlorine, bromine, iodine or trifluoromethanesulfonyloxy, in the presence of a suitable palladium catalyst, a ligand and a base, and in a suitable solvent.

19. A process for the preparation of a compound of formula (I) according to claim 1, wherein G is $C(X^a)$—$R^a$ or $C(X^b)$—$X^c$—$R^b$, wherein $X^a$, $X^b$ and $X^c$ are oxygen, $R^a$ is $C_1$-$C_6$alkyl, $C_2$-$C_6$alkenyl, $C_2$-$C_6$alkynyl, $C_3$-$C_6$cycloalkyl or $C_1$-$C_4$alkoxy$C_1$-$C_4$alkyl, and $R^b$ is $C_1$-$C_6$alkyl, $C_3$-$C_6$alkenyl, $C_3$-$C_6$alkynyl, $C_3$-$C_6$cycloalkyl or $C_1$-$C_4$alkoxy$C_1$-$C_4$alkyl, which comprises treating a compound of the formula (A)

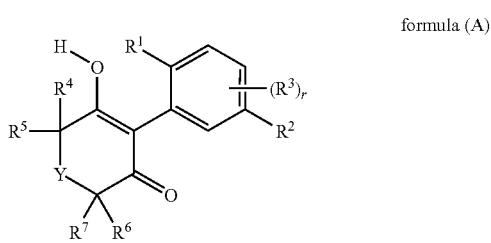

formula (A)

with an acylating agent, in the presence or absence of at least one equivalent of a base.

20. A method of controlling grasses and weeds in crops of useful plants, which comprises applying a herbicidally effective amount of a compound of formula (I) as defined in claim 1, or of a composition comprising such a compound, to the plants or to the locus thereof.

21. A herbicidal composition, which, in addition to comprising formulation adjuvants, comprises a herbicidally effective amount of a compound of formula I as defined in claim 1.

22. A herbicidal composition according to claim 21, which, in addition to comprising the compound of formula I, comprises a further herbicide as mixing partner.

23. A herbicidal composition according to claim 21, which, in addition to comprising the compound of formula I, comprises a safener.

24. A herbicidal composition according to claim 21, which, in addition to comprising the compound of formula I, comprises a further herbicide as mixing partner and a safener.

25. A compound according to claim 1, wherein $R^2$ is phenyl substituted at the para-position by halogen and is optionally further substituted by halogen, nitro, $C_1$-$C_2$alkyl, $C_1$-$C_2$haloalkyl, $C_1$-$C_2$alkoxy or $C_1$-$C_2$haloalkoxy.

26. A compound according to claim 1, wherein $R^2$ is phenyl substituted at the para-position by chlorine and is optionally further substituted by halogen, nitro, $C_1$-$C_2$alkyl, $C_1$-$C_2$haloalkyl, $C_1$-$C_2$alkoxy or $C_1$-$C_2$haloalkoxy.

27. A compound according to claim 1, wherein $R^3$ is hydrogen, which means that r is 0.

28. A compound according to claim 1, wherein Y is O.

29. A compound according to claim 1, which is selected from compound numbers A-2 to A-25, A-27, A-28, A-31, A-35, A-36, A-38, A-40 to A-45, A-47 to A-67, A-69, A-70, A-72 to A-77, A-79, A-81, A-82, A-87 to A-90, A-92, A-95 to A-103, A-113 to A-117, A-119, A-131, A-132, A-135 to A-139, A-141, A-142, A-144, A-147, A-149 to A-160, A-165 to A-168, D-1 to D-17, D-19 to D-26, D-28, D-31, D-32, D-33, and D-36 to D-39, whose structures are as shown below:

| Compound Number | Structure |
|---|---|
| A-2 | 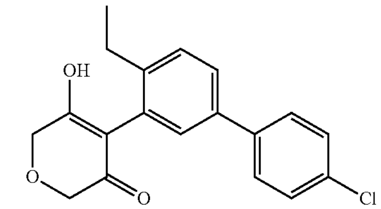 [SMILES: CCc1ccc(-c2ccc(Cl)cc2)cc1C1=C(O)COCC1=O] |
| A-3 | 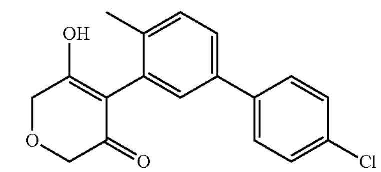 [SMILES: Cc1ccc(-c2ccc(Cl)cc2)cc1C1=C(O)COCC1=O] |
| A-4 | 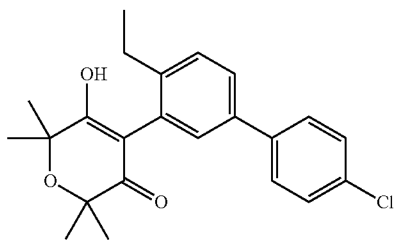 |
| A-5 | 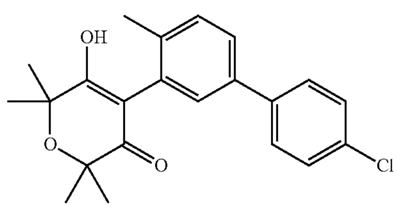 [SMILES: Cc1ccc(-c2ccc(Cl)cc2)cc1C1=C(O)C(C)(C)OC(C)(C)C1=O] |
| A-6 | 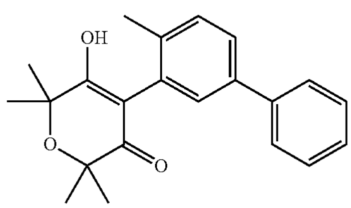 [SMILES: Cc1ccc(-c2ccccc2)cc1C1=C(O)C(C)(C)OC(C)(C)C1=O] |
| A-7 | 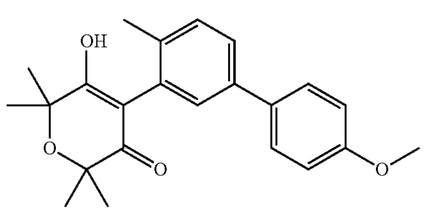 |
| A-8 | 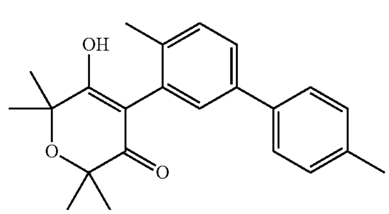 |
| A-9 | |
| A-10 | |
| A-11 | |
| A-12 | |
| A-13 | |
| A-14 | |
| A-15 | |

-continued

| Compound Number | Structure |
|---|---|
| A-16 | 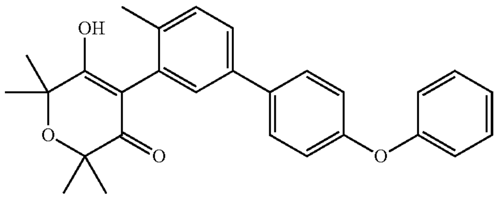 [SMILES: Cc1ccc(-c2ccc(Oc3ccccc3)cc2)cc1C1=C(O)C(C)(C)OC(C)(C)C1=O] |
| A-17 | 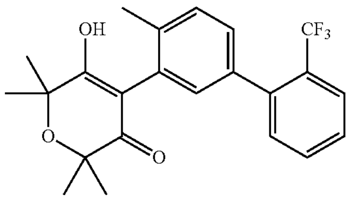 [SMILES: Cc1ccc(-c2ccccc2C(F)(F)F)cc1C1=C(O)C(C)(C)OC(C)(C)C1=O] |
| A-18 | 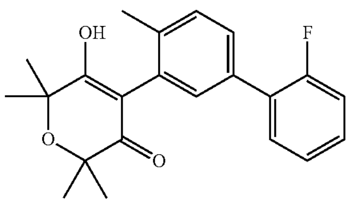 [SMILES: Cc1ccc(-c2ccccc2F)cc1C1=C(O)C(C)(C)OC(C)(C)C1=O] |
| A-19 | 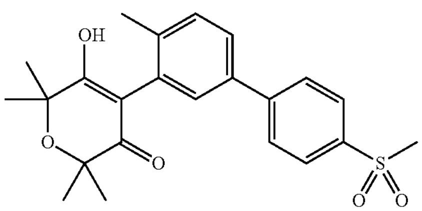 |
| A-20 | 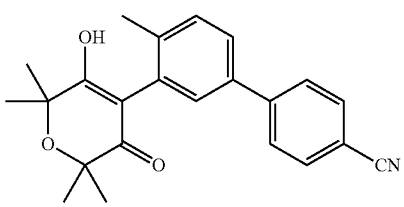 [SMILES: Cc1ccc(-c2ccc(C#N)cc2)cc1C1=C(O)C(C)(C)OC(C)(C)C1=O] |
| A-21 | 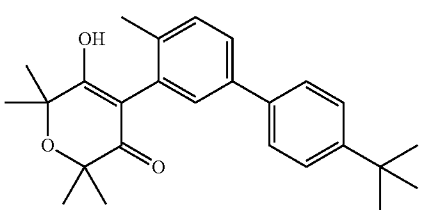 [SMILES: Cc1ccc(-c2ccc(C(C)(C)C)cc2)cc1C1=C(O)C(C)(C)OC(C)(C)C1=O] |
| A-22 | 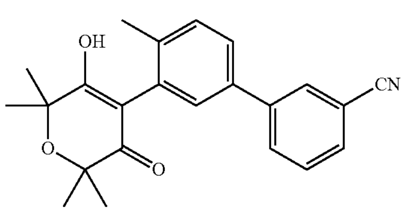 [SMILES: Cc1ccc(-c2cccc(C#N)c2)cc1C1=C(O)C(C)(C)OC(C)(C)C1=O] |

-continued

| Compound Number | Structure |
|---|---|
| A-23 | 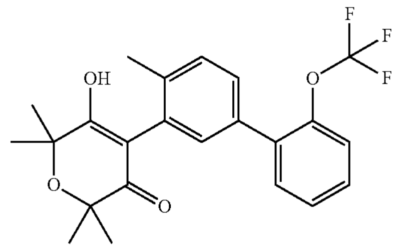 [SMILES: Cc1ccc(-c2ccccc2OC(F)(F)F)cc1C1=C(O)C(C)(C)OC(C)(C)C1=O] |
| A-24 | 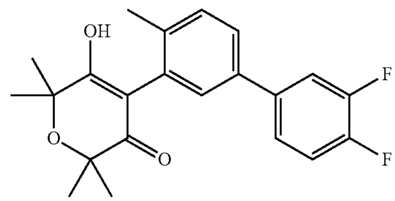 [SMILES: Cc1ccc(-c2ccc(F)c(F)c2)cc1C1=C(O)C(C)(C)OC(C)(C)C1=O] |
| A-25 | 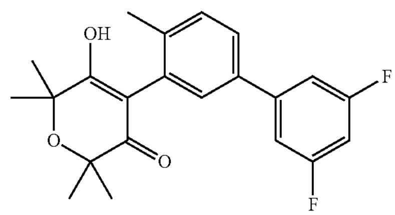 [SMILES: Cc1ccc(-c2cc(F)cc(F)c2)cc1C1=C(O)C(C)(C)OC(C)(C)C1=O] |
| A-27 | 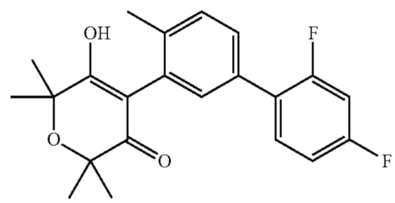 [SMILES: Cc1ccc(-c2ccc(F)cc2F)cc1C1=C(O)C(C)(C)OC(C)(C)C1=O] |
| A-28 | 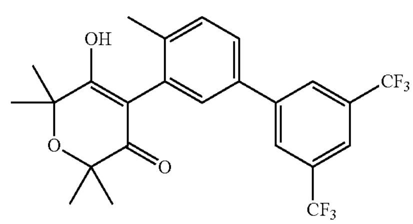 [SMILES: Cc1ccc(-c2cc(C(F)(F)F)cc(C(F)(F)F)c2)cc1C1=C(O)C(C)(C)OC(C)(C)C1=O] |
| A-31 | 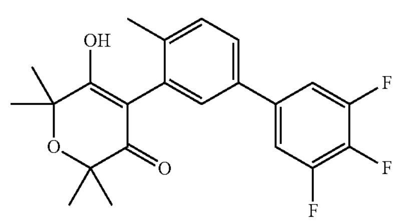 [SMILES: Cc1ccc(-c2cc(F)c(F)c(F)c2)cc1C1=C(O)C(C)(C)OC(C)(C)C1=O] |

| Compound Number | Structure |
|---|---|
| A-35 | 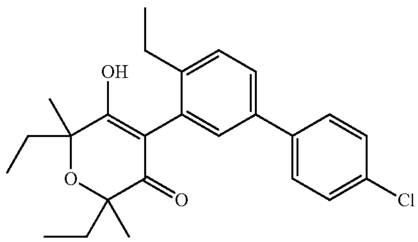 [SMILES: CCc1ccc(-c2ccc(Cl)cc2)cc1C1=C(O)C(C)(CC)OC(C)(CC)C1=O] |
| A-36 | 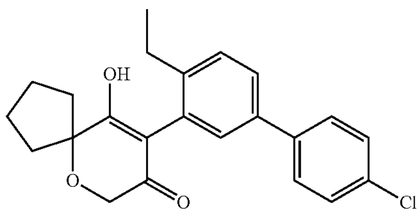 [SMILES: CCc1ccc(-c2ccc(Cl)cc2)cc1C1=C(O)C2(CCCC2)OCC1=O] |
| A-38 | 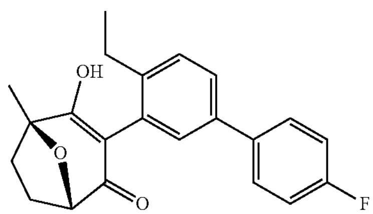 [SMILES: CCc1ccc(-c2ccc(F)cc2)cc1C1=C(O)[C@@]2(C)CC[C@H](O2)C1=O] |
| A-40 | 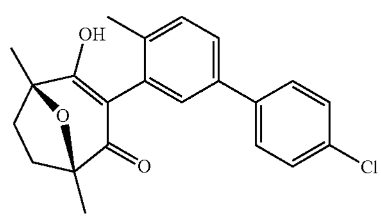 [SMILES: Cc1ccc(-c2ccc(Cl)cc2)cc1C1=C(O)[C@@]2(C)CC[C@](C)(O2)C1=O] |
| A-41 | 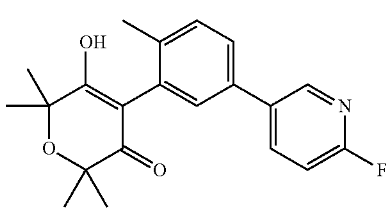 [SMILES: Cc1ccc(-c2ccc(F)nc2)cc1C1=C(O)C(C)(C)OC(C)(C)C1=O] |
| A-42 | 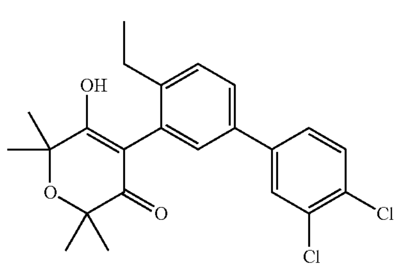 [SMILES: CCc1ccc(-c2ccc(Cl)c(Cl)c2)cc1C1=C(O)C(C)(C)OC(C)(C)C1=O] |

| Compound Number | Structure |
|---|---|
| A-43 | 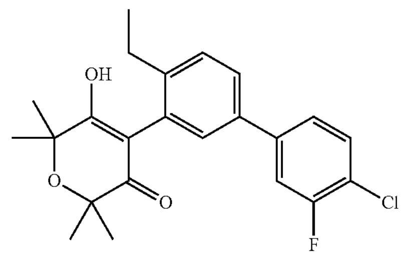 [SMILES: CCc1ccc(-c2ccc(Cl)c(F)c2)cc1C1=C(O)C(C)(C)OC(C)(C)C1=O] |
| A-44 | 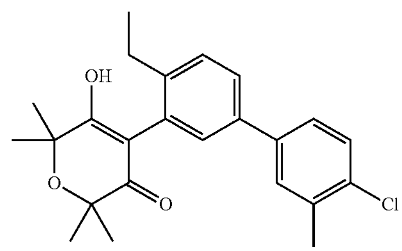 [SMILES: CCc1ccc(-c2ccc(Cl)c(C)c2)cc1C1=C(O)C(C)(C)OC(C)(C)C1=O] |
| A-45 | 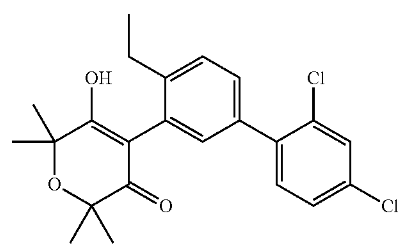 [SMILES: CCc1ccc(-c2ccc(Cl)cc2Cl)cc1C1=C(O)C(C)(C)OC(C)(C)C1=O] |
| A-47 | 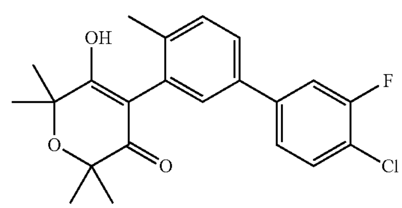 [SMILES: Cc1ccc(-c2ccc(Cl)c(F)c2)cc1C1=C(O)C(C)(C)OC(C)(C)C1=O] |
| A-48 | 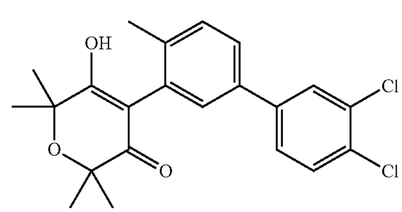 [SMILES: Cc1ccc(-c2ccc(Cl)c(Cl)c2)cc1C1=C(O)C(C)(C)OC(C)(C)C1=O] |
| A-49 | 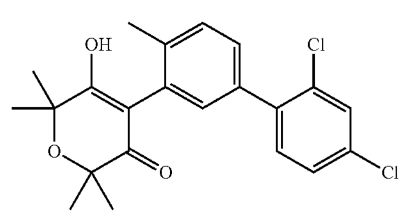 |

| Compound Number | Structure |
|---|---|
| A-50 | 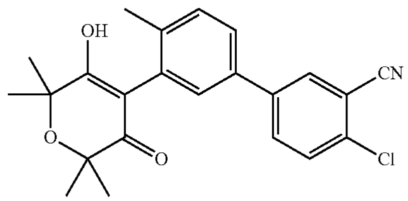 [SMILES: Cc1ccc(-c2ccc(Cl)c(C#N)c2)cc1C1=C(O)C(C)(C)OC(C)(C)C1=O] |
| A-51 | 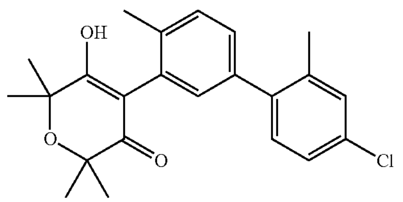 [SMILES: Cc1ccc(-c2ccc(Cl)cc2C)cc1C1=C(O)C(C)(C)OC(C)(C)C1=O] |
| A-52 | 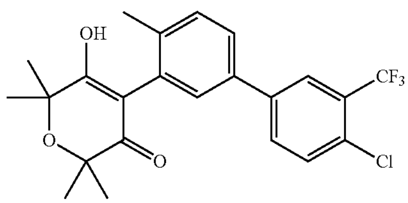 [SMILES: Cc1ccc(-c2ccc(Cl)c(C(F)(F)F)c2)cc1C1=C(O)C(C)(C)OC(C)(C)C1=O] |
| A-53 | 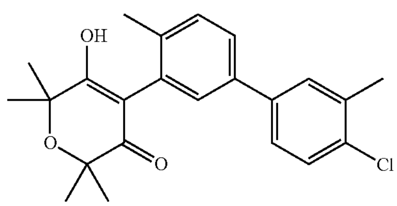 |
| A-54 | 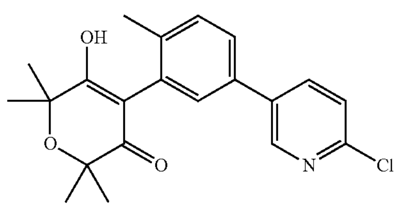 [SMILES: Cc1ccc(-c2ccc(Cl)nc2)cc1C1=C(O)C(C)(C)OC(C)(C)C1=O] |
| A-55 | 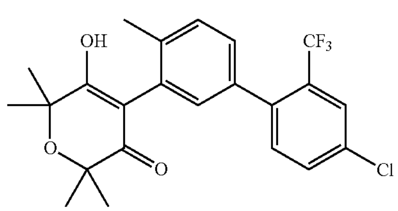 |
| A-56 | 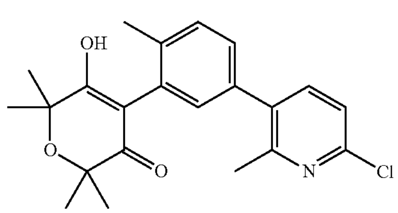 |
| A-57 | |
| A-58 | |
| A-59 | |
| A-60 | |
| A-61 | |
| A-62 | |
| A-63 | |

| Compound Number | Structure |
|---|---|
| A-64 | 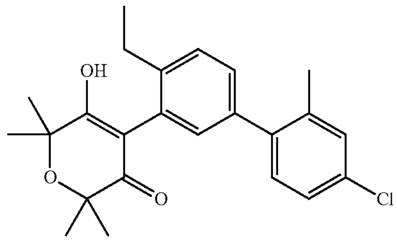 [SMILES: CCc1ccc(-c2ccc(Cl)cc2C)cc1C1=C(O)C(C)(C)OC(C)(C)C1=O] |
| A-65 | 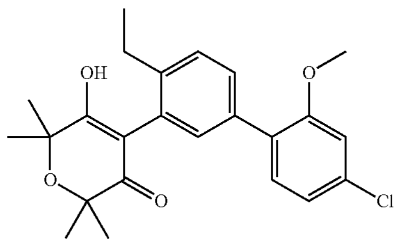 [SMILES: CCc1ccc(-c2ccc(Cl)cc2OC)cc1C1=C(O)C(C)(C)OC(C)(C)C1=O] |
| A-66 | 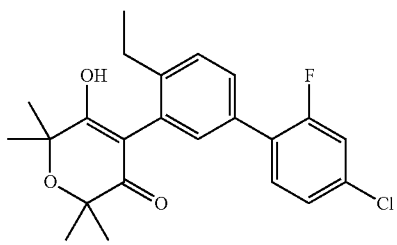 |
| A-67 | 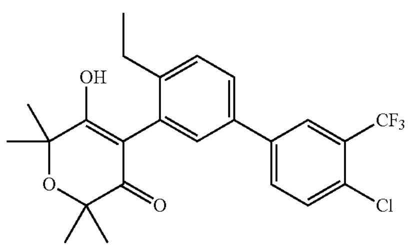 [SMILES: CCc1ccc(-c2ccc(Cl)c(C(F)(F)F)c2)cc1C1=C(O)C(C)(C)OC(C)(C)C1=O] |
| A-69 | 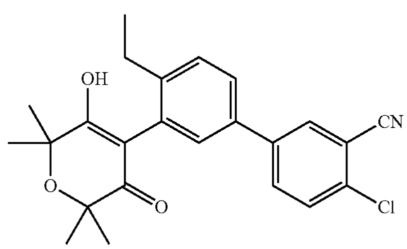 [SMILES: CCc1ccc(-c2ccc(Cl)c(C#N)c2)cc1C1=C(O)C(C)(C)OC(C)(C)C1=O] |
| A-70 | 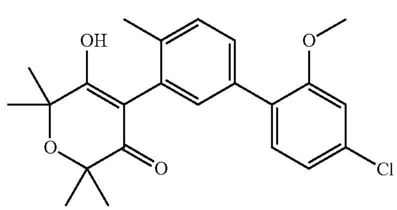 [SMILES: COc1cc(Cl)ccc1-c1ccc(C)c(C2=C(O)C(C)(C)OC(C)(C)C2=O)c1] |

| Compound Number | Structure |
|---|---|
| A-72 | 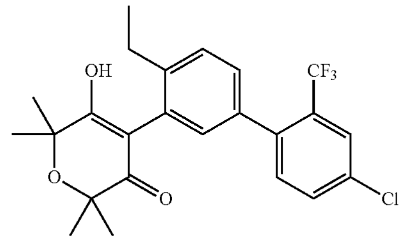 [SMILES: CCc1ccc(-c2ccc(Cl)cc2C(F)(F)F)cc1C1=C(O)C(C)(C)OC(C)(C)C1=O] |
| A-73 | 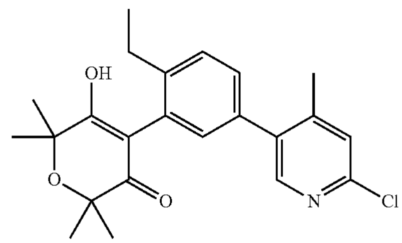 [SMILES: CCc1ccc(-c2cnc(Cl)cc2C)cc1C1=C(O)C(C)(C)OC(C)(C)C1=O] |
| A-74 | 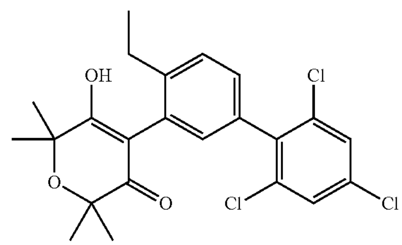 [SMILES: CCc1ccc(-c2c(Cl)cc(Cl)cc2Cl)cc1C1=C(O)C(C)(C)OC(C)(C)C1=O] |
| A-75 | 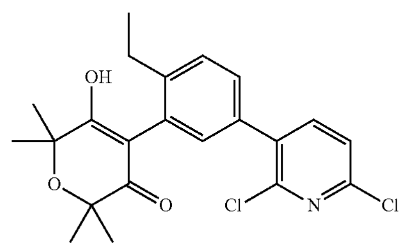 [SMILES: CCc1ccc(-c2ccc(Cl)nc2Cl)cc1C1=C(O)C(C)(C)OC(C)(C)C1=O] |
| A-76 | 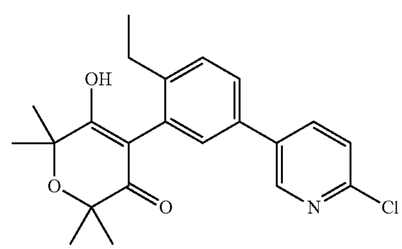 [SMILES: CCc1ccc(-c2ccc(Cl)nc2)cc1C1=C(O)C(C)(C)OC(C)(C)C1=O] |
| A-77 | 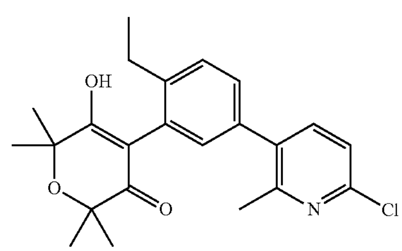 |

| Compound Number | Structure |
|---|---|
| A-79 | 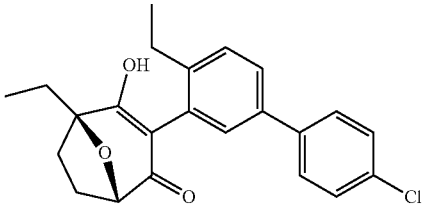 [SMILES: CCc1ccc(-c2ccc(Cl)cc2)cc1C1=C(O)[C@@]2(CC)CC[C@H](O2)C1=O] |
| A-81 | 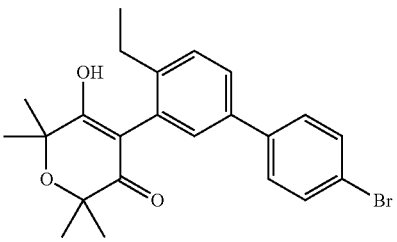 [SMILES: CCc1ccc(-c2ccc(Br)cc2)cc1C1=C(O)C(C)(C)OC(C)(C)C1=O] |
| A-82 | 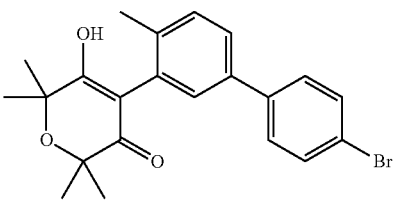 [SMILES: Cc1ccc(-c2ccc(Br)cc2)cc1C1=C(O)C(C)(C)OC(C)(C)C1=O] |
| A-87 | 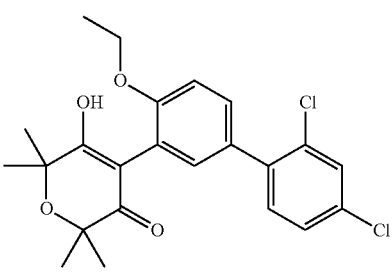 |
| A-88 | 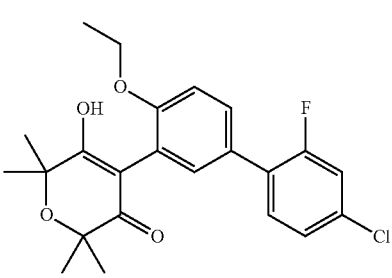 [SMILES: CCOc1ccc(-c2ccc(Cl)cc2Cl)cc1C1=C(O)C(C)(C)OC(C)(C)C1=O] |
| A-89 | 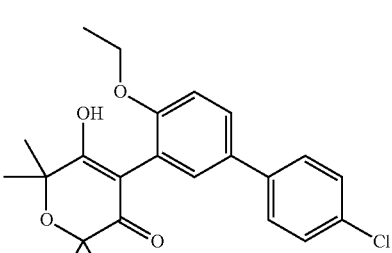 |
| A-90 | 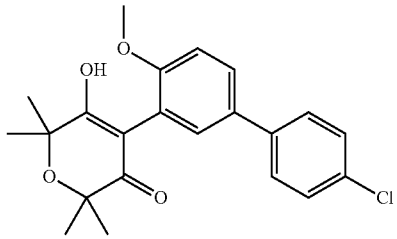 [SMILES: COc1ccc(-c2ccc(Cl)cc2)cc1C1=C(O)C(C)(C)OC(C)(C)C1=O] |
| A-92 | 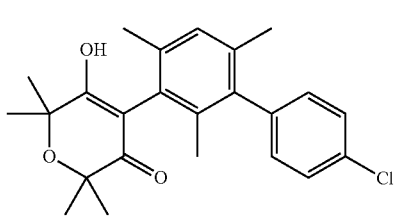 [SMILES: Cc1cc(C)c(-c2ccc(Cl)cc2)c(C)c1C1=C(O)C(C)(C)OC(C)(C)C1=O] |
| A-95 | 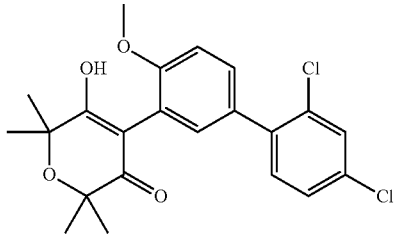 |
| A-96 | 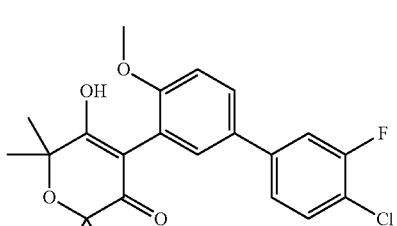 |
| A-97 | 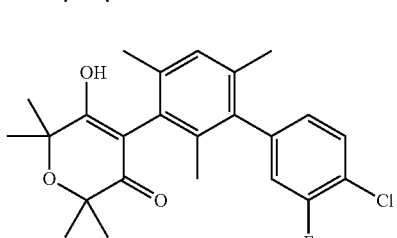 |
| A-98 | 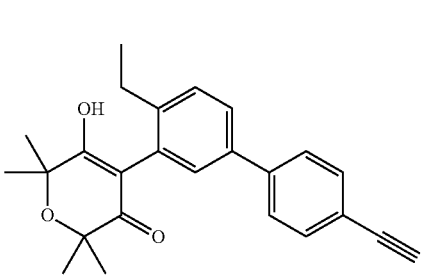 [SMILES: C#Cc1ccc(-c2ccc(CC)c(C3=C(O)C(C)(C)OC(C)(C)C3=O)c2)cc1] |

-continued
| Compound Number | Structure |
|---|---|
| A-99 | 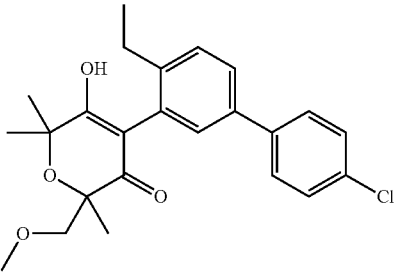 [SMILES: CCc1ccc(-c2ccc(Cl)cc2)cc1C1=C(O)C(C)(C)OC(C)(COC)C1=O] |
| A-100 | 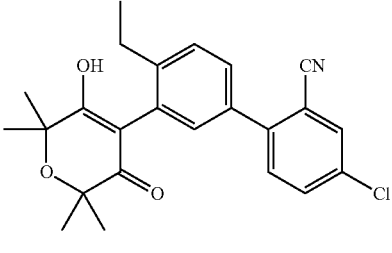 [SMILES: CCc1ccc(-c2ccc(Cl)cc2C#N)cc1C1=C(O)C(C)(C)OC(C)(C)C1=O] |
| A-101 | 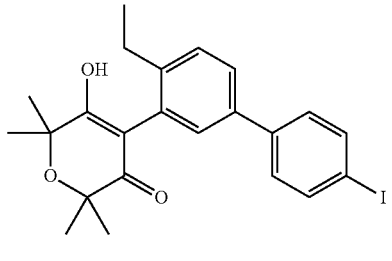 [SMILES: CCc1ccc(-c2ccc(I)cc2)cc1C1=C(O)C(C)(C)OC(C)(C)C1=O] |
| A-102 | 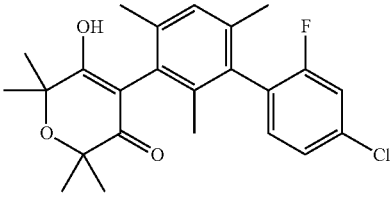 [SMILES: Cc1cc(C)c(-c2ccc(Cl)cc2F)c(C)c1C1=C(O)C(C)(C)OC(C)(C)C1=O] |
| A-103 | 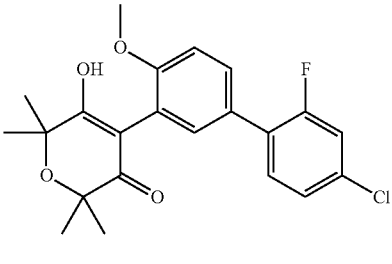 [SMILES: COc1ccc(-c2ccc(Cl)cc2F)cc1C1=C(O)C(C)(C)OC(C)(C)C1=O] |
| A-113 | 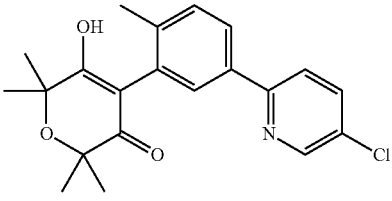 |
| A-114 | 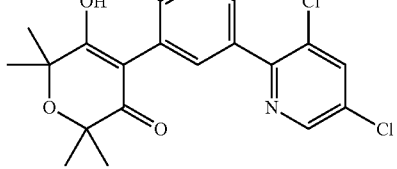 |
| A-115 | 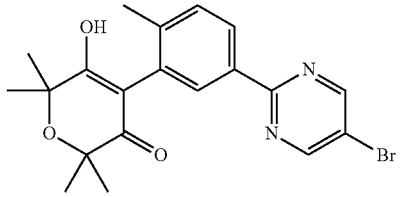 [SMILES: Cc1ccc(-c2ncc(Br)cn2)cc1C1=C(O)C(C)(C)OC(C)(C)C1=O] |
| A-116 | 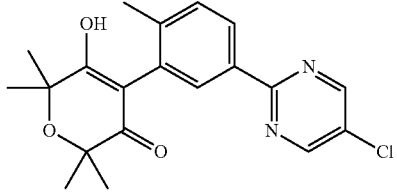 [SMILES: Cc1ccc(-c2ncc(Cl)cn2)cc1C1=C(O)C(C)(C)OC(C)(C)C1=O] |
| A-117 | 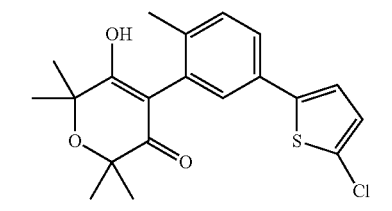 [SMILES: Cc1ccc(-c2ccc(Cl)s2)cc1C1=C(O)C(C)(C)OC(C)(C)C1=O] |
| A-119 | 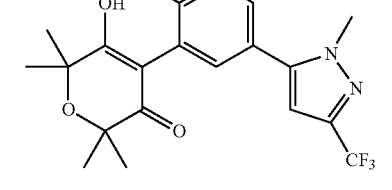 |
| A-131 | 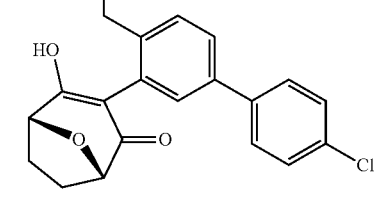 |
| A-132 | 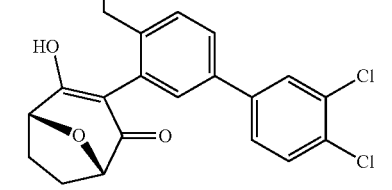 |

| Compound Number | Structure |
|---|---|
| A-135 | 4-[2-ethyl-5-(4-chloro-3-methoxyphenyl)phenyl]-5-hydroxy-2,2,6,6-tetramethyl-2H-pyran-3(6H)-one |
| A-136 | 4-[2-ethyl-5-(4-chloro-3-nitrophenyl)phenyl]-5-hydroxy-2,2,6,6-tetramethyl-2H-pyran-3(6H)-one |
| A-137 | 4-[2-ethyl-5-(2,3,4-trichlorophenyl)phenyl]-5-hydroxy-2,2,6,6-tetramethyl-2H-pyran-3(6H)-one |
| A-138 | 4-[2-ethyl-5-(2-chloro-3-fluoro-4-chlorophenyl)phenyl]-5-hydroxy-2,2,6,6-tetramethyl-2H-pyran-3(6H)-one |
| A-139 | 4-[2-ethyl-5-(3,4,5-trichlorophenyl)phenyl]-5-hydroxy-2,2,6,6-tetramethyl-2H-pyran-3(6H)-one |
| A-141 | 4-[2-chloro-5-(2-fluoro-4-chlorophenyl)phenyl]-5-hydroxy-2,2,6,6-tetramethyl-2H-pyran-3(6H)-one |
| A-142 | 4-[2-chloro-5-(4-chlorophenyl)phenyl]-5-hydroxy-2,2,6,6-tetramethyl-2H-pyran-3(6H)-one |
| A-144 | 4-[2-ethyl-5-(2,4,5-trichlorophenyl)phenyl]-5-hydroxy-2,2,6,6-tetramethyl-2H-pyran-3(6H)-one |
| A-147 | 4-[2-ethyl-5-(4-difluoromethylphenyl)phenyl]-5-hydroxy-2,2,6,6-tetramethyl-2H-pyran-3(6H)-one |
| A-149 | 4-[2-bromo-5-(4-chlorophenyl)phenyl]-5-hydroxy-2,2,6,6-tetramethyl-2H-pyran-3(6H)-one |
| A-150 | 4-[2-ethyl-5-(5-chloropyridin-2-yl)phenyl]-5-hydroxy-2,2,6,6-tetramethyl-2H-pyran-3(6H)-one |
| A-151 | 4-[2-ethyl-5-(4-difluoromethoxyphenyl)phenyl]-5-hydroxy-2,2,6,6-tetramethyl-2H-pyran-3(6H)-one |

| Compound Number | Structure |
|---|---|
| A-152 | 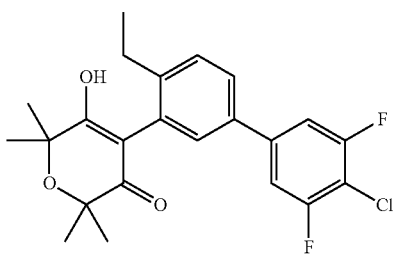 [SMILES: CCc1ccc(-c2cc(F)c(Cl)c(F)c2)cc1C1=C(O)C(C)(C)OC(C)(C)C1=O] |
| A-153 | 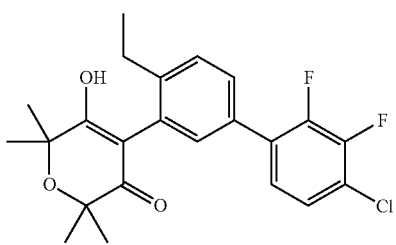 |
| A-154 | 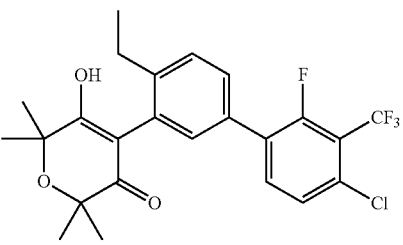 [SMILES: CCc1ccc(-c2ccc(Cl)c(C(F)(F)F)c2F)cc1C1=C(O)C(C)(C)OC(C)(C)C1=O] |
| A-155 | 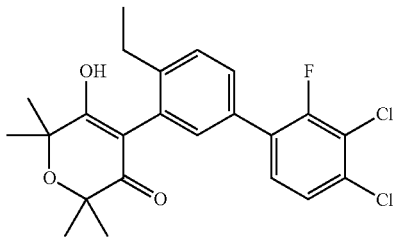 [SMILES: CCc1ccc(-c2ccc(Cl)c(Cl)c2F)cc1C1=C(O)C(C)(C)OC(C)(C)C1=O] |
| A-156 | 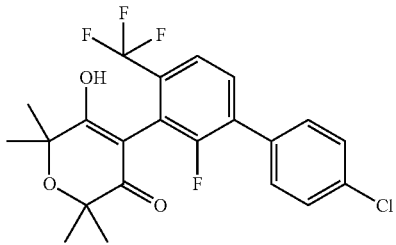 [SMILES: CC1(C)OC(C)(C)C(O)=C(c2c(C(F)(F)F)ccc(-c3ccc(Cl)cc3)c2F)C1=O] |
| A-157 | 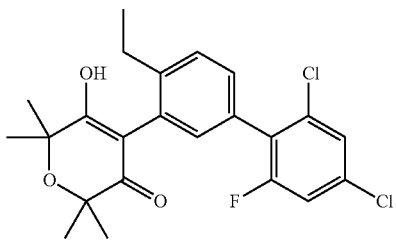 |
| A-158 | 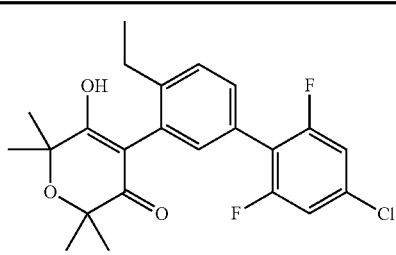 |
| A-159 | 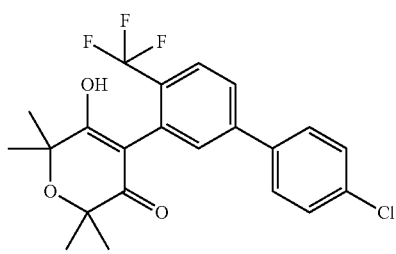 [SMILES: CC1(C)OC(C)(C)C(O)=C(c2cc(-c3ccc(Cl)cc3)ccc2C(F)(F)F)C1=O] |
| A-160 | 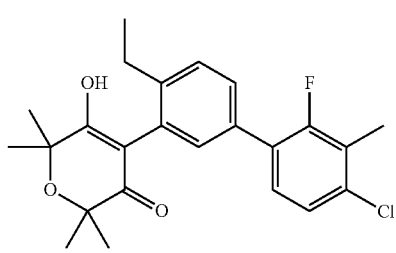 [SMILES: CCc1ccc(-c2ccc(Cl)c(C)c2F)cc1C1=C(O)C(C)(C)OC(C)(C)C1=O] |
| A-165 | 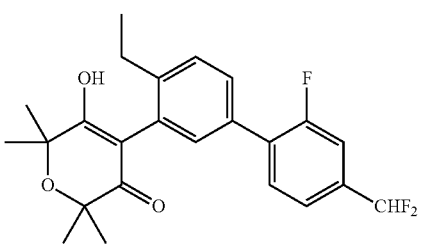 [SMILES: CCc1ccc(-c2ccc(C(F)F)cc2F)cc1C1=C(O)C(C)(C)OC(C)(C)C1=O] |
| A-166 | 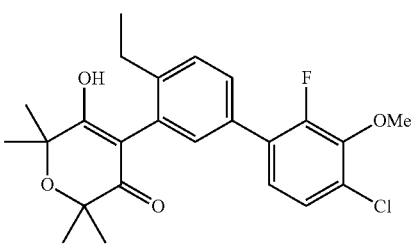 [SMILES: CCc1ccc(-c2ccc(Cl)c(OC)c2F)cc1C1=C(O)C(C)(C)OC(C)(C)C1=O] |
| A-167 | 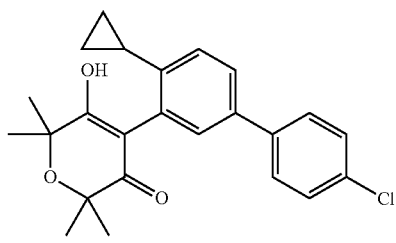 [SMILES: CC1(C)OC(C)(C)C(O)=C(c2cc(-c3ccc(Cl)cc3)ccc2C2CC2)C1=O] |

| Compound Number | Structure |
|---|---|
| A-168 | 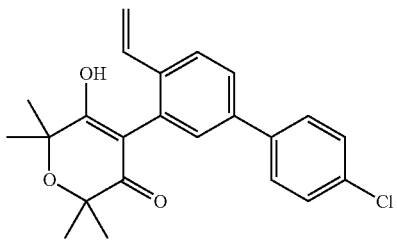 [SMILES: C=Cc1ccc(-c2ccc(Cl)cc2)cc1C1=C(O)C(C)(C)OC(C)(C)C1=O] |
| D-1 | 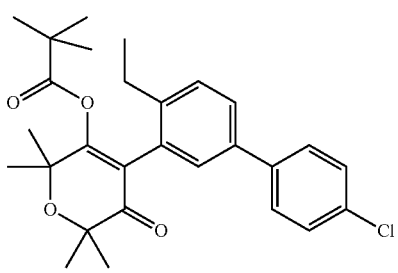 [SMILES: CCc1ccc(-c2ccc(Cl)cc2)cc1C1=C(OC(=O)C(C)(C)C)C(C)(C)OC(C)(C)C1=O] |
| D-2 | 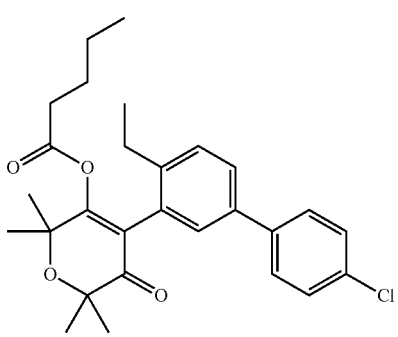 [SMILES: CCCCC(=O)OC1=C(c2cc(-c3ccc(Cl)cc3)ccc2CC)C(=O)C(C)(C)OC1(C)C] |
| D-3 | 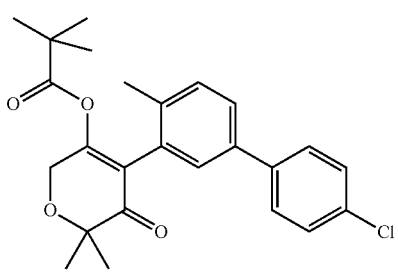 [SMILES: Cc1ccc(-c2ccc(Cl)cc2)cc1C1=C(OC(=O)C(C)(C)C)COC(C)(C)C1=O] |
| D-4 | 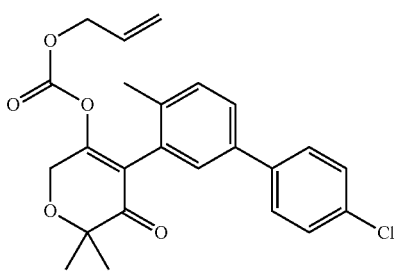 [SMILES: C=CCOC(=O)OC1=C(c2cc(-c3ccc(Cl)cc3)ccc2C)C(=O)C(C)(C)OC1] |
| Compound Number | Structure |
|---|---|
| D-5 | 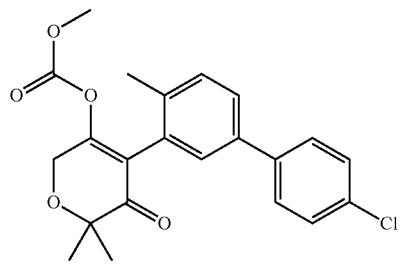 [SMILES: COC(=O)OC1=C(c2cc(-c3ccc(Cl)cc3)ccc2C)C(=O)C(C)(C)OC1] |
| D-6 | 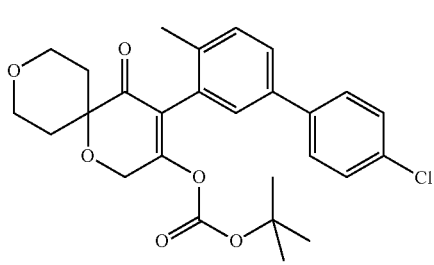 [SMILES: Cc1ccc(-c2ccc(Cl)cc2)cc1C1=C(OC(=O)OC(C)(C)C)COC2(CCOCC2)C1=O] |
| D-7 | 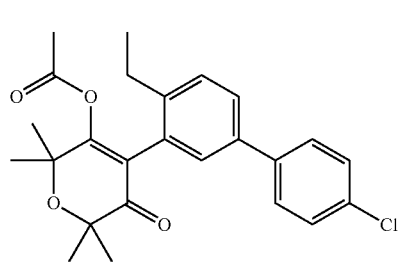 [SMILES: CCc1ccc(-c2ccc(Cl)cc2)cc1C1=C(OC(C)=O)C(C)(C)OC(C)(C)C1=O] |
| D-8 | 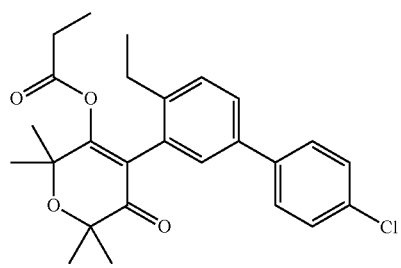 [SMILES: CCC(=O)OC1=C(c2cc(-c3ccc(Cl)cc3)ccc2CC)C(=O)C(C)(C)OC1(C)C] |
| D-9 | 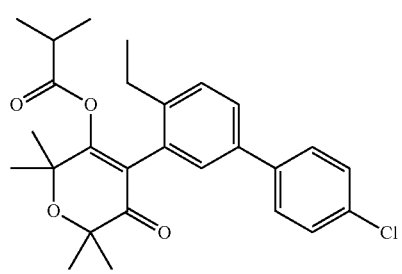 [SMILES: CCc1ccc(-c2ccc(Cl)cc2)cc1C1=C(OC(=O)C(C)C)C(C)(C)OC(C)(C)C1=O] |

-continued
| Compound Number | Structure |
|---|---|
| D-10 | 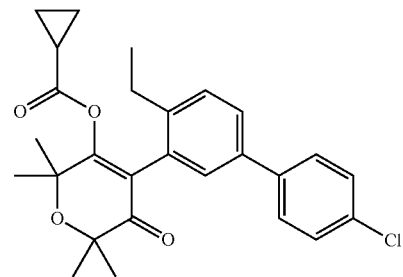 [SMILES: CCc1ccc(-c2ccc(Cl)cc2)cc1C1=C(OC(=O)C2CC2)C(C)(C)OC(C)(C)C1=O] |
| D-11 | 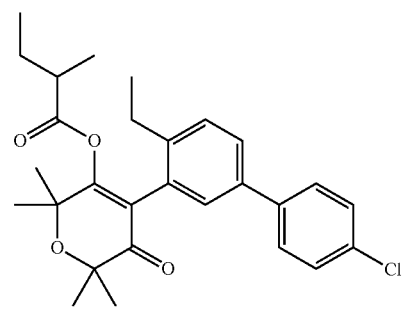 |
| D-12 | 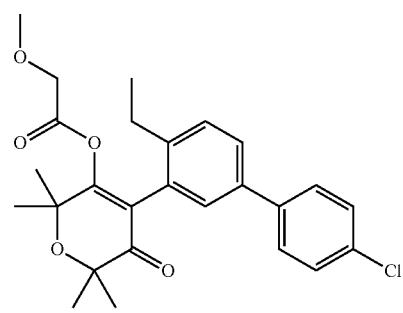 [SMILES: CCc1ccc(-c2ccc(Cl)cc2)cc1C1=C(OC(=O)COC)C(C)(C)OC(C)(C)C1=O] |
| D-13 | 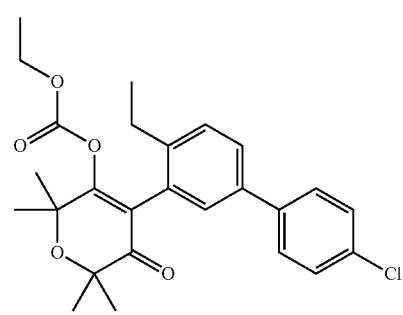 |
| D-14 | 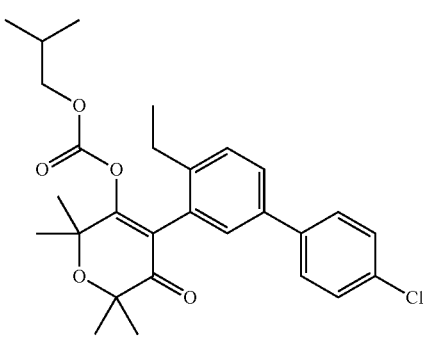 [SMILES: CCc1ccc(-c2ccc(Cl)cc2)cc1C1=C(OC(=O)OCC(C)C)C(C)(C)OC(C)(C)C1=O] |
-continued
| Compound Number | Structure |
|---|---|
| D-15 | 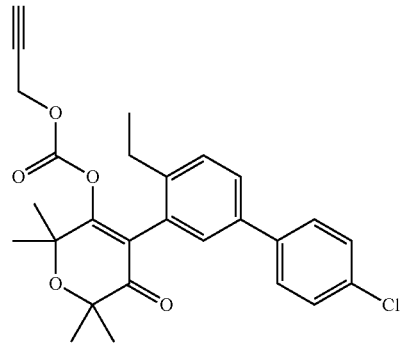 [SMILES: C#CCOC(=O)OC1=C(c2cc(-c3ccc(Cl)cc3)ccc2CC)C(=O)C(C)(C)OC1(C)C] |
| D-16 | 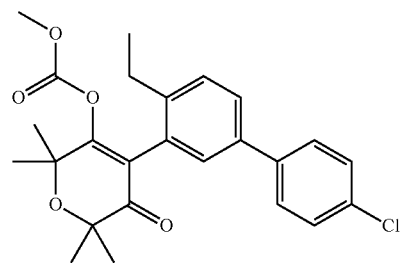 [SMILES: CCc1ccc(-c2ccc(Cl)cc2)cc1C1=C(OC(=O)OC)C(C)(C)OC(C)(C)C1=O] |
| D-17 | 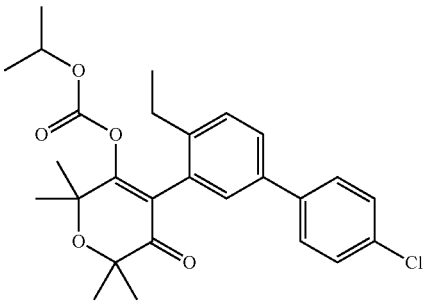 [SMILES: CCc1ccc(-c2ccc(Cl)cc2)cc1C1=C(OC(=O)OC(C)C)C(C)(C)OC(C)(C)C1=O] |
| D-19 | 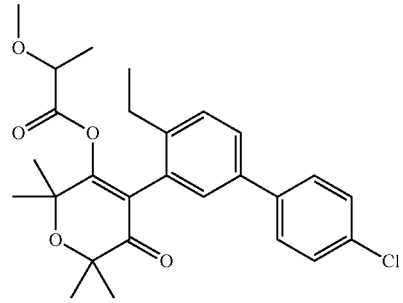 [SMILES: CCc1ccc(-c2ccc(Cl)cc2)cc1C1=C(OC(=O)C(C)OC)C(C)(C)OC(C)(C)C1=O] |
| D-20 | 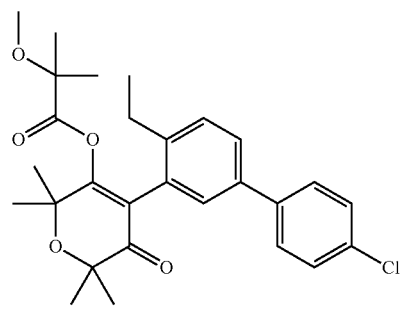 [SMILES: CCc1ccc(-c2ccc(Cl)cc2)cc1C1=C(OC(=O)C(C)(C)OC)C(C)(C)OC(C)(C)C1=O] |

| Compound Number | Structure |
|---|---|
| D-21 | |
| D-22 | |
| D-23 | |
| D-24 | |
| D-25 | |
| D-26 | 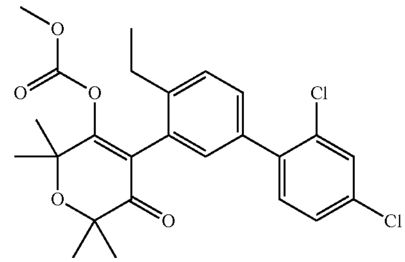 [SMILES: CCc1ccc(-c2ccc(Cl)cc2Cl)cc1C1=C(OC(=O)OC)C(C)(C)OC(C)(C)C1=O] |
| D-28 | 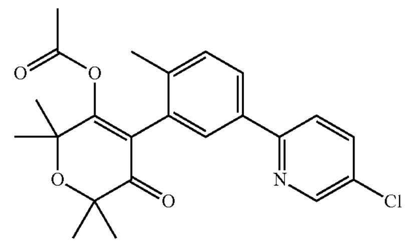 [SMILES: CC(=O)OC1=C(c2cc(-c3ccc(Cl)cn3)ccc2C)C(=O)C(C)(C)OC1(C)C] |
| D-31 | 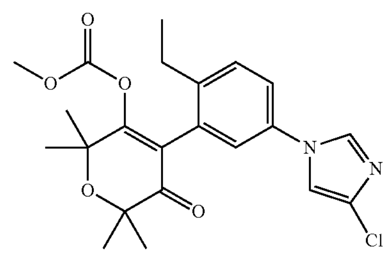 [SMILES: CCc1ccc(-n2cnc(Cl)c2)cc1C1=C(OC(=O)OC)C(C)(C)OC(C)(C)C1=O] |
| D-32 | 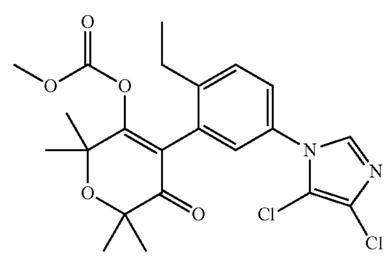 [SMILES: CCc1ccc(-n2cnc(Cl)c2Cl)cc1C1=C(OC(=O)OC)C(C)(C)OC(C)(C)C1=O] |
| D-33 | 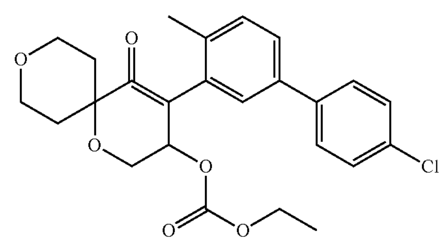 |
| D-36 | 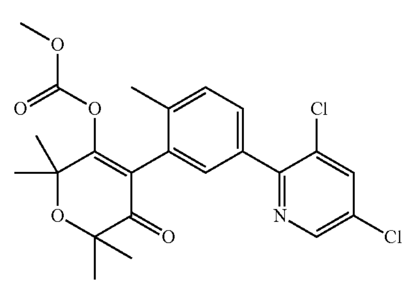 [SMILES: COC(=O)OC1=C(c2cc(-c3ncc(Cl)cc3Cl)ccc2C)C(=O)C(C)(C)OC1(C)C] |

-continued

| Compound Number | Structure |
|---|---|
| D-37 | 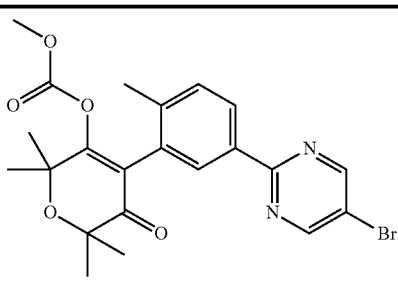 |
| D-38 | 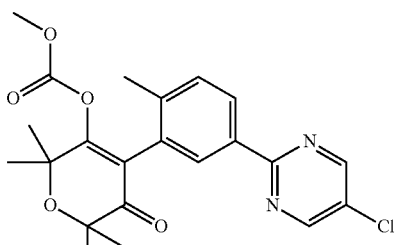 |
| D-39 | 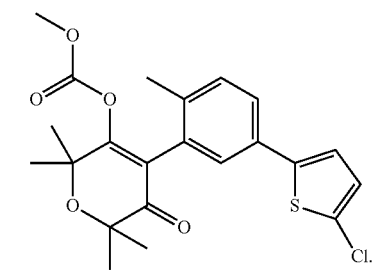 [SMILES: COC(=O)OC1=C(c2cc(-c3ccc(Cl)s3)ccc2C)C(=O)C(C)(C)OC1(C)C] |

30. A compound according to claim 1, which is compound number A-4, whose structure is:

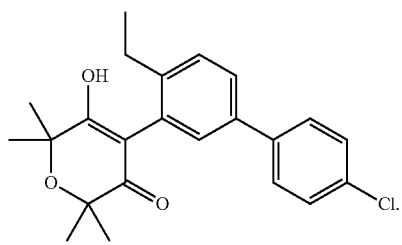 [SMILES: CCc1ccc(-c2ccc(Cl)cc2)cc1C1=C(O)C(C)(C)OC(C)(C)C1=O]

31. A compound according to claim 1, which is compound number A-45, whose structure is:

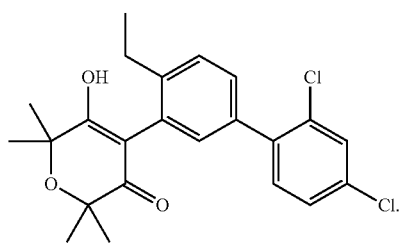 [SMILES: CCc1ccc(-c2ccc(Cl)cc2Cl)cc1C1=C(O)C(C)(C)OC(C)(C)C1=O]

32. A compound according to claim 1, which is compound number A-66, whose structure is:

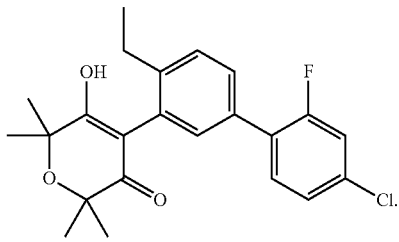 [SMILES: CCc1ccc(-c2ccc(Cl)cc2F)cc1C1=C(O)C(C)(C)OC(C)(C)C1=O]

33. A compound according to claim 1, which is compound number A-167, whose structure is:

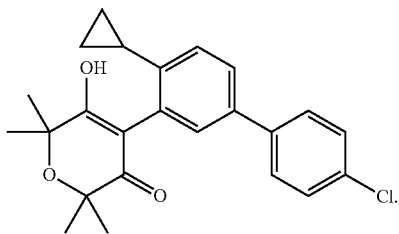 [SMILES: CC1(C)OC(C)(C)C(O)=C(c2cc(-c3ccc(Cl)cc3)ccc2C2CC2)C1=O]

34. A compound according to claim 1, which is compound number D-7, whose structure is:

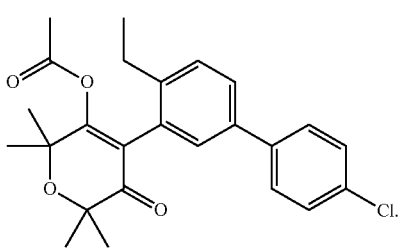 [SMILES: CCc1ccc(-c2ccc(Cl)cc2)cc1C1=C(OC(C)=O)C(C)(C)OC(C)(C)C1=O]

35. A compound according to claim 1, which is compound number D-16, whose structure is:

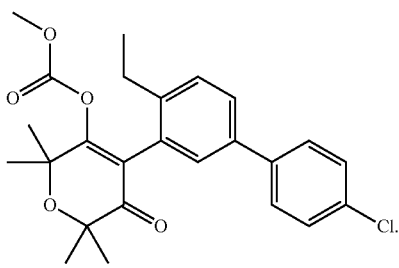 [SMILES: CCc1ccc(-c2ccc(Cl)cc2)cc1C1=C(OC(=O)OC)C(C)(C)OC(C)(C)C1=O]

36. A compound according to claim 1, which is compound number D-23, whose structure is:

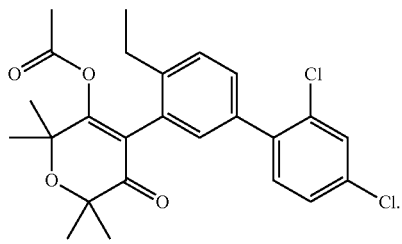 [SMILES: CCc1ccc(-c2ccc(Cl)cc2Cl)cc1C1=C(OC(C)=O)C(C)(C)OC(C)(C)C1=O]

37. A compound according to claim 1, which is compound number D-26, whose structure is:

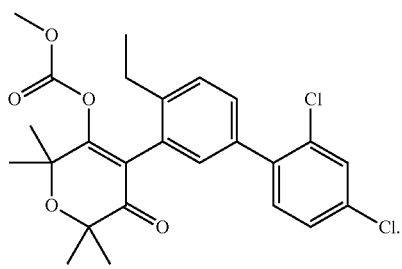 [SMILES: CCc1ccc(-c2ccc(Cl)cc2Cl)cc1C1=C(OC(=O)OC)C(C)(C)OC(C)(C)C1=O]

38. A mixture comprising a compound of formula (I), as defined in claim 1, in combination with another herbicide, wherein the mixture is selected from one of the following mixtures of the compound of formula (I):

a compound of formula I+acetochlor, a compound of formula I+acifluorfen, a compound of formula I+acifluorfen-sodium, a compound of formula I+aclonifen, a compound of formula I+acrolein, a compound of formula I+alachlor, a compound of formula I+alloxydim, a compound of formula I+allyl alcohol, a compound of formula I+ametryn, a compound of formula I+amicarbazone, a compound of formula I+amidosulfuron, a compound of formula I+aminopyralid, a compound of formula I+amitrole, a compound of formula I+ammonium sulfamate, a compound of formula I+anilofos, a compound of formula I+asulam, a compound of formula I+atrazine, formula I+aviglycine, formula I+azafenidin, a compound of formula I+azimsulfuron, a compound of formula I+beflubutamid, a compound of formula I+benazolin, formula I+bencarbazone, a compound of formula I+benfluralin, a compound of formula I+benfuresate, a compound of formula I+bensulfuron, a compound of formula I+bensulfuron-methyl, a compound of formula I+bensulide, a compound of formula I+bentazone, a compound of formula I+benzfendizone, a compound of formula I+benzobicyclon, a compound of formula I+benzofenap, a compound of formula I+bifenox, a compound of formula I+bilanafos, a compound of formula I+bispyribac, a compound of formula I+bispyribac-sodium, a compound of formula I+borax, a compound of formula I+bromacil, a compound of formula I+bromobutide, formula I+bromophenoxim, a compound of formula I+bromoxynil, a compound of formula I+butachlor, a compound of formula I+butafenacil, a compound of formula I+butamifos, a compound of formula I+butralin, a compound of formula I+butroxydim, a compound of formula I+butylate, a compound of formula I+cacodylic acid, a compound of formula I+calcium chlorate, a compound of formula I+cafenstrole, a compound of formula I+carbetamide, a compound of formula I+carfentrazone, a compound of formula I+carfentrazone-ethyl, a compound of formula I+chlorflurenol, a compound of formula I+chlorflurenol-methyl, a compound of formula I+chloridazon, a compound of formula I+chlorimuron, a compound of formula I+chlorimuron-ethyl, a compound of formula I+chloroacetic acid, a compound of formula I+chlorotoluron, a compound of formula I+chlorpropham, a compound of formula I+chlorsulfuron, a compound of formula I+chlorthal, a compound of formula I+chlorthal-dimethyl, a compound of formula I+cinidon-ethyl, a compound of formula I+cinmethylin, a compound of formula I+cinosulfuron, a compound of formula I+cisanilide, a compound of formula I+clethodim, a compound of formula I+clodinafop, a compound of formula I+clodinafop-propargyl, a compound of formula I+clomazone, a compound of formula I+clomeprop, a compound of formula I+clopyralid, a compound of formula I+cloransulam, a compound of formula I+cloransulam-methyl, a compound of formula I+cresol, a compound of formula I+cumyluron, a compound of formula I+cyanamide, a compound of formula I+cyanazine, a compound of formula I+cycloate, a compound of formula I+cyclosulfamuron, a compound of formula I+cycloxydim, a compound of formula I+cyhalofop, a compound of formula I+cyhalofop-butyl, a compound of formula I+daimuron, a compound of formula I+dalapon, a compound of formula I+dazomet, a compound of formula I+desmedipham, formula I+desmetryn, a compound of formula I+dicamba, a compound of formula I+dichlobenil, a compound of formula I+ortho-dichlorobenzene, a compound of formula I+para-dichlorobenzene, a compound of formula I+dichlorprop, a compound of formula I+dichlorprop-P, a compound of formula I+diclofop, a compound of formula I+diclofop-methyl, a compound of formula I+diclosulam, a compound of formula I+difenzoquat, a compound of formula I+difenzoquat metilsulfate, a compound of formula I+diflufenican, a compound of formula I+diflufenzopyr, a compound of formula I+dimefuron, a compound of formula I+dimepiperate, a compound of formula I+dimethachlor, a compound of formula I+dimethametryn, a compound of formula I+dimethenamid, a compound of formula I+dimethenamid-P, a compound of formula I+dimethipin, a compound of formula I+dimethylarsinic acid, a compound of formula I+dinitramine, a compound of formula I+dinoterb, a compound of formula I+diphenamid, formula I+dipropetryn, a compound of formula I+diquat, a compound of formula I+diquat dibromide, a compound of formula I+dithiopyr, a compound of formula I+diuron, a compound of formula I+endothal, a compound of formula I+esprocarb, a compound of formula I+ethalfluralin, a compound of formula I+ethametsulfuron, a compound of formula I+ethametsulfuron-methyl, formula I+ethephon, a compound of formula I+ethofumesate, a compound of formula I+ethoxyfen, a compound of formula I+ethoxysulfuron, a compound of formula I+etobenzanid, a compound of formula I+fenoxaprop-P, a compound of formula I+fenoxaprop-P-ethyl, a compound of formula I+fentrazamide, a compound of formula I+ferrous sulfate, a compound of formula I+flamprop-M, a compound of formula I+flazasulfuron, a compound of formula I+florasulam, a compound of formula I+fluazifop, a compound of formula I+fluazifop-butyl, a compound of formula I+fluazifop-P, a compound of formula I+fluazifop-P-butyl, formula I+fluazolate, a compound of formula I+flucarbazone, a compound of formula I+flucarbazone-sodium, a compound of formula I+flucetosulfuron, a compound of formula I+fluchloralin, a compound of formula I+flufenacet, a compound of formula I+flufenpyr, a compound of formula I+flufenpyr-ethyl, formula I+flumetralin, a compound of formula I+flumetsulam, a compound of formula I+flumiclorac, a compound of formula I+flumiclorac-pentyl, a compound of formula I+flumioxazin, formula I+flumipropin, a compound of formula I+fluometuron, a compound of formula I+fluoroglycofen, a compound of formula I+fluoroglycofen-ethyl, formula I+fluoxaprop, formula I+flupoxam, formula I+flupropacil, a compound of formula I+flupropanate, a compound of formula I+flupyrsulfuron, a compound of formula I+flupyrsulfuron-methyl-sodium, a compound of formula I+flurenol, a compound of formula I+fluridone, a compound of formula I+fluorochloridone, a compound of formula I+fluoroxypyr, a compound of formula I+flurtamone, a compound of formula I+fluthiacet, a compound of formula I+fluthiacet-methyl, a compound of formula I+fomesafen, a compound of formula I+foramsulfuron, a compound of formula I+fosamine, a compound of formula I+glufosinate, a compound of formula I+glufosinate-ammonium, a compound of formula I+glyphosate, a compound of formula I+halosulfuron, a compound of formula I+halosulfuron-methyl, a compound of formula I+haloxyfop, a compound of formula I+haloxyfop-P, a compound of formula I+hexazinone, a compound of formula I+imazamethabenz, a compound of formula I+imazamethabenz-methyl, a compound of formula I+imazamox, a compound of formula I+imazapic, a compound of formula I+imazapyr, a compound of formula I+imazaquin, a compound of formula I+imazethapyr, a compound of formula I+imazosulfuron, a compound of formula I+indanofan, a compound of formula I+iodomethane, a compound of formula I+iodosulfuron, a compound of formula I+iodosulfuron-methyl-sodium, a compound of formula I+ioxynil, a compound of formula I+isoproturon, a compound of formula I+isouron, a compound of formula I+isoxaben, a compound of formula I+isoxachlortole, a compound of formula I+isoxaflutole, formula I+isoxapyrifop, a compound of formula I+karbutilate, a compound of formula I+lactofen, a compound of formula I+lenacil, a compound of formula I+linuron, a compound of formula I+mecoprop, a compound of formula I+mecoprop-P, a compound of formula I+mefenacet, a compound of formula I+mefluidide, a compound of formula I+mesosulfuron, a compound of formula I+mesosulfuron-methyl, a compound of formula I+mesotrione, a compound of formula I+metam, a compound of formula I+metamifop, a compound of formula I+metamitron, a compound of formula I+metazachlor, a compound of formula I+methabenzthiazuron, formula I+methazole, a compound of formula I+methylarsonic acid, a compound of formula I+methyldymron, a compound of formula I+methyl isothiocyanate, a compound of formula I+metobenzuron, formula I+metobromuron, a compound of formula I+metolachlor, a compound of formula I+S-metolachlor, a compound of formula I+metosulam, a compound of formula I+metoxuron, a compound of formula I+metribuzin, a compound of formula I+metsulfuron, a compound of formula I+metsulfuron-methyl, a compound of formula I+molinate, a compound of formula I+monolinuron, a compound of formula I+naproanilide, a compound of formula I+napropamide, a compound of formula I+naptalam, a compound of formula I+neburon, a compound of formula I+nicosulfuron, formula I+nipyraclofen, formula I+n-methyl glyphosate, a compound of formula I+nonanoic acid, a compound of formula I+norflurazon, a compound of formula I+oleic acid (fatty acids), a compound of formula I+orbencarb, a compound of formula I+orthosulfamuron, a compound of formula I+oryzalin, a compound of formula I+oxadiargyl, a compound of formula I+oxadiazon, a compound of formula I+oxasulfuron, a compound of formula I+oxaziclomefone, a compound of formula I+oxyfluorfen, a compound of formula I+paraquat, a compound of formula I+paraquat dichloride, a compound of formula I+pebulate, a compound of formula I+pendimethalin, a compound of formula I+penoxsulam, a compound of formula I+pentachlorophenol, a compound of formula I+pentanochlor, a compound of formula I+pentoxazone, a compound of formula I+pethoxamid, a compound of formula I+petrolium oils, a compound of formula I+phenmedipham, a compound of formula I+phenmedipham-ethyl, a compound of formula I+picloram, a compound of formula I+picolinafen, a compound of formula I+pinoxaden, a compound of formula I+piperophos, a compound of formula I+potassium arsenite, a compound of formula I+potassium azide, a compound of formula I+pretilachlor, a compound of formula I+primisulfuron, a compound of formula I+primisulfuron-methyl, a compound of formula I+prodiamine, a compound of formula I+profluazol, a compound of formula I+profoxydim, formula I+prohexadione-calcium, a compound of formula I+prometon, a compound of formula I+prometryn, a compound of formula I+propachlor, a compound of formula I+propanil, a compound of formula I+propaquizafop, a compound of formula I+propazine, a compound of formula I+propham, a compound of formula I+propisochlor, a compound of formula I+propoxycarbazone, a compound of formula I+propoxycarbazone-sodium, a compound of formula I+propyzamide, a compound of formula I+prosulfocarb, a compound of formula I+prosulfuron, a compound of formula I+pyraclonil, a compound of formula I+pyraflufen, a compound of formula I+pyraflufen-ethyl, formula I+pyrasulfotole, a compound of formula I+pyrazolynate, a compound of formula I+pyrazosulfuron, a compound of formula I+pyrazosulfuron-ethyl, a compound of formula I+pyrazoxyfen, a compound of formula I+pyribenzoxim, a compound of formula I+pyributicarb, a compound of formula I+pyridafol, a compound of formula I+pyridate, a compound of formula I+pyriftalid, a compound of formula I+pyriminobac, a compound of formula I+pyriminobac-methyl, a compound of formula I+pyrimisulfan, a compound of formula I+pyrithiobac, a compound of formula I+pyrithiobac-sodium, formula I+pyroxasulfone (KIN-485), formula I+pyroxulam, a compound of formula I+quinclorac, a compound of formula I+quinmerac, a compound of formula I+quinoclamine, a compound of formula I+quizalofop, a compound of formula I+quizalofop-P, a compound of formula I+rimsulfuron, a compound of formula I+sethoxydim, a compound of formula I+siduron, a compound of formula I+simazine, a compound of formula I+simetryn, a compound of formula I+sodium arsenite, a compound of formula I+sodium azide, a compound of formula I+sodium chlorate, a compound of formula I+sulcotrione, a compound of formula I+sulfentrazone, a compound of formula I+sulfometuron, a compound of formula I+sulfometuron-methyl, a compound of formula I+sulfosate, a compound of formula I+sulfosulfuron, a compound of formula I+sulfuric acid, a compound of formula I+tar oils, a compound of formula I+tebutam, a compound of formula I+tebuthiuron, a compound of formula I+tefuryltrione, a compound of formula I+tembotrione, a compound of formula I+tepraloxydim, a compound of formula I+terbacil, a compound of formula I+terbumeton, a compound of formula I+terbuthylazine, a compound of formula I+terbutryn, a compound of formula I+thenylchlor, a compound of formula I+thiazafluoron, a compound of formula I+thiazopyr, a compound of formula I+thifensulfuron, a compound of formula I+thiencarbazone, a compound of formula I+thifensulfuron-methyl, a compound of formula I+thiobencarb, a compound of formula I+tiocarbazil, a compound of formula I+topramezone, a compound of formula I+tralkoxydim, a compound of formula I+tri-allate, a compound of formula I+triasulfuron, a compound of formula I+triaziflam, a compound of formula I+tribenuron, a compound of formula I+tribenuron-methyl, a compound of formula I+tricamba, a compound of formula I+triclopyr, a compound of formula I+trietazine, a compound of formula I+trifloxysulfuron, a compound of formula I+trifloxysulfuron-sodium, a compound of formula I+trifluralin, a compound of formula I+triflusulfuron, a compound of formula I+triflusulfuron-methyl, a compound of formula I+trihydroxytriazine, a compound of formula I+trinexapac-ethyl, a compound of formula I+tritosulfuron, a compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester, a compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one, a compound of formula 1+2-chloro-5-[3,6-dihydro-3-methyl-2,6-dioxo-4-(trifluoromethyl)-1(2H)-pyrimidinyl]-4-fluoro-N-[[methyl(1-methylethyl)amino]sulfonyl]benzamide, and a compound of formula I+4-hydroxy-3-[[2-(3-methoxypropyl)-6-(difluoromethyl)-3-pyridinyl]carbonyl]bicyclo[3.2.1]oct-3-en-2-one;

and wherein the mixing partner for the compound of formula (I) is optionally in the form of a salt thereof.

39. A method of controlling grasses and weeds in crops of useful plants according to claim 20, which comprises applying a herbicidally effective amount of a compound of formula (I) as defined in claim 29, or of a composition comprising such a compound, to the plants or to the locus thereof.

40. A method for the selective control of grasses in crops of rice plants, which comprises treating the rice plants or the area under cultivation or the locus thereof with a compound of formula (I) as defined in claim 1.

41. A method for the selective control of grasses in crops of rice plants, which comprises treating the rice plants or the area under cultivation or the locus thereof with a compound of formula (I) as defined in claim 29.

42. A method for the selective control of grasses in crops of rice plants, which comprises treating the rice plants or the area under cultivation or the locus thereof with a compound of formula (I) as defined in claim 30, 31, 32, 33, 34, 35, 36 or 37.

* * * * *